(12) United States Patent
Ahuja et al.

(10) Patent No.: US 7,393,634 B1
(45) Date of Patent: Jul. 1, 2008

(54) SCREENING FOR DISEASE SUSCEPTIBILITY BY GENOTYPING THE CCR5 AND CCR2 GENES

(75) Inventors: Sunil Ahuja, San Antonio, TX (US); Enrique Gonzales, San Antonio, TX (US); Srinivas Mummidi, San Antonio, TX (US); Matthew J. Dolan, San Antonio, TX (US); Mike Bamshad, Salt Lake City, UT (US)

(73) Assignees: United States of America as represented by the Secretary of the Air Force, Washington, DC (US); The University of Texas System, Board of Regents, Austin, TX (US); The University of Utah Research Foundation, Salt Lake City, UT (US)

( * ) Notice: Subject to any disclaimer, the term of this patent is extended or adjusted under 35 U.S.C. 154(b) by 364 days.

(21) Appl. No.: 10/089,595

(22) PCT Filed: Oct. 12, 2000

(86) PCT No.: PCT/US00/28158

§ 371 (c)(1),
(2), (4) Date: Sep. 23, 2002

(87) PCT Pub. No.: WO01/27330

PCT Pub. Date: Apr. 19, 2001

Related U.S. Application Data

(60) Provisional application No. 60/159,137, filed on Oct. 12, 1999.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6; 435/91.1; 435/91.2; 536/23.1; 536/24.3

(58) Field of Classification Search ................. None
See application file for complete search history.

(56) References Cited

U.S. PATENT DOCUMENTS 6,372,435 B1 * 4/2002 Kaslow et al. ............ 435/6

FOREIGN PATENT DOCUMENTS

| WO | WO 98/05798 | 2/1988 |
|----|----|----|
| WO | WO 99/09162 | 2/1999 |
| WO | WO 99/23253 | 5/1999 |
| WO | WO 01/12857 | 2/2001 |

(Continued)

OTHER PUBLICATIONS

Mummidi et al; Nature Medicine, vol. 4, Jul. 1998, pp. 786-793.*

(Continued)

*Primary Examiner*—Jehanne S Sitton
(74) *Attorney, Agent, or Firm*—Myers Bigel Sibley & Sajovec, P.A.

(57) ABSTRACT

Provided are compositions, methods and uses for identifying persons at an increased risk of infection by, transmission of, or accelerated progression of a disease caused by an HIV-1 virus. Diagnostic, prognostic and combined therapeutic kits are also provided.

7 Claims, 4 Drawing Sheets

```
           CCR5 human
          haplogroups (HH)

CCR2  927 208 303 627 630 676  ORF
                29
       HHG
       HHG*1 64V  G G A C C A C  WT
       HHG*2 64V  G G A C C A C Δ32

HHF
       HHF*1 64V  A G A C C A T  WT
       HHF*2 64I  A G A C C A T  WT

HHE   64V  A G A C C A C  WT

HHD   64V  A T G T T A C  WT

HHB   64V  A T G T C A C  WT
       HHC   64V  A T G T C G C  WT

HHA   64V  A G G T C A C  WT

64V  A G G T C A C  WT
```

FOREIGN PATENT DOCUMENTS

WO        WO 01/77125     *  4/2001      .................... 435/6

OTHER PUBLICATIONS

Buseyne et al; Journal of Infectious Diseases, Oct. 1998, vol. 178, pp. 1019-1023.*
Hogg et al; The Lancet, vol. 349, p. 1294, 1997.*
Gonzalez et al; PNAS, vol. 96, pp. 12004-12009; Oct. 12, 1999.*
Szalai et al; Pediatric Research, Jul. 1999; vol. 46, 82-84.*
Daly et al., "High-Resolution Haplotype Structure in the Human Genome," *Nature Genetics*, 29:229-232, 2001.
Dean et al., "Genetic Restriction of HIV-1 Infection and Progression to AIDS by a Deletion Allele of the *CKR5* Structure Gene," *Science*, 273:1856-1862, 1996.
Garred et al., "CC Chemokine Receptor 5 Polymorphism in Rheumatoid Arthritis," *J. Rheumatol.*, 25(8):1462-1465, 1998.
Gomez-Reino et al., "Association of Rheumatoid Arthritis with a Functional Chemokine Receptor, CCR5," *Arthritis & Rheumatism*, 42(5):989992, 1999.
Gonzalez et al., "Global Survey of Genetic Variation in *CCR5*, *RANTES*, and *MIP-1α*: Impact on the Epidemiology of the HIV-1 Pandemic," *PNAS*, 98(9):5199-5204, 2001.
Gonzalez et al., "Race-Specific HIV-1 Disease-Modifying Effects associated with *CCR5* Haplotypes," *PNAS*, 96(21):12004-12009, 1999.
Hall et al., "Association of CCR5 Δ32 with Reduced Risk of Asthma," *The Lancet*, 354:1264-1265, 1999.
Helms, "CCR5-Δ32 Polymorphism in Asthma," *The Lancet*, 357:802, 2001.
Jiang et al., "Chemokine Receptor Expression in Cultured Glia and Rat Experimental Allergic Encephalomyelitis," *J. Neuroimmunol.*, 86:1-12, 1998.
Johnson et al., "Haplotype Tagging for the Identification of Common Disease Genes," *Nature Genetics*, 29:233-237, 2001.
Karpas et al., "Are Anti-HIV Drugs an Effective Treatment," *Nature Medicine*, 3(10):1052-1053, 1997.
Kostrikis et al., "A Polymorphism in the Regulatory Region of the CC-Chemokine Receptor 5 Gene Influences Perinatal Transmission of Human Immunodeficiency Virus Type 1 to African-American Infants," *J. Virol.*, 73(12):10264-10271, 1999.
Liu et al., "Homozygous Defect in HIV-1 Co receptor Accounts for Resistance of Some Multiple-Exposed Individuals to HIV-1 Infection," *Cell*, 86:367-377, 1996.
Mangano et al., "Concordance Between the CC Chemokine Receptor 5 Genetic Determinants that Alter Risks of Transmission and Disease Progression in Children Exposed Perinatally to Human Immunodeficiency Virus," *J. Infect. Disease*, 183:1574-1585, 2001.
Martin et al., Genetic Acceleration of AIDS Progression by a Promoter Variant of *CCR5*, *Science*, 282:1907-1911, 1998.
McDermott et al., "CCR5 Promoter Polymorphism and HIV-1 Disease Progression," *The Lancet*, 352:866-870, 1998.
Mummidi et al., "Evolution of Human and Non-Human Primate CC Chemokine Receptor 5 Gene and mRNA," *J. Biol. Chem.*, 275(25):18946-18961, 2000.
Mummidi et al., "Genealogy of the *CCR5* Locus and Chemokine System Gene Variants Associate with Altered Rates of HIV-1 Disease Progression," *Nature Medicine*, 4(7):786-793, 1998.
Mummidi et al., "The Human CC Chemokine Receptor 5 (CCR5) Gene," *J. Biol. Chem.*, 272(49):30662-30671, 1997.
Nguyen et al., "Phenotypic Expressions of *CCR5-Δ32/ Δ32* Homozygosity," *JAIDS*, 22:75-82, 1999.
Sabbe et al., "Donor- and Ligand-Dependent Differences in C-C Chemokine Receptor 5 Reexpression," *J. Virol.*, 75(2):661-671, 2001.
Samson et al., "Resistance to HIV-1 Infection in Caucasian Individuals Bearing Mutant Alleles of the CCR-5 Chemokine Receptor Gene," *Nature*, 382:722-725, 1996.
Segerer et al., "Expression of Chemokines and Chemokine Receptors During Human Renal Transplant Rejection," *Am. J. Kidney Diseases*, 37(3):518-531, 2001.
Tang et al., "Allelic Variants of Human Beta-Chemokine Receptor 5 (CCR5) Promoter: Evolutionary Relationships and Predictable Associations with *HIV*-1 Disease Progression," *Genes and Immunity.*, 1:20-27, 1999.
Tran et al., "Induction of Experimental Autoimmune Encephalomyelitis in C57BL/6 Mice Deficient in Either the Chemokine Macrophage Inflammatory Protein-1α or its CCR5 Receptor," *Eur. J. Immunol.*, 30:1410-1415, 2000.
International Search Report for PCT Application Serial No. PCT/US00/28158, Jun. 28, 2001.
Anzala et al. CCR2-64I allele and genotype association with delayed AIDS progression in African women *The Lancet* 351:1632-1633 (1998).
Biti et al. "HIV-1 infection in an individual homozygous for the *CCR5* deletion allele" *Nature Medicine* 3(3):252-253 (1997).
Dean et al. "Genetic Restriction of HIV-1 Infection and Progression to AIDS by Deletion Allele of the *CKR5* Structural Gene" *Science* 273:1856-1862 (1996).
Esposito et al. "Role of *CCR5* Chemokine Receptor Gene in Vertical Human Immunodeficiency Virus Type 1 Transmission and Disease Progression" *The Pediatric Infectious Disease Journal* 17(9):847-849 (1998).
Eugen-Olsen et al. "Heterozygosity for a deletion in the CKR-5 gene leads to prolonged AIDS-free survival and slower CD4 T-cell decline in a cohort of HIV-seropositive individuals" *AIDS* 11:305-310 (1997).
Eugen-Olsen et al. "Chemokine Receptor CCR2b 64I Polymorphism and its Relation to CD4 T-Cell Counts and Disease Progression in a Danish Cohort of HIV-Infected Individuals" *J. Acquir. Immune Def. Syndr. Hum. Retrovirol.* 18:110-116 (1998).
Garred et al. "Dual effect of CCR5 Δ32 gene deletion in HIV-1-infected patients" *The Lancet* 349:1884 (1997).
Garred et al. "Chemokine-receptor polymorphisms: clarity or confusion for HIV-1 prognosis?" *The Lancet* 351:2-3 (1998).
Hendel et al. "Distinctive Effects of *CCR5, CCR2 and SDF1* Genetic Polymorphisms in AIDS Progression" *J. Acquir. Immune Def. Syndr. Hum. Retrovirol.* 19:381-386 (1998).
Huang et al. "The role of a mutant CCR5 allele in HIV-1 transmission and disease progression" *Nature Medicine* 2(11):1240-1243 (1996).
Husman et al. "Association between CCR5 Genotype and the Clinical Course of HIV-1 Infection" *Annals of Internal Medicine* 127(10):882-890 (1997).
Ioannidis et al. "Genetic effects on HIV disease progression" *Nature Medicine* 4(5):536 (1998).
Just et al. "Influence of host genotype on progression to acquired immunodeficiency syndrome among children infected with human immunodeficiency virus type 1" *The Journal of Pediatrics* 127(4):544-549 (1995).
Katzenstein et al. "HIV-Infected Individuals With the CCR Δ32/CCR5 Genotype Have Lower HIV RNA Levels and Higher CD4 Cell Counts in the Early Years of the Infection Than Do Patients With the Wild Type" *J. Acquir. Immune Defic. Syndr. Hum. Retrovirol.* 16:10-14 (1997).
Kostrikis et al. "A chemokine receptor CCR2 allele delays HIV-1 disease progression and is associated with a CCR5 promoter mutation" *Nature Medicine* 4(3):350-353 (1998).
Libert et al. "The Δccr5 mutation conferring protection against HIV-1 in Caucasian populations has a single and recent origin in Northeastern Europe" *Human Molecular Genetics* 7(3):399-406 (1998).
Lucotte, G. "Frequencies of the CC chemokine receptor 5 Δ32 allele in various populations of defined racial background" *Biomed & Pharmacother* 51:469-473 (1997).
Mandl et al. "Possible influence of the Mutant CCR5 Allele on Vertical Transmission of HIV-1" *Journal of Medical Virology* 55:51-55 (1998).
Mangano et al. "Distribution of *CCR-5 Δ32* allele in Argentinian children at risk of HIV-1 infection: its role in vertical transmission" *AIDS* 12:109-123 (1998).
Meyer et al. "Early protective effect of *CCR-5 Δ32* heterozygosity on HIV-1 disease progression: relationship with viral load" *AIDS* 11:F73-F78 (1997).

Michael et al. "The role of *CCR5* and *CCR2* polymorphisms in HIV-1 transmission and disease progression" *Nature Medicine* 3(10):1160-1162 (1997).

Michael et al. "The role of viral phenotype and *CCR-5* gene defects in HIV-1 transmission and disease progression" *Nature Medicine* 3(3):338-340 (1997).

Misrahi et al. "CCR5 Chemokine Receptor Variant in HIV-1 Mother-to-child Transmission and Disease Progression in Children" *JAMA* 279(4):277-280 (1998).

Morawetz et al. "Genetic polymorphism of CCR5 gene and HIV disease: the heterozygous (CCRS/Δccr5) genotype is neither essential nor sufficient for protection against disease progression" *Eur. J. Immunol.* 27:3223-3227 (1997).

O'Brien et al. "HIV-1 infection in a man homozygous for CCR5Δ32" *The Lancet* 349:1219 (1997).

Pal et al. "Inhibition of HIV-1 infection by the β-Chemokine MDC" *Science* 278:695-698 (1997).

Philpott et al. "CCR5 Genotype and Resistance to Vertical Transmission of HIV-1" *J. Acquir. Immune Defic. Syndr.* 21:189-193 (1999).

Quillent et al. "HIV-1-resistance phenotype conferred by combination of two separate inherited mutations of *CCR5* gene" *The Lancet* 351:14-18 (1998).

Rizzardi et al. "CCR2 Polymorphism and HIV Disease" *Nature Medicine* 4(3):252-253 (1998).

Rousseau et al. "CCR5del32 in Perinatal HIV-1 Infection" *J. Acquir. Immune Defic. Syndr. Hum. Retrovirol.* 16:239-242 (1997).

Shearer et al. "Cytokine Profiles in HIV Type 1 Disease and Protection" *AIDS Res. Hum. Retroviruses* 14(Suppl 2):S149-S152 (1998).

Shearer et al. "CCR5 HIV-1 Vertical Transmission" *J. Acquir. Immune Def. Syndr. Hum. Retroviol.* 17:180-181 (1998).

Smith et al. "Contrasting Genetic Influence of CCR2 and CCR5 Variants on HIV-1 Infection and Disease Progression" *Science* 277(5328):959-965 (1997).

Tang et al. "Distribution of Chemokine Receptor *CCR2* and *CCR5* Genotypes and Their Relative Contribution to Human Immunodeficiency Virus Type 1 (HIV-1) Seroconversion, Early HIV-1 RNA Concentration in Plasma, and Later Disease Progression" *Journal of Virology* 76(2):662-672 (2002).

Theodorou et al. "HIV-1 infection in an individual homozygous for CCR5Δ32" *The Lancet* 349:1219-1220 (1997).

Van Rij et al. "Role of CCR2 Genotype in the Clinical Course of Syncytium-Inducing (SI) or Non-SI Human Immunodeficiency Virus Type 1 Infection and in the Time to Conversion to SI Virus Variants" *JID* 178:1806-1811 (1998).

Winkler et al. "Genetic Restriction of AIDS Pathogenesis by an SDF-1 Chemokine Gene Variant" *Science* 279:389-393 (1998).

Zimmerman et al. "Inherited Resistance to HIV-1 Conferred by an Inactivating Mutation in CC Chemokine Receptor 5: Studies in Populations with Contrasting Clinical Phenotypes, Defined Racial Background, and Quantified Risk" *Mol. Med.* 3(1):23-36 (1997).

* cited by examiner

FIG. 1C

Unique CCR5 haplotypes

| | 28 | 27 | 26 | 25 | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | |
|---|---|---|---|---|---|---|---|---|---|---|---|---|---|---|---|---|---|---|---|---|---|---|---|---|---|---|---|---|---|
| | . | . | . | . | T | T | T | T | T | T | T | T | . | . | . | . | . | . | . | . | . | . | . | . | . | . | . | . | C — 927 |
| | A | . | . | . | . | . | . | . | . | . | . | . | . | . | . | . | . | . | . | . | . | . | . | . | . | . | . | . | — 925 |
| | . | . | . | . | . | . | . | . | . | . | . | . | . | . | . | . | . | . | . | . | . | . | . | . | A | . | . | . | — 922 |
| | . | . | . | . | . | . | G | . | . | . | . | . | . | . | . | . | . | . | . | . | . | . | . | . | . | . | . | . | AG-A-G-C — 895 |
| | . | . | . | . | . | A | . | . | . | . | . | . | . | . | . | . | . | . | . | . | . | . | . | . | . | . | . | . | — 891 |
| | . | . | . | . | . | . | . | G | . | . | . | . | . | G | . | . | . | . | . | . | . | . | . | . | . | . | . | . | T — 890 |
| | . | . | . | . | . | . | . | . | . | C | C | . | . | . | . | . | . | . | . | . | . | . | . | . | . | . | . | . | A-T-T — 880 |
| | . | . | . | . | . | . | . | . | . | . | . | . | . | . | . | . | . | . | . | . | . | . | . | . | . | . | . | . | — 772 |
| | . | . | . | . | . | . | G | . | . | . | . | . | . | . | . | . | . | . | . | . | . | C | . | . | . | . | . | . | A-T — 756 |
| | . | . | . | . | . | . | . | . | . | . | . | . | . | . | . | . | . | . | . | . | . | . | . | . | . | . | . | . | — 718 |
| | . | . | . | . | . | . | . | . | . | . | . | C | . | . | . | . | . | . | . | . | . | . | . | . | . | . | . | . | T — 686 |
| | . | . | . | . | . | . | . | . | . | . | . | . | . | . | . | . | . | . | G | G | G | G | . | . | . | . | . | . | A — 676 |
| | . | . | . | . | . | . | . | . | . | . | . | . | . | T | T | T | T | . | . | . | . | . | . | . | . | . | . | . | — 630 |
| | C | C | C | C | C | C | C | C | C | C | C | C | C | C | C | C | C | . | . | . | . | . | . | . | . | . | . | . | T-C — 627 |
| | . | . | . | . | . | . | . | . | . | . | . | . | . | . | . | . | . | . | . | . | . | . | . | C | . | . | . | . | — 546 |
| | . | . | . | . | . | . | . | . | . | . | . | . | . | . | . | . | T | . | . | . | . | . | . | . | . | . | . | . | T-T-C — 524 |
| | . | . | . | . | . | . | . | . | . | . | . | . | . | . | . | . | . | . | . | . | . | . | . | . | . | . | . | . | T — 494 |
| | . | . | . | . | . | . | . | . | . | . | C | C | . | . | . | . | . | . | . | . | . | . | . | . | . | . | . | . | T-T — 434 |
| | . | . | . | . | . | . | . | . | . | . | . | C | . | . | . | . | . | . | . | . | . | . | . | . | . | . | . | . | G-T — 410 |
| | . | . | . | . | . | . | . | . | . | . | . | . | . | . | . | . | . | . | . | . | . | . | . | . | . | A | . | . | — 385 |
| | . | . | . | . | . | . | . | . | . | . | . | . | . | . | . | . | . | . | . | . | . | . | . | . | C | . | . | . | — 381 |
| | . | . | . | . | . | . | . | . | . | . | . | . | . | . | . | . | . | . | . | . | . | . | . | . | . | . | . | . | C — 374 |
| | . | . | . | . | . | . | . | . | . | . | . | . | A | . | . | . | . | . | . | . | . | . | . | . | . | . | . | . | A-G-G — 361 |
| | A | A | A | A | A | A | A | A | A | A | A | A | A | A | . | . | A | . | . | . | . | . | . | . | . | . | . | . | — 303 |
| | . | . | . | . | . | . | . | . | . | . | . | . | . | . | G | . | . | . | . | . | . | . | . | . | . | . | . | . | — 292 |
| | . | . | . | . | . | . | . | . | . | . | . | . | . | . | . | . | . | . | . | . | . | . | . | . | . | C | . | . | T — 239 |
| | . | . | . | . | . | . | . | . | . | . | . | . | . | . | . | . | . | T | T | T | T | T | T | T | T | . | . | . | — 209 |
| | . | . | . | . | . | . | . | . | . | . | . | C | . | . | . | . | . | . | . | . | . | . | . | . | . | . | . | . | A-C — 208 |
| | . | . | . | . | . | . | . | . | . | . | . | . | . | . | . | . | . | . | . | . | . | . | . | . | . | . | . | . | — 200 |
| | . | . | . | . | . | . | G | . | . | . | . | . | . | . | . | . | . | . | . | . | . | . | . | . | . | . | . | . | — 177 |
| | . | . | . | . | . | . | . | . | . | . | . | . | . | . | . | . | . | T | . | . | . | . | . | . | . | . | . | . | T — 94 |
| | . | . | . | . | . | . | G | . | . | . | . | . | . | . | . | . | . | . | . | . | . | . | . | . | . | . | . | . | — 45 |
| | G | G | G | G | . | . | . | . | . | . | . | . | . | . | . | . | . | . | . | . | . | . | . | . | . | . | . | . | A-T-A-C-A-GT-T — 29 |

FIG. 1D

CCR5 human haplogroups (HH)

| | CCR2 | | 29 | 208 | 303 | 627 | 630 | 676 | 927 | ORF |
|---|---|---|---|---|---|---|---|---|---|---|
| HHG | | 64V | G | G | A | C | C | A | C | WT |
| HHG*1 | | 64V | G | G | A | C | C | A | C | WT |
| HHG*2 | | 64V | G | G | A | C | C | A | C | Δ32 |
| HHF | | | | | | | | | | |
| HHF*1 | | 64V | A | G | A | C | C | A | T | WT |
| HHF*2 | | 64I | A | G | A | C | C | A | T | WT |
| HHE | | 64V | A | G | A | C | C | A | C | WT |
| HHD | | 64V | A | T | G | T | T | A | C | WT |
| HHB | | 64V | A | T | G | T | C | A | C | WT |
| HHC | | 64V | A | T | G | T | C | G | C | WT |
| HHA | | 64V | A | G | G | T | C | A | C | WT |
| | | 64V | A | G | G | T | C | A | C | WT |

Haplotype pairs in Caucasians

HIV-1 disease association retardation      neutral      acceleration

Haplotype pairs in African Americans

HIV-1 disease association retardation      neutral      acceleration

*CCR5 haplotype pairs that influence mother-to-child HIV transmission*

CCR5 haplotype pairs

Transmission retardation — neutral — acceleration

*CCR5 haplotype pairs that influence disease progression*

CCR5 haplotype pairs

Disease progression retardation — neutral — acceleration

SCREENING FOR DISEASE SUSCEPTIBILITY BY GENOTYPING THE CCR5 AND CCR2 GENES

The present application is a nationalization of PCT Application Serial No. PCT/US00/28158, filed Oct. 12, 2000, which claims priority to U.S. provisional application Ser. No. 60/159,137, filed Oct. 12, 1999, the entire text, figures and sequences of which applications are incorporated herein by reference without disclaimer.

The U.S. government owns rights in the present invention pursuant to grant numbers AI43279 and AI46326 from the National Institutes of Health.

BACKGROUND OF THE INVENTION

1. Field of the Invention

The present invention relates generally to the fields of molecular biology and genetics. More particularly, the invention provides compositions, methods and uses for identifying persons at an increased risk of infection by, transmission of, or accelerated progression of a disease caused by an HIV-1 virus. Diagnostic, prognostic and combined therapeutic kits are also provided.

2. Description of Related Art

Infection with HIV and the resulting diseases, including full-blown AIDS, remain a significant worldwide health problem. Methods are urgently needed to further understand the infection and transmission process and factors that predispose certain individuals to increased risks.

Results from studies on the viral and host genetic and immunological factors that influence in HIV pathogenesis have been reported (Cairns and D'Souza, 1998; Berger, 1997; Fauci, 1996; Cohen et al., 1997; Buchacz et al., 1998; Rosenberg and Walker, 1998; Ferbas, 1998; Shearer and Clerici, 1998; Graziosi et al., 1998). Among the host factors that influence HIV-1 pathogenesis are non-MHC genetic determinants (chemokine system gene variants), MHC genetic determinants (HLA and linked genes), and chemokine related inhibition of HIV-1.

Several chemokine receptors have been identified as co-receptors with CD4 for HIV (Deng et al., 1996; Doranz et al., 1996; Moore et al., 1997; Cairns and D'Souza, 1998; Berger, 1997; Cohen et al., 1997; Feng et al., 1996; Choe et al., 1996; Deng et al., 1997; Zhang et al., 1998; Garzino-Demo et al., 1998; Berger et al., 1998; Unutmaz et al., 1998; Bjorndal et al., 1997; D'Souza and Harden, 1996; Fauci, 1996). These include CCR5, used preferentially by macrophage-tropic strains (M-tropic; non-synctium inducing (NSI); R5), and CXCR4, utilized by T-cell-tropic strains (T-tropic; synctium inducing (SI); X4). In addition, several R5 strains can use CCR2B or other co-receptors, although the role of this expanded receptor repertoire in vivo is not clear.

Analyses of different receptor alleles in HIV-1 patients have led to conflicting information regarding their importance to infectivity and disease progression (Dean et al., 1996; Michael et al., 1997a; 1997b; Zimmerman et al., 1997; de Roda Husman et al., 1997; Rizzardi et al., 1998; Meyer et al., 1997; Katzenstein et al., 1997; Eugen-Olsen et al., 1997; 1998; Hendel et al., 1998; Huang et al., 1996; Smith et al., 1997; Kostrikis et al., 1998; Anzala et al., 1998; van Rij et al., 1998; Rizzardi et al., 1998; Hendel et al., 1998).

In the U.S., the genetic determinants of HIV-1 in adults have been examined primarily in three different cohorts, each differing in risk factors for HIV-1 (Dean et al., 1996; Huang et al., 1996; Michael et al., 1997a; 1997b; Smith et al., 1997; Zimmerman et al., 1997; Winkler et al., 1998; Kostrikis et al., 1998; Martin et al., 1998; McDermott et al., 1998). They include multi-center cohort studies biased towards homosexual, Caucasian men (Multicenter AIDS cohort study (MACS); San Francisco City Cohort); hemophiliacs (Multi-center Hemophilia Cohort Study); and the single African-American cohort that is biased heavily towards an intravenous drug using population (AIDS link to Intravenous Experience (ALIVE)).

Despite such multi-center studies, it is unclear whether the results of the reported associations can be generalized to other ethnic/population groups. More recent publications have proposed associations of certain receptor promoter polymorphisms with an accelerated disease course in Caucasians (Martin et al., 1998; McDermott et al., 1998). However, as with the studies described above, the promoter studies attempt to correlate the association of promoter polymorphisms with an accelerated disease course, without consideration of the complete genotypic information present in the study group.

Therefore, it is evident that the art still needs improved methods of correlating the risk of infection by, transmission of, or accelerated progression of diseases caused by HIV-1. In particular, correlative methods that take into consideration all of the relevant genotypic (haplotype pairs) information, thus providing a stronger correlation, would represent a significant advance in this field.

SUMMARY OF THE INVENTION

The present invention overcomes these and other shortcomings in the art by providing improved compositions, kits, methods and uses for determining the genotype of a human subject at the CCR5 locus. The invention thus preferably allows for the identification of individuals and populations that are at increased risk of infection by HIV-1, increased risk of transmission of HIV-1, and/or increased risk of accelerated HIV-1 disease progression. The invention accomplishes this by providing methods of identifying the complete CCR5 genotype (both haplotype pairs), and correlating the complete CCR5 genotype with the risk of becoming infected by HIV-1, transmitting HIV-1, or having an accelerated or retarded HIV-1 disease progression. Comparing both haplotype pairs (or alleles) of the CCR5 genotype to HIV-1 disease risk, as provided by this invention, results in a much stronger correlation to the risk of HIV-1 infection, transmission and/or accelerated disease progression.

The invention thus provides a composition comprising at least a first nucleic acid segment or primer that detects a human CCR5 polymorphism, for use in identifying the genotype, particularly, detecting polymorphisms on both CCR5 alleles of a human subject, and for correlating polymorphisms on both CCR5 alleles with the risk of HIV-1 infection, transmission or disease progression in humans.

The compositions may comprise at least a first nucleic acid segment or primer that detects a human CCR5 polymorphism by detecting an HHE allele, an HHC allele, an HHF*1 allele, an HHD allele or an HHG*2 allele of human CCR5. Compositions that comprise at least a first nucleic acid segment or primer that detects a human CCR5 polymorphism by detecting an HHA allele, an HHB allele, an HHF*2 allele or an HHG*1 allele of human CCR5 are also provided.

Such compositions may comprise at least a first and second nucleic acid segment or primer that each detect a distinct human CCR5 polymorphism; or at least three or four such segments or primers; up to and including a plurality of nucleic acid segments or primers that detect distinct human CCR5 polymorphisms. Within the plurality, at least five, six, seven or eight, up to about nine or more nucleic acid segments or primers that detects a CCR5 polymorphism may readily be included.

The HHA, HHB, HHC, HHD, HHE, HHF*1 HHF*2, HHG*1 and HHG*2 alleles of human CCR5 may be readily determined according to the present disclosure. The chimpanzee reference sequence of 925 bp is provided herein as SEQ ID NO:64. The human consensus sequence of 927 bp is provided herein as SEQ ID NO:65. Initially considering the CCR5 sequence, the sequence of HHA is provided herein as SEQ ID NO:66; HHB is SEQ ID NO:67; HHC is SEQ ID NO:68; HHD is SEQ ID NO:69; HHE is SEQ ID NO:70; HHF is SEQ ID NO:71; and HHG is SEQ ID NO:72. These sequences are provided so that the spatial relationship of the signature motifs can be readily identified irrespective of any arbitrary numbering system that may later be assigned to this region of the CCR5 sequence.

The HHA, HHB, HHC, HHD, HHE, HHF*1 HHF*2, HHG*1 and HHG*2 CCR5 human haplogroups may also be identified by their signature motifs themselves. The CCR5 "signature motif", as used herein, refers to the 7-letter SNP signature motif that defines the nucleotides at CCR5 positions 29, 208, 303, 627, 630, 676, and 927, as disclosed herein. Therefore, the motifs do not represent a contiguous 7-mer, but are a shorthand notation to define the nucleotides at positions 29, 208, 303, 627, 630, 676 and 927, irrespective of the intervening sequences. The signature motifs of HHA (AGGTCAC), HHB (ATGTCAC), HHC (ATGTCGC), HHD (ATGTTAC), HHE (AGACCAC), HHF (AGACCAT) and HHG (GGACCAC) are shown in FIG. 1D.

Accordingly, HHA can be described as having the CCR5 sequence based upon SEQ ID NO:65 and tolerating G or C at position 374, G or A at position 385, T or C at position 546 and G or A at position 922. HHB can be described as having an obligate requirement for T at position 208, and HHC can be described as having an obligate requirement for T at position 208 and G at position 676, but tolerating a T or C at position 239 and a T or C at position 756. HHD has an obligate requirement for T at position 208 and T at position 630; and may tolerate T or C at position 45, T or C at position 381 and C or T at position 524. HHE has an obligate requirement for A at position 303 and C at position 627; and may tolerate C or T at position 177 and T or C at any of positions 410, 434 and 494. HHF has an obligate requirement for A at position 303, C at position 627 and T at position 927; and may tolerate A or G at positions 94 and 200, T or C at position 209, A or G at position 292, G or A at position 361, T or C at positions 686, 772, and 880, A or G at positions 890 and 895. HHG has an obligate requirement for G at position 29, A at position 303 and C at position 627; and may tolerate A or G at position 718, G or A at position 891, and G or A at position 925.

Exemplary alleles of the unique CCR5 haplotypes have been illustrated in FIG. 1C. These include, for example, allele #1 (an HHA allele) that can properly be described as having the CCR5 sequence based upon SEQ ID NO:65, where position 374 is preferably a C, and position 385 is preferably an A. Similarly, allele #3 (also an HHA allele), can be described as having the CCR5 sequence based upon SEQ ID NO:65, where position 546 is preferably a C and position 922 is preferably an A. Likewise, allele #20, an HHF allele, preferably has a G at both positions 292 and 890, while allele #23, a distinctly different HHF allele, preferably has a G at both positions 94 and 200 and a C at position 880. Another HHF allele, #24, preferably has a C at position at 772 and a G at position 895.

As shown in FIG. 1D, all haplotypes within a haplogroup have identical nucleotide sequences at CCR5 positions 29, 208, 303, 627, 630, 676, and 927 (the signature motif. HHF*2 and HHG*2 designate the subset of haplotypes within HHF and HHG that are in linkage disequilibrium with the CCR2-64I and CCR5-Δ32 polymorphisms, respectively. Thus, the 7-letter SNP signature motif for HHF*2 and HHG*2 have the prefix, 64I and the suffix, Δ32, respectively.

The compositions of the invention may also be combined with one or more other HIV diagnostic or prognostic indicators, exemplified, but not limited to, other nucleic acid segments or primers, discriminating antibodies, and the like. Biological materials, such as one, two or a plurality of nucleic acid segments, primers or discriminating antibodies that detect human CCR2 polymorphisms and human CCR2 polymorphisms at both alleles are particular examples.

The present invention further provides uses of any of the foregoing compositions in the preparation of diagnostic or prognostic formulations for use in identifying human subjects at increased risk of HIV-1 infection, transmission and/or disease progression. Such uses include the preparation of diagnostic, prognostic and medicinal test kits for identifying human subjects with increased risk of HIV-1 infection, transmission or disease progression.

Methodologically, the invention further provides methods of assessing the risk of a human subject for HIV-1 infection or disease progression, comprising identifying the genotype of both CCR5 alleles of the subject, wherein the genotype of both CCR5 alleles is indicative of the risk of said subject for HIV-1 infection or disease progression. Particular methods include identifying a human subject at increased risk of HIV-1 infection, transmission, and/or disease progression, comprising identifying the genotype of both CCR5 alleles of the patient, wherein certain CCR5 allelic combinations (haplotype pairs) are indicative of or associated with an increased risk of HIV-1 infection or accelerated disease progression.

In the compositions, uses and methods of the invention, where the human subject is a Caucasian, the presence of two HHE alleles of CCR5 is particularly indicative of an increased risk of being infected by an HIV-1 virus or for accelerated HIV-1 disease progression. In the compositions, uses and methods wherein the human subject is an African-American, the presence of an HHC and an HHF*1 allele, an HHC and an HHE allele, two HHC alleles, or an HHC and an HHD allele of CCR5 is particularly indicative of an increased risk of being infected by an HIV-1 virus or for accelerated HIV-1 disease progression. In compositions, uses and methods wherein the human subject is a child, particularly a South American or Argentinean child or a child of southern European descent, the presence of an HHC and an HHE allele, two HHE alleles, or an HHE allele and an HHG*2 allele of CCR5 is particularly indicative of an increased risk of being infected by an HIV-1 virus or for accelerated HIV-1 disease progression.

The present invention also provides compositions, uses and methods of identifying a child at increased risk for transmission of an HIV-1 virus from the mother while the child is in utero, comprising identifying the genotype of both CCR5 alleles of the child, wherein the presence of an HHC and an HHE allele, two HHE alleles, or an HHE allele and an HHG*2 allele of CCR5 is indicative of an increased risk of transmission of the HIV-1 virus from the mother while the child is in utero.

Human subjects that are at an increased risk of infection by or the accelerated progression of a disease caused by the HIV-1 virus are candidates for therapy, optionally, more aggressive therapy, with one or more anti-HIV-1 therapeutics, such as anti-reverse transcriptase agent(s). Therefore, the present invention further provides methods, uses, compositions and combinations for reducing or preventing infection by, or the accelerated progression of a disease caused by, an HIV-1 virus in human subjects. Such embodiments generally comprise identifying a susceptible human subject by determining the genotype of both CCR5 alleles of the subject, and treating the susceptible human subject with a biologically effective amount of at least a first anti-viral, particularly anti-HIV, agent.

A "susceptible human subject" in this context is a candidate human subject that has an increased risk of infection by or accelerated progression of a disease caused by the HIV-1 virus, as identified by determining the genotype of both CCR5 alleles of the subject, as disclosed herein. The CCR5 allelic combinations (haplotype pairs) particularly indicative of or associated with increased risks in groups of Caucasians, African-Americans and children are as set forth above and disclosed herein in detail. "Treating" the susceptible human subject includes providing at least a first anti-viral or anti-HIV therapeutic agent and, optionally, providing aggressive therapy with at least a first anti-viral or anti-HIV therapeutic agent. Such agents are exemplified by, but not limited to, those listed in Section IV of the Illustrative Embodiments, herein.

Diagnostic, prognostic and medicinal test kits, and combined diagnostic-therapeutic kits, form further aspects of the invention. Preferred kits of the invention comprise only the instructions for correlating CCR5 polymorphisms on both CCR5 alleles of a human subject with the risk of infection by, transmission of, or accelerated progression of a disease caused by an HIV-1 virus. The one or more nucleic acid segments or primers that detect a CCR5 polymorphism on both CCR5 alleles of a human subject may be separated obtained for use by the practitioner, or may also be supplied with the kit.

The diagnostic, prognostic, medicinal and combined diagnostic-therapeutic kits may also comprise, in a suitable container, the at least a first nucleic acid segment or primer that detects a CCR5 polymorphism on both CCR5 alleles of a human subject. Preferably, these kits will comprise both the first nucleic acid segment or primer and the instructions for correlating CCR5 polymorphisms on both CCR5 alleles with risk of infection, transmission or accelerated HIV-1 disease progression. Instructions for executing the detection step, i.e., the detection of CCR5 polymorphisms on both CCR5 alleles of a human subject may also be included with any type of kit.

In common with the foregoing compositions, methods and uses, the kits may comprise at least a first and at least a second nucleic acid segment or primer that detects a CCR5 polymorphism on both CCR5 alleles of a human subject, wherein the at least a first and at least a second nucleic acid segment or primer detect distinct CCR5 polymorphisms. As the inventors have elucidated nine CCR5 haplotypes, in preferred aspects of the invention, the diagnostic, prognostic and medicinal kits may comprise at least three, at least four, at least five, at least six, at least seven, at least eight, or nine nucleic acid segments or primers that detects a CCR5 polymorphism.

In addition to nucleic acid primers that detect CCR5 polymorphisms, the diagnostic, prognostic and medicinal kits may further comprise at least a second, third or plurality of agents capable of providing diagnostic or prognostic information concerning HIV infection, transmission and/or progression. Nucleic acid segments or primers that detect CCR2 polymorphisms on both CCR2 alleles of a human subject are particularly preferred.

As human subjects that are identified as being at an increased risk of infection by or the accelerated progression of a disease caused by the HIV-1 virus are candidates for therapy, optionally, more aggressive therapy, with one or more anti-HIV-1 agent(s), the present invention also provides combined diagnostic-therapeutic kits. In general, these kits comprise at least a first anti-viral therapeutic agent, preferably an anti-HIV agent, such as a reverse transcriptase inhibitor, in addition to the CCR5 diagnostic nucleic acids and preferred correlation instructions.

That is, one or more anti-viral agents in combination with at least a first nucleic acid segment or primer that detects a CCR5 polymorphism on both CCR5 alleles of a human subject and instructions for correlating CCR5 polymorphisms on both CCR5 alleles of a human subject with the risk of infection by, transmission of, or accelerated progression of a disease caused by an HIV-1 virus. One, two, three, four or a plurality of anti-viral, anti-HIV or reverse transcriptase inhibitory therapeutic agents, optionally, increased doses thereof, may be used. Such agents are exemplified by, but not limited to, those listed in Section IV of the Illustrative Embodiments, herein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. All figures, and the entire text of the supporting figure legends from U.S. provisional application Ser. No. 60/159,137, filed Oct. 12, 1999, are also incorporated herein by reference without disclaimer.

FIG. 1A, FIG. 1B, FIG. 1C, FIG. 1D and FIG. 1E. CCR5 gene map and phylogenetic network of CCR5 haplotypes and haplogroups. FIG. 1A. Schema of CCR2 and CCR5 loci on chromosome 3 (not to scale; the hatched marks denote gaps). The four CCR5 exons (open boxes) and two introns (black boxes) are numbered; the open reading frame (ORF) is in exon 4. CCR5 numbering is based on GenBank Accession numbers AF031236 and AF031237 (Example 3). Downward pointing arrows indicate the common polymorphisms found in CCR5 ORF, CCR2 ORF, and in a cis-regulatory region spanning from CCR5 +1 to +927 (Examples 3 and 4). The arrow above the gene map denotes the downstream CCR5 promoter (Example 3). FIG. 1B. A phylogenetic tree depicting the relationships among the seven CCR5 human haplogroups (HHA-HHG). A chimpanzee CCR5 allele was used as an outgroup. The sequences of 28 unique CCR5 alleles were used to generate the phylogenetic tree. Each allele was assigned a number (1 through 28) that is displayed at the tips of the branches. The CCR5 alleles that have a common evolutionary history clustered together and are boxed. Each cluster of CCR5 alleles therefore defined a unique CCR5 haplogroup, and all haplotypes within a haplogroup share several distinct genetic features. The CCR5 cis-regulatory polymorphism(s) that define a haplogroup and the bootstrap support for each branch are denoted at the branch point. The subset of haplotypes within HHF and HHG that are in linkage disequilibrium with the CCR2-64I and CCR5-Δ32 polymorphisms, respectively are indicated by a suffix following their identification number. The CCR2-64I and CCR5-Δ32 polymorphisms were genotyped as described in Example 4. FIG. 1C. A schematic representation of the nucleotide sequences of the unique human CCR5 alleles (+1 to +927). The sequences of human CCR5 alleles were compared to those found in the homologous region of chimpanzee CCR5. The numbers at the bottom of the figure correspond to human CCR5 sequence. The sequence found at the corresponding nucleotide positions in chimpanzee CCR5 are shown. Dashes represent gaps introduced, and dots denote identity between human and chimpanzee CCR5 sequences for the indicated nucleotide position. Each row is numbered serially (1 through 28) and represents the sequence for the 28 alleles displayed in the phylogenetic tree. CCR5 SNPs common to several human alleles are boxed, whereas those that are unique to individual alleles are unboxed. CCR5 alleles that form a haplogroup are bracketed. FIG. 1D. classification of CCR5 human haplogroups. All haplotypes within a haplogroup have identical nucleotide sequences at CCR5 positions 29, 208, 303, 627, 630, 676, and 927. This cassette of nucleotide sequences is designated by a 7-letter SNP signature motif. Therefore, each haplotype within a haplogroup is characterized by the constellation of invariant polymorphisms indicated but differ from each other by additional SNPs. The sequences within a SNP signature motif that are common to those found in the ancestral CCR5 haplotype, designated as HHA are shown. HHF*2 and HHG*2 designate the subset of haplotypes within HHF and HHG that are in linkage disequilibrium with the CCR2-64I and CCR5-Δ32 polymorphisms, respectively. The 7-letter SNP signature motif for HHF*2 and HHG*2 have the prefix, 64I and the suffix, Δ32, respectively. The sequence for the allele representing HHG*2 is derived from a CCR5 genomic DNA clone (GenBank Accession number AF009962). The HHB haplotype was found by genotyping over 2000 individuals (Example 7), and confirmed by sequencing. The sequences of the HHB alleles derived from two individuals who were heterozygous for HHB were identical (allele number 7). The sequence for the remaining 26 CCR5 alleles were derived from individuals homozygous or heterozygous for either CCR5 29G or 927T. FIG. 1E. A model illustrating the evolution of human CCR5 haplogroups. HHB, HHC and HHD differ from HHA by having a 208T mutation. However, unlike HHC or HHD, HHB is not mutated at either CCR5 630 or 676. HUB may therefore be ancestral to HHC and HHD. HHG*1 and HHF*1 are likely to be ancestral to HHG*2 and HHF*2, respectively.

DETAILED DESCRIPTION OF ILLUSTRATIVE EMBODIMENTS

Figure 1A:
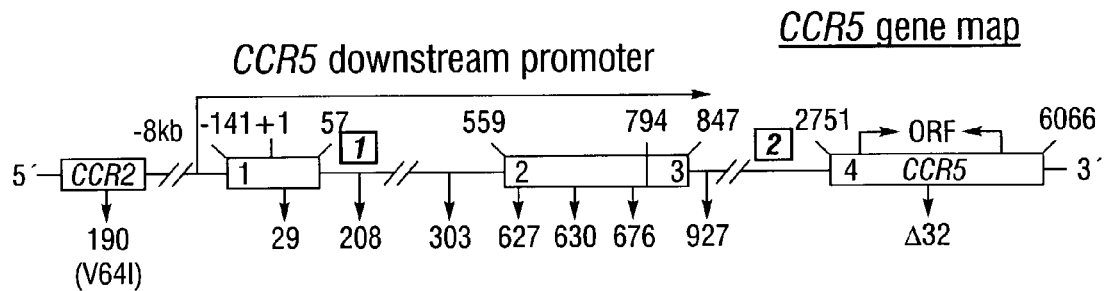

I. Markers of HIV-1 Infection and Progression

Host genetic and immunological factors that influence HIV-1 pathogenesis include MHC and non-MHC genetic determinants. Of the non-MHC determinants, the chemokine system gene variants and chemokine related inhibition of HIV-1 are of reported relevance. However, the published data in this field is conflicting and there is little or no reliable indication as to which genes and particular markers could be developed into reliable diagnostic and prognostic tests. Such tests are urgently needed in themselves, and would also allow appropriate therapeutic treatments to be designed on an individual basis, thus allowing the spread of HIV infection in the population at large to be counteracted.

In light of such needs, the present inventors undertook a detailed analysis of the published literature in this area. Of the chemokine receptors reported to be co-receptors for HIV (Deng et al., 1996; Doranz et al., 1996; Moore et al., 1997; Cairns and D'Souza, 1998; Berger, 1997; Cohen et al., 1997; Feng et al., 1996; Choe et al., 1996; Deng et al., 1997; Zhang et al., 1998; Garzino-Demo et al., 1998; Berger et al., 1998; Unutmaz et al., 1998; Bjorndal et al., 1997; D'Souza and Harden, 1996; Fauci, 1996), the two principal components are believed to be CCR5 and CXCR4. An expanded receptor repertoire, including CCR2B, has also been connected with, several strains.

The inventors reason that homozygosity, but not heterozygosity, for a 32-bp deletion in the CCR5 gene (CCR5-Δ32) leads to loss of CCR5 surface expression, and is associated with strong resistance to HIV infection by M-tropic isolates (Dean et al., 1996; Liu et al., 1996; Samson et al., 1996). The CCR5-Δ32 allele is rarely found in individuals of African and Asian ancestry (Martinson et al., 1997; Lucotte, 1997). In contrast, ~15% of Caucasians are heterozygous and 1% are homozygous for this allele. When situated in trans with CCR5-Δ32, the CCR5 m303 mutation also eliminates CCR5 expression and accounts for resistance against infection (Quillent et al., 1998). Other rare variants of the CCR5 ORF have also been described, but their relevance to HIV-1 pathogenesis is unknown (Ansari-Lari et al., 1997; Carrington et al., 1997). Most highly exposed HIV-negative individuals are not homozygous for the CCR5-Δ32 allele (Dean et al., 1996; McNicholl et al., 1997) suggesting that there are other important genetic resistance factors.

Despite the prevailing view that heterozygosity for the CCR5-Δ32 allele, and a common allelic variant of CCR2 (CCR2-64I) delays disease progression, the inventors' careful scrutiny of these studies suggested otherwise. A protective role for CCR5-Δ32 heterozygosity is evident in some reports (Dean et al., 1996; Michael et al., 1997b; Zimmerman et al., 1997; de Roda Husman et al., 1997), but transient/weak (Rizzardi et al., 1998; Meyer et al., 1997; Katzenstein et al., 1997; Eugen-Olsen et al., 1997; Hendel et al., 1998) or not confirmed in other studies (Huang et al., 1996). Similarly with regards to the presence of the CCR2-64I allele, a protective role is evident in some reports (Smith et al., 1997; Kostrikis et al., 1998; Anzala et al., 1998; van Rij et al., 1998), but not confirmed in other studies (Michael et al., 1997a; Rizzardi et al., 1998; Hendel et al., 1998; Eugen-Olsen et al., 1998).

From the U.S. analyses of genetic determinants of HIV-1 infection in adults in different risk groups (Dean et al., 1996; Huang et al., 1996; Michael et al., 1997a; 1997b; Smith et al., 1997; Zimmerman et al., 1997; Winkler et al., 1998; Kostrikis et al., 1998; Martin et al., 1998; McDermott et al., 1998), it is not possible to generalize the published results to ethnic/population groups other than the precise groups studied (homosexual, Caucasian men, San Francisco City Cohort, hemophiliacs and a single African-American cohort, heavily biased towards intravenous drug use).

More recently, there have been additional publications that have described the association of CCR5 promoter polymorphisms with an accelerated disease course in Caucasians (Martin et al., 1998; McDermott et al., 1998). Martin et al. (1998) described a CCR5 allele designated as the P1 allele that was associated with an accelerated disease course. However, these studies also attempt to correlate the association of CCR5 promoter polymorphisms with an accelerated disease course, without consideration of the complete genotypic information present in the study group.

Thus, realizing that improved methods of correlating the increased risk of HIV-1 infection, transmission and/or accelerated disease progression were needed, the present inventors developed more rigorous studies. Analyses taking into consideration all of the relevant genotypic (haplotype pairs) information allowed the inventors to delineate stronger correlations without the ambiguity that existed in the art. Specifically, the present inventors found that comparing both haplotype pairs (or alleles) of the CCR5 genotype to HIV-1 disease risk is necessary to provide reliable correlations of the risk of HIV-1 infection and/or accelerated disease progression.

II. Nucleic Acid Segments

Aspects of the present invention concern isolated DNA segments that hybridize to one or more coding or non-coding regions of the human CCR5 and/or CCR2 gene(s). As used herein, the term "DNA segment" refers to a DNA molecule that has been isolated free of total genomic DNA of a particular species. Therefore, for example, a DNA segment that hybridizes to one or more coding or non-coding regions of the human CCR5 and/or CCR2 gene(s) refers to a DNA segment that is isolated away from, or purified free from, total genomic DNA. Included within the term "DNA segment", are DNA segments and smaller fragments of such segments, such as probes and primers, and the like, that are chemically synthesized.

Excepting flanking regions, and allowing for the degeneracy of the genetic code, sequences that have between about 70% and about 79%; or more preferably, between about 80% and about 89%; or even more preferably, between about 90% and about 99%; of nucleotides that are identical to the nucleotides of the disclosed nucleic acid sequences will be sequences that are "essentially as set forth in" these sequences.

Sequences that are essentially the same as those set forth in the disclosed nucleic acid sequences may also be functionally defined as sequences that are capable of hybridizing to a nucleic acid segment containing the complement of the disclosed nucleic acid sequences under relatively stringent conditions. Suitable relatively stringent hybridization conditions will be well known to those of skill in the art, as disclosed herein.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Another exemplary, but not limiting, standard hybridization is incubated at 42° C. in 50% formamide solution containing dextran sulfate for 48 hours and subjected to a final wash in 0.5×SSC, 0.1% SDS at 65° C.

Naturally, the present invention also encompasses DNA segments that are complementary, or essentially complementary, to the sequence set forth in the disclosed nucleic acid sequences. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the disclosed nucleic acid sequences under relatively stringent conditions such as those described herein.

The nucleic acid segments of the present invention, regardless of the length of the "hybridizing" or "complementary"

sequence itself, may be combined with other DNA sequences, such as additional restriction enzyme sites, and the like, such that their overall length may vary somewhat.

For example, nucleic acid fragments may be prepared that include a short contiguous stretch identical to or complementary to the disclosed nucleic acid sequences, such as about 8, about 10 to about 14, or about 15 to about 20 nucleotides, and that are up to about 30, or about 50, or about 100 nucleotides in length, with segments of about 25 nucleotides being preferred in certain cases. DNA segments with total lengths of about 75, about 60, about 45, about 40 and about 35 nucleotides in length (including all intermediate lengths) are also contemplated to be useful.

It will be readily understood that "intermediate lengths", in these contexts, means any length between the quoted ranges, such as 9, 10, 11, 12, 13, 16, 17, 18, 19, 21, 22, 23, 24, 26, 27, 28, 29, 31, 32, 33, 34, 36, 37, 38, 39, 41, 42, 43, 44, 46, 47, 48, 49, 51, 52, 53, etc.; 100, 101, 102, 103, etc. and the like.

The various primers designed around the disclosed nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 ... and so on. For a 15-mer, the probes correspond to bases 1 to 15, 2 to 16, 3 to 17 ... and so on. For a 20-mer, the probes correspond to bases 1 to 20, 2 to 21, 3 to 22 ... and so on.

III. Nucleic Acid Amplification

As used herein, the term "oligonucleotide directed amplification procedure" refers to template-dependent processes that result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety. Nucleic acids, used as a template for amplification methods, may be isolated from cells according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to the CCR5 and/or CCR2 genes are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the sequences present in a given template sample. One of the best-known amplification methods is the polymerase chain reaction (referred to as PCR™) which is described in detail in U.S. Pat. Nos. 4,683,195, 4,683,202 and 4,800,159, each incorporated herein by reference in entirety.

Briefly, in PCR™, two primer sequences are prepared that are complementary to regions on opposite complementary strands of the target sequence. An excess of deoxynucleoside triphosphates is added to a reaction mixture along with a DNA polymerase, e.g., Taq polymerase. If the particular target sequence is present in a sample, the primers will bind to the target sequence and the polymerase will cause the primers to be extended along the sequence by adding on nucleotides. By raising and lowering the temperature of the reaction mixture, the extended primers will dissociate from the target sequence to form reaction products, excess primers will bind to the target sequence and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in Eur. Pat. Appl. No. 320308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase (QβR), described in Intl. Pat. Appl. Publ. No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alphathio]-triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744,311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in Great Britain Patent 2202328, and in Intl. Pat. Appl. Publ. No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact, available to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double-stranded DNA, and then transcribed once again with an RNA polymerase such as T7 or SP6. The resulting products, whether truncated or complete, indicate target specific sequences.

Davey et al., Eur. Pat. Appl. No. 329822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase 1), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion exchange and molecular sieve, and many specialized techniques for using them including column, paper, thin-layer and gas chromatography.

Amplification products must be visualized in order to confirm amplification of the target sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified target sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (Sambrook et al., 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

IV. Anti-HIV Therapeutic Agents

The instant methods identify patients at risk for HIV-1 infection, transmission and/or disease progression, and who are therefore candidates for treatment with one or more of the well-known reverse transcriptase inhibitors. Two pharmacological classes of inhibitor molecules, nucleoside and non-nucleoside, have been found to be effective in halting the enzymatic function of the reverse transcriptase (Larder, 1993). Nucleoside inhibitors such as AZT (zidovudine, azidothymidine; Boucher et al., 1993; Fischl et al., 1987, 1990; Lambert et al., 1990; Meng et al., 1990; Skowron et al., 1993; Furman et al., 1988; Yarchoan et al., 1986), ddC (Zalcitabine, 2',3'-dideoxycytidine, Hivid), ddI (didanosine, 2',3'-dideoxyinosine, Videx), and d4T (Stavudine, 2',3'-didehydro-2',3'-dideoxythymine) are chemically similar to the normal nucleosides and therefore can be converted to their triphosphate form and then used in the synthesis of DNA during reverse transcription. However, elongation of the DNA chain is blocked since these compounds lack a 3'-OH group that is essential for incorporation of additional nucleotides. Problems of cellular toxicity together with development of drug resistant variants of the virus have compromised the effective utility of these drugs.

A number of pharmacologically active non-nucleoside inhibitors (NNI) have also been identified. Many of these inhibitors appear highly potent, relatively nontoxic, and specifically inhibit HIV reverse transcriptase. Examples of such compounds include, but are not limited to, nevirapine (BI-RG-587, 11-cyclopropyl-5, 11-dihydro-4-methyl-6H-dipyrido[3,2-b:2',3']-e(1,4)diazepin-6-one), TIBO (Tetrahydroimidazo[4,5,1-jk][1,4]benzodiazepin-2(1H)-one), HEPT (1-[(2-hydroxyethoxymethyl)]-6-(phenylthio)thymine), BHAP (bis(heteroaryl)piperazine), and alpha-APA (alpha-anilinophenylacetamide). However, the rapid emergence of HIV strains resistant to these compounds in vitro has become a major concern that may affect further development of these types of drugs (Larder, 1993). Rapid mutations, in some cases within weeks or months, in the HIV-1 RT have been reported upon exposure of HIV-infected cells to these compounds.

Therapeutic compounds and reverse transcriptase inhibitors and metabolites thereof useful in any of the methods of the invention also include, but are not limited to dideoxynucleotide triphosphate analogs, including 2',3'-dideoxynucleoside 5'-triphosphates (Izuta et al., 1991); including, for example, dideoxyinosine and dideoxycytidine (Shirasaka et al., 1990); anti-reverse transcriptase antibodies and sFvs; Carbovir (carbocyclic analog of 2',3'-didehydro-2',3'-dideoxyguanosine; White et al., 1990); 3'-azido-3'-deoxythymidine triphosphate, (Furman et al., 1986); 3'-azido-3'-deoxythymidine (Mitsuya et al., 1985; Tavares et al., 1987); , thymidine 5'-[α,β-imido]-triphosphate, 3'-azido-3'-deoxythymidine 5'-[α,β-imido]-triphosphate, dideoxythymidine 5'-[α,β-imido]-triphosphate, 3'-azidothymidine 5'-[β,γ-imido]-triphosphate, thymidine 5'-[α,β:β,γ-diimido]-triphosphate (Ma et al., 1992); R82913 ((+)-S-4,5,6,7-tetrahydro-9-chloro-5-methyl-6-(3-methyl-2-butenyl)-imidazo[4,5,1-jk][1,4]-benzodiazepin-2(1H)-thione (a TIBO derivative); (White et al., 1991); 3'-deoxy-2',3'-didehydrothymidine 5'-triphosphate, 2',3'-dideoxycytidine 5'-triphosphate; 2',3'-dideoxyadenosine 5'-triphosphate; 2',3'-dideoxyguanosine 5'-triphosphate; 2',3'-dideoxythymidine 5'-triphosphate; (Reardon, 1992); 5'-triphosphate of carbovir (the carbocyclic analog of 2'-3'-didehydro-2'-3'-dideoxyguanosine; Parker et al., 1991, White et al., 1991); threo- and erythro-isomers of 3'-azido-3'-deoxythimidine triphosphate (Vrang et al., 1987); 2',3'-didehydro-2',3'-dideoxythimidine (D4T) (Wainberg et al., 1990); purines comprising a 2',3'-dideoxyribose moiety, nucleosides comprising a 2',3'-didehydro-2',3'-deoxyribose moiety, 2',3'-dideoxythymidinene (ddE Thd) (Masood et al., 1989); galolyl derivatives of quinic acid, particularly 3',4',5-tri-O-galoylquinic acid (Tri GQA), and 3,4-di-O-galloyl-5-digalloylquinic acid, Tetra GQA plus 3'-azido-3-deoxy thymidine triphosphate or phosphonoformic acid (Parker et al., 1989); Merck compound L-697,661 (Olsen et al., 1992); 3'-azido-2', 3'-dideoxyadenosine AZA (Shirasaka et al., 1990); 3'-azido-2'-3'-dideoxyguanosine (AZG), carbovir monophosphate; (-Et, -nPr, -nPre, -iPre, -Ce) 5'-triphosphates of 5'-substituted 2'-deoxy-uridine; phosphonoacidic acid and phosphonoformic acid (Pei-Zhen, 1989); 3-amino-thymidine 5'-triphosphate (Lacey et al., 1992); zidovudine monophosphate and diphosphate; 2',3'-dideoxynucleosides; R 12913; Ribavirin poly(A).poly(U), (Hovanessian et al., 1991); AZT plus interferon; anhydro-AZT; phosphoformate ("Foscarnet"); deoxythiacytidine (Wainberg et al., 1990); anhydro-N3, -UdR and the nonnucleoside inhibitors shown in U.S. Pat. No. 5,917,033 (incorporated herein in its entirety by reference).

Any combination of the above reverse transcriptase inhibitors can be used in the treatment methods disclosed herein.

V. Pharmaceutical Compositions and Routes of Administration

The present invention contemplates the use of pharmaceutical compositions that comprise a dosage range of the reverse transcriptase inhibitors detailed above that provide a beneficial prophylactic or therapeutic effect.

The active agents are preferably dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or preferably a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Among the preferred routes of administration are intravenous and subcutaneous injection. Thus, the reverse transcriptase inhibitors or other anti-HIV-1 therapeutic agents may be administered "parenterally". Parenteral administration also includes intramuscular or even intraperitoneal routes. The preparation of an aqueous composition that contains an anti-HIV-1 therapeutic agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Anti-HIV agents can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. This is envisioned to have particular utility in e.g., facilitating the treatment of needle stick injuries of health care workers. In this regard, the use of DMSO as solvent is possible as this will result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like. Upon formulation of any suitable pharmaceutical, administration of therapeutically effective amounts compatible with the dosage formulation will be known to those of ordinary skill in the art in light of the present disclosure.

In certain embodiments, active compounds may be administered orally. This is contemplated for agents that are generally resistant, or have been rendered resistant, to proteolysis by digestive enzymes. For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Further exemplary suitable treatment method involves the use of nasal solutions or sprays, aerosols or inhalants. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines.

Inhalations and inhalants are pharmaceutical preparations designed for delivering a drug or compound into the respiratory tree of a patient. A vapor or mist is administered to deliver agents into the systemic circulation. Inhalations may be administered by the nasal or oral respiratory routes. Another group of products, also known as inhalations, and sometimes called insulations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered dose of the inhalation is propelled into the respiratory tract of the patient.

The administration of inhalation solutions is most effective if the droplets are sufficiently fine and uniform in size so that the mist reaches the bronchioles. Particle size is of importance in the administration of this type of preparation. It has been reported that the optimum particle size for penetration into the pulmonary cavity is of the order of 0.5 to 7 µm. Fine mists are produced by pressurized aerosols and hence their use in considered advantageous.

VI. Diagnostic and Therapeutic Kits

Diagnostic and therapeutic kits comprising, in at least a first suitable container, one or more nucleic acid segment(s) or primer(s) specific for one or more human CCR5 and/or CCR2 haplotypes, as defined herein, along with instructions that correlate the identified human CCR5 and/or CCR2 haplotype pair (genotype) to the risk of HIV-1 infection, transmission or disease progression, represent another aspect of the invention. Such nucleic acid primers may be DNA or RNA, and may be either native, recombinant, or mutagenized nucleic acid segments.

The kits may comprise a single container that contains a solution of the CCR5 and/or CCR2 nucleic acid segment or primer. The single container may contain a dry, or lyophilized, CCR5 and/or CCR2 nucleic acid segment or primer, which may require pre-wetting before use.

Alternatively, the kits of the invention may comprise a distinct container for each component. In such cases, separate or distinct containers would contain the CCR5 and/or CCR2 nucleic acid segments or primers, either as a sterile solution or in a lyophilized form. The kits may also comprise a third container for containing an acceptable buffer, diluent or solvent. Such a solution may be required to formulate the CCR5 and/or CCR2 acid segment or nucleic acid primer compositions into a more suitable form for amplifying particular CCR5 and/or CCR2 haplotype DNA segments. It should be noted, however, that all components of a kit could be supplied in a dry form (lyophilized). Thus, the presence of any type of buffer or solvent is not a requirement for the kits of the invention.

As the CCR5 and/or CCR2 nucleic acid segments or primers, along with the information correlating the completely identified CCR5 and/or CCR2 genotype (haplotype pairs) to the risk of HIV-1 infection, transmission or disease progression, identify subjects that are at an increased risk of HIV-1 infection, transmission or disease progression and thus candidates for anti-HIV-1 therapy, in certain aspects of the present invention the kits further comprise one or more anti-HIV-1 therapeutic agents, including, but not limited to, reverse transcriptase inhibitors as described in detail herein.

The container(s) will generally be a container such as a vial, test tube, flask, bottle, syringe or other container, into which the components of the kit may placed. The CCR5 and/or CCR2 nucleic acid segment(s) or primer(s) may also be aliquoted into smaller containers, should this be desired. The kits of the present invention may also include material for containing the individual containers in close confinement for commercial sale, such as, e.g., injection or blow-molded plastic containers into which the desired vials or syringes are retained.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

CCR5 Regulation and Promoter Variants in HIV-1 Infection

It is now clear that viral, immune and host genetic factors may influence a person's risk of becoming infected with HIV-1, as well as the rate of disease progression once infected (Fauci, 1996; Feng et al., 1996; Alkhatib et al., 1996; Choe et al., 1996; Doranz et al., 1996; Deng et al., 1996; Bleul et al., 1996; Oberlin et al., 1996; Liu et al., 1996; Dean et al., 1996; Samson et al., 1996; Huang et al., 1996; Zimmerman et al., 1997; Connor et al., 1997; Michael et al., 1997; Garred et al., 1997; Ansari-Lari et al., 1997; Martinson et al., 1997; Theodorou et al., 1997; O'Brien et al., 1997; Biti et al., 1997; Smith et al., 1997; Cocchi et al., 1995). For example, homozygous polymorphisms in the coding region of CCR5, especially homozygosity for the 32-nucleotide deletion (Δ32; −/− genotype) play an important role in HIV-1 transmission and pathogenesis (Liu et al., 1996; Dean et al., 1996; Samson et al., 1996; Huang et al., 1996; Zimmerman et al., 1997; Connor et al., 1997; Michael et al., 1997; Garred et al., 1997; Ansari-Lari et al., 1997; Martinson et al., 1997; Theodorou et al., 1997; O'Brien et al., 1997; Biti et al., 1997; Smith et al., 1997).

The work presented herein is significant because it takes a multi-disciplinary approach to addressing some fundamental questions related to CCR5, a critical host-determinant of the virus. For example, what are the key molecular determinants of CCR5 gene expression and how can they be targeted to mimic the protective Δ32/Δ32 phenotype? Do transcriptional mutants in the regulatory regions of CCR5 account for the observed inter-individual differences in cell surface expression of CCR5? Is differential expression of CCR5 in M-tropic HIV-1 target cells related to differential promoter utilization?

Recognizing that information gained in "surrogate" cellular environments for HIV-1 target cells may not accurately reflect the cellular milieu of a primary HIV-1 target cell, the inventors also use novel "physiologically relevant ex-vivo cellular environments" that they have developed, i.e., human CD34+ progenitor cell-derived monocytes/dendritic cells (DCs), to examine the transcriptional regulation of human CCR5.

A. Introduction

1. The Chemokine Receptor/HIV-1 Nexus

It is now clear that HIV-1 interacts—through its envelop protein gp120—with at least two cell surface receptors: the type I membrane protein CD4 and a seven-membrane spanning G-protein coupled chemokine receptor (Fauci, 1996; Feng et al., 1996; Alkhatib et al., 1996; Choe et al., 1996; Doranz et al., 1996; Deng et al., 1996; Bleul et al., 1996; Oberlin et al., 1996; Samson et al., 1996; Raport et al., 1996; Combadiere et al., 1996). The type of chemokine receptor that is able to support HIV-1 entry into target cells depends on the viral isolate. The HIV-1 strains that cause most transmissions of viruses are called macrophage tropic (M-tropic) viruses (Fauci, 1996). These M-tropic HIV-1 strains can replicate in primary CD4+ T cells and macrophages and use CCR5 (Feng et al., 1996; Alkhatib et al., 1996; Choe et al., 1996; Doranz et al., 1996; Deng et al., 1996). The T-tropic viruses can also replicate in CD4+ T cells but can in addition infect established CD4+ T cell lines in vitro by engaging another chemokine receptor called CXCR4 (Feng et al., 1996). Some strains can use other co-receptors such as CCR3 and CCR2B.

CCR5 binds the CC chemokines, MIP-1α, MIP-1β, and RANTES, the three chemokines identified as responsible for CD8+ T cell inhibition of infection by M-tropic but not T-tropic isolates (Cocchi et al., 1995). Similarly, stromal cell-derived factor 1 is the recently identified ligand for CXCR4, and it inhibits infection by T-tropic strains (Bleul et al., 1996; Oberlin et al., 1996). Thus, the selective use of co-receptor molecules for HIV-1 entry provides a basis for the cellular determinants of target tropism.

2. Targeting Human CCR5

The Δ32 mutation results in a truncated protein and loss of CCR5 molecules on the cell surface of −/− individuals, and thus confers near absolute protection (Liu et al., 1996; Dean et al., 1996; Samson et al., 1996; Huang et al., 1996; Zimmerman et al., 1997; Connor et al., 1997; Michael et al., 1997; Garred et al., 1997; Ansari-Lari et al., 1997; Martinson et al., 1997; Theodorou et al., 1997; O'Brien et al., 1997; Biti et al., 1997). Furthermore, individuals who display the −/− genotype do not have any detectable immunological defect, suggesting that a strategy designed to mimic a CCR5 null mutation may be a viable therapeutic approach. At a conceptual level CCR5 can be targeted at one of the following points along the cascade of: gene-RNA-Protein-Function (surface (co-receptor expression) activity).

3. Targeting CCR5 Co-Receptor Activity

Several groups have initiated programs designed to block CCR5 co-receptor activity using CCR5-based peptides, modified chemokines, or small molecules (Rucker et al., 1996; Gosling et al., 1997; Farzan et al., 1997; Speck et al., 1997; Alkhatib et al., 1997 Lu et al., 1997; Atchison et al., 1996; Simmons et al., 1997). The inventors have started to identify the CCR5/HIV-1 interaction sites, since this information may help guide the design of novel anti-HIV-1 compounds that target CCR5/HIV interactions. The findings of the inventors studies (Alkhatib et al., 1997), and that of several other groups (Rucker et al., 1996; Gosling et al., 1997; Farzan et al., 1997; Alkhatib et al., 1997; Lu et al., 1997; Atchison et al., 1996), indicate that the determinants of CCR5 HIV-1 co-receptor activity are likely to be complex, involving several extracellular domains and perhaps, transmembrane domains as well.

This extensive plasticity of the HIV-1 binding sites on CCR5, and given the virus's notorious propensity to mutate, it is conceivable that a strategy designed to target CCR5/HIV interactions might facilitate escape from co-receptor antagonists. Alternatively, it is conceivable that a drug that blocks HIV-1 entry to one part of CCR5 may permit entry through another. Another concern about the strategy of using modified chemokines is that there is marked variability in the sensitivity of different HIV strains to these "natural" antagonists, conceivably permitting a particular infecting strain to escape the effects of a modified chemokine. Taken together, these concerns/findings all point to the need to develop multiple strategies aimed at targeting CCR5 at different levels.

4. Targeting CCR5 Gene Expression

Since the amount of CCR5 protein expressed is likely to be a direct function of the amount of CCR5 mRNA expressed, targeting CCR5 gene expression is an attractive strategy to mimic the −/− genotype. It is likely that regulation of CCR5 on the surface occurs at many levels (Murphy, 1996). As is the case for other GPCRs, the cell surface expression of CCR5 may be regulated at the protein level, over the short term, through mechanisms such as receptor internalization, sequestration and desensitization. However, longer term regulation of CCR5 is likely to be achieved through regulation of transcription, stability of the mRNA and translation efficiency.

The most common way to regulate gene expression is by modulating the activity of transcription factors that recognize specific cis-acting elements in the control regions of the genes. Two general approaches can be used for developing drugs targeting the transcriptional machinery in the cells: i) Inhibition of an activator of a gene thus abrogating its expression; and ii) stimulation of a repressor of a gene that in turn inhibits its expression. Examples of drugs that can modulate gene expression are now in clinical trials (Peterson and Baichwal, 1993; Bustin and McKay, 1994).

Towards developing a strategy to mimic the −/− genotype, first one should develop a comprehensive understanding of the cis-elements and trans-acting factors that regulate CCR5 expression. To this end, the inventors have identified the mRNA composition of CCR5, defined its gene structure, and broad DNA regions that function as gene promoters (Example 3). This Example describes a series of experiments designed to understand better the basis for the constitutive and IL-2 stimulated expression of CCR5.

One of the novel features of this application is the use of "ex vivo" cellular environments that the inventors have developed, i.e., CD34+ derived monocytes/DCs, to study CCR5 gene regulation. These studies are relevant because the results of experiments conducted in "surrogate" cellular environments (cell lines) may not mimic the in vivo environment, whereas, the ex vivo cellular environment used herein does so, and the use of monocytes/DCs is particularly relevant in that they are major target cells for M-tropic HIV-1 strains.

These studies not only dissect the factors that modulate constitutive/differential CCR5 gene expression, but also identify cis-responsive elements that are responsible for the stimulated CCR5 expression that occurs in response to IL-2. It is known that the state of activation of CD4+ T cells affects not only HIV-1, but also co-receptor expression. Quiescent CD4+ T cells express CCR5 only minimally or not at all, however, activation with IL-2 causes strong, sustained up-regulation of CCR5 expression (Carroll et al., 1997; Wu et al., 1997). This allows for the identification of agents that block the interaction of specialized, cell-specific regulatory sequence elements with corresponding trans-acting factors. The intervention may be at the level of the DNA-binding, protein dimerization (which is involved in protein-DNA interactions), or binding the activation site on the transcription factors.

The importance of CCR5 cell surface expression is often viewed in the context of an all-or-none phenomenon. There is no doubt that complete absence of CCR5 is protective, and that complete or partial presence serves as a portal of entry of M-tropic strains of HIV-1. However, whether the absolute numbers of CCR5 molecules available on the cell surface of target cells influence efficiency of HIV-1 entry, replication in host cells and hence, disease progression is not absolutely clear.

The levels of CCR5 surface expression on T cells of +/− individuals is lower than that in individuals with the wild-type genotype, however, there is no evidence that the +/− genotype protects against transmission (Liu et al., 1996; Dean et al., 1996; Samson et al., 1996; Huang et al., 1996; Zimmerman et al., 1997). Furthermore, the +/− genotype may have only a limited protective role in disease progression. In one study, the heterozygous state delayed the onset of progression of AIDS by 2 to 4 years (Dean et al., 1996).

However, as pointed out in a recent study, a problem in determining whether the heterozygous state plays a protective role in disease progression in seroprevalent subjects is that the time of seroconversion is usually unknown (Huang et al., 1996). This limitation was corrected for by analyzing a cohort of HIV-1-positive individuals in whom the time of seroconversion was known (within 6 months). In this analysis, there was a general shift towards slower loss of CD4+ T cells in the heterozygotes (P=0.04). Furthermore, the plasma viral loads 9-18 months post-conversion was lower in heterozygotes than those who had the wild-type genotype (P=0.05). However, in Kaplan-Meir analysis of time to AIDS or death in these seroconverters, the +/− genotype did not appear to be protective. This could have been due to small numbers of +/− individuals in the seroconverters. Nevertheless, a higher proportion were AIDS-free at year 10 (Huang et al., 1996).

In vivo animal studies supporting the notion that in heterozygous individuals viral replication may be slower were recently published (Lu et al., 1997). Reconstitution of the human PBL-Scid mice with cells from CCR5 +/Δ32 individuals delayed replication of M-tropic HIV-1, whereas reconstitution with cells from CCR5 Δ32/Δ32 individuals were resistant to HIV-1. In these studies, variations in CCR5 surface expression levels were noted among heterozygous individuals (Lu et al., 1997). Furthermore, the effect of the differences in expression levels were more apparent with certain viral isolates, suggesting that differences in cell surface expression levels could be more protective against disease progression with certain isolates.

Recent in vitro findings also support the notion that the amount of expression of CCR5 on the cell surface correlates with ease of infectability with HIV-1 (Wu et al., 1997). Using anti-CCR5 mAbs, it was shown that compared to normal cells (+/+), T cells obtained from heterozygotes (+/−) have markedly reduced expression of CCR5 (Wu et al., 1997). Furthermore, low levels of CCR5 surface expression correlated with the reduced infectability of T cells with M-tropic strains in vitro. A striking finding is the considerable inter-individual variability in CCR5 expression on T cells obtained from individuals with the +/+ and +/− genotype, and interestingly, in some instances, the levels of expression from +/+ individuals were comparable to the low levels observed on cells from +/− individuals. Trkola et al. have reported similar findings, and found that the amount of CCR5 expression on the cell surface of activated CD4+ T cells as measured by MIP-1β binding can vary by 20-fold in individuals with the +/+ genotype (Trkola et al., 1996).

In summary, findings from HIV-1 infected subjects, mice reconstitution studies, and in vitro experiments all suggest that the level of CCR5 surface expression may influence efficiency of HIV-1 entry and/or disease progression. Thus, viewing the importance of CCR5 expression levels in HIV-1 pathogenesis as a purely −/− or +/±=off/on=protective/non-protective phenomenon may be premature. Mechanistically, it is thought that HIV-1 first interacts through its envelope protein gp120 with CD4, and that this interaction exposes the CCR5-binding site of gp120. The subsequent binding of gp120 to CCR5 then relieves a conformational constraint of the envelope protein gp41, which can then insert through its fusion domain in the target cell membrane thereby initiating viral fusion. From a purely mechanistic and mathematical perspective, the exact number/density of CCR5 molecules required for viral fusion to ultimately occur remains unknown. Nevertheless, levels of CCR5 extending along a spectrum of absent-low-moderate-or-high are all likely to influence virus entry.

Because of the observed wide inter-individual variability in cell surface expression of CCR5 in +/− and +/+ individuals, in addition to the Δ32 mutation, other factors—genetic or immune—likely accounts for these differences. Additional factors also account for the finding that 80% of highly exposed uninfected individuals analyzed to date are not CCR5-Δ32/Δ32 homozygotes (Huang et al., 1996). Furthermore, >60% of "long-term" survivors are homozygous for the wild-type allele (Dean et al., 1996; Huang et al., 1996; Zimmerman et al., 1997).

Clarifying what these other factors are have important consequences for HIV-1 transmission and AIDS pathogenesis, as they provide clues to factors that could increase resistance to disease. For example, an explanation for these variations in CCR5 levels of endogenously secreted MIP-1α, MIP-1β, and RANTES, which in turn can modulate the CCR5 expression levels. An alternative explanation, which invokes a genetic basis for this variability in CCR5 expression levels, is discussed below.

5. Polymorphisms in the Regulatory Regions of CCR5 Provide a Genetic Basis for the Variations in CCR5 Surface Expression in +/+ and +/− Individuals The CCR5 promoter regions (~4 kb) from 6 individuals (5+/+ and 1+/−) have been sequenced. What is striking is that in all six individuals the regulatory sequences were different, and are characterized by extensive polymorphisms. Similar polymorphic changes were also detected in both the 5'- and 3'-untranslated regions of the RNA.

Several studies have clearly demonstrated that genes can be polymorphic not only in their coding regions, but also in important cis-regulatory sequences (Leen et al., 1994; Sloan et al., 1992; Angotti et al., 1994; Naganawa et al., 1997; Song et al., 1996; In et al., 1997; Inoue et al., 1997; Dallinga-Thie et al., 1997; Kazazian, 1990; McGuire et al., 1994). Furthermore, transcriptional mutants may profoundly affect the promoter strengths of particular alleles by altering the affinity of regulatory proteins for these elements, and in some instances a single nucleotide change in a critical regulatory region can result in up to one order of magnitude difference in transcriptional activity of two otherwise identical promoters. As discussed below, this, in turn, can have a profound affect on protein synthesis.

One of the most striking examples of transcriptional mutants affecting protein synthesis came in the wake of the cloning of the human β-globin gene nearly 20 years ago, where in addition to mutations in the coding region, single mutations in the regulatory regions were shown to decrease the amount of β-globin produced by red cells, leading to the blood disorder called β-thalassemia (Kazazian, 1990). It is interesting, that to date, over 300 β-thalassemia alleles have been discovered, including 12 transcriptional mutants, which account for the molecular basis of the marked heterogeneity of the β-thalassemia syndrome.

Transcriptional mutants that lead to an increase in protein expression have also been described. For example, studies have linked the variant allele for the TNF-α gene, referred to as TNF2, to increased serum levels of TNF-α, and a poor prognosis for several infections, such as malaria (McGuire et al., 1994).

Thus, different CCR5 genotype-phenotype outcomes may, in part, account for the observed variability of cell surface expression, and hence its co-receptor activity. These "natural" mutants may also point to important cis-acting regions that regulate CCR5 transcription in vivo, and may rapidly pave the way for identifying transcriptional factors that bind to these "mutated" regions. For example, even though 12 transcriptional mutations are now known in the β-globin gene, none has yet been found in the "CCAAT" box, even though it was one of the first to be implicated in in vitro studies of promoter activity.

It should be noted that, in addition to the predominant Δ32 mutation, several additional mutations/polymorphisms in the coding region of CCR5 have now been described (Ansari-Lari et al., 1997). Thus, similar to the β-globin gene, where mutations in both the coding and non-coding regions account for the heterogeneity in β-globin protein expression, molecular heterogeneity in different regions of the CCR5 gene may play an important role in its expression, and consequently, efficiency of HIV-1 entry. This Example defines the molecular heterogeneity in the regulatory regions of CCR5, and the consequent phenotype of the transcriptional mutants. In the coding regions of highly exposed uninfected individuals, the −/− genotype has been found in only 20% of such individuals. A transcriptional mutant in a +/+ individual could result in decreased protein expression, and even a complete absence of protein expression.

6. Factors that Regulate Differential Expression of CCR5

The profound resistance resulting from absence of CCR5 may be related to the differential expression of CCR5 and CXCR4 on target cells for M-tropic strains of HIV-1 (Carroll et al., 1997; Wu et al., 1997; Bleul et al., 1997). Primary infection may be confined to cells expressing CCR5 rather than CXCR4. This would result in the preferential selection of M-tropic strains from a mixture of different HIV-1 strains deposited at the site of exposure. Thus, when HIV-1 is acquired through intravenous routes, the initial infection is in the reticuloendothelial system and lymphoid organs, and the target cells are likely monocytes/DCs, which are known to express abundant amounts of CCR5 and be largely resistant to T-tropic viruses.

Recent studies suggest that preferential/differential expression of CCR5 in primary target cells explains the critical role of CCR5 in HIV-1 entry. Memory subsets of T cells (CD45RO+), key HIV-1 target cells, were shown express much more CCR5 than naive T cells (CD45RA+; Bleul et al., 1997). In contrast, CXCR4 expression is less variable among T cell subsets. The studies described herein suggest that differential promoter utilization determines tissue/cell-specific expression of CCR5. Additionally, the precise factors that account for the differential expression patterns of CCR5 are identified. Interfering with transcription of the CCR5 gene is reasoned by the inventors to be an attractive strategy to modulate the expression of CCR5 on target cells.

B. Results

1. CCR5 mRNA Composition

Transcript analysis revealed that alternative splicing events generated multiple CCR5 mRNA isoforms that differ only in their 5'-UTR sequences. Based on the exon composition, these isoforms were segregated into 3 classes: those with exons 1+2+3+4, designated CCR5A; those with exons 1+3+4, designated CCR5B; and cDNAs containing portions of exons 2 and 3, collectively designated as "truncated isoforms" as they lacked exon 1. Conversely, transcripts containing exon 1 were designated as "full-length isoforms". The human CCR5 gene was found to be composed of 4 exons and 2 introns.

2. Alternatively Spliced CCR5 Transcripts Expressed in HIV-1 Target Cells

As all of the CCR5 cDNA clones identified contained exon 4 and portions of exon 3, and the additional length contributed by exons 1 and/or 2 to CCR5A or CCR5B is not substantial, the proportion of transcripts in cells that are either "full-length" or "truncated" could not be readily ascertained by size differences on northern blots. To demonstrate the tissue distribution of CCR5A and CCR5B, RT-PCR was used on total RNA derived from PBMCs, lymphocytes, monocytes, CD34+ progenitor cell-derived DCs, and activated CD4+ T cells. The upper and lower bands were subcloned and sequenced, and corresponded to CCR5A and CCR5B, respectively. It should be noted that this RT-PCR analysis is qualitative, and although minor to moderate variations in the proportion of the transcripts containing these exons were observed, there was no clear-cut pattern of tissue-specific utilization.

3. CCR5 Isoforms are Initiated by Two Promoters of Different Strengths

CCR5-firefly luciferase chimeric plasmids were constructed from portions of the gene upstream of exon 1, designated as pA1-4, and the ability of these promoter constructs to drive the expression of the reporter gene (firefly luciferase) were tested in the following cell lines: THP-1, a human monocytic leukemia cell line, a surrogate for monocytes; K-562, a human chronic myelogenous leukemia cell line, a surrogate for undifferentiated hemopoietic cells; and Jurkat, which is a human T cell leukemia cell line. To correct for differences in transfection efficiency, the promoter constructs and the promoterless vector pGL3-Basic were co-transfected with pRL-CMV, a construct that contains the renilla luciferase gene downstream of a CMV promoter. Lysates prepared from cells transfected with constructs pA1-4 exhibited weak luciferase activity. This genomic region upstream of exon 1 is designated as the upstream promoter ($P_U$).

Because a large number of 5'-RACE clones terminated either in exon 3 or at the 3'-end of exon 2, these transcripts may represent distinct isoforms that are initiated because of the usage of an alternative promoter. To study this, a series of promoter constructs were constructed. In some instances these constructs contain portions of $P_U$, intron 1, and exon 2, and the distal end of each of these constructs resides within exon 3. Cell culture and transfections were as described previously (Ahuja et al., 1994a). The firefly and renilla luciferase activities were determined according to manufacturer's instructions (Dual-Luciferase Reporter Assay System, Promega) in a luminometer. The protein concentration in the cell lysates as measured by the Bradford method were comparable between and within experiments. The "relative luciferase activity" is derived from the equation: (firefly luciferase activity of CCR5 promoters/renilla luciferase activity of co-transfected pRL-CMV)/(firefly luciferase of promoterless vector pGL3-Basic/renilla luciferase activity of co-transfected pRL-CMV). Experiments with $P_U$ and $P_D$ were conducted in parallel.

The results showed that pA1-4 are weak promoters ($P_U$); relative to pA1-4, pB1-5 are strong promoters ($P_D$); and the $P_D$ constructs are significantly more active in K562 cells, suggesting that they may be differentially regulated. In contrast to $P_U$, the region upstream of exon 3, designated as the downstream promoter ($P_D$), had strong luciferase activity in all the three cell lines tested. Maximal promoter activity was consistently observed in the cell lysates from K-562 cells, especially with those transfected with pB3 and pB4. The promoter activity for these two constructs in K562 cells was ~8- to 10-fold more than that detected in cells transfected with pB1, pB2 or pB5. The increase in luciferase activity in THP-1 and Jurkat cell lines transfected with pB3 and pB4 was not as prominent as that observed for these two promoter constructs in K-562 cells. Relative to pB3 and pB4, pB5 exhibited weak promoter activity. This suggests that the sequences between pB4 and pB5 contain important cis-acting elements for CCR5 promoter activity. Since all the $P_D$ constructs contain all or portions of exon 2, it is likely that cis-elements within this non-coding exon play an important role in modulating gene expression. The promoters of CCR5 lack classical TATA or CCAAT motifs and are AT-rich.

4. Polymorphisms in the Non-Coding Regions of CCR5

The alignment of nucleotide sequences of the cloned human CCR5 gene and sequences of the cDNA clones derived by RT-PCR and 5' RACE revealed polymorphisms in the 5'-UTRs of CCR5. To confirm this finding, the promoter regions (~4 kb) of CCR5 from 6 individuals (5+/+ and 1+/−) were PCR amplified and sequenced. Similar and/or different polymorphisms were noted in the non-coding sequences. The sequence of a portion of chromosome 3p (~150,000 bp), submitted under the GenBank accession number U95626, contains several chemokine receptors and the entire coding and non-coding portions of CCR5. Sequence comparisons in this case also confirmed the presence of polymorphisms (insertions/deletions/substitutions) in the promoter regions.

To extend these observations, studies were conducted using single-strand conformation polymorphism (SSCP) on genomic DNA obtained from the founders of 40 original multigenerational families that belong to the Paris-based Cente d'Etude du Polymorphisme Humain (CEPH; French acronym for Human Polymorphism Study Center). Primers were used to amplify exon 2 (~200 bp) for an SSCP analysis. In this study, out of 126 genomic DNA samples tested, at least 6 different polymorphisms were detected.

5. CCR5 Surface Expression is Regulated During the Differentiation of CD34+ Progenitor Cells Towards Different Target Cells, Including Dendritic Cells To better understand the expression of CCR5 during myelopoiesis, cytokine-stimulated CD34+ progenitor cells were used as an ex vivo differentiation model. The stem cells are harvested as previously described (Ahuja et al., 1996), except for one difference: the column used to isolate CD34+ cells is obtained from CellPro (Ceprate SC column). In brief, after obtaining informed consent, healthy normal donors were apheresed and the light density mononuclear cells in their blood were harvested. Normal donors received G-CSF for 5 days prior to apheresis. These peripheral blood progenitors were enriched for CD34+ cells by positive selection, using the immunoaffinity column (CellPro, Inc., Bothell, Wash.). $5 \times 10^6$ cells were labeled with 5 µg/ml anti-human CCR5 monoclonal antibody (murine IgG2b subtype, clone 45549.111, R&D), CXCR4 monoclonal antibody, followed by FITC conjugated anti-mouse and then analyzed on a FACScan. The isolated CD34+ cells were >99% pure and 27.5% of cells express CXCR4, whereas CCR5 expression was minimal (1.37%). A differential expression pattern was observed for CCR5 and CXCR4: staining for CCR5 expression was minimal, whereas abundant expression of CXCR4 was observed on freshly isolated CD34+ cells; the CD34+ cells were unresponsive to MIP-1β, a CC chemokine specific to CCR5. CD34+ progenitor cells thus express minimal amounts of CCR5.

CD34+ progenitor cell-derived DCs express CCR5. The inventors have described protocols to differentiate CD34+ cells towards the monocytic lineage (Ahuja et al., 1996), and have shown that these cells respond to CC chemokines such as MIP-1α (Ahuja et al., 1996), and RANTES. To differentiate CD34+ cells towards the dendritic cell lineage, the cells were cultured in IMDM and 20% FBS, and supplemented with the following human growth factors: SCF, 100 ng/ml; GM-CSF, 100 ng/ml; TNF α, 10 ng/ml. The finding that cell surface marker expression on these cells was similar to that described by other investigators (Steinman, 1991; Steinman et al., 1993) confirmed that the CD34+ cells were indeed DCs.

Importantly, these CD34+ progenitor cell derived DCs were able to stimulate the proliferation of autologous CD4+ lymphocytes in mixed lymphocytic reactions, and they exhibited chemokine responses characteristic of DCs (Sozzani et al., 1995), including MIP-1β. The functional chemokine responses of these DCs clearly demonstrate the cell surface expression of CCR5. Other investigators have shown that at an RNA level, CD34+ cells do not express CCR5 (Deichmann et al., 1997), whereas DCs express abundant amounts of CCR5 mRNA (Granelli-Piperno et al., 1996).

6. CCR5 Surface Expression on PBMCs is Highly Variable

In these studies, PBMCs were isolated from three normal donors, and then stimulated with DCs for 3d. Following this the cells were maintained in IL-2 100 units/ml for an additional 5d. On day 8, 1 million cells were labeled with 5 µg/ml of antihuman CCR5 monoclonal antibody (murine IgG2b subtype, clone 45549.111, R&D) followed by FITC conjugated goat anti-mouse and analyzed on the FACScan. CCR5 surface expression levels were 7%, 25% and 29%.

7. Cellular Models to Examine CCR5 Gene Transcription

CD34+ progenitor cells differentiated towards different leukocyte lineages are transfectable using both electroporation and the lipofectamine reagent. The inventors have previously demonstrated that CD34+ cells differentiated towards the monocytic, neutrophilic and eosinophilic phenotype can be transfected with IL-8R (CXCR1 and CXCR2)-CAT constructs (Ahuja et al., 1994b). Lipofectamine based (Gibco) techniques have been used transfect similar cells with luciferase constructs. These findings demonstrate the ability of using CD34+ progenitor-derived cells for gene regulation studies, as these cells are transfectable, and CAT and luciferase activity, surrogate markers for gene promoter activity, can be measured.

After a single apheresis between 80-300 million CD34+ cells are typically harvested. In a typical experiment between 1-2 million CD34+ cells are used. After differentiation towards the DC lineage, i.e., by day 10-14 there is a 20-50 fold expansion of the cell number, yielding approximately 20-100 million cells. Using the Dual luciferase assay system, and the lipofectamine reagent, 20-100 million CD34+ cells are sufficient for at least 40-100 transfections.

8. HIV-1 Infection Assays

Studies were conducted to define β-chemokine receptors involved in SIVagm viral fusion with HeLa-T4 cell lines. Cell lines were developed that co-express one of the CC chemokine receptors CCR-1, CCR-2b, CCR-3, CCR-4, and CCR-5 along with CD4. The HeLa cell line is suitable for studying SIVagm entry because some isolates (i.e., SIVagm(tyo-1)) do not infect HeLa-T4, whereas these cells support replication of HIV-1/IIIB due to the high levels of CXCR4 expressed on their surface. Only low level expression of SIVagm(tyo-1) was observed with HeLa-T4/CCR-5. However, SIVagm(sab-4br) isolated from the brain of a naturally infected monkey, and which is primarily macrophage-tropic, also infected HeLa-T4/CCR-5 and high levels of virus expression was observed. These data are similar to studies with the macrophage-tropic HIV-1/BaL. In comparison, SIVagm(sab-41n) derived from the lymph node (replicate poorly in macrophages) of the same animal replicated well in each of the CCR containing cell lines, albeit to a lower level in HeLa-T4 without CCR transfection. HIV-1/IIIB also had the same pattern of replication. The constitutive expression of CXCR4 on HeLa cells may define the co-receptor usage for SIVagm(sab-41n) like HIV-1/IIIB. These findings suggest that at least some of the SIVagm viruses have similar requirements for co-receptors in viral entry.

The inventors have recently compared receptor usage on HEK 293 cells transfected with CCR5 or CCR2B using HIV-1/BaL, SIVagm(sab-4), SIVagm(tyo-1). The sab-4 isolate was derived from a naturally infected African green monkey by co-cultivation with Molt4c18 human T cell line. Of interest is the ability of SIVagm(sab-4) to infect 293 cells transfected with both CCR5 and CD4, but not cells transfected with CCR2B and CD4. While sab-4 was isolated on a non-CCR5 bearing T cell line, it nevertheless utilized CCR5 in this assay. These results are also consistent with recent studies reporting two new chemokine receptors that are preferentially used by SIVagm and SIVmac viruses (Bonzo and Bob). SIVagm(tyo-1) was reported to use Bonzo (STRL33) and so may be more restricted in its tropism than is sab-4 (Deng et al., 1997). Importantly, these studies also indicate the reproducible nature of BaL infectivity for CCR5 expressing cell types and its usefulness in in vitro studies.

Studies were conducted to determine CCR5's genomic and mRNA organization. Previous studies have identified a single CCR5 mRNA isoform whose open reading frame (ORF) is intronless. The studies described herein demonstrate the following: 1) Complex alternative splicing and multiple transcription start sites give rise to several distinct CCR5 transcripts that differ in their 5'-untranslated regions (UTR); 2) The gene is organized into four exons and two introns. Exons 2 and 3 are not interrupted by an intron. Exon 4 and portions of exon 3 are shared by all isoforms. Exon 4 contains the ORF, 11 nucleotides of the 5'-UT and the complete 3'-UTR; 3) The transcripts appear to be initiated from two distinct promoters: an upstream promoter ($P_U$), upstream of exon 1, and a downstream promoter ($P_D$), that includes the "intronic" region between exons 1 and 3; 4) $P_U$ and $P_D$ lacked the canonical TATA or CAAT motifs, and are AT-rich; 5) $P_D$ demonstrated strong constitutive promoter activity, whereas $P_U$ was a weak promoter in all three leukocyte cell environments tested (THP-1, Jurkat and K562); 6) Evidence is provided for polymorphisms in the non-coding sequences, including the regulatory regions and 5'-UTRs; 7) Cellular systems were developed to study CCR5 gene regulation in more "physiologically relevant" cellular milieus.

It is clear from the study of several diverse gene systems that alternative promoter usage resulting in alternative transcripts is an important evolutionary mechanism to create diversity in the regulatory control of gene expression. In these systems, alternative promoter usage has been shown to be an important transcriptional mechanism for regulating either tissue- or cell-type specific expression, the level of expression, the developmental stage-specific (temporal) expression, the specific capacity to respond to a particular cellular or metabolic conditions, or the translational efficiency of the mRNA. The inventors reasoned that several possible scenarios exist for CCR5. It is possible that the level of CCR5 expression is regulated at a transcriptional level by the usage of promoters of different strengths, such as the promoters described above. In addition, although the protein encoded by the different CCR5 transcripts is likely to be identical in different cell types, they may be regulated differentially in these different cell types by various extracellular signals, such cytokines or chemokines. Understanding these fundamental issues have important implications for CCR5 expression, and hence HIV-1 entry.

9. Mechanisms that Regulate CCR5 Gene Expression in HIV-1 Target Cells

The cell type distribution and amount of RNA encoding CCR5 are key determinants for entry of M-tropic HIV-1 strains in vivo. This is clearly underscored by the high levels of CCR5 transcripts that are detected in Northern blot hybridization of RNA from resting dendritic cells and monocytes but not neutrophils (Combadiere et al., 1996; Granelli-Piperno et al., 1996). This differential expression pattern of CCR5 may help explain why its absence confers such profound resistance to HIV-1.

This section studies factors that regulate CCR5 transcription in HIV-1 target cells at two levels: constitutive/differential expression; and stimulated expression (after IL-2). It is preferable to examine CCR5 gene expression in "native" cell types, an as discussed above, cellular model systems that take advantage of the fact that CD34+ progenitor cells, stimulated with different cytokine-regimens, can be differentiated along different myeloid lineages, such as monocytes and DCs, have been developed. In the studies described below, the following cellular models are used to dissect the factors that regulate CCR5 gene expression: 1) Cell lines that serve as "surrogates" for HIV-1 target cells: THP-1 (myeloid), Jurkat/PM1 (T cell), and K562 (undifferentiated); 2) Ex vivo cellular model/differentiation model: CD34+ progenitor cells differentiated towards DCs/monocytes; and 3) Stimulated CCR5 expression models: PBMC's stimulated with PHA±IL-2 and Jurkat/PM1 cells stimulated with PHA±IL-2

DNA recognition is one of the central points in the regulation of a gene, and thus, the thrust of these studies are towards sorting out the factors responsible for the constitutive/differential and stimulated expression of CCR5. For studies related to defining factors that regulate the constitutive transcription of CCR5, the minimal sequence, i.e., transcriptional unit needed to mediate constitutive transcription of CCR5, is identified; sites of protein binding to segments of the promoter are identified by the approach of DNase I footprinting; the regions in the promoter regions that bind to nuclear proteins are identified by the approach of EMSA (electrophoretic mobility shift assay, also referred as gel-mobility shift assay); the importance of the cis-elements identified are confirmed by site-directed mutagenesis studies; and the importance of the regulatory regions determined in the aforementioned studies are characterized in CD34+ progenitor derived monocytes/DCs.

Similar approaches are taken to define the IL-2 responsive elements that account for the stimulated transcription of CCR5 in PBMCs. In addition, the mechanisms (transcriptional and/or post-transcriptional) by which IL-2 affects the steady-state levels of CCR5 mRNA are determined. To determine CCR5 mRNA synthesis that occurs in response to IL-2 in PBMCs nuclear transcript elongation assays are performed. To examine whether post-transcriptional mechanisms play a role in IL-2 mediated increases in CCR5 mRNA, the effects of IL-2 on the stability of CCR5 cytoplasmic mRNA is studied. The most direct method involves monitoring CCR5 mRNA abundance after inhibition of RNA synthesis. Alternatively, stability may also be assessed by pulse-decay assays.

Constitutive transcription is regulated by distinct segments of the promoter, and stimulated transcription employs many or all of these same elements, plus an additional set of stimulus responsive elements. The strategy is to systematically narrow the focus to those response elements/transcription factors that are most likely to be functional in regulating the expression of CCR5. The rationale for this strategy is that there are too many candidate sites identified by computer-assisted analysis to explore each of them by site-directed mutagenesis. Looking directly for an interaction between protein and DNA by gel mobility shift assays (EMSA) is often the quickest way to identify the important sequences in a regulatory region. However, EMSA has some limitations. It cannot identify the position at which the protein binds along the DNA, nor can it be used to determine whether the shifted band is the result of two proteins binding to different sites on the same fragment. The technique of DNA footprinting addresses these questions.

10. Deletion/Transient Transfection Analyses

In the studies described above, broad regions of CCR5 were identified that are functional promoters, hence, these studies are conducted to find the minimal promoter sequence(s) and other regulatory regions within $P_U$ and $P_D$, that support/regulate the full expression of the CCR5-luciferase promoter constructs, in unstimulated THP-1, Jurkat, and K562 cell lines.

The approach is similar to the one described above. Briefly, using a combination of convenient restriction sites and PCR a series of deletion constructs are made in the promoter regions, and these DNA fragments are fused to the pGL3 Basic vector. The constructs are transiently transfected into the aforementioned cell lines by electroporation, and the ability of these constructs to drive firefly luciferase expression is determined. The promoterless pGL3-Basic vector serves as the baseline control for constitutive expression in unstimulated cells. This method has the limitation that introns, exon (e.g., exon 4) and the 3'-flanking sequences are not included in the fusion gene. Among the advantages are the ease of analysis of reporter gene expression, and since there is minimal or no firefly luciferase activity in eukaryotic cells, the presence of firefly luciferase activity is a direct measure of the luciferase gene transcription directed by the recombinant vectors.

The region between +430 to +635 in $P_D$ is likely to be important in regulating CCR5 expression. Within this region, consensus sequences representing binding sites for transcription factors such as Oct-1 and GR-β are present. Transient transfection is used to demonstrate some response elements, while stable integration of fusion genes is used to demonstrate other regulatory elements. In transient transfection, nearly all of the transfected DNA remains extrachromosomal and is subject to degradation by cellular nucleases. Nevertheless, for a short interval (12 to 48 h) these cells may express the fusion gene and provide a means of analyzing these regulatory elements. In stable transfection, recombinant DNA molecules are integrated into genomic DNA, replicate with the genome and may be expressed and regulated in a fashion analogous to the native gene.

The CCR5-constitutive transcription studies are studied in two distinct cellular environments: 1) "surrogate" leukocyte environments, e.g., THP-1, Jurkat/PM1, and K562 cells; and 2) "physiologically relevant ex-vivo cellular environments", e.g., CD34+ progenitor derived monocytes/DCs that permit a more physiologic dissection of the elements required for CCR5 gene expression in HIV target cells. Mature DCs constitute a very small fraction of circulating leukocytes (<1%), and therefore harvesting them directly from the periphery is difficult. Furthermore, since monocytes and mature DCs are terminally differentiated cells, and are not actively proliferating, they cannot be cultivated in culture for a long duration. This limitation is overcome by using cellular environments such those described above. These cellular environments, i.e., CD34+ differentiating monocytes/DCs, are practical, since the methods required for isolation and growth of CD34+ progenitor cells have been established; the components of the cytokine-cocktails/regimens required for differentiating the cells towards the DC/monocyte lineage have been determined; and the conditions and cell numbers required for transfecting similar CD34+ progenitor cell-derived leukocyte populations have been determined.

Because, these cell types are a rare resource, instead of electroporation, these cells are transfected using the lipofectamine reagent. The advantage is that a relatively small number of cells can be transfected. Before transfection the leukocyte composition of the cytokine-treated cultures are analyzed by FACS analysis for cell surface markers thought to be characteristic of DCs, and leukocyte-specific stains as previously described (Ahuja et al., 1996). This allows for the ability to control for differences in the degree of differentiation that the CD34+ cells may have undergone.

First, it is determined whether IL-2 mediated increases in CCR5 mRNA are transcriptionally and/or post-transcriptionally mediated. To do this, the following assays are performed: nuclear transcript elongation assays; assays that monitor CCR5 mRNA abundance after inhibition of RNA synthesis. Alternatively, stability may also be assessed by pulse-decay analysis. If the increase is transcriptionally mediated, the IL-2 responsive elements in the promoters are defined.

For studies to determine the IL-2 responsive elements, dose response (e.g., IL-2, 25-500 U/ml) analysis is initially performed. These studies are performed in Jurkat cells and the PM1 cell (T cell lines). The optimal time for IL-2 addition to the transfected cells is determined (e.g., immediately after transfection or 24 h after transfection). In these studies, the optimal time for harvesting cells for luciferase assay is determined. Because the IL-2 response elements may not necessarily reside in the minimal promoter, CCR5-pGL3 constructs of varying lengths are used. The baselines for stimulated transcription studies are the values obtained with each construct in cells incubated in medium alone, i.e., unstimulated cells. For both the stimulated and unstimulated transcription studies, a positive control is included (the pA3 construct described above).

The aforementioned studies allow for the identification of the minimal sequences required for basal level of transcription, as well as sequences required for stimulation of transcription during IL-2 treatment. To verify the functional importance of the element(s), the nucleotide sequence of the element(s) are altered by site-directed mutagenesis (created by PCR). Loss of effect of IL-2 or basal transcription caused by a focused mutation in the context of the promoter construct is verifies that the elements are important for CCR5 transcription.

It is important to demonstrate that faithful initiation and transcription of the luciferase gene occurs in transfected cells. Measurement of luciferase activity is a rapid method of screening a large number of transfected cells and gives a reasonable approximation of the rate of transfection of the luciferase gene. However, reporter genes allow only an indirect measure of promoter activity, and it is necessary to analyze RNA levels and the structure of the RNA produced from the transfected gene. Accordingly, in selected cultures, luciferase mRNA in CCR5-luciferase transfectants is analyzed (by primer extension and S1 nuclease protection) to ascertain the location of the transcription start site. The levels of CCR5 promoter/luciferase mRNA and luciferase activity are compared in transfected cells with and without treatment with IL-2 to verify that the luciferase activity is a valid method of assessing transcription.

For deletion/transfection studies, the efficiency of transfection may vary from sample to sample. To minimize this: all luciferase assays are done using the same stocks of plasmid DNAs; the optimal time at which peak luciferase activity can be demonstrated is defined in each cellular environment; for each independent experiment, the "surrogate" and "physiologic" cellular environments are transfected on the same day with the same construct, and in certain studies, the luciferase activity is measured on the same day; relative luciferase activity is normalized against a transfection control, by co-transfecting the plasmid pRL-CMV (Promega) with the CCR5-luciferse gene chimeras and determination of the renilla activity in the extracts; to minimize the trans-effects between the promoters of the co-transfected *Renilla* luciferase vector and the CCR5 promoter constructs, the *Renilla* luciferase expression vectors (renilla driven by CMV, SV40, and or TK promoters) that has the least trans-effect is determined.

11. Protein/DNA Interactions that Regulate the Constitutive and IL-2 Stimulated Expression of CCR5 a. DNase I Protection Assays

The power of this approach derives from the fact it is not necessary to know the nucleotide sequence of the transcription factor binding sites prior to the examination, and is thus more specific than EMSA. DNase I protection analysis involves incubation of the 5'-end labeled DNA containing CCR5 regulatory element(s) (100-200 bp) with nuclear extracts that might contain the putative binding protein, followed by the addition of pancreatic DNaseI. Samples are then analyzed on urea-polyacrylamide DNA sequencing gels to identify proteins that protect DNA regions from digestion and to localize these elements. The labeled DNA is protected from DNase I digestion due to the binding of the protein and the protected region appears as a "gap" or "footprint" on autoradiography. The exact sequence where the protection occurred can be determined by correlating it with the markers generated by the chemical sequencing of the probe itself. Nuclear extracts are prepared from several cell lines and tested for the presence of nuclear factors that can confer DNase I protection.

b. EMSA (Gel Mobility Shift Assay)

The approach of EMSA is that on gel electrophoresis one can determine whether a radioactive DNA fragment binds nuclear proteins, and to what extent this binding is sequence specific. Briefly, a synthetic double-stranded oligonucleotide version of each sequence to be tested is prepared and examined for its ability to bind protein factor(s) from nuclear extracts of cells, by gel mobility shift assay, in which differential migration of protein-DNA complexes and free DNA is assessed in a non-denaturing gel system. Probes of differing lengths are end-labeled with $^{32}$P-ATP and T4 polynucleotide kinase. Nuclear extracts from the cells are prepared and the binding reaction is incubated at room temperature for 20 min and subjected to electrophoresis through a 6% polyacrylamide gel.

Several possible band patterns may result from this analysis. Ideally, a band near the top of the gel representing a sequence specific DNA interaction is accompanied by a second heavy band at the bottom of the gel reflecting an excess unbound probe. In addition, other bands may appear which may represent: 1) protein-DNA interaction that is non-sequence-specific; 2) dissociation of protein-DNA complexes; 3) existence of protein-protein complexes that bind to the element. To establish the relative specificity of the interactions, competition studies are performed using constant amounts of labeled DNA and extract but with increasing mass of cold competitor DNA containing either the element or a non-specific sequence. Protein binding that is sequence specific is competed out much more readily by unlabeled specific sequence than by an equal concentration of a non-specific sequence of similar length. To determine if specific sequences in the CCR5 promoter regions are distinct from other well-known sequences, competition studies using unlabeled competition sequences identical to those previously identified from other genes are conducted. The identity of such binding factors is confirmed by performing super-shift assays using a specific antibody. The affinity of the binding element as well as a negative control oligonucleotide is evaluated on the basis of their relative dissociation constant (kd). The kd is a function of the relative ability of the different unlabeled oligonucleotides to displace the labeled element from its high affinity binding protein. Radioactive bands from the gels are excised and radioactivity measured by scintillation counting and binding data measured by the method of Scatchard.

12. IL-2 Effects on the Steady-State Levels of CCR5 mRNA in PBMCs a. Nuclear Transcript Elongation Analysis This procedure allows the detection of RNA transcripts that are initiated prior to cell lysis and elongated during the transcription assay, and provides a fairly accurate measure of in vivo gene transcription rate. PBMCs are incubated with IL-2±PHA for various time intervals to include time points before and after peak abundance of the mRNA (e.g., 1, 3, 5, 7 days). At each time point, nuclei are isolated (Cook et al., 1985). Isolated nuclei are incubated with $^{32}$P-UTP and unlabeled NTPs to label nascent RNA transcripts (McKnight and Palmiter, 1979). In some studies, alpha-amanitin (1 µg/ml) is used to inhibit RNA polymerase II in transcription reaction mixtures. Radiolabeled RNA is isolated as specific transcripts detected by hybridization to excess CCR5 cDNA (5 µg) immobilized on a filter membrane. To determine if there is preferential transcription of CCR5A or CCR5B, labeled RNA is hybridized to exon 2 specific DNA prepared by PCR. Immobilized pBluescript vector DNA (Stratagene) without any insert is used as a non-specific control, and cDNA probes for actin also serve as controls. Specific radioactivity is quantitated by liquid scintillation counting and the intensity of the CCR5 signal is compared to that of control probes. Relative CCR5 mRNA synthesis is expressed as parts per million (ppm). CCR5 specific transcription is corrected for hybridization efficiency determined by including a [$^3$H]-cRNA in all samples.

Whether induction of CCR5 gene transcription is dependent on de novo protein synthesis is studied by treating PBMCs with cycloheximide (10 mg/ml) concurrently with PHA±IL-2, then harvesting nuclei for in vitro transcription assays. Duplicate cultures are treated with cycloheximide alone. If treatment with cycloheximide blocks the induction of CCR5 transcription by PHA±IL-2, these cytokines may act by inducing de novo synthesis of one or more proteins required for induction of CCR5 gene transcription in PBMCs. It is possible that cycloheximide may enhance gene transcription, either by itself or in conjunction with IL-2+PHA; such "superinduction" may be seen when the process of mRNA decay is dependent on de novo protein synthesis.

b. Rate of Degradation of CCR5 mRNA

Inhibition of RNA Synthesis

PBMCs are incubated with optimal doses of IL-2 or with medium alone, for a time period before and after maximal induction of CCR5 mRNA. Further synthesis of mRNA is blocked by dichloro-ribofuranosyl benzimidazole (DRB) and the rate of disappearance of CCR5 mRNA is determined (Rodgers et al., 1985). Inhibition is determined from the incorporation of $^3$H-uridine into RNA in the absence and presence of inhibitor. After treatment, RNA is extracted after 0.25, 0.5, 1, and 2 h. Half-life is determined from the first disappearance of CCR5 mRNA.

Inherent in this type of analysis is the assumption that the inhibitor has no effect on mRNA degradation. Data from inhibitor studies is interpreted with caution because of possible secondary effects, which can include inhibition of mRNA degradation (Saini et al., 1990). This method, however, is technically easier than the pulse-decay method.

Pulse-Decay Analysis

CCR5 mRNA stability (half-life) is also assessed by $^3$H-uridine pulse-decay analysis according to modification of the glucosamine-uridine method of Levis and Perman (Levis and Penman, 1977). This method requires i) preincubation with glucosamine to deplete the UTP pool; ii) incubation with $^3$H-uridine to radiolabel newly synthesized RNA; iii) incubation with glucosamine after the $^3$H-uridine pulse-labeling to inhibit further $^3$H-UTP incorporation into RNA; and iv) incubation with uridine and cytidine during the "chase" to minimize reincorporation of released radioactive uridine. Cells are incubated for 2 h (short-term treatment) or 8 h (long-term treatment) in fresh culture medium with or without test agents. The cultures are pulse-labeled with $^3$H-uridine (100 uCi/dish, 50 Ci/mmol). After 15 min, cultures are washed and a "chase" period is initiated after the addition of fresh medium containing 5 mM each of cytidine and uridine. Cultures are harvested at time intervals during the "chase" for analysis of radioactivity remaining in total RNA and CCR5 mRNA. The half-life of CCR5 mRNA is calculated from the disappearance of $^3$H-labeled CCR5 specific transcripts by hybridization with excess CCR5 cDNA as discussed for nuclear transcription elongation assays. Labeled transcripts are also hybridized to exon 2 oligonucleotides to determine if there is differential stability of the transcripts.

When using the pulse-chase method to determine mRNA degradation, it is important to select an appropriate time to pulse-label the cells before starting the "chase" period. Although it is usually convenient and desirable to pulse-label for several half-lives or more before the "chase", a relatively short pulse-labeling is preferred for short-lived mRNAs, and when there are two or more species of specific mRNAs which have different half-lives, as may be the case for CCR5. Labeling for a long-time (relative to $t_{1/2}$) reduces the relative signal for short-lived mRNAs and may obscure their presence. To avoid these problems, a short pulse-labeling is required. The data for steady-state levels of cytoplasmic mRNA, and rates of decay of CCR5 mRNA is expressed as changes relative to the values observed for PBMCs in the absence of IL-2 and/or early time points of IL-2 administration (i.e., fold increase or decrease).

The levels of CCR5 mRNA in freshly isolated cells is constitutively skewed towards certain cell types that can also be targets for HIV, such as DCs and monocytes. Thus, while mechanisms exist for fine tuning the levels of CCR5 in mature leukocytes such as DCs, the events regulating CCR5 receptor gene expression may occur in lineage-committed myeloid precursor cells during differentiation in the bone marrow. Thus, gene regulation of CCR5 is studied in human progenitor derived leukocytes. To verify that the regulatory sequences identified by in vitro DNase footprinting are relevant in vivo, in vivo DNase footprinting and in vivo methylation are conducted. Such studies include analysis of all segments of CCR5 that are important. Screening of cDNA expression libraries with a putative DNA element allows further characterization of DNA binding proteins.

13. Polymorphisms/Mutations in CCR5 Regulatory Regions

As described above, extensive polymorphisms were identified in the regulatory regions of CCR5. In this section, the importance of these polymorphisms as it relates to HIV-1 infection is studied. Certain genotypes display different levels of chemokine receptors (CCR5), which may directly influence infectivity and hence virus expression. The amount of CCR5 expression directly influences the numbers of cells infected and the amount of virus produced (Wu et al., 1997). In the end, these factors may profoundly effect disease progression. Macaques infected with SIVmac vary in their virus expression in vitro, which directly correlates with the rate of progression to simian AIDS in these individual monkeys (Lifson et al., 1997). The inventors reasoned that similar patterns may emerge in humans.

The genetic analysis of the CCR5 regulatory region defines genetic variants linked to differences in the following phenotypes: transcriptional activity, as determined by reporter assays; protein expression, as determined by cell surface expression by FACS analysis; and co-receptor activity, as determined by in vitro HIV-1 infection assays.

There appears to be a significant interplay between genetic backgrounds and ease of infectability with HIV-1. Thus, in addition to structural mutations such as the Δ32 mutation, molecular variations in the regulatory and other non-structural regions of the gene may also play a significant role in CCR5 gene expression and protein synthesis, and therefore HIV-1 infection. Hence, study of these genetic variants helps shed more light on the basis for the variations in individual susceptibility to HIV-1.

a. Genetic Variation Within the CCR5 Regulatory Region

The extent of genetic variation is determined in the CCR5 regulatory regions. Rather than carrying out DNA sequencing on every individual in the study population (CCR5+/+ or +/−, and HIV-1 negative), a genetic "pre-screen" is employed. To do this, assays for single-strand conformation polymorphisms (SSCP) are used. Study of the pattern of the SSCP variations allows the determination of a "bar code" distinguishing the extent of genetic versions of the CCR5 regulatory region in the study population. Since the SSCP variants are in genetic disequilibrium with the DNA sequence variants that affect promoter activity, this scheme pre-selects the maximum number of individuals with different CCR5 regulatory regions. By genetically profiling the approximately 150 individuals in the study population, ~30 individuals are identified with the broadest spectrum of variations in the CCR5 regulatory region. The complete promoter region of these individuals is then DNA sequenced, and the promoters and PBMCs are assessed for phenotypic variations. Based on the frequency of the sequence patterns (genotypes) observed, the regulatory regions are classified as silent polymorphisms linked to wild type CCR5 promoter activity, polymorphisms associated with the Δ32 mutation, or polymorphisms linked to CCR5 promoter activity variants. These polymorphisms are likely not somatic in nature, and similar to the Δ32 mutation are acquired by germ-line transmission. This is verified by performing segregation analysis of SSCP variants using genomic DNA from reference pedigrees: 40 original multi-generational families from the Paris-based Cente d'Etude du Polymorphisme Humain (CEPH; French acronym for Human Polymorphism Study Center) (Dausset, 1986), and the San Antonio Family Diabetes Study (SAFADS), which represent San Antonians of Mexican American descent who have been identified in a prior epidemiological survey (Haffner et al., 1986; Stem et al., 1989).

Genomic DNA and PBMCs is available from several unrelated normal donors known to be HIV-1 negative (all ethnic groups). The criteria for inclusion of the normal adult donors in this study are that they be HIV-1 negative, have no major illness (i.e., inflammatory/infectious states that may alter CCR5 expression), ingest no medication for a chronic or acute illness, and finally be up-to-date on their immunization (since immunization of tetanus toxoid renders PBMCs from uninfected individuals more susceptible to HIV in vitro). The genomic DNA from the PBMCs of these individuals is extracted and screened by PCR for the Δ32 mutation. Individuals with the −/− genotype are excluded from analysis. The genomic DNA from the +/+ and +/− individuals from the study population described above is screened for SSCP variants. This screen utilizes approximately 20 pairs of oligonucleotide PCR primers that span the CCR5 gene promoter regions, $P_U$ and $P_D$, a total of ~4 kb of DNA.

DNA samples are arrayed in a 96-well format so that PCR assays are set up with 8-channel pipetting tools in a polycarbonate 96-well microtiter plate (Techne Hi-Temp 96), which is transferred to a 96-well thermal cycler for PCR amplification. For SSCP analysis, [$\gamma$-$^{32}$P] radiolabeled PCR products are heat-denatured and loaded onto a 0.5× Mutation Detection Enhancement Gel (MDE™ gel; FMC Bioproducts, PA) and subjected to electrophoresis at 2 watts at 25° C. for 14 h. The SSCP patterns are compared for each individual and a "bar code" is assigned. These "bar codes" define the full range of genetic versions of the CCR5 regulatory region in the study population.

These studies define the sequence of the CCR5 regulatory regions of the two alleles from a single individual, i.e., define the haplotype. For this analysis the genomic DNA is re-amplified from the individuals that represent the broadest spectrum of genetic variants. Unlike the SSCP studies, only two PCR primer sets are used that amplify the $P_U$ and $P_D$ regions as a complete DNA segment, i.e., ~2 kb each. The PCR primers include linkers at either end to facilitate cloning into the reporter vector, pGL3-Basic.

There are two options for defining the sequence of the CCR5 regulatory region on each allele. The first option is to sequence a few clones at random. This option, though practical, is quite expensive. Instead, a few DNA "mini-prep" clones representative of $P_U$ and $P_D$ are "typed" from a single individual by the SSCP assay. This allows "pre-selection" of the DNA clones that need to be sequenced. It should be noted that the sequences of $P_U$ and $P_D$ overlap over a short region, and that in this region several polymorphisms were identified.

b. Transcriptional Activity of Genotype Variations

These studies determine the phenotype, i.e., transcriptional activity of the regulatory regions of CCR5. Since the regulatory sequences in both alleles of an individual may be different, and since two different regulatory regions, i.e., $P_U$ and $P_D$, from a single individual are tested, from a single individual a total of four (Choe et al., 1996) promoter constructs are tested in reporter assays. Constructs that encompass the complete $P_U$ and $P_D$ sequences are studied initially. Where polymorphisms are detected in critical cis-elements or in the minimal promoter, constructs to test the functional significance of these mutations are designed. Transcriptional activity is measured by luciferase activity in the lysates of cells transfected with the promoter constructs. The cell types used are THP-1 (monocyte) or Jurkat (lymphocyte).

To decrease variability in the normalized luciferase activity measured, the variables discussed above are followed, and the following factors are controlled for: (a) only cells growing in the log phase are transfected; (b) the cell numbers for transfection are kept constant; (c) as differences in DNA preps may give variable results, large preps of highly pure DNA (Qiagen) are made for transfection; and (d) experiments are in triplicate dishes for each construct and each construct is tested a minimum of three times. The luciferase activity of the various constructs is compared by ANOVA, and significant differences are compared by Student's t test. Using rigorous statistical tests, a rank is assigned for the promoter activity of each construct tested.

c. CCR5 Surface Expression of Genotype Variations

Previous studies show that the conditions under which PBMCs are grown effects the level of CCR5 expression. These studies demonstrate that addition of exogenous IL-2 increases CCR5 expression on PBMCs, whereas PHA alone has little effect. Furthermore, stimulating PBMCs with PHA (5-10 μg/ml) or anti-CD3 (Wu et al., 1997) followed by IL-2 (100 U) causes a high level of CCR5 expression in PBMC that is evident at 3 weeks. There is some concern that by activating cells the nature of CCR5 expression is disturbed that may mask subtle differences between genotypes. However, most cells in the peripheral blood are inactive. The ability of cells to respond to insult by activating cell surface markers including adhesion molecules, CD26, and other memory or effector phenotypes, may correlate with disease progression if those individuals are infected with HIV-1. Moreover, the studies of Wu et al. (1997) and studies in macaques suggest that the stimulation is necessary for infectivity but that this is the basal level from which to assess HIV-1 infection. That is, PHA and IL-2 stimulate PBMC to express CCR5, the level of which is genetically programmed by genotype. This is addressed by examining the role each of these play in CCR5 expression. This includes titrating PHA and IL-2 on PBMC from normal human subjects and assessing how these factors influence CCR5 expression. At the same time CXCR4 is assessed as a control. Expression of CXCR4 is also important for the comparison of infection with both M- and T-tropic HIV-1 strains. In addition, activation of PBMCs is compared using anti-CD3 (Wu et al., 1997). In this case, PBMC are incubated in the presence of anti-CD3 coated tissue culture plates for 4 days followed by the addition of IL-2.

Cell surface expression of CCR5 is determined on PBMCs obtained from +/+ or +/− individuals. The methods for CCR5 FACS analysis are discussed above. As a positive control, in each run a HEK 293 cell line stably expressing CCR5 is also stained (Alkhatib et al., 1997).

d. In Vitro Infectability of PBMCs with HIV-1 of Genotype Variations

The role of genotypic variation of CCR5 cell surface expression on human PBMC in the infectious process is analyzed by studying their infectability using M- and T-tropic strains of HIV-1. An important consideration in these studies is the reduction of any free chemokine expression in these cultures that might interfere with HIV-1 infectivity. It has been reported that chemokines downregulate CCR5 (RANTES) and CXCR4 (SDF-1), which might result in low virus titers due to HIV suppression. To reduce the possible negative effects of CD8+ T cell populations, the CD8 fraction from PBMC is removed by immunomagnetic bead separation (Dynabeads, Dynal; Great Neck, N.Y.). This technique when performed sequentially removes greater than 99% of CD8 expressing PBMCs and is performed essentially as recommended by the manufacturer. The number of beads used is at a ratio of 30:1 (e.g., 215 µl beads/$1\times10^6$ cells; the beads are supplied at about $1.4\times10^6$ beads/ml). After adding the beads to the cells, the cells are gently rocked at 4° C. for 45 minutes. Subsequently the cell-bead mixture is incubated with a Dynal magnet for 2-3 minutes and the nonattached cells (CD4+) are harvested and the process repeated.

HIV-1 isolates BaL, 89.1 and IIIB(LAV) are used for in vitro infectivity studies. Virus stocks of HIV-1/IIIB and HIV-1/BaL were generated, and virus preparations from samples sent from the AIDS repository are made. The HIV-1/BaL stock (NIH AIDS Repository) has been expanded by infection of primary human macrophages. This stock was used to successfully infect CCR5 transfected HeLa cells and HEK 293 cells, and BaL was titered based on Ag p24. 89.6 was selected since it has been shown to be dual-tropic, infecting both CD4+ T cell lines and macrophages and is more promiscuous in regard to CC chemokine receptor usage. As a control, IIIB is compared for infection of primary PBMC cell cultures. IIIB is primarily T cell line tropic and has been propagated in Molt3 T cell lines and stocks titrated and frozen at $-135°$ C.

PBMCs from heparinized human blood are isolated by Ficoll Hypaque gradient centrifugation. The protocol involves stimulation in PHA followed by IL-2 for 15-21 days. Following this, $2\times10^5$ PBMCs are centrifuged at 1700×g to remove the growth medium, resuspended in virus stock culture or culture medium (250 µl) for 2 hours at 37° C. and then the volume adjusted with culture medium to a cell density of $2\times10^6$/ml. After overnight incubation, the cells are washed 5 times and the contents of the last wash harvested as the zero time point. Every 3-4 days, culture supernatants are harvested and frozen at $-80°$ C. until analysis for virus by HIV-1 p24 antigen capture ELISA as per the manufacturers instructions. The antigen capture kits are sold by the NIH AIDS Repository and NCI-Frederick. Results are compared with a standard curve generated according to the manufacturer's instructions. In cases where the OD values of the samples are out of range (over), serial 10 fold dilutions are analyzed to obtain a value situated within the standard curve, which gives a direct measure of virus present in PBMC cultures. Infection of HEK293 cells stably expressing CCR5 resulted in relatively low levels of virus expression (1-10 ng/ml). For PBMC cultures, infection with BaL or IIIB leads to 10-100 fold higher antigen levels at 10-14 days post-infection.

All infections are performed in triplicate for statistically representative sampling. This is important in assessing whether certain genetic variants are more commonly linked to changes in HIV-1 infection/expression. Other non-membrane factors may also influence viral replication and expression, however, it has not been shown that cellular factors directly or profoundly effect HIV-1 expression in studies performed on PBMCs. Other cell surface molecules could serve as co-receptors and may have genetic linkage. Therefore a control well is included for each sample that includes pre-treatment of cells with anti-CCR5 (100 µg/ml) to inhibit infection in PBMC from the various genotypes. This ensures that the variation in HIV-1 infectability is linked to the use of CCR5 in viral entry. In addition, recombinant chemokines RANTES, MIP-1α, and MIP-1β (200 ng/ml) are incubated during the infection period to determine if infection proceeds through CCR5 or related CCR-like molecules. RANTES may block M-tropic viruses but not 89.6 or IIIB variants. These genotype-phenotype analyses shed light on novel molecular determinants that alter/influence levels of CCR5 transcription, surface expression levels and co-receptor activity, and thus have important implications for the understanding of the host determinants of HIV-1 entry.

Example 2

Host Genetic Determinants of HIV Pathogenesis

This Example describes that genetic resistance to HIV-1 in African Americans is conferred by a MIP-1α allele. MIP-1α, RANTES and MIP-1β are the three ligands for CC chemokine receptor 5 (CCR5), the major co-receptor for HIV-1 entry (Raport et al., 1996; Samson et al., 1996; Combadiere et al., 1996; Alkhatib et al., 1996; Deng et al., 1996; Dragic et al., 1996; Doranz et al., 1996). In vitro, these ligands have, in general, anti-HIV-1 properties (Alkhatib et al., 1996; Moore et al., 1997). By extensive sequencing, an allele was identified that includes single nucleotide polymorphisms (SNPs) in the gene for MIP-1α. The distribution of this allele is restricted to African Americans.

This allele was not found in HIV-1 seropositive African Americans (n=421). In contrast, in HIV-1 seronegative individuals of African descent (n=240 African Americans and 100 Africans), the allele frequency was 5%. This suggests that this allele is likely to be an HIV-1 resistance factor in African Americans. Since the majority (~96%) of highly-exposed, seronegative individuals tested are not homozygous for the CCR5-Δ32 mutation (a genetic resistance factor for Caucasians) other resistance factors must exist. For example, a cohort of Kenyan sex-workers have been identified who, despite documented heavy exposure to HIV-1, remain seronegative (Fowke et al., 1996). The binding sites of MIP-1α, RANTES and MIP-1β on CCR5 overlap with those for HIV-1 (Alkhatib et al., 1997). Thus, this MIP-1α allele may be linked to polymorphisms in the cis-regulatory region of MIP-1α that lead to over-expression of MIP-1α protein and hence inhibit binding of HIV-1 to CCR5. Alternatively, this allele is in linkage disequilibrium with polymorphisms in another gene that is also on chromosome 17q and HIV-1 resistance is mediated by this gene. Several CC chemokine genes are found on chromosome 17q.

This Example also details that the ancestral CCR5 haplotype designated as CCR5 Human haplogroup A (CCR5-HHA) is associated with HIV-disease retardation in African Americans but not Caucasians. The phenotypic effects of CCR5 HHA appears to be race-specific, i.e., is associated with disease retardation in African Americans but not in Caucasians, and that this effect is independent of phenotypic effects of the CCR5 haplotype that carries the CCR2-64I mutation. The CCR2-64I allele is associated with disease-retardation in African Americans but not Caucasians (Example 4). The highest allele frequency of CCR5 HHA is in African Pygmies. The frequency of CCR5 HHA was highest in individuals of African descent ($\geqq 0.22$), and was maximum in Mbuti and Biaka pygmies (0.71).

It is noteworthy that the frequency of HHA haplotypes is highest in African pygmies living near the origin of HIV-1, and in whom the prevalence of HIV-1 infection is very low. HIV-1 is believed to have arisen by cross-species transmission of a closely related SIV strain (SIVcpz), whose reservoir is thought to be a subspecies of chimpanzees (P.t. troglodytes) found in regions of Africa co-inhabited by pygmies (Gao et al., 1999). Among 1430 pygmies tested for infection with HIV-1, only two confirmed cases of HIV-1 were found (Kowo et al., 1995; Ndumbe et al., 1993; Brun-Vezinet et al., 1986; Gonzalez et al., 1987). Yet, among pygmies there is a high prevalence of other blood-borne infections such as HBV, HCV and HTLV-1 (Kowo et al., 1995 Ndumbe et al., 1993). The close relationships (>98% nucleotide similarity) among some STLV-I strains from chimpanzees and HTLV-I subtype B strains present in pygmies suggests that zoonotic transmission of other primary lentiviruses (e.g., SIVcpz) from chimpanzees to pygmies may have occurred (Koralnik et al., 1994; Saksena et al., 1994). Thus, despite presumably intimate contact with a SIVcpz/HIV-1 reservoir for thousands of years, the frequency of zoonotic transmission of SIVcpz/HIV-1 to pygmies appears to be very low. One possible scenario is that the frequency of SIVcpz/HIV infection in chimpanzees is low, and/or the nature of pygmy exposure to this virus is relatively inefficient for transmission. Another possibility is that pygmies harbor an HIV-1 resistance factor. These results described herein indicate that HHA haplotypes are associated with a delay in disease progression in individuals of African descent, although there is no evidence that HHA haplotypes are associated with a reduction in transmission risk. Nonetheless, the highest prevalence of HHA haplotypes was in African populations with the very highest frequency in pygmy populations of Central and West Africa. Thus, protection against HIV-1 infection in pygmies could have been afforded, in part, by HHA haplotypes.

The cohort described herein is the largest cohort of HIV-1 infected individuals followed at a single medical center (n=1158). This and other features of the cohort make it ideally suited for genetic epidemiological studies. In this regard it is important to note that the genetic determinants of HIV-1 disease in U.S. adults have been examined primarily in cohorts comprised of hemophiliacs, injection-drug-using African American populations, and Caucasian homosexual men (Dean et al., 1996; Huang et al., 1996; Michael et al., 1997a; 1997b; Smith et al., 1997; Zimmerman et al., 1997; Winkler et al., 1998; Kostrikis et al., 1998; Rizzardi et al., 1998; Morawetz et al., 1997; Martin et al., 1998; McDermott et al., 1998). Consequently, apparent associations with the rate of HIV disease progression could be secondary to an association with susceptibility to developing a specific AIDS-defining condition. For example, Kaposi's sarcoma is epidemiologically almost entirely confined to homosexual men (Spijkerman et al., 1996; Dawkins et al., 1998), while extra-pulmonary TB is more prevalent among African American intravenous drug users (Shafer and Edlin, 1996; Schwoebel et al., 1995). Thus, the varied patterns of clinical disease exhibited by different cohorts could confound genotype-phenotype association studies. Another limitation of many genotype-phenotype association studies is the practice of pooling together several heterogeneous cohorts in order to increase the sample size of haplotype groups. Individual cohorts may differ greatly in influential factors such as access to medical care, injection drug use, duration of and loss to follow-up, and adherence to medical therapy (Jones et al., 1998; Hu et al., 1995; Joyce et al., 1999; Bozzette et al., 1998; Cunningham et al., 1995). One possible effect of this practice of aggregation is that it might obscure the signature of associations that may be population-specific.

Several factors serve to reduce confounding effects for genetic analysis of the WHMC cohort used for these studies. First, recruitment was not based on a single HIV risk factor. Second, recruitment was not biased toward a specific race, ethnic group, or geographic region. The cohort was drawn from a mixed North American population and then stratified by race. Third, recruitment was from a pool of individuals who were otherwise healthy, thus reducing the effects of co-morbid illnesses (e.g., hemophilia). Fourth, the age and gender (predominantly male) distributions of African Americans and Caucasians in the cohort were comparable. Fifth, all cohort members had equal and ready access to health care and anti-retroviral therapy, and were prospectively followed at a single medical center. Sixth, the concordance of CCR5 haplotype frequencies are checked by comparing the distribution of CCR5 haplotypes of African Americans and Caucasians in the WHMC cohort to the CCR5 haplotype distributions of uninfected African-Americans, and U.S. and European Caucasians, respectively. Last, CCR5 haplotypes are organized in an evolutionary framework to minimize the confounding that might occur by mixing SNPs and/or haplotypes with different evolutionary histories and phenotypic effects.

Over the last decade a considerable amount of information about the pathogenesis of HIV-1 infection has been assimilated. However, many fundamental questions about the observed variation in host response to HIV-1 remain unanswered. For example, it is unclear what factors (e.g., genetic, environmental) are responsible for the observed inter-individual and inter-population differences in susceptibility to infection and/or disease progression. A growing body of evidence suggests that host genetic factors (i.e., genetic polymorphisms) play an important role in determining susceptibility to HIV-1 infection and disease progression. Earlier studies suggested that HLA alleles and closely linked genes of the major histocompatibility complex (MHC) influenced HIV-1 transmission and disease progression. More recently, several studies have shown a powerful influence of chemokine system gene variants in HIV-1 transmission and disease progression. As shown in Example 4, polymorphisms in the regulatory regions of CC chemokine receptor 5 (CCR5), the major co-receptor for HIV entry, as well as the coding region of CCR2B, and the non-coding region of the chemokine SDF are associated with altered rates of disease progression.

Preliminary studies demonstrated that the amount and complexity of sequence variation at CCR5 is considerably more than currently appreciated, the disease-accelerating and disease-retarding effects of the CCR5 haplotypes can be race-specific, the genes encoding the HIV-1 suppressive CC chemokines are polymorphic, and an allele that includes polymorphisms in MIP-1α, a ligand for CCR5, is associated with protection against transmission of HIV-1 in African Americans.

Human populations have varied evolutionary histories and more importantly, have co-evolved with different combinations of microbial pathogens. Hence, the repertoire of alleles that afford resistance or susceptibility to pathogens may vary in different populations (Hill, 1998). For example, the spread of *Plasmodium falciparum* malaria throughout Africa and Asia resulted in selection for alleles that reduce the risk of dying from malaria. Consequently, many malaria resistance genes show marked allele frequency differences among populations. Natural selection may have had similar effects on the genes encoding proteins that affect susceptibility to HIV-1, especially in African populations where cross-species transmission of HIV-like retroviruses likely first occurred (Gao et al., 1999).

The search for population/ethnic-specific determinants of HIV-1 infection has a high priority for planning public health policies. Failure to stratify risk for disease progression and transmission in cohorts used to evaluate HIV-1 treatment strategies could obscure the real host responses to AIDS intervention and management approaches. The changing epidemiology of HIV-1 makes stratification for population-specific disease-modifying genetic determinants more compelling. In the U.S., AIDS is evolving from a disease that once predominately affected homosexual Caucasian men to one that now largely strikes minority groups (HIV/AIDS Surveillance Report CDC, 1998). For example, African Americans constitute 12 percent of the U.S. population but account for 45 percent of new cases of AIDS, and AIDS has been the leading killer of African Americans between the ages of 25 and 44 for most of the last decade. Furthermore, it is estimated that 1 of 50 African American men and 1 of 160 African American women are infected with HIV-1. Thus, identification of genetic determinants associated with population-specific effects on HIV-1 disease could be an important step toward stratifying disease risk in African Americans.

A. Introduction

Defining the genetic basis of individual susceptibility to HIV involves the same problems encountered in the study of most common chronic diseases. Each case of HIV/AIDS has a complex multi-factorial etiology, with genetic, viral or environmental components influencing the final outcome. Even complete knowledge of an individual's genetic constitution would not enable an accurate prediction of the risk of HIV transmission, or progression, or severity of disease. HIV transmission and disease progression develops as a consequence of interactions between the "initial" conditions, coded in the genome and the infecting viral strain, and influenced by variations in the environment (e.g., co-infections, sexual practices, drug use, access to health care) indexed by the individual. This emphasizes that the genome is not an isolated source of fixed, one-way information and that predicting the outcome of a multi-factorial disease such as HIV without consideration of environmental or viral factors is incomplete. Thus, unexplained genotype-phenotype differences may be attributable to epigenetic modifiers of HIV disease. In this respect, steps have been taken to minimize these concerns, including serious consideration of: 1) the invariant features of the gene at the population level. This includes a clear appreciation of the extent of genetic variability present in a particular chemokine or co-receptor locus in different populations; 2) context-dependent features at the sub-population level (e.g., cohort, race). One of the significant aspects of this study is the nature of the cohort. In the U.S., the genetic determinants of HIV-1 in adults have been examined primarily in three different cohorts, each differing in risk factors for HIV-1 (Dean et al., 1996; Huang et al., 1996; Michael et al., 1997a; 1997b; Smith et al., 1997; Zimmerman et al., 1997; Winkler et al., 1998; Kostrikis et al., 1998; Martin et al., 1998; McDermott et al., 1998). They include multi-center cohort studies biased towards homosexual, Caucasian men (Multicenter AIDS cohort study (MACS); San Francisco City Cohort); hemophiliacs (Multicenter Hemophilia Cohort Study); and the single African-American cohort that is biased heavily towards an intravenous drug using population (AIDS link to Intravenous Experience (ALIVE)). Whether the results of these association studies can be generalized to other ethnic/population groups is unclear.

In contrast to these cohorts, the present cohort is not biased towards a particular risk factor and has a racially balanced composition. It represents the largest cohort of 141V seropositive patients (1,158) followed prospectively at a single medical center (Blatt et al., 1993a; 1993b; 1995; Dolan et al., 1993; Dolan et al., 1995; Example 4). This large sample size increases the power of detecting variants that significantly affect HIV transmission and pathogenesis. Also, because of the unique nature of the cohort, additional factors that influence genotype-phenotype studies (e.g., unequal access to medical care and anti-retroviral therapy, length of follow-up, very low loss to follow-up) are minimized. In the last five years, more studies have likely been published about the association between different host genetic variants and HIV than about any other infectious pathogen (Hill, 1998; Roger, 1998; Just, 1995; Weatherall et al., 1997; Weatherall, 1996a; 1996b). However, the majority of these studies were completed in Caucasian homosexual populations, and there are very few studies that have reported genetic risk factors in patients of African descent (Hill, 1998; Roger, 1998; Just, 1995; Mann et al., 1998; Achord et al., 1996; Anzala et al., 1998; Brackin et al., 1995). The present cohort is well suited to determine the genetic risk factors in African-Americans, a population in which the incidence of HIV infection continues to rise in the U.S. Taken together, the present cohort represents a novel resource that not only complements, but also extends significantly, the HIV-1 genotype-phenotype studies conducted in the aforementioned cohorts.

The viral, and host genetic and immunological factors that influence in HIV pathogenesis have been studied extensively (Cairns and D'Souza, 1998; Berger, 1997; Fauci, 1996; Cohen et al., 1997; Buchacz et al., 1998; Rosenberg and Walker, 1998; Ferbas, 1998; Shearer and Clerici, 1998; Graziosi et al., 1998). Among the factors that influence HIV-1 pathogenesis are non-MHC genetic determinants (chemokine system gene variants), MHC genetic determinants (HLA and linked genes), and chemokine related inhibition of HIV-1.

Several chemokine receptors have been identified as co-receptors with CD4 for HIV (Deng et al., 1996; Doranz et al., 1996; Moore et al., 1997; Cairns and D'Souza, 1998; Berger, 1997; Cohen et al., 1997; Feng et al., 1996; Choe et al., 1996; Deng et al., 1997; Zhang et al., 1998; Garzino-Demo et al., 1998; Berger et al., 1998; Unutmaz et al., 1998; Bjorndal et al., 1997; D'Souza and Harden, 1996; Fauci, 1996). Of these, the two principal co-receptors are CCR5, used preferentially by macrophage-tropic strains (M-tropic; non-synctium inducing (NSI); R5), and CXCR4, utilized by T-cell-tropic strains (T-tropic; synctium inducing (SI); X4). In addition, several R5 strains can use CCR2B or other co-receptors, although the role of this expanded receptor repertoire in vivo is not clear.

Homozygosity, but not heterozygosity, for a 32-bp deletion in the CCR5 gene (CCR5-Δ32) leads to loss of CCR5 surface expression, and is associated with strong resistance to HIV infection by M-tropic isolates (Dean et al., 1996; Liu et al., 1996; Samson et al., 1996). The CCR5-Δ32 allele is rarely found in individuals of African and Asian ancestry (Martinson et al., 1997; Lucotte, 1997). In contrast, 15% of Caucasians are heterozygous and 1% are homozygous for this allele. When situated in trans with CCR5-Δ32, the CCR5 m303 mutation also eliminates CCR5 expression and accounts for resistance against infection (Quillent et al., 1998). Other rare variants of the CCR5 ORF have also been described, but their relevance to HIV-1 pathogenesis is unknown (Ansari-Lari et al., 1997; Carrington et al., 1997). Most highly exposed HIV-negative individuals are not homozygous for the CCR5-Δ32 allele (Dean et al., 1996; McNicholl et al., 1997) suggesting that there are other important genetic resistance factors.

Despite the prevailing view that heterozygosity for the CCR5-Δ32 allele, and a common allelic variant of CCR2 (CCR2-64I) delays disease progression, careful scrutiny of these studies suggest otherwise. A protective role for CCR5-

Δ32 heterozygosity is evident in some reports (Dean et al., 1996; Michael et al., 1997b; Zimmerman et al., 1997; de Roda Husman et al., 1997) but transient/weak (Rizzardi et al., 1998; Meyer et al., 1997; Katzenstein et al., 1997; Eugen-Olsen et al., 1997; Hendel et al., 1998) or not confirmed in other studies (Huang et al., 1996). Similarly with regards to the presence of the CCR2-64I allele, a protective role is evident in some reports (Example 4; Smith et al., 1997; Kostrikis et al., 1998; Anzala et al., 1998; van Rij et al., 1998) or not confirmed in other studies (Michael et al., 1997a; Rizzardi et al., 1998; Hendel et al., 1998; Eugen-Olsen et al., 1998). In the present cohort, the CCR2-64I allele delayed disease progression to AIDS and death in African-Americans but not Caucasians. Interestingly, the CCR2-64I allele is more prevalent in individuals of African, Asian, Hispanic ancestry than in Caucasians (Smith et al., 1997; Example 4).

The inventors were the first to demonstrate the complex genomic and RNA organization of CCR5 and provide evidence for polymorphisms in the regulatory region of CCR1 (Example 3). The CCR5 and CCR2 genes are closely linked on chromosome 3p21-22 (i.e., separated by ~8-kb). Because of this physical proximity and the notion that CCR2 is thought to play a minor role in HIV pathogenesis. The inventors reasoned that the CCR2-64I mutation mediates its effects via linkage to polymorphisms in the regulatory region of CCR5. As detailed above (Examples 3 and 4): CCR5 is a multi-allelic locus with distinct alleles that are characterized by a constellation of multiple polymorphisms in the regulatory region; the CCR2-64I allele is linked to CCR5 +927T, a polymorphism situated in an intronic region, in agreement with published reports (Kostrikis et al., 1998); the linkage between CCR2-64I and CCR5 +927 is not complete, and CCR5 +927T-bearing individuals who lacked a CCR2-64I polymorphism had an accelerated disease course; and the CCR5-Δ32 mutation is in linkage disequilibrium with CCR5 +29G, a polymorphism also located in the regulatory region of CCR5. The CCR5 +29G polymorphism, like the CCR5-Δ32 allele, was associated with a weak delay in disease progression.

More recently, there have been additional publications that have described the association of CCR5 promoter polymorphisms with an accelerated disease course in Caucasians (Martin et al., 1998; McDermott et al., 1998). Martin et al. (1998) described a CCR5 allele designated as the P1 allele that was associated with an accelerated disease course. However, as was shown herein above, because of linkage disequilibrium to two evolutionarily distinct polymorphisms, each associated with different disease outcomes, the P1 allele is a composite of at least three different haplotypes. Similarly, the polymorphism described by McDermott et al. (1998) is also found on three different haplotype backgrounds.

The influence of the polymorphism in the chemokine, SDF, the ligand for CXCR4 (Oberlin et al., 1996; Bleul et al., 1996) is unclear. Winkler et al. (1998) found that this polymorphism was associated with disease retardation, whereas the inventors found it to be associated with disease acceleration (Example 4). A similar disease accelerating phenotype was also observed independently in another cohort (van Rij et al., 1998). Recently, Liu et al. reported two SNPs in the gene for RANTES, and provided data suggesting that one of these alleles might be associated with a delay in disease progression in a cohort of HIV-1 seropositive individuals of Japanese descent (Liu et al., 1999). The two polymorphisms identified by this group are identical to those described herein above. However, this study by Liu et al. is limited in that the association was between an allele and differences in CD4 counts, and not progression to AIDS or death. Furthermore, the possibility that this SNP might be in linkage disequilibrium to other SNPs in 17q was not considered. Another limitation of this study is that there was no consideration of the disease-modifying effects of CCR5 haplotypes.

The MHC locus is comprised of tightly-linked HLA genes that encode proteins associated with intercellular recognition of T-lymphocytes (Corzo et al., 1995; Tomlinson and Bodmer, 1995). MHC class I and class II loci are highly polymorphic in human populations. Since the MHC gene products are critical in regulating many antiviral immune reactions, it is possible that the MHC-coded molecules influence the course of HIV infection (Westby et al., 1996; Keet et al., 1996; Rowland-Jones et al., 1995). A number of MHC loci have been associated with increased or decreased susceptibility to HIV infection (Roger, 1998; Just, 1995; Mann et al., 1998; Westby et al., 1996; Hill, 1996; Just et al., 1992; Just et al., 1995; Kaslow et al., 1990; Kaslow et al., 1996; Puppo et al., 1991; Steel et al., 1988; Cameron et al., 1988; Cameron et al., 1990; Fabio et al., 1992; Mann et al., 1992); Mann et al., 1990; Saah et al., 1998; Nelson et al., 1997; Kaplan et al., 1990; Donald et al., 1992; Brettle et al., 1996; McNeil et al., 1996; Itescu et al., 1992; Itescu et al., 1994; Itescu et al., 1995; Klein et al., 1994; Louie et al., 1991). However, there are very few studies that have examined associations between HLA types and HIV-disease in African-Americans (Roger, 1998; Just, 1995; Hill, 1996; Carrington et al., 1999).

It is clear that polymorphisms in chemokine/co-receptors, and MHC genes play an important role in HIV pathogenesis. Although the role of homozygosity for CCR5-Δ32 in transmission is apparent, the role of the other chemokine system gene polymorphisms in disease progression, either alone or in various combinations, is becoming increasingly complex and to some extent controversial. The situation is similar for HLA association studies. The reasons for this are as detailed below.

In part, the difficulty of interpreting CCR5 polymorphism data is a consequence of an incomplete understanding of the structure of genetic variation at the CCR5 locus (because of extensive linkage disequilibrium among CCR5 polymorphisms, it is not appropriate to perform single nucleotide association studies, emphasizing the need to have a complete understanding of the complex links between haplotype variation in the cis-regulatory region and ORF of CCR5), and differences in haplotype frequencies between populations that are unequally represented in the disease cohorts. With regard to HLA heterogeneity, the MHC locus is highly polymorphic. Consequently, several of the concerns noted above with respect to studies of CCR5 and ethnicity are likely to be true for HLA genes. Additionally, with regard to viral heterogeneity, an important confounder of association studies may be the substantial polymorphism of the HIV strains and their high rate of within-host diversification. For example, if the virus is presenting different epitopes in HLA-identical individuals, genotype-phenotype correlations may be weaker.

When comparisons are made of studies examining the broad outcome of AIDS across risk groups, different patterns of clinical disease exhibited by different risk groups could affect genotype-phenotype studies (e.g., Kaposi sarcoma is more common in homosexual males whereas extra-pulmonary TB is more common among intravenous drug users). Consequently, in HIV-disease outcome studies it is possible that an association with AIDS may be secondary to an association with susceptibility to developing specific AIDS-defining conditions independent of HIV (Spijkerman et al., 1996; Dawkins et al., 1998; Shafer and Edlin, 1996; Schwoebel et al., 1995; Mehra, 1990; Kaloterakis et al., 1995; Papasteriades et al., 1984; Iannetti et al., 1988), and inconsistent associations across risk groups may simply reflect different patterns of clinical disease in different risk groups.

Possible exposures to co-factors (e.g., infectious agents, and therapeutic or recreational drugs) and routes of infection vary by risk group and may contribute to the inconsistency of findings among studies. Response to treatment and prophylaxis for AIDS-related conditions could also be genetically determined.

Likely mechanisms mediating the effects of chemokine/co-receptor polymorphisms include genetically-mediated alterations in expression levels and/or protein structures of chemokines/co-receptors. The paradigm that expression levels of CCR5 profoundly influence HIV infection is now well established. In part, control of CCR5 expression may be genetically mediated. Because there is substantial overlap in CCR5 expression (Wu et al., 1997; Trkola et al., 1996; Paxton et al., 1998), polymorphisms in the regulatory region that modulate gene expression are likely to influence HIV infection. It should be noted that there is strong precedence linking genetic variation in the cis-regulatory regions and pathogenesis of infectious diseases, including one form of genetic resistance to malaria that is mediated by a mutation in the GATA site of the chemokine receptor DARC (Tournamille et al., 1995).

CC chemokine binding to co-receptors can essentially mediate the same effect as genetic mutations in CCR5. That is, receptor down-modulation via ligand-induced endocytosis or interference with a post-binding fusion step may contribute to the inhibition of viral replication by blocking the virus fusion and entry (Cocchi et al., 1995; Amara et al., 1997; Oravecz et al., 1996; Malnati et al., 1997; Furci et al., 1998; Furci et al., 1997). There are several studies that lend credence to the notion that vigorous production of suppressive CC-chemokines may help in controlling disease progression (Zagury et al., 1998). However, in contrast to the inhibitory effects of CC chemokines in T cells found by Cocchi et al. (1995), other groups have found that MIP-1α, MIP-1β, and RANTES fail to inhibit and even enhance in vitro replication of primary HIV strains in macrophages (Moriuchi et al., 1996; Schmidtmayerova et al., 1996), emphasizing that additional research is needed to clarify the in vivo role of CC chemokines in susceptibility to HIV infection.

Nevertheless, given the established importance of CCR5, and a potentially important role of its ligands in HIV pathogenesis, the following scenario may be operative: in response to HIV antigens, CD4+ effector T cells release anti-viral levels of chemokines at the site of virus production. This release not only protects local target cells, but also protects activated effector cells by inducing down-regulation of CCR5. The induction of this response may produce an asymptomatic state for some period. However, a more broader/robust response may lead to non-progression or, in some cases, protection from infection. Conversely, a weaker response may lead to an accelerated course. Thus, genetic mutations in MIP-1α, MIP-1β, and RANTES may result in either high or low CC chemokine responses. Mutations regulating differences in chemokine levels may act in concert with genetic mutations in CCR5 or other chemokine/co-receptor genes to modulate infection.

HIV evolves during the course of infection to use an expanded repertoire of co-receptors for infection, and this adaptation is associated with progression to AIDS (Connor et al., 1997; Glushakova et al., 1998; Scarlatti et al., 1997). The factors that favor the evolution of HIV-1 towards CXCR4 usage may involve polymorphisms in CCR5 or its ligands, which are known to possess potent anti-HIV properties.

B. Results

1. Nature of the Ancestral CCR5 Allele

A limitation of previous attempts to understand the evolution of human CCR5 alleles has been a lack of an appropriate outgroup to root the ancestral CCR5 haplotype (McDermott et al., 1998). The present studies define the ancestral CCR5 haplotype relative to four important events in human evolution: the divergence of humans from great apes, orangutans, Old and New World monkeys. The region corresponding to human CCR5 +1 to +927 was cloned and sequenced from a total of 45 non-human primates (apes (Chimpanzee, Gorilla, Orangutan, gibbon), and selected species within Old and New World Monkeys). Additional non-human primates (including 20 chimpanzees) were genotyped for polymorphisms corresponding to human CCR5 +29, +208, +627, +927 and Δ32.

All Old World Monkeys (one exception), and all Greater and Lesser apes examined had a CCR5 genotype characterized by 29A, 208G, 303G, 627T, 630C, 676A, 927C and wild-type CCR5 ORF, suggesting strongly that this is the genotype for the ancestral CCR5 allele. Interestingly, this ancestral CCR5 haplotype in man in not associated with alterations in HIV disease progression. In contrast to previous assertions, it is unlikely that CCR5 +303A represents an allele ancestral to CCR5 +303G (McDermott et al., 1998).

2. Structure of the Genetic Variability at Human CCR5

A limitation of previous attempts to understand CCR5 evolution has been the reliance on incomplete data on sequence variation, and failure to integrate genotypic data into an evolutionary context. Complete sequencing offers the ultimate level of resolution of differences among CCR5 haplotypes. A total of 54 CCR5 alleles were sequenced, in part, from Caucasian and African-American individuals that were homozygous for at least one of two variable sites in the cis-regulatory region of CCR5 (i.e., CCR5 +29 or CCR5 +927).

The genetic variability at CCR5 was found to be more complex than currently appreciated. A total of 34 variable sites in the cis-regulatory region (+1 to +927) of CCR5 defined 26 unique human haplotypes. The amount of sequence variation found among these 26 haplotypes is considerably more than has been previously appreciated in ad hoc surveys of HIV-1 cohorts (Martin et al., 1998; McDermott et al., 1998). Moreover, the ascertainment bias introduced by sampling from individuals homozygous at a given single nucleotide polymorphism (SNP) suggests that the amount of variation observed among these sequences is a conservative estimate of the total genetic variation at this locus. Nevertheless, these data suggest that identification of a variant site or combination of sites, that directly influence the risk of disease progression within and among human populations could be more challenging than is currently acknowledged.

CCR5 haplotypes are organized into at least 5 separate haplogroups. Sequence data from the cis-regulatory region of the 26 unique CCR5 haplotypes were used to construct a phylogenetic network depicting the evolutionary relationships among each allele. The network was rooted with a chimpanzee haplotype that represents the ancestral state for all nucleotides in the human sequences. Virtually identical networks were obtained using neighbor-joining, parsimony, and maximum likelihood methods. Phylogenetic analysis clearly separates the 26 unique CCR5 haplotypes into distinct clusters that were categorized into 5 separate human haplogroups (CCR5-HHA through CCR5-HHE). Previously described CCR5 SNPs/polymorphisms were labeled on the branches delimiting the major clusters of this network. Each haplogroup is delimited by at least one SNP. Thus, a CCR5 haplogroup is an aggregate of several distinct haplotypes that share a common ancestry. Hence, each haplotype within a haplogroup is characterized by the constellation of polymorphisms but differ from each other by additional SNPs. For example, the CCR2-64I mutation is found only on a subset of haplotypes in haplogroup D (designated as HHD*2) while the distribution of CCR5 haplotypes on which the CCR5-Δ32 mutation occurred is even more restricted. All else being equal, this suggests that the CCR2-64I mutation predated the CCR5-Δ32 mutation.

There is a distinct racial distribution of the different CCR5 haplogroups. Using PCR-RFLP and molecular beacon technology, the entire WHMC cohort (1158 individuals) was genotyped for positions CCR2-64I, CCR5 +29, +208, +627, +927 and CCR5-Δ32. Based on this genotypic data, 39 different genotypes were identified. Of these, 18 genotypes were present in at least 10 or more individuals, and represented 92% of the entire cohort. Using this genotypic data and the haplotype tree, the two haplotypes associated with each individual were assigned. The CCR5 haplogroups are widely distributed in all human populations at appreciable frequencies (i.e., they are common variant sites). Haplogroup A is defined by the ancestral CCR5 haplotypes and is found at substantially higher frequencies in African-Americans (0.22). Haplotypes in haplogroup B are the most common alleles in African-Americans (0.28) and Caucasians (0.36). Haplotypes in haplogroups C, D, and E are found at varying frequencies in African-Americans (0.18, 0.19, and 0.05) and Caucasians (0.33, 0.09, and 0.11). Among 1199 HIV-1 uninfected individuals from Africa, Asia, and Europe, the prevalence of HHA haplotypes was highest in individuals of African descent ($\geq 0.22$), reaching its maximum in Mbuti and Biaka pygmies (0.71).

In contrast to recent reports, the number of CCR5 haplotypes is substantially more than ten (Martin et al., 1998). The recently reported P1 allele (Martin et al., 1998) that was shown to be associated with accelerated disease progression is a composite of CCR5 haplogroups -C, -D, and -E (minus those that have CCR2-64I and CCR5-Δ32). Similarly, the CCR5 +303A allele associated with accelerated disease progression is also a composite of at least three haplogroups (McDermott et al., 1998).

The inventors have organized the complex patterns of CCR5 SNPs/polymorphisms into biologically and evolutionarily meaningful relationships that are used to develop an appropriate nomenclature of CCR5 haplotypes for disease association studies. This is not a trivial issue, especially when one considers the world-wide interest in defining the role of CCR5 polymorphisms in HIV disease pathogenesis, and the potential for confusion without an appropriate CCR5 nomenclature for these association studies. By comparing the distribution of CCR5 haplotypes in uninfected and infected HIV-1 individuals from the U.S. and relevant world-wide populations, haplotypes or haplotype combinations associated with resistance to infection are identified. This approach provides important information regarding the genetic determinants of HIV-1 pathogenesis.

3. Influence of Genetic Variation of CCR5 on HIV Disease Progression

The phylogenetic network of CCR5 haplotypes provides the biological framework for defining the relationships between CCR5 alleles and HIV pathogenesis. The end points analyzed were AIDS (1987 definition) and death. The groups analyzed were the seroconverting group and a group including both seroconverters and seroincident cases. The outcome for the entire cohort was examined, and the outcomes were then stratified by race (African Americans and Caucasians). The statistical approaches are as described herein (Example 4).

There are no previously reported data regarding the HIV disease modifying effects of CCR5 haplogroups CCR5-HHA, -HHB or -HHC. The CCR5-HHB haplogroup is delimited by CCR5 +208T. Presence of this haplotype (homozygous or heterozygous state) is associated with a strong disease-accelerating effect in African Americans but not Caucasians. The effect for homozygosity is more pronounced, with rapid acceleration to AIDS and death in African Americans. The CCR5-HHC haplogroup is delimited by CCR5 +303A and +627C. Homozygosity for this haplogroup is associated with slight disease acceleration in Caucasians, but not African Americans. An allele designated as P1 (Martin et al., 1998) that is a composite of CCR5-HHC, -HHD, and -E (excluding CCR2-64I and CCR5-Δ32) was also shown to also have a weak deleterious effect in Caucasians. CCR5 +927T-bearing individuals (CCR5-HHD) who lack the CCR2-64I allele have an accelerated disease course.

The CCR5-HHD haplotype is delimited by the CCR5 +927T polymorphism with or without linkage to CCR2-64I. Presence of this haplotype (as a whole) in this cohort is associated with disease-retardation, however the effects are demonstrable only in African-Americans, not in Caucasians. This protective effect, based on statistical analysis, is due to the dominant effect of CCR2-64I. In fact, when adjusted for the protective effects of CCR2-64I, the CCR5 +927T allele is associated with disease acceleration. Thus, the effect of CCR2-64I may be independent of its linkage to CCR5 +927T and may be due to linkage to some other as yet unknown polymorphism in CCR5. The results of these studies and others (Michael et al., 1997a; Rizzardi et al., 1998; Hendel et al., 1998; Eugen-Olsen et al., 1998) are in contrast to other studies that have reported a protective effect of the CCR2-64I allele in Caucasians (Smith et al., 1997; Kostrikis et al., 1998; van Rij et al., 1998). In the one cohort that contains a large number of African Americans (ALIVE), the follow-up may not have been long enough to demonstrate an effect of this allele (Smith et al., 1997). However, a recent report found that the CCR2-64I allele was associated with delayed AIDS progression in African women (Anzala et al., 1998).

The CCR5-HHE haplotype is delimited by the CCR5 +29G polymorphism with or without linkage to CCR5-Δ32. This haplotype is associated with weak disease retardation, however, the effects are only demonstrable in Caucasians, not in African Americans. The Δ32 allele is also associated with a delay in disease progression.

In the entire cohort, HHA haplotypes (combining +/+ and +/−) were associated with a delay in progression to AIDS (adjusted for the protective effects of CCR2-64I and CCR5-Δ32 bearing haplotypes, P=0.04; RH=0.77; CI=0.60-0.99) and death (adjusted P=0.04; RH=0.79; CI=0.62-0.99). This association was demonstrable in African Americans, but not Caucasians (for AIDS, adjusted for CCR2-64I, P=0.71; for death, adjusted P=0.94).

These findings suggest that HHA haplotypes in African Americans are associated with disease retardation, and that this association is independent of the effect of the CCR2-64I alleles (HHD*2). However, the finding did not exclude the possibility of an additive and/or interactive effect between HHA and HHD*2 (CCR2-64I) haplotypes. Thus, the African American and Caucasian patients were stratified into 4 groups, with each group composed of a different pair-wise haplotype combination. For African Americans, the three groups that contain an HHA and/or HHD*2 haplotype were each associated with a delay in progression to AIDS and death, with the combination of HHA and HHD*2 providing the greatest advantage. In Caucasians there are no demonstrable differences between various combinations of these two.

These CCR5-HIV association studies demonstrate a powerful influence of different CCR5 haplotypes in disease progression. Both disease-accelerating (CCR-5-HHB, CCR5-HHC, CCR5 +927T/CCR2-64V) as well as disease-retarding (CCR5-HHA; +927C/CCR2-64I (HHD*2); CCR5-HHE) haplotypes were identified, and the effects of these haplotypes were shown to be race-specific. Thus, these studies extend significantly the paradigm of race-specificity for the disease-modifying effects of CCR5 haplotypes.

4. Genetic Variability of Chemokines and HIV Disease Pathogenesis

The host response to HIV is likely to be polygenic, and analogous to the significant influence of genetic variation in CCR5 regulatory regions, polymorphisms in the regulatory regions (or other regions) of chemokines may also be associated with alterations in the rate of HIV disease progression or transmission. Given the importance of CCR5 and CXCR4 and their associated ligands in HIV pathogenesis, these studies first defined the extent of genetic variability in MIP-1α, MIP-1β and RANTES, and then determined the influence of this variability on HIV transmission and disease progression.

As described herein below, a polymorphism in the 3'-UTR of SDF is associated with accelerated disease progression. To determine the presence of polymorphisms in the regulatory regions of RANTES, bulk sequencing was employed. 458-bp of the RANTES promoter was cloned and sequenced from >24 individuals. Differences among these sequences, and also between these sequences and previously published sequences (Nelson et al., 1993; Moriuchi et al., 1997) were found. There were two polymorphisms (at −28 and at −401), and two insertions. The insertions are likely to be sequencing errors in the published sequences.

The genes for MIP-1α and MIP-1β have been previously cloned and sequenced (Hirashima et al., 1992; Nomiyama et al., 1993; Nakao et al., 1990). There is a high degree of sequence homology between these two genes. Gene-specific primers were designed to PCR amplify MIP-1α and MIP-1β. Using these primers, the coding and non-coding regions of these two genes were PCR amplified and sequenced. By bulk sequencing (from several individuals) polymorphisms in the genes for MIP-1β and MIP-1β were identified. One allele that includes non-coding polymorphisms in the gene for MIP-1α is associated with genetic resistance to HIV-1, i.e., it is a HIV-1 resistance factor. Possession of even a single allele is associated with protection, i.e., homozygosity, is not essential for protection.

Molecular beacon technology to detect polymorphisms was according to published protocols (Tyagi et al., 1998; Kostrikis et al., 1998; Piatek et al., 1998; Tyagi and Kramer, 1996). Time-to-event statistical issues and other pertinent analyses were performed according to published protocols (Dolan et al., 1993; 1995). In large part, the methods utilizing molecular tools for HLA-typing use commercially available reagents/kits, and it is relatively easy to do large numbers of samples in a high-through-put fashion. The technique is based on PCR amplification with sequence-specific primers and subsequent hybridization with sequence-specific oligonucleotide probes (PCR-SSOP; (Bozon et al., 1996). In brief, using locus-specific primers, different regions of short arm of chromosome 6 (HLA loci) arc PCR amplified in 100 µl reactions. After confirming the fidelity of the PCR reaction, 5 µl of the amplicon is dot-blotted to a positively charged nylon membrane using a multi-channel pipettor. The membranes are air-dried, denatured, cross-linked, and then hybridized with alkaline phosphatase-labeled oligonucleotide probes (LifeCodes). Non-specific hybridization is removed by pre-washing the membranes with TMAC followed by treatment with Lumiphos 480 (Life Codes, Stamford, Conn.), and then exposed to x-ray film. Using a DOT scan computer program (Life Codes), the hybridizing signals are coded by the program and allele(s) assigned. Based on the hybridizing patterns, the computer program resolves homozygosity or heterozygosity. The hybridization is performed in two steps. In the first step, oligonucleotide probes that resolve the haplotypes at low resolution are used. The results obtained at this point are generally comparable to that reported previously by serological methods. For higher resolution of the alleles, another round of hybridization is performed using locus-specific oligonucleotides.

5. CCR5 Haplotypes that Influence HIV-1 Transmission and Disease Progression

The genetic basis of inter-individual and inter-population variation in HIV transmission and disease progression is poorly understood. Since CCR5 is the first portal for HIV entry it is expected that genetic polymorphisms in CCR5 may produce different phenotypes at the functional level (e.g., surface expression) and the biological level (e.g., differences in transmission of HIV or disease progression). Thus, the inventors reasoned that there is a correlation between CCR5 haplotypes and HIV transmission and disease progression. Therefore, the evolutionary history of genetic variation at the CCR5 locus in HIV seropositive and seronegative cohorts was defined, and appropriate statistical approaches were used to determine the influence of different CCR5 haplotypes on HIV transmission and disease progression.

Since not all polymorphisms in CCR5 affect the function of CCR5, it is important to identify the specific genetic variants that do affect CCR5 function and be able to distinguish the relative importance of their effects. In other words, polymorphisms at a particular locus (e.g., CCR5) do not necessarily represent independent disease-altering genetic variants. Rather, combinations of specific polymorphisms may be in linkage disequilibrium with each other contingent on the evolutionary history of the locus and the demographic history of the population that is being sampled. Failure to consider either the evolutionary history of a haplotype or the demographic history of a population will lessen the power of genotype-phenotype associations. For example, individuals in disease cohorts that have been defined by the presence or absence of a single SNP may be composed of subsets of different haplotypes. Since the haplotype defines the biologically active unit of the locus, conflating/fusing different haplotypes into a single haplotype reduces the power of detecting a significant association (Martin et al., 1998; McDermott et al., 1998). Thus, understanding the complex relationships among different polymorphisms in the coding and non-coding regions of CCR5 is a prerequisite to determining the definitive relationships between CCR5 haplotypes and HIV transmission and disease progression.

By understanding that the complex relationships between genotypic variation in CCR5 and HIV susceptibility, the understanding of HIV pathogenesis is greatly increased. Because of the powerful influence that genetic variation at CCR5 may have on HIV susceptibility, this information is important for evaluating effective AIDS management strategies, especially in non-Caucasian populations. Biologically relevant stratification of uninfected and disease cohorts used for the evaluation of preventive, and treatment strategies, respectively, requires knowledge of the underlying genetic basis of the variation in host response to HIV. Indeed, polymorphisms in the CCR5 are likely to become important variables of a biologically-based stratification system. Without this stratification, favorable host responses to prevention and intervention strategies may be over-looked.

All CCR5 haplotypes are related to each other and the observed genetic variation among CCR5 haplotypes has been produced by a combination of mutation and recombination. Phylogenetic and population genetic methods provide the analytical tools necessary to reconstruct the evolutionary history of CCR5 alleles and allow a better understanding of the relationships between different CCR5 haplotypes and the forces that have distributed them to varying frequencies among different human populations.

Different CCR5 haplotypes may be associated with the same disease phenotype. In other words, different adaptive molecular strategies may have been exploited by components of the human immune repertoire to defend against HIV or similar viral pathogens. This process is called evolutionary convergence. CCR5 alleles that have converged toward a similar strategy to impede or block HIV transmission and/or disease progression may reveal important targets against which interventional strategies could be developed.

The magnitude of association between CCR5 haplotypes and disease phenotype may vary substantially. Some CCR5 haplotypes may have strong disease-modifying effects while other haplotypes may have only modest effects. The combined effects of two haplotypes produce the phenotype of each individual. The effects of these haplotypes may be independent (additive) or there may be an additional epistatic effect (interactive). Such effects can only be critically investigated if the evolutionary relationships between different CCR5 haplotypes are known clearly.

By using a unique cohort of HIV seropositive individuals, this multi-disciplinary approach advances significantly the current working paradigms related to the influence of polymorphisms in CCR5 and HIV-1 transmission and disease progression. This phylogenetic approach to understanding the influence of different CCR5 haplogroups in HIV-1 pathogenesis is efficient because it circumvents the need to sequence each allele in the HIV cohort (1158 individuals=2316 alleles).

6. CCR5 Haplotype Analysis

Cohorts broadly labeled as HIV seropositive and seronegative are studied. The HIV seropositive cohort is the Wilford Hall Medical Center cohort whose unique epidemiological features are extensively reviewed herein. The HIV seronegative cohort comprises ~600 Caucasians and ~400 African-Americans. Most of these DNA samples were collected from normal donors (no-identifiers except for race and sex). The limitation of this seronegative cohort is that the HIV status has not been documented. However, based on the ascertainment history there is an overriding likelihood that the vast majority of the samples are HIV seronegative. Since most of the samples at WHMC are likely to have been prescreened for HIV (before entry into the U.S. Air Force), the vast majority of these individuals will likely be HIV seronegative.

The major CCR5 haplogroups are delimited based upon polymorphisms ascertained by sequence analysis of the region extending from CCR5 +1 and +927. In preliminary studies, five major haplogroups were defined, however, there is evidence to suggest that there may be additional CCR5 haplogroups (see additional Examples herein). For example, CCR5 haplogroup B may represent a single haplogroup or it may be composed of two distinct haplogroups (based on additional mutations at CCR5 +630 or +676) that may display different HIV-related phenotypes. This is important considering that the haplotype B is associated with accelerated disease progression in African-Americans but not in Caucasians.

The genetic survey of CCR5 is extended by additional bulk DNA sequencing and multiple single-marker analysis (by PCR-RFLP and molecular beacon strategy). The entire WHMC cohort for is genotyped for CCR5-630 (C/T) and CCR5-676 (A/G). The seronegative cohort is genotyped for CCR2-64I, CCR5 +29, +208, +627, +630, +676, +927, and Δ32. This genotypic information is required to determine the influence of CCR5 haplotypes on HIV transmission.

The expectation-maximization algorithm is utilized to estimate CCR5 haplotypes from phase-unknown (family data are rarely available from individuals in disease and ethnic cohorts) genotypic data collected from disease and seronegative cohorts. Subsequently, the CCR5 haplotypes defined by sequencing are used to reconstruct a CCR5 haplotype phylogeny. This CCR5 haplotype tree is used as a tool to assign each individual's haplotype combination, understand further the derivation of CCR5 haplotypes (e.g., the identification of haplotypes that have been generated by recombination may be easier to recognize), test the evolutionary significance of CCR5 haplotypes that are unevenly distributed among different racial groups, and identify those mutations that are associated with differences in HIV transmission or disease.

7. Influence of CCR5 Haplotypes in HIV Transmission and Disease Course

To verify that specific CCR5 haplotypes determine, in part, the risk of HIV infection, it is determined if specific haplotypes in the HIV cohort are under-represented (decreased transmission), equally-represented (non-protective) or over-represented (increased transmission). A detailed analysis of the haplotypes in the WHMC and non-HIV cohort reveals specific haplotypes that play a role in transmission. This is consistent with the significant role that CCR5 plays in HIV entry and given the precedent that homozygosity for the CCR5-Δ32 containing haplotype results in increased resistance to HIV infection. Despite this finding, the mechanisms of resistance in many high-risk populations remain unknown. For example, it remains unclear why many of the sex-workers of Nairobi remain uninfected despite high-risk practices (Fowke et al., 1996). Although they are known to have intact CCR5 ORFs, it remains unknown whether they have polymorphisms in the cis-regulatory region of CCR5 that may afford protection.

8. CCR5 Determinants of HIV Progression

The statistical approaches to determine the association between disease progression (AIDS 1987 criteria and death) and specific haplotypes are illustrated herein. The additive effects of and/or interaction between different haplotypes are determined. Prognostic modeling that takes into consideration genotypic, immunological (e.g., CD4), and viral (e.g., viral load) is also performed.

An overriding concern of any association study is the uncertainty of whether the association between a gene variant and disease is a direct causal relationship, or that the variant is merely a marker for an as yet unidentified molecular variant. The present approach of integrating extensive sequencing and genotyping data into an evolutionary context minimizes these concerns. In order to test the effects of specific mutations or sequence motifs on the HIV-related phenotypes of transmission or progression, the ideal control population is one that has an identical haplotype background except for the polymorphism to be tested. Such control populations can only be identified if the evolutionary relationships among CCR5 haplotypes are understood. In other words, the simple presence or absence of a specific CCR5 polymorphism may provide little information about how closely related are two CCR5 haplotypes. This problem confounds virtually all association studies of others completed to date.

9. CCR5 Haplotypes Responsible for Differential Racial Susceptibility to HIV-1 Infection There is an increasing appreciation of inter-population heterogeneity in infectious disease resistance or susceptibility alleles (Hill, 1992a; 1996; 1998; Bellamy and Hill, 1998; Hill et al., 1994; 1997; McGuire et al., 1994; Abel and Dessein, 1997). At least some of the genetic correlates of HIV transmission and disease progression are likely to be more pronounced in different racial groups. Some of these genetic determinants may be deleterious in a given environment, although of selective advantage in different environments. The search for these determinants is of high priority in a public health setting to develop molecular markers to identify those at risk, novel approaches to anti-HIV strategies, and tools for balanced stratification in cohort studies analyzing these strategies. Of note, current studies evaluating vaccine or therapeutic efficiencies do not take into consideration the powerful influence that genetic variation at CCR5 may have on HIV transmission or progression.

The present studies show that there are race-specific CCR5 genetic correlates of HIV susceptibility and progression. The basis for this can be understood by placing genetic variation at CCR5 in the context of human evolution. It is likely that infectious diseases have been important selective forces during human evolution. Host-parasite interactions are an attractive explanation for the existence of genetic polymorphisms in populations because they are ubiquitous and may exert strong selection pressures. In Europeans, tuberculosis has been a major selective force. In Africans, malaria was a major selective force, and has led to striking differences in the prevalence of some malaria-resistance alleles in different populations (Hill, 1992b; 1998; Weatherall et al., 1997; Weatherall, 1996a; 1996b; Bellamy and Hill, 1998; Hill et al., 1994; 1997; Hill, 1996; McGuire et al., 1994). By analogy, evolutionary forces acting on CCR5 may have generated genetic differences among Africans and Caucasians. Identification of these race/population-specific genetic correlates, and the evolutionary forces responsible for these patterns, enables tailored strategies for disease prevention and treatment to specific racial groups. One example is the striking difference in the distribution of CCR5 HHA haplotypes in pygmy and non-pygmy African populations and difference in prevalence of HIV-1 in these two populations.

The present studies present evidence that CCR5 alleles exhibit race specific disease-modifying effects. The CCR5-Δ32 allele is found primarily in Caucasians and homozygosity provides strong protection against HIV transmission, whereas heterozygosity, in some cohorts is associated with a delay in disease progression. The studies detailed herein above have shown that the CCR2-64I polymorphism is associated with disease retardation in African-Americans but not Caucasians, CCR5 haplogroup B is associated with accelerated progression to AIDS and death in African-Americans but not Caucasians, and CCR5 haplogroup C is associated with accelerated disease course in Caucasians but not African-Americans. Therefore, these studies define the genetic basis for the differential race-specific disease susceptibility associated with the CCR2-64I allele, CCR5 haplogroup B, and CCR5 haplogroup C. Given the results described above regarding the protective effects associated with HHA as well as the high allele frequency in African pygmies, differences in the genetic determinants in HHA from African-American, pygmy and non-pygmy Africans, and Caucasians is also determined.

The hallmark feature of genetic variation at CCR5 is linkage disequilibrium. This feature can be exploited to dissect the genetic determinants that account for the differential effects of CCR2-64I, and the CCR5-B and -C haplogroups. The DNA sequence spanning CCR2 to CCR5 is known (~8 kb; GenBank accession number U95626). This long stretch of DNA is scanned to identify the race-specific polymorphisms that are in linkage disequilibrium to CCR2-64I, and CCR5-B and -C haplogroups. The genomic DNA from individuals of African-American and Caucasian ancestry who are homozygous for the markers that delimit these three haplotypes/haplogroups are used to identify race-specific polymorphisms and/or sequence motifs. Six to eight individuals (3-4 African-American; 3-4 Caucasians) are sequenced from each of these four groups (total ~18-24). In addition, individuals from different racial groups that are homozygous for markers that delimit the CCR5-A, and -E haplogroups are sequenced (total ~12-18). Since the haplotype tree described above created by genotypic data is based on only ~1 kb of sequence, this sequencing strategy allows for the generation of an "extended" CCR2/CCR5 haplotype tree. This tree allows for the further definition of the CCR5 haplotypes associated with altered rates of disease progression/transmission in specific racial groups.

By sequencing the ~3 kb region upstream of CCR5 ORF, some of the patterns of complex linkage disequilibrium among CCR5 polymorphisms were resolved, and identified that the CCR5 +927T polymorphism is in linkage disequilibrium with CCR2-64I. By extensive genotyping for CCR5 +927T, CCR5 +927T-bearing individuals who lacked the CCR2-64I polymorphism were identified; individuals with this extended haplotype (CCR2-64V/CCR5+927T) had an accelerated disease course. Additionally, it was determined that the CCR5-Δ32 is in linkage disequilibrium with the CCR5 +29G mutation. By genotyping for CCR5 +29G it was shown that there are a significant number of individuals with CCR5 +29G that lacked the CCR5-Δ32 mutation, and that this 29G polymorphism was associated with a delay in disease progression. Based on the success of this approach to identifying CCR5 variants in this ~1 kb region that are associated with disease-modification, by determining the "extended" CCR2/CCR5 haplotypes, race-specific haplotypes associated with disease-modifications are defined.

CCR5 sequence-specific sense- and anti-sense primer pairs that span overlapping ~1.5 kb regions are designed. Using these primer pairs the region between CCR2 and CCR5 was PCR amplified and sequenced. Since the region is ~8 kb it requires approximately 10 PCR reactions to scan this region. Using CCR5-specific primers, these overlapping PCR amplicons are sequenced using automated double-stranded sequencing. The individual sequences are aligned and examined for the presence or absence of polymorphisms. PCR-RFLPs or molecular beacons are designed to identify the mutations that are haplotype and/or race specific. The HIV+ and HIV- cohorts are scanned to identify the prevalence of the haplotypes as well as the racial specificity of these markers. The aforementioned genotype/haplotype data is used in association studies to determine if there is a significant relationship between these markers and altered rates of HIV transmission and/or disease progression. Evidence of long-range control of gene activities is becoming increasingly common. For example, one of the key regulatory regions of the globin gene resides several kb upstream of its traditional promoter region (Versaw et al., 1998; Dillon et al., 1997).

A complementary approach to identifying race-specific markers takes advantage of a group of highly polymorphic markers that are tightly linked to CCR2 and CCR5. These are called microsatellites and consist of tandemly repeated arrays of one-to-six nucleotides (Csink and Henikoff, 1998; Jorde et al., 1998; Schlotterer, 1998; Goldstein and Pollock, 1997; Freimer and Slatkin, 1996). Microsatellite markers are currently an important tool for most genetic mapping studies and for studies of the evolution of human populations. The majority of the microsatellite mutational changes likely occur via the insertion or deletion of one or more repeat units by a process called replication slippage. These microsatellite markers can be in strong linkage disequilibrium with flanking sequences including genes and other microsatellite markers. There are several microsatellite loci that are tightly linked to CCR2 and CCR5 and can be used to further explore the genetic diversity of extended haplotypes (Libert et al., 1998; Stephens et al., 1998). For example, by genotyping a microsatellite locus tightly linked to CCR2/CCR5, the inventors have demonstrated that the same CCR2/CCR5 haplotype may be associated with different microsatellite alleles. At least one of these alleles is in strong linkage disequilibrium with the CCR5 +29G and CCR5-Δ32 polymorphism. These findings are consistent with the data of Libert et al. who examined the CCR5 loci in a non-infected cohort of Europeans (Libert et al., 1998) and found that these microsatellite alleles could differentiate at least 13 different alleles. Because the variation at each microsatellite locus is very high (and thus these markers are very informative for resolving relationships among human populations), an alternative strategy of finding race-specific haplotypes is to sequence the specific CCR2/CCR5-microsatellite haplotypes whose distribution is limited to African-Americans or Caucasians.

10. Influence of Genetic Variability in CC Chemokines and MHC Genes on HIV-1 Pathogenesis The inventors gained insights on the number of resistance/susceptibility genes that influence HIV pathogenesis from previous studies on malarial disease and human genetic variation. The genetic basis of inter-individual variation in susceptibility to malaria is determined by alleles at many different loci (Hill, 1998; Weatherall et al., 1997; Weatherall, 1996a; 1996b; Hill, 1992b). Thus, the inventors reasoned that susceptibility to HIV infection is likely to be determined by alleles at many different loci. Indeed, it is likely that since neither genes nor pathogens are found in isolation from other genes or pathogens, that the balance between different variants of the human immune system and various pathogens is maintained by many different loci whose products interact with one another. For example, the studies detailed herein, a polymorphism in SDF was shown to be associated with accelerated disease progression. Thus, identification of chemokine system gene loci other than CCR5 and SDF that influence HIV pathogenesis provides important insights into disease mechanisms and may suggest new approaches for prophylactic or therapeutic interventions in HIV. Therefore, focused studies that dissect the polygenic nature of variable HIV susceptibility in humans are conducted, and mechanisms that mediate the resistance to HIV-1 transmission associated with a chromosome 17q allele that includes polymorphism in MIP-1α are identified.

Both MHC and non-MHC genes are likely to be important in the immune response to HIV infection. There are several candidate non-MHC genes for infectious disease resistance and susceptibility, many of which have documented functional polymorphisms (Hill, 1998; Hill, 1992b; Fernandez-Reyes et al., 1997). It is likely that among these genes, several may play a role in HIV pathogenesis. However, a prerequisite to understanding the combined effects of different genes is to determine the effect of each gene independently.

11. Role of Polymorphisms in CC Chemokine Genes in HIV Pathogenesis

High production levels of MIP-1α, MIP-1β and RANTES in response to HIV infection have been postulated to be important immunological defenses against this pathogen (Garzino-Demo et al., 1998; Paxton et al., 1998; Cocchi et al., 1995; Oravecz et al., 1996; Zagury et al., 1998; Garzino-Demo et al., 1998; Paxton and Koup, 1997; Paxton et al., 1996a; 1996b; Paxton et al., 1998). For example, Paxton et al. observed that CD8-depleted (CD4+) PBMC from highly exposed uninfected individuals were less susceptible to infection with primary HIV-1 than PBMCs from non-exposed controls, and that this resistance was associated with an increased production of CC chemokines MIP-1α, MIP-1β and RANTES by these cells (Paxton et al., 1996a). In another recent study of 14 seronegative hemophiliacs highly exposed to HIV-1, Zugary et al. showed that these individuals lacked the CCR5-Δ32 mutation but that in most of them there was an overproduction of the CCR5 ligands (Zagury et al., 1998). Analogous to the variation in CCR5 expression levels, variation in the level of production of CC chemokines could, in part, be genetically-mediated. It is for this reason that the influence of mutations in these genes on HIV transmission and progression were determined. Importantly, a polymorphism associated with reduced risk in disease transmission was identified.

MIP-1α, MIP-1β and RANTES are closely linked genes on chromosome 17q21.1-q21.3 (Hirashima et al., 1992) and therefore, it is likely that polymorphisms in one of these chemokine genes will be in linkage disequilibrium with those in another CC chemokine gene. Hence, the important caveats regarding linkage disequilibrium in CCR5 and HIV disease association studies also apply to these polymorphic chemokine loci. Thus, the phylogenetic strategy outlined for CCR5 is adopted to dissect the genetic variability in these three chemokines, and then the influence of this variability in HIV pathogenesis is determined.

Several novel polymorphisms in CC chemokines were identified by bulk sequencing. This work is extended by additional bulk sequencing of the coding and non-coding regions of the RANTES, MIP-1α and MIP-1β. This is important since several key cis-acting elements reside further upstream (Nelson et al., 1993; Moriuchi et al., 1997), and considering the powerful anti-HIV properties of high levels of these chemokines, it is important to identify the complete repertoire of mutations that are associated with alterations in disease progression. Some of these mutations may reside in critical promoter regions. In addition, the coding region of MIP-1α, MIP-1β and RANTES are sequenced from individuals who carry the protective haplotype already identified by the inventors.

Genotyping is performed using PCR-RFLP and molecular beacon techniques. Analysis of the ~500 bp of genomic DNA sequence upstream of the RANTES ORF identified two polymorphisms (i.e., −28 and −401). The polymorphisms in RANTES do not create or destroy a naturally-occurring restriction enzyme site. A PCR-RFLP was designed by introducing a single bp change in the PCR primer that spans these mutations, and these mutations were scanned in the WHMC cohort. To determine the role, if any of these polymorphisms in transmission, the prevalence of these polymorphisms are determined in the seronegative cohort and compared to the prevalence in the HIV cohort. The relationship of these RANTES polymorphisms to those in MIP-1α and MIP-1β is determined.

The prevalence of different haplotypes in the HIV-1 seronegative and seropositive cohorts are compared. Survival analyses (with AIDS and death endpoints) are conducted. Appropriate adjustments for the HIV-1 disease-modifying effects of the CCR5 haplotypes are also made.

12. The Protective MIP-1α Allele Mediates Resistance to HIV-1 Infection

Mechanism(s) that may account for the reduction in transmission risk associated with the protective MIP-1α allele are determined. Nucleotide substitutions in the regulatory regions of MIP-1α, MIP-1β or RANTES could result in enhanced or reduced transcriptional activity, and hence differences in protein expression levels. Consequently, these differences in expression levels could affect expression levels of HIV-1 co-receptors such as CCR5 and in turn, profoundly influencing HIV transmission and progression. PBMCs from normal individuals known to be homozygous or heterozygous for the protective allele are studied for the parameters listed below. As a control, samples from individuals known to lack this allele are studied.

In brief, flat-bottomed 96-well plates triplicate wells of 200 μl of $1.5\times10^6$ cell/ml ($3\times10^5$ PBMCs/well) are stimulated with medium alone or with PHA-M (Sigma) in RPMI supplemented with 2.5% human AB serum (ABS) (Sigma). Levels of MIP-1α, MIP-1β, and RANTES in culture supernatants are determined by ELISA (kits from R & D) after 48 hours as per manufacturers instructions.

CCR5 and CXCR4 expression levels are determined by FACS as described in Example 4. Variation in CCR5 expression levels on fresh versus frozen samples derived from the same donor varied less than 5-10% and that the levels of CCR5 expression in individuals with or without the CCR2-64I polymorphism were similar (Example 4). CCR5 expression levels are determined on various leukocyte subsets (e.g., CD4+ and CD8+ cells).

The PHA-activated PBMCs derived from individuals who possess or lack the protective MIP-1α allele are infected with three log dilutions of the following viruses: R4 (T-tropic), dual-tropic and R5 (M-tropic) strains. Supernatants are harvested on days 0, 4, 8, 12, and 16 post-infection for determination of p24 antigen levels. The role of genotypic variation of MIP-1α alleles in the infectious process is addressed by studying their infectability using M- and T-tropic strains of HIV-1. Blood samples from non-infected individuals representing selected genotypes of MIP-1α but similar CCR5 genotypes are evaluated for HIV-1 infectivity.

HIV-1 isolates BaL, 89.1 and IIIB (LAV) are used for in vitro infectivity studies. The inventors have generated virus stocks of HIV-1/IIIB and HIV-1/BaL and made virus preparations from samples sent from the AIDS repository. The HIV-1/BaL stock (NIH AIDS Repository) has been expanded by infection of primary human macrophages. This stock was used to successfully infect CCR5 transfected HeLa cells and HEK 293 cells, and BaL was titrated based on Ag p24. 89.6 was selected since it has been shown to be dual-tropic, infecting both CD4+ T cell lines and macrophages and is more promiscuous in regard to CC chemokine receptor usage. As a control, IIIB is compared for infection of primary PBMC cell cultures. IIIB is primarily T cell line tropic and has been propagated in Molt3 T cell lines and stocks titrated and frozen at −135° C.

PBMCs from heparinized human blood are isolated by Ficoll Hypaque gradient centrifugation. The protocol involves stimulation in PHA followed by IL-2 for 15-21 days. Following this, $2\times10^5$ PBMCs are centrifuged at 1700×g to remove the growth medium, resuspended in virus stock culture or culture medium (250 μl) for 2 hours at 37° C. and then the volume adjusted with culture medium to a cell density of $2\times10^6$/ml. After overnight incubation, the cells are washed 5 times and the contents of the last wash harvested as the zero time point. Every 3-4 days, culture supernatants are harvested and frozen at −80° C. until analysis for virus by HIV-1 p24 antigen capture ELISA as per the manufacturers instructions. Results are then compared with a standard curve generated according to the manufacturer's instructions. In cases where the OD values of the samples are out of range (over), serial 10 fold dilutions are analyzed to obtain a value situated within the standard curve, which gives a direct measure of virus present in PBMC cultures.

All infections are performed in triplicate so that statistically representative sampling is obtained. This is important in assessing if certain genetic variants are more commonly linked to changes in HIV-1 infection. Other non-membrane factors may also influence viral replication and expression, however, it has not been shown that cellular factors directly or indirectly effect HIV-1 expression in studies performed on PBMCs. Other cell surface molecules could serve as co-receptors and may have genetic linkage. Therefore, a control well for each sample is included that includes pre-treatment of cells with anti-CCR5 to inhibit infection in PBMC from the various genotypes. This ensures that the variation in HIV-1 infectability is linked to the use of CCR5 in viral entry. In addition, recombinant chemokines RANTES, MIP-1α and MIP-1β (200 ng/ml) are incubated during the infection period to determine if infection proceeds through CCR5 or related CCR-like molecules. RANTES and MIP-1α might block M-tropic viruses but not 89.6 or IIIB variants.

13. Role of Polymorphisms in MHC Genes in HIV-1 Pathogenesis

Because many of the HLA genes are known to function in the immune response to HIV, there is growing evidence that it is related to both disease susceptibility and progression. Knowledge of the MHC influences can, by reverse genetics, offer a way of identifying crucially important antigens. For example, identification of virus-derived, HLA-restricted peptides from individuals who resist disease progression has the potential for the development of vaccines. That such an approach might work is suggested by data from cancer vaccine studies. HLA-restricted peptides of the E7 protein of human papilloma virus, which stimulate a strong T cell response, have been used in a vaccine to protect mice against cervical cancer (Ressing et al., 1996a; 1996b). From a therapeutic standpoint, elucidating the mechanisms through which certain MHC alleles influence outcome of HIV infection is also of importance. It allows for the design of boosting strategies for protective responses or blocking strategies for immuno-pathological responses. A general problem in HLA-HIV studies is that most published association studies have been too small to detect convincing allelic associations. This lack of power is particularly problematic with HLA studies where there is a requirement to make statistical correction for comparison of multiple alleles. Most reported HLA studies are with ~100 cases and similar numbers of controls. Another limitation is that most studies are based on cohorts composed primarily of Caucasians (Roger, 1998; Just, 1995).

To determine the influence of HLA haplotypes in transmission and disease progression, the present studies overcome several of the aforementioned limitations: the sample size is large, there are adequate numbers of matched controls, and there are large numbers of both African-Americans and Caucasians. These studies also provide insights into the role of gene-gene interactions between HLA and CCR5/chemokine haplotypes. These interactions may account in part, for the race-specific disease-modifying effects associated with certain CCR5 haplotypes.

Initially, HLA-HIV studies are performed in the African-American subset of the WHMC cohort, followed by analysis in the Caucasians. There are three categories of genes in the HLA region. Class I, encoding (among others) for HLA-A (109 alleles), -B (240 alleles), -C (67 alleles), -E (5 alleles) and -G (13 alleles). Class II, encoding (among others) for HLA D (alleles: 2 DRA, 257 DRB, 19 DQA, 38 DQB, 13 DPA, 82 DPB, 4 DMA, 5 DMB), 5 TAP 1, 4 Tap 2. Class III, which contains (among others) the genes encoding for the complement system (C2 and C4). The tumor necrosis factor (TNF) gene is also located in this region. Analogous to CCR5, the hallmark feature of the HLA and other genes in the MHC is linkage disequilibrium. The total number of possible combinations of all these alleles is enormous, but fortunately certain combinations occur more frequently than would be expected if the segregation of these alleles was random. Serological assays were traditionally used to type HLA molecules. These assays do not sample the human genome directly, but instead analyze the protein products encoded by certain HLA alleles. More recently developed methods utilizing standard molecular biological techniques allow for a more, rapid and systematic analysis of HLA loci. Furthermore, these methods have increased the sensitivity and specificity of detecting genetic variants as compared to serological techniques. HLA-typing protocols are such that they are very amenable to analyzing large samples in a time- and -energy efficient manner.

For HLA-A, HLA-B, HLA-C, HLA-DRB and HLA-DQB commercial typing kits are used (Lifecodes Corp) that employ a PCR-SSOP (sequence specific oligonucleotide probes) based strategy. For HLA-E, HLA-G, HLA-DQA, HLA-DPA and HLA-DPB a PCR-SSOP strategy is used, except that the primers and oligonucleotide probes are synthesized based on previously reported sequences. For HLA-DRA, HLA-DMA, HLA-DMB, TNF-α, TAP 1 and TAP 2 a PCR-RFLP and/or PCR-SSOP-based analysis is used. Again, previously established PCR-RFLPs and/or PCR-SSOP sequence primers are used.

The HLA frequencies in the WHMC cohort are compared to those found in large studies of African Americans and Caucasians (Granja et al., 1996). Additionally, randomly collected DNA samples from ~400 African-Americans, and about ~600 Caucasians, are available as controls for this study. Because of the large number of samples analyzed in both cohorts (HIV− and HIV+), a very robust analysis is conducted. The analysis includes determining the influence of HLA markers on disease progression and transmission, with a special statistical consideration for multiple comparisons. Also considered are MHC-chemokine/co-receptor interactions.

Because of the extensive linkage disequilibrium, HLA alleles associated with disease outcomes are not by definition cofactors, but may merely be linked with genes that play a causal role in HIV-1 disease progression. A technical issue is the signal-to-noise ratios related to the hybridization procedures. To address this, additional washes with SSC were included, and some hybridizations may be repeated. To resolve the assignment of anomalous haplotype patterns by the computer program, the membranes are scanned visually, since the anomalous patterns may represent novel alleles.

Example 3

The Human CC Chemokine Receptor 5 (CCR5) Gene

Multiple Transcripts with 5'-End Heterogeneity, Dual Promoter Usage, and Evidence for Polymorphisms within the Regulatory Regions and Non-Coding Exons Human CC chemokine receptor 5 (CCR5), mediates the activation of cells by the chemokines MIP-1α, MIP-1β and RANTES, and serves as a fusion cofactor for macrophage-tropic strains of HIV-1. To understand the molecular mechanisms that regulate human CCR5 gene expression, studies were conducted to determine its genomic and mRNA organization. Previous studies have identified a single CCR5 mRNA isoform whose open reading frame (ORF) is intron-less. The inventors now report the following novel findings. (1) Complex alternative splicing and multiple transcription start sites give rise to several distinct CCR5 transcripts that differ in their 5'-untranslated regions (UTR). (2) The gene is organized into four exons and two introns. Exons 2 and 3 are not interrupted by an intron. Exon 4 and portions of exon 3 are shared by all isoforms. Exon 4 contains the ORF, 11 nucleotides of the 5'-UTR and the complete 3'-UTR. (3) The transcripts appear to be initiated from two distinct promoters: an upstream promoter ($P_U$), upstream of exon 1, and a downstream promoter ($P_D$), that includes the "intronic" region between exons 1 and 3. (4) $P_U$ and $P_D$ lacked the canonical TATA or CAAT motifs, and are AT-rich. (5) $P_D$ demonstrated strong constitutive promoter activity, whereas $P_U$ was a weak promoter in all three leukocyte cell environments tested (THP-1, Jurkat and K562). (6) Evidence is provided for polymorphisms in the non-coding sequences, including the regulatory regions and 5'-UTRs. The structure of CCR5 was strikingly reminiscent of the overall structure of other chemokine/chemoattractant receptors, underscoring an important evolutionarily conserved function for a prototypical gene structure. This is the first description of functional promoters for any CC chemokine receptor gene, and the complex pattern of splicing events and dual promoter usage likely functions as a versatile mechanism to create diversity and flexibility in the regulation of CCR5 expression.

A. Introduction

CC chemokine receptor 5 (CCR5), a receptor for the CC chemokines macrophage inflammatory protein-1α, macrophage inflammatory protein-1β and RANTES (Samson et al., 1996; Combadiere et al., 1996; Raport et al., 1996), also serves as a fusion cofactor for the entry of macrophage-tropic strains of HIV-1 (Alkhatib et al., 1996; Dragic et al., 1996; Deng et al., 1996; Choe et al., 1996; Doranz et al., 1996). The level of CCR5 cell surface expression may have a direct influence on the relative ease with which an individual acquires HIV-1 infection (Liu et al., 1996; Samson et al., 1996; Dean et al., 1996; Huang et al., 1996): individuals homozygous for a 32-bp deletion (denoted ΔCCR5) in the open reading frame (ORF) do not express the protein on the cell surface, and are relatively resistant to developing HIV-1 infection. In contrast, individuals who display the CCR5/ΔCCR5 genotype can develop HIV-1 infection however, their progression to AIDS may be slower. Interestingly, in individuals who display the CCR5/CCR5 genotype, the cell surface expression of CCR5 can be highly variable (Wu et al., 1997), however, whether this heterogeneity in protein expression also correlates with differences in HIV-1 infection/transmission in vivo is not known. These observations suggest that a therapeutic or preventive strategy based on targeting CCR5 cell surface expression could potentially be quite beneficial. Towards this end, the inventors have initiated studies to define the structural organization of CCR5 and molecular factors that regulate its expression.

Phylogenetic analysis of the G-protein coupled receptor (GPCR) superfamily indicates that replication of a progenitor gene may have given rise to clusters of evolutionarily related receptor genes (Murphy, 1994; Murphy, 1996). Two such GPCR clusters are members of the chemokine receptor subclass, and receptors for the classical chemoattractants, such as the N-formyl peptide receptor (FPR). To date, the complete mRNA and genomic organization of only a limited number of chemokine receptors has been described (Iwamoto et al., 1995, 1996; Ahuja et al., 1992, 1994; Wong et al., 1997), however, a comparison of their structural organization with that of the receptors for the classical chemoattractants reveals some striking similarities (Gerard et al., 1993; Mutoh et al., 1993; Pang et al., 1995; Murphy et al., 1993). 1) Their ORFs are usually intronless or contain a single intron interrupting the amino-terminal coding region, as is the case for the C5a receptor (Gerard et al., 1993). 2) Their 5'-untranslated regions (UTR) can have a surprisingly complex organization. Unlike most GPCRs, the 5' UTRs for these genes reside on multiple exons and alternative splicing may generate multiple mRNA isoforms. 3) Splicing of the untranslated exons to form the mature transcripts occurs at a common 3'-splice junction that is a short distance upstream of the start of the translation. Thus, the transcription and translation start sites can be separated by long intervening sequences. 4) Although they are products of distinct genes, they tend to be physically clustered on a single chromosome (Murphy, 1994, 1996; Ahuja et al., 1992; Gerard et al., 1993; Samson et al., 1996). For example, CCR5 and several other CCRs co-localize on chromosome 3p21.3-p24 (Samson et al., 1996) whereas several of the chemoattractant receptors co-localize to 19q13.3 (Gerard et al., 1993). These similarities suggest that despite coding for receptors that have diverse ligand-receptor relationships, these two subclasses of receptors have retained a remarkably conserved structural organization.

Some of these prototypical structural features also appear to be true for human CCR5. First, a partial length gene (1376-bp) has been cloned and it has an intronless CCR5 ORF (Samson et al., 1996; position 240 to 1298). Second, cDNA clones for CCR5 have been cloned and reported by two groups (Combadiere et al., 1996; Raport et al., 1996). Comparison of the partial CCR5 sequence with that of the cDNA clones, and restriction mapping of P1 clones suggests the presence of a single ~1.9-kb intron between position −11 and −12 relative to the start of translation (Samson et al., 1996; Combadiere et al., 1996; Raport et al., 1996). To delineate the full extent of the 5'-UTR of human CCR5, Raport et al. also performed 5' RACE (5' rapid amplification of cDNA ends) on human spleen cDNA, and by this method the longest 5'-UTR identified was 54 nucleotides (nt) in length (Raport et al., 1996). The cDNA clone reported by Raport et al. also contains a poly(A) tail, suggesting a full-length 3'-end (Raport et al., 1996). Nevertheless, the exact location of the remainder of the reported CCR5 5'-UTR sequence on the gene, and the nature of the cis-acting elements is not known.

Expression of CCR5 at the mRNA level suggests that CCR5 may contain tissue-specific cis-acting elements. An ~4 kb human CCR5 transcript has been observed in several human cell lines, and in human thymus, spleen, small intestine, and peripheral blood leukocytes (Samson et al., 1996; Combadiere et alt, 1996; Raport et al., 1996; Alkhatib et al., 1996). Combadiere et al. have shown that human CCR5 transcripts are present in primary adherent monocytes but are absent from the primary neutrophils and eosinophils (Combadiere et al., 1996). Carroll et al. have reported recently that human unstimulated CD4+ cells do not express CCR5 mRNA (Carroll et al., 1997). However, CD4+ cells activated by phytohemagglutinin (PHA)/IL-2 expressed CCR5 mRNA, whereas those co-stimulated with immobilized antibodies to CD3/CD28 did not. Both unstimulated CD4+ cells and CD4+ cells co-stimulated with CD3/CD28 were resistant to infection by macrophage-tropic strains of HIV-1 in vitro, whereas PHA/IL-2 activated CD4+ cells could be infected, further highlighting the importance of understanding the molecular mechanisms that regulate CCR5 expression.

Unlike reported previously, the present studies demonstrate that the mRNA structure of human CCR5 is not monomorphic. Instead transcript analysis by 5'-RACE and RT-PCR (reverse transcriptase-polymerase chain reaction) revealed complex alternative splicing patterns in the 5'-UTRs of CCR5: alternative splicing of four exons that span ~6 kb of CCR5 give rise to multiple CCR5 transcripts that differ in their 5'-UTRs. Although the generation of multiple CCR5 transcripts has no effect on the protein sequence of CCR5, it does have consequences for the regulation of the gene as it is demonstrated that CCR5 transcription is regulated by at least two promoters, and an important role is ascribed for the 5'-UTR and intron sequences in regulating CCR5 expression. In this Example evidence is provided that the regulatory sequences and non-coding exons of CCR5 are polymorphic.

B. Materials and Methods

1. Cells and Cell Culture

After obtaining informed consent, normal adult donors were pre-treated with granulocyte colony stimulating factor (Amgen; 10 µg/kg body weight, subcutaneously) for 5 days, and then their low density cells in the peripheral blood were collected by apheresis. These cells were enriched for CD34+ progenitor cells by positive selection, using the Ceprate SC column (CellPro, Bothell, Wash.). The purified CD34+ cells were differentiated into dendritic cells by culturing them in a cytokine cocktail for 7 days. The cytokine cocktail contained stem cell factor (20 ng/ml), granulocyte macrophage colony stimulating factor (20 ng/ml), and tumor necrosis factor-α (TNF-α) (2 ng/ml; R & D Systems). The culture conditions were similar to those described previously (Ahuja et al., 1996), and included Iscove's Modified Dulbecco's Medium and 20% fetal calf serum (Life Technologies). It was confirmed that the cells derived from the cytokine-stimulated CD34+ cells had a dendritic cell phenotype by two independent criteria: first, by FACS they expressed a high percentage of cell surface markers characteristic of dendritic cells; and second, dendritic cells pulsed with tetanus toxoid and purified-protein derivative stimulated the proliferation of autologous T cells. Density gradient ficoll centrifugation was used to isolate peripheral blood mononuclear cells (PBMCs) from whole blood and the cells obtained from the apheresis flow-through. Monocytes were isolated from PBMCs by plastic adherence for 6 hours. CD4+ cells were purified by positive selection using the Ceprate LC4 column (CellPro). To prepare activated CD4+ T lymphocytes, resting CD4+ T lymphocytes were stimulated with irradiated autologous dendritic cells. Lymphocytes, monocytes and PBMCs were cultured in RPMI and 10% fetal bovine serum.

2. RNA Extraction

Total RNA was extracted from human leukocytes, including dendritic cells and the cell lines (THP-1 and Jurkat), using commercially purchased reagents according to instructions of the manufacturer (Trizol; Life Technologies).

3. 5' RACE and RT-PCR

The template for 5' RACE was total RNA (1 µg) isolated from dendritic cells. For RT-PCR, the template was 1 µg of total RNA isolated from human leukocytes, including dendritic cells. A 5'-RACE kit (5'-RACE System, Life Technologies) was used per instructions of the manufacturer. The sequences of the reverse and forward primers (primary and nested) corresponded to the amino-terminus of the CCR5 ORF and the anchor primer, respectively. The 5'-RACE products were subcloned into pBlueScript II SK(+) and the nucleotide sequence was determined on both strands. To confirm the sequence composition of the 5'-RACE products, RT-PCR reactions were performed on the aforementioned RNA templates. A reverse primer complementary to the amino-terminus of CCR5 was first extended by AMV reverse transcriptase (Invitrogen), and then PCR was performed with a forward primer that was specific to the 5'-most unique sequence segment identified by 5'-RACE and a reverse primer specific to the CCR5 ORF; semi-nested PCR was then performed on this PCR template with primers specific to the 5'-UTR. The RT-PCR products were subcloned into pBlueScript II SK(+) and sequenced. Oligonucleotides were synthesized by the Advanced DNA Technology Unit, University of Texas Health Science Center at San Antonio, Tex. DNA sequence analysis was performed by the dideoxy method according to the manufacturer's instructions (U.S. Biochemical Corp.) and also by the Dye Terminator Cycle Sequencing method using an automated fluorescent sequencer (Applied Biosystem 373).

4. Characterization of CCR5 Gene

The genomic region upstream of the 5'-UTR sequence reported by Raport et al. (1996) was cloned by using the Human PromoterFinder Kit (CLONTECH) according to the manufacturer's protocols. The forward and reverse primers (primary and nested) were complementary to the adaptor ligated to the genomic DNA fragments in each library, and the 5'-UTR sequence reported by Raport et al. (1996), respectively. A series of overlapping genomic DNA amplification products were generated using PCR primer sets specific to the following regions: 1) 5'-UTR and amino-terminus of the ORF; 2) amino-terminus and the intracellular carboxyl-tail of the ORF (Alkhatib et al., 1997); and 3) the intracellular carboxyl-tail of the ORF and a reverse primer whose 3'-terminus is immediately upstream to the polyadenylation signal sequence AAATAA in the 3'-UTR. The PCR amplification products were subcloned into pBlueScript II SK(+) and the nucleotide sequence was obtained for both strands. Nucleotide sequences were analyzed by algorithms in the GCG software (BLAST, FASTA, BestFit) and GeneWorks (Intelli-Genetics, CA). The promoter sequences were analyzed for the presence of potential transcription factor binding sites by the SIGSCAN (http://bimas.dert.nih.gov/molbio/signal; Prestridge, 1991) and MatInspector (http://transfac.gbf-braunschweig.de/TRANSFAC/; Quandt et al., 1995) programs.

5. Construction of CCR5 Promoter Constructs

Convenient restriction endonuclease sites and/or PCR was used to create a series of gene fragments of varying lengths from different regions of CCR5, and they were cloned into the promoterless pGL3-Basic vector (Promega) upstream of the firefly luciferase gene. Nucleotide fidelity was confirmed by sequencing.

6. Transient Transfection of Cell Lines and Luciferase Assays

The cell lines (K-562, Jurkat, and THP-1) were obtained from ATCC (Rockville, Md.). The promoter constructs were transfected into the cell lines as described previously (Ahuja et al., 1994). Transfection efficiency was normalized by co-transfecting either the promoterless vector pGL3-Basic or the CCR5 promoter constructs with 0.5 µg of renilla luciferase vector, pRL-CMV (Promega). Forty hours post-transfection the cells were pelleted, washed in Dulbecco's phosphate buffered saline and lysed in 1× passive lysis buffer (Promega). The firefly and renilla luciferase activities were determined according to manufacturer's instructions (Dual-Luciferase Reporter Assay System, Promega) in a luminometer (Turner TD-20/20). In initial experiments, the protein concentration in the cell lysates as measured by the Bradford method were comparable between and within experiments. The "relative luciferase activity" reported is derived from: (firefly luciferase activity of CCR5 promoter construct/renilla luciferase activity of co-transfected pRL-CMV)/(firefly luciferase of promoterless vector pGL3-Basic/renilla luciferase activity of co-transfected pRL-CMV).

C. Results

1. Heterogeneity in the 5'-UTR of Human CCR5 mRNA

A single CCR5 mRNA isoform that contains a 5'-UTR of 54-nt in length has been reported (Raport et al., 1996). Since alternative splicing in the 5'-UTRs appears to be a feature common to several human chemokine and chemoattractant receptors (Ahuja et al., 1994; Mutoh et al., 1993; Murphy et al., 1993), the inventors reasoned that this might also be true for CCR5. To test this, a strategy was designed that involved 5'-RACE and RT-PCR techniques, and the diversity in the CCR5 mRNA structure was probed in several primary human cell types and the human cell lines THP-1 and Jurkat. By this strategy, PCR products of ~100 to ~350 bp in length were identified from human dendritic cells, suggesting the possibility of novel 5'-UTR sequences. These PCR products were subcloned. Based on sequence analysis and criteria outlined below, these cDNA clones were segregated into two categories, representing either "fill-length" or "truncated" CCR5 transcripts.

Specifically, the boundaries of the exons and the length of the non-coding exons were determined. The ORF resides in exon 4 and also contains 11 bp of the 5'-UTR and the entire 3'-UTR. The transcripts that contained exon 1 sequence were designated as "full-length" transcripts, whereas the individual transcripts that lacked exon 1 were designated as "truncated" isoforms. The 5'-termini of each "truncated" isoform identified, relative to its position in CCR5A was determined. The 5'-terminus of the longest reported 5'-UTR was also determined (Raport et al., 1996).

The two "full-length" CCR5 transcripts, designated as CCR5A and CCR5B, shared three sequence segments but differed by the presence or absence of a 235-bp sequence segment in the 5'-UTR. As demonstrated later, these sequence segments were identified on CCR5, and based on their location on the gene they were designated as exons 1-4; exon 2 corresponded to the 235-bp sequence segment that is unique to CCR5A. Exons 1, 3 and 4 were common to both CCR5-A and -B, and the ORF, 11-bp of the 5'-UTR and the 3'-UTR resided in exon 4.

The cDNA clones that lacked sequences corresponding to the 5'-most unique sequence segment, i.e., exon 1, were arbitrarily classified as "truncated" CCR5 mRNA isoforms. The 5'-termini of the truncated clones relative to their position on CCR5A were determined. It should be emphasized that the "truncated" CCR5 transcripts could also represent incomplete cDNA synthesis by the reverse transcriptase. However, two findings suggest that this may not be the case. 1) From a single RT-PCR, products were cloned whose lengths were significantly longer than the "truncated" transcripts. 2)

Except in a single instance, several clones had identical 5'-termini, suggesting that they may represent transcripts that originate from distinct transcription start sites. It should also be noted that the presence of additional CCR5 isoforms that may have unique 5'-non-coding exons or novel splice patterns cannot be excluded.

The cDNA sequence reported by Raport et al. lacked in-frame stop codons in the 5'-UTR, raising the possibility of a longer CCR5 ORF initiated at an upstream methionine (Raport et al., 1996). In-frame stop codons were identified 26 and 12 amino acids (aa) upstream of the currently assigned translation initiation codon in CCR5A and CCR5B, respectively. None of the upstream in-frame amino-acids were a methionine, excluding the possibility of a longer transcript that could encode a protein isoform with an amino-terminal extension. Interestingly, four upstream AUG triplets were found in the 5'-UTR of both CCR5A and CCR5B, but they were followed by downstream termination codons, and the two longest minicistrons were 9 and 15 aa in length.

The 5'-UTR sequences of the "full-length" and "truncated" CCR5 transcripts appeared to be highly conserved in evolution as GenBank database analysis revealed strong sequence homology with the 5'-UTRs of mouse and rat CCR5 cDNAs. The mouse and rat cDNA GenBank Accession numbers are D83648, and Y12009, respectively. The 5'-termini of the 5'-UTRs of mouse and rat cDNAs reside in a region that corresponds to exon 2 of human CCR5A. Whether additional upstream mRNA sequences exists in these two species is not known. It is interesting that 12 bp upstream of the start of the translation start site, all the human CCR5 cDNA clones had a 4 bp insertion (CCCC) relative to the mouse and rat cDNAs.

2. Tissue Distribution of Human CCR5 mRNA Isoforms

All the CCR5 cDNA clones identified contained exon 4 and portions of exon 3, and the additional length contributed by exons 1 and/or 2 to CCR5A or CCR5B was not substantial. This implied two points. First, that the proportion of transcripts in human cell types that are either "full-length" or "truncated" cannot be readily ascertained by size differences on northern blots. Second, since CCR5A and CCR5B can be differentiated only by the presence or absence of exon 2, a RT-PCR strategy could be designed to evaluate exon usage in different human leukocyte populations. However, the latter strategy would not be helpful in defining the relative abundance of the truncated transcripts, as portions of exon 3 are common to all isoforms. To illustrate the first point, when a probe was used that corresponded to exon 1, an ~4.0 kb hybridizing band was visualized in human poly(A)+ mRNA derived from bone marrow, peripheral blood mononuclear cells, thymus, lymph node and spleen, and corresponded to the transcript size seen in the identical tissues hybridized with an ORF/3' UTR probe (Raport et al., 1996).

The second point is illustrated by the demonstration of splicing patterns, i.e., exon usage, of CCR5 mRNA. In RT-PCR, total RNA derived from primary human cell types (PB-MCs, lymphocytes, monocytes, CD34+ progenitor cell-derived dendritic cells, activated CD4+ T cells, and the THP-1 and Jurkat cell lines) was used as a PCR template. The forward and reverse primers were specific to exon 1 and 3, respectively. In these studies, two bands were observed in these cell types. A single PCR product of ~800 bp was detected when human genomic DNA was amplified with the identical primers, suggesting that the RNA templates used to perform RT-PCR were free of genomic DNA contamination. Each RT-PCR included a negative control that lacked the cDNA template.

To confirm the exon composition of the ethidium bromide stained PCR products, the two bands were subcloned that were amplified from dendritic cells and the THP-1 cell line. Sequence analysis revealed that the upper and lower band corresponded to isoforms that contained exons 1+2+3 (CCR5A) or exons 1+3 (CCR5B), respectively. It should be noted that this analysis is qualitative, and although minor variations in the proportion of the transcripts containing these exons were observed, there was no clear pattern of tissue-specific utilization of either CCR5A or CCR5B.

3. The Human CCR5 Gene

Using PCR overlapping fragments of human CCR5 were amplified, cloned and sequenced, that together comprised an ~8 kb contiguous stretch of CCR5. The 5'-UTR sequences detected by 5' RACE and RT-PCR, and the cDNA sequence reported by Raport et al. (1996) were identified on this genomic contig. This genomic contig spanned 8035-bp, and originated ~1.9 kb upstream of exon 1 and terminated immediately upstream of the polyadenylation signal. The gene is organized into four exons and two introns. Both introns interrupt the 5'-UTR. Interestingly, exons 2 and 3 are contiguous and are not interrupted by an intron. The exon/intron splice junctions in CCR5 conform to the consensus sequences for 5'-(CAG<u>GT</u>RAGT) and 3'-(Y$_n$NY<u>AG</u>) splice sites. Interestingly, a region upstream of exon 1, had strong sequence homology (~89%) with sequences in the 3'-flanking region of CCR5 (GenBank accession number U95626). Note that the 3'-flanking sequence is in the reverse complement orientation.

The 5'- and 3'-flanking regions of CCR5 were compared with sequences deposited in GenBank. This analysis revealed identity or close homology between the CCR5 sequences that were characterized in this study and two unpublished gene sequences that were submitted while this work was in progress. 1) The entire 8035-bp sequence that was cloned was colinear with a portion of a human genomic DNA contig sequenced as part of the Advanced Genome Sequence Analysis Course, Cold Spring Harbor Laboratory, NY (GenBank Accession number U95626); this unpublished contig is 143,068-bp in length and in addition to CCR5, it contains CCR2A, CCR2B and an orphan chemokine receptor gene. The present CCR5 sequence ends just proximal to the polyadenylation signal. However, alignment of the sequence contig with the sequences contained in GenBank Accession number U95626 revealed that the nucleotides that follow the end of the present clone are identical to the polyadenylation signal sequence AAATAA. 2) A 227-bp sequence that is upstream of the *Macaca mulatta* CCR5 ORF (GenBank Accession number U77672) had a high degree of homology with the region that corresponds to intron 2 of human CCR5. The 5'- and 3'-flanking sequences reported previously by Samson et al. (1996) were 239-bp and 78-bp in length, respectively, and identical sequences were found in the CCR5 that was characterized herein. A region in intron 2 also had strong sequence homology with Alu repeats.

The exact location of the exon/intron boundary between intron 2 and exon 4 in human CCR5 appears to be conserved in mouse. Comparison of the mouse CCR5 cDNA and genomic sequences (GenBank Accession numbers D83648 and U68565) revealed an intron between −11 and −12 upstream of the translation start codon, a position that is identical for intron 2 in the human CCR5. Interestingly, the 554-bp mouse intron sequence had no homology with human CCR5 sequences, whereas, the 5'-UTRs of human and mouse CCR5 are highly conserved.

4. Evolutionary Conservation in the mRNA and Genomic Structure of Human CCR5 with that of Other Human Chemokine/Chemoattractant Receptors The mRNA and gene organization of human CCR5 is remarkably similar to that described for several other human chemokine and chemoattractant receptors (Iwamoto et al., 1995, 1996; Ahuja et al., 1994; Wong et al., 1997; Mutoh et al., 1993; Murphy et al., 1993), suggesting a selective evolutionary pressure for these receptors to retain a conserved gene architecture. It should be appreciated that, to date, the gene and mRNA structures (human) of only one CCR, CCR2 (Wong et al., 1997), two CXCRs, CXCR1 and CXCR2 (Ahuja et al., 1992, 1994), and the Duffy antigen receptor for chemokines (DARC; Iwamoto et al., 1995, 1996) have been described. The genomic organization of the C5a receptor (Gerard et al., 1993) has also been determined. The functional promoters for only two human chemokine receptors, CXCR1 and CXCR2, have been described (Ahuja et al., 1994). As described below, two promoters for CCR5, designated as $P_U$ and $P_D$, have been characterized. Interestingly, as is the case for the promoters for CXCR2 (Ahuja et al., 1994) and platelet-activating factor receptor gene (Mutoh et al., 1993, Pang et al., 1995), the two CCR5 promoters are also tandemly arranged on the gene. Another feature that is common to both CCR5 and CXCR2 is that they contain exon-exon units that are uninterrupted by an intron. For example, exon 2 of CCR5A, resides in the "intronic" region for CCR5B, and exon 5 of the CXCR2-3 isoform, resides in the intronic region for CXCR2-1, -2, and -4 isoforms.

5. Molecular Dissection of Functional Promoters for CCR5

The genomic region upstream of exon 1 should potentially contain the cis-acting elements important in the promoter activity of CCR5A and CCR5B. Therefore, CCR5-firefly luciferase chimeric plasmids were constructed from portions of the gene upstream of exon 1, designated as pA1-4. The ability of these promoter constructs to drive the expression of the reporter gene (firefly luciferase) were tested in the following cell lines: 1) THP-1, a human monocytic leukemia cell line, a surrogate for monocytes; 2) K-562, a human chronic myelogenous leukemia cell line, a surrogate for undifferentiated hemopoietic cells; and 3) Jurkat, which is a human T cell leukemia cell line. To correct for differences in transfection efficiency, the promoter constructs and the promoterless vector pGL3-Basic were co-transfected with pRL-CMV, a construct that contains the renilla luciferase gene downstream of a CMV promoter. Lysates prepared from cells transfected with constructs pA1-4 exhibited weak luciferase activity. This genomic region upstream of exon 1, which has weak promoter activity, is designated as the upstream promoter ($P_U$).

Because a large number of 5'-RACE clones terminated either in exon 3 or at the 3'-end of exon 2, these transcripts may represent distinct isoforms that are initiated because of the usage of an alternative promoter. To test this, another series of promoter constructs were constructed. It should be noted that in some instances these constructs contain portions of $P_U$, intron 1, and exon 2, and that the distal end of each of these constructs resides within exon 3.

In contrast to $P_U$, the region upstream of exon 3, designated as the downstream promoter ($P_D$), had strong luciferase activity in all the three cell lines tested. Maximal promoter activity was consistently observed in the cell lysates from K-562 cells, especially with those transfected with pB3 and pB4. The promoter activity for these two constructs in K562 cells was ~8- to 10-fold more than that detected in cells transfected with pB1, pB2 or pB5. The increase in luciferase activity in THP-1 and Jurkat cell lines transfected with pB3 and pB4 was not as prominent as that observed for these two promoter constructs in K-562 cells. Relative to pB3 and pB4, the construct pB5 exhibited weak promoter activity. This finding suggests that the sequences between pB4 and pB5 may contain important cis-acting elements for CCR5 promoter activity. It is important to note that since all the $P_D$ constructs contain all or portions of exon 2, it is likely that this non-coding exon may play an important role in modulating gene expression.

6. Analysis of the $P_U$ and $P_D$ Sequences

It is important to appreciate that because of the complex genomic and mRNA organization of CCR5, it is difficult to unambiguously assign certain regions of CCR5 as an exon, intron or promoter. Notwithstanding this caveat, $P_U$ and $P_D$ lacked canonical TATA and CCAAT motifs. However, in $P_D$ there was a non-consensus TATA-box (TTTATA). Unlike most TATA-less promoters, which have a high GC content, $P_U$ and $P_D$ were GC-poor. The overall G+C content of $P_U$ and $P_D$ was 46 and ~40%, respectively. Several pyrimidine-rich segments were identified in both $P_U$ and $P_D$. Pyrimidine-rich sequences have been observed in the proposed promoter for DARC (Iwamoto et al., 1995), and several other genes that are abundantly expressed in myeloid cells, including FPR (Murphy et al., 1993). $P_U$ and $P_D$ contained consensus sequences for several transcription factor DNA binding sites (e.g., AP-1, Oct-1, $P_U$F, PU.1, and NF-κB-like). The PU.1 transcription factor has been found to be important in the promoter activity of several genes expressed in myeloid cells, including M-CSF, and CD11b genes (Orkin, 1995). Multiple binding sites for GATA-1, an important transcription factor in the development of hematopoietic cells (Orkin, 1995), and for Sp1 were also noted.

7. Polymorphisms in CCR5 Non-Coding Sequences

The nucleotide sequences of the CCR5 gene were aligned with gene sequences in GenBank Accession number U95626, and the sequences of the cDNA clones derived by RT-PCR and 5' RACE. This alignment revealed extensive nucleotide differences in the non-coding sequences of the gene. The relative positions of the nucleotide substitutions, deletions or insertions detected in the 5'-non-coding sequences were determined. Differences in the 3'-flanking regions of the two gene sequences were also noted. The nucleotide differences noted in the cDNAs obtained from the non-related donors and the THP-1 cell line were not random, as sequence of multiple cDNA clones identified differences only at those positions where the two gene sequences diverged. This also suggests that these differences were probably not due to mutations introduced by the Taq polymerase. Sequence analysis of the genomic region upstream of exon 3 in 5 additional unrelated donors revealed polymorphic changes at the same and/or additional nucleotide positions.

D. Discussion

In this Example, novel CCR5 transcripts were identified, their splicing patterns were defined, and the organization of CCR5 was determined. The striking conservation in gene structure of CCR5 and related chemokine/chemoattractant receptors was also illustrated. This is the first description of functional promoters for any CC chemokine receptor gene. With regard to the molecular nature of the cis-acting elements that regulate the constitutive CCR5 expression in human leukocytes, a complex picture is emerging, one which may involve alternative promoter usage with regulatory elements residing on both sides of the 5'-most exon, implicating an important role for "intronic" and 5'-UTR sequences. In addition, evidence is provided for the presence of polymorphic nucleotides in the non-coding sequences of CCR5.

It is likely that a single gene encoding multiple transcripts allows for genetic parsimony while maximizing the mechanisms by which gene expression can be modulated (Ayoubi and Van De Ven, 1996). The "full-length" and "truncated" transcripts are initiated from $P_U$ and $P_D$, respectively, and those initiated from $P_U$ undergo alternative splicing, giving rise to CCR5-A and CCR5-B. The number of "truncated" isoforms may be even greater if one considers the possibility of additional transcription start sites within $P_D$. Nevertheless, as alluded to earlier, it is important to emphasize that distinguishing whether these "truncated" isoforms are transcribed in vivo or merely represent premature termination of cDNA synthesis by the reverse transcriptase is difficult.

The structural similarities in the gene and mRNA organization of CCR5 and several other chemokine/chemoattractant receptor genes, underscores an important evolutionary conserved function for this prototypical gene structure, the propensity for alternatively spliced isoforms, and usage of multiple promoters. It is likely that these receptors arose from an initial gene duplication event, with subsequent tandem duplication of an ancestral gene on chromosome 3p giving rise to several CCRs. It should be noted that in addition to these two GPCR subclasses, alternative splicing within the 5'-UTR has been described for a few other human GPCR genes (Curnow et al., 1995; Ball et al., 1995).

From an evolutionary perspective, it is intriguing that in addition to their ORFs, the 5'UTRs of mouse, rat and human CCR5 share strong sequence homology. To date, murine homologues for CCR1-5 have been cloned (Nibbs et al., 1997). The 5'-UTR sequences for murine CCR1 are not available in GenBank, nevertheless, unlike the strong interspecies homology of the 5'-UTRs of CCR5, the 5'-UTRs of mouse and human CCR2, CCR3, and CCR4 do not share significant sequence homology. These observations point towards a selective pressure for both mouse and human CCR5 to retain similar non-coding exons, which at least in humans, may participate in CCR5 gene regulation.

It is likely that CCR5 regulation may occur at many levels (Murphy, 1994, 1996). As is the case for other GPCRs, the cell surface expression of CCR5 may be regulated at the protein level, over the short term, through mechanisms such as receptor internalization, sequestration and desensitization. Longer term, regulation of these receptors is likely to be achieved through regulation of the rate of transcription of the gene, stability of the mRNA and translation efficiency, and there is increasing evidence that the sequences in the 5'- and 3'-UTRs may influence these processes (Jackson, 1993).

There are at least two possible mechanisms by which the 5'-UTRs of CCR5 may regulate gene expression. First, the 5'-UTR of CCR5-A and -B have several structural features that may exert a negative effect on the efficiency of translation. Kozak has examined factors in the 5'-UTRs that promote efficient translation (Kozak, 1989; 1991), which include the observation that: 1) most eukaryotic mRNAs have a short 5'-UTR, and 2) there are no AUGs upstream of the translation initiation site of the major ORF. Both CCR5A and CCR5B, the two "full-length" transcripts, have relatively long 5'-UTRs, and they belong to the unusual class of mRNAs (<10% vertebrate RNAs characterized) that contains AUG triplets upstream of the AUG that initiates the major ORF. The presence of translation initiation codons followed immediately by termination codons creates short upstream ORFs in the 5'-UTR. As reported in other gene systems (Oliveira and McCarthy, 1995; Parola and Kobilka, 1994) these short upstream ORFs could lead to reduced protein output through a mechanism of abortive translation. For example, a product of a short upstream ORF encoding a 19 aa leader peptide inhibits the translation of the β2 adrenergic receptor (Parola and Kobilka, 1994). Since some of the "truncated" isoforms lack short upstream ORFs, it is conceivable that preferential initiation of transcripts from $P_D$ may represent a potential mechanism by which CCR5 expression is modulated, as this would by-pass the possible inhibitory effects of the upstream minicistrons.

A second mechanism includes the possibility that differences in the secondary structures of the 5'-UTRs of the distinct CCR5 transcripts may influence translation efficiency. It is known that a Gibbs free energy of formation (AG) of less than −50 kcal/mol can impair the passage of the ribosomal 40S subunits as they scan from the cap site (Kozak, 1986). Algorithms developed by Zuker (Zuker, 1989) were used to analyze the 5'-UTRs of CCR5A and CCR5B for their tendency to undergo secondary structure. These algorithms predict that the AG of CCR5A and CCR5B are −69.5 kcal/mol and −48.7 kmol/mol, respectively, suggesting that relative to CCR5B, CCR5A has a higher propensity to form a very stable structure.

Two CCR5 promoter regions were identified that were active in all three cellular environments tested: $P_U$, a weak promoter that resides proximal to exon 1, and $P_D$, a stronger promoter that is located upstream of exon 3. It is conceivable that regions further upstream of exon 1, or constructs shorter than those tested, may support strong promoter activity for $P_U$. The region between +429 to +634 has an important role in regulating CCR5 expression. Although within this region, consensus sequences representing binding sites for transcription factors such as Oct-1 and GR-β are present, the precise cis-acting elements that confer this activity remain to be elucidated. It should be noted, that several of the constructs designed to test $P_D$ had intron 1 and exon 2 sequences, implicating an important function for these two regions in the regulation of CCR5. An important role for "intronic" sequences in the regulation of several genes has been described, including for CXCR2 (Ahuja et al., 1994).

The promoter sequences of CCR5 have two interesting features. First, a region in $P_U$ has sequence homology to a region in the 3'-UTR, the significance of which, if any, remains unclear. Second, characteristic of several GPCRs, neither $P_U$ nor $P_D$ had classical TATA or CCAAT motifs, although $P_D$ does contain a non-consensus TATAA-box. Most genes that are TATA-deficient can be divided into two classes on the basis of their upstream GC content (Smale and Baltimore, 1989). GC-rich promoters, found primarily in housekeeping genes, are very complex and prevalent; their promoters contain several binding sites for the ubiquitous transactivating Sp1 protein and have several transcription start sites. In contrast, the remainder of the genes that are TATA-deficient and are not GC rich, tend to be regulated during differentiation or development; many of their promoters are not constitutively active and initiate at only one or a few very tightly clustered start sites. The AT-rich composition of the CCR5 promoters, $P_U$ or $P_D$, suggests that they belongs to the latter class of promoters. However, in contrast to this subclass of TATA-deficient promoters, $P_U$ or $P_D$ appear to be constitutively active, are possibly initiated at several transcription start sites, and there is no conclusive evidence, to date, to suggest that CCR5 requires strict activation and inactivation during cellular differentiation and development.

It is clear from the study of several diverse gene systems that alternative promoter usage resulting in alternative transcripts is an important evolutionary mechanism to create diversity in the regulatory control of gene expression (Ayoubi and Van De Ven, 1996). In these systems, alternative promoter usage has been shown to be an important transcriptional mechanism for regulating either tissue- or cell-type specific expression, the level of expression, the developmental stage-specific (temporal) expression, the specific capacity to respond to a particular cellular or metabolic conditions, or the translational efficiency of the mRNA. Several possible scenarios for CCR5 can be envisaged. It is possible that the level of CCR5 expression is regulated at a transcriptional level by the usage of promoters of different strengths, such as those described.

Although the protein encoded by the different CCR5 transcripts is likely to be identical in different cell types, they may be regulated differentially in these different cell types by various extracellular signals, such cytokines or chemokines. To test this latter possibility, the inventors determined whether cytokine stimulation alters the constitutive promoter activity of a single promoter construct (pB3). The promoter activity of pB3 in Jurkat cells stimulated with PHA, PHA and phorbol myristic acid, ionomycin and phorbol myristic acid, or CD3/CD28 was similar to that observed in unstimulated Jurkat cells transfected with pB3 (n=3). Similarly, the cell lysates of THP-1 cells transfected with pB3 and stimulated with lipopolysaccharide, TNF-α, interleukin-6, and interferon-γ exhibited promoter activities similar to the cell lysates from the unstimulated THP-1 cells transfected with pB3 (n=3).

Several polymorphisms have been described in the CCR5 ORF (Samson et al., 1996; Dean et al., 1996; Huang et al., 1996; Ansari-Lari et al., 1997). The studies described in this Example provide evidence for polymorphisms in the flanking regions of CCR5. Several studies have clearly demonstrated that genes can be polymorphic not only in their coding regions, but also in important cis-regulatory sequences (Leen et al., 1994; Sloan et al., 1992; Angotti et al., 1994; Naganawa et al., 1997; Song et al., 1996; Inoue et al., 1997; Dallinga-Thie et al., 1997; Kazazian, 1990; McGuire et al., 1994). Furthermore, transcriptional mutants, may profoundly affect the promoter strengths of particular alleles by altering the affinity of regulatory proteins for these elements, and in some instances a single nucleotide change in a critical regulatory region can result in up to one order of magnitude difference in transcriptional activity of two otherwise identical promoters. As discussed below, this in turn, can have a profound affect on protein synthesis.

One of the most striking examples of transcriptional mutants affecting protein synthesis came in the wake of the cloning of the human β-globin gene nearly 20 years ago, where in addition to mutations in the coding region, single mutations in the regulatory regions were shown to decrease the amount of β-globin produced by red cells, leading to the blood disorder called β-thalassemia (Kazazian, 1990). It is interesting that, to date, over 300 β-thalassemia alleles have been discovered, including 12 transcriptional mutants, which account for the molecular basis of the marked heterogeneity of the β-thalassemia syndrome. Transcriptional mutants that lead to an increase in protein expression have also been described. For example, studies have linked the variant allele for the TNF-α gene, referred to as TNF2, to increased serum levels of TNF-α, and a poor prognosis for several infections, such as malaria (McGuire et al., 1994). Thus, it is conceivable that the polymorphisms in the regulatory regions of CCR5 may, in part, explain the observed variability in CCR5 expression in individuals who display the CCR5/CCR5 genotype (Wu et al., 1997; Trkola et al., 1996), and may therefore, influence the clinical outcome of HIV-1.

Example 4

Genealogy of the CCR5 Locus and Chemokine System Gene Variants Associated with Altered Rates of HIV-1 Disease Progression Allelic variants for the HIV-1 co-receptors CC chemokine receptor (CCR) 5 and CCR2, as well as the ligand for the co-receptor CXCR4, stromal-derived factor (SDF-1) have been associated with a delay in disease progression. This study was conducted to test the hypothesis that polymorphisms in the CCR5 regulatory regions influence the course of HIV-1 disease, as well as to examine the role of the previously identified allelic variants in 1,090 HIV-1 infected individuals. This Example describes the evolutionary relationships between the phenotypically important CCR5 alleles, defines precisely the CCR5 promoter sequences that are linked to the CCR5-Δ32 and CCR2-64I polymorphisms, and identifies genotypes associated with altered rates of HIV-1 disease progression. The disease-retarding effects of the CCR2-64I allele was demonstrable in African Americans but not in Caucasians, and the SDF1-3'A/3'A genotype was associated with an accelerated progression to death. In contrast, the CCR5-Δ32 allele, as well as a CCR5 promoter mutation with which it is tightly linked, were associated with limited disease-retarding effects. Taken together, these findings highlight a complex array of genetic determinants in HIV-host interplay.

A. Introduction

HIV-1 uses several chemokine co-receptors such as CCR5 for cell entry, and the ligands of these co-receptors generally exhibit anti-HIV-1 properties (Moore et al., 1997; Berger, 1997; Alkhatib et al., 1996; Deng et al., 1996; Dragic et al., 1996; Doranz et al., 1996; Feng et al., 1996; Bleul et al., 1996; Oberlin et al., 1996). Several studies have ascribed an important role for CCR5 surface expression levels in HIV-1 entry and pathogenesis (Liu et al., 1996; Samson et al., 1996; Dean et al., 1996). Interestingly, CCR5 surface expression levels on cells from individuals with the CCR5/CCR5 genotype are highly variable (Moore, 1997), and there appears to be a general correlation between the level of expression and in vitro infectability with R5-HIV strains (Wu et al., 1997; Berger et al., 1998). In this context, the inventors recently found evidence for polymorphisms in the regulatory regions of CCR5 (Example 3), and suggested that these polymorphisms mediate the wide variation in CCR5 expression levels, and thus, influence HIV-1 disease progression. This hypothesis was tested in a large cohort of HIV-1 seropositive individuals followed prospectively at a single U.S. medical center. Because of the unique nature of this cohort, the subjects share several pertinent environmental variables, mitigating some of the inherent problems of multi-center, genetic-epidemiologic investigations.

Recognizing that this cohort is ideally suited for ascertaining the genetic underpinnings of HIV-1 disease progression, the role of the previously identified allelic variants of the chemokine system was also examined for two reasons. First, despite the prevailing view that heterozygosity for the CCR5-Δ32 allele delays disease progression, a careful scrutiny of these studies suggests otherwise. A protective role for CCR5-Δ32 heterozygosity is evident in some reports (Dean et al., 1996; Zimmerman et al., 1997; de Roda Husman et al., 1997; Michael et al., 1997a), but transient (Meyer et al., 1997; Katzenstein et al., 1997; Eugen-Olsen et al., 1997), weak (Morawetz et al., 1997) or not confirmed (Huang et al., 1996) in other studies (Garred, 1998). Similarly, with regard to the role of the CCR2-64I allele in delaying disease progression, two studies have demonstrated a protective effect (Smith et al., 1997; Kostrikis et al., 1998), whereas protection was not apparent in two others (Michael et al., 1997b; Rizzardi et al., 1998). Finally, the disease-retarding role of homozygosity for the mutant SDF-3'A allele (Winkler et al., 1998) has not been confirmed in other cohorts.

B. Materials and Methods

1. Patients

HIV-infected patients participating in this study were volunteers from the US Air Force component of the Tri-Service HIV Natural History Study. The voluntary, fully informed consent of the subjects used in this research was obtained as required by Air Force Regulation (AFR) 169-9. Wilford Hall Medical Center is the referral hospital for all Air Force personnel developing infection with HIV. All HIV-infected USAF personnel undergo an evaluation at WHMC every 6 months while on active duty and at 12- to 18-month intervals, or as clinically required, when medically retired. As part of this evaluation, a variety of clinical, immunological and virological parameters are entered into a database, and associated with stored blood samples. Anti-retroviral therapy was provided without expense to all the patients, and usage was guided by contemporary public health service recommendations. Only those individuals with a minimum of 365 days of follow up were included for analysis in this study. By definition, all HIV-1 seroconverters had a previous negative HIV-1 test prior to their positive HIV-1 antibody test. The study population had 1,090 patients, including 620 seroprevalent and 470 seroincident cases. Demographically, this cohort was 54% Caucasian, 37% African American, 6.5% Hispanic and 2.5% from other racial groups. The median age was 28 years (range, 18 to 59 years). Ninety-four percent of the subjects were male. The median follow-up time was 5.9 years (range, 1.0 to 13.5 years) for the entire cohort. It was 6.3 years (range, 1.3 to 11.1 years) for the seroconvertor subset using the estimated seroconversion date (the midpoint between the last negative and first positive HIV test) as the initial time-point. The median time from last negative HIV test to estimated seroconversion was 10.5 months. 41% percent of this cohort progressed to AIDS (1987 criteria) and 34% died during the study period.

2. Genotype Analysis

Genomic DNA was extracted from frozen peripheral blood mononuclear cells (PBMCs) with a proprietary reagent (Qiagen) as recommended by the manufacturer's protocol. The CCR2-G190A polymorphism was genotyped as a BsaBI PCR-restriction fragment length polymorphism (RFLP) (Primers: 5'-CTCCGCTCTACTCGCTGGTGT-TCATCTTTGGTTTTGTGGGCAACATGATGG-3' (SEQ ID NO:32) and 3'-TCAACTGACCACGAAAGT-5' (SEQ ID NO: 33)) (Smith et al., 1997); the PCR amplicon was 679-bp. The CCR5-A29G transition creates a BamHI RFLP which was examined in a 337-bp PCR amplicon (Primers: 5'-GAGCCAAGGTCACGGAAGCCC-3' (SEQ ID NO:34) and 3'-CCTGGGTCCTA GAATCAC-5' (SEQ ID NO:35)). The CCR5-627T polymorphism was genotyped by a HindIII PCR-RFLP (Primers: 5'-GTGGGATGAGCAGAGAA-CAAAAACAAAA TAATCCAGTGAGAAAAGCCCG-TAAATAAAG-3' (SEQ ID NO:36) and 3'-CTATTAACAT-ACTCGTGAACCAC-5' (SEQ ID NO:37)); the PCR amplicon was 392-bp. The CCR5-C927T was genotyped by an EcoRV PCR-RFLP (Primers: 5'-GTTGGTTTAAGTTG-GCTT-3' (SEQ ID NO:38) and 3'-TAGAATTTCTAATAT AAAATTCTATTAACATACTCGTGAACCA-CAAACGGTCTA-5' (SEQ ID NO:39)); the PCR amplicon was 635-bp. The CCR5-Δ32 polymorphism was analyzed by size differences within the PCR amplicons (Primers: 5'-CAAAAAGAAG GTCTTCATTACACC-3' (SEQ ID NO:40) and 3'-AGTGTTCGGGTGTCTATAAAG GAC-5' (SEQ ID NO:41)); the PCR amplicons were 552-bp for wtCCR5 and 520-bp for CCR5-Δ32. The SDF1-G801A transition (SDF1-3'A allele) resides in the 3'-UTR of SDF-1 (Winkler et al., 1998) and was detected by a Msp1 RFLP in a 751 bp PCR amplicon (Primers: 5'-TGGCGACACGTAG-CAGCTTAG-3' (SEQ ID NO:42) and 3'-TTCCTGGTGC-CGAGACTAGTC-5' (SEQ ID NO:43)). The PCR cycling conditions were: 94° C. for 3 min, followed by 35 cycles of 94° C. for 30 s, 55° C. for 30 s, and 72° C. for 30 s. The PCR amplicons were visualized by ethidium bromide staining and ultraviolet light transillumination after electrophoresis on a horizontal submarine 2% agarose gel. The minor differences in the total number of individuals bearing the different alleles shown in Tables 1 and 2 are accounted by unsuccessful PCR amplification from a few individuals.

3. CCR5 Sequence and Evolutionary Analysis

Regions upstream of the CCR5 coding region were PCR amplified and subcloned into the Topo 2.1 Vector (Invitrogen). For sequencing data, CCR5 spanning from −731 to +981 was subcloned. To identify individual alleles, the BamHI RFLP in exon 1 of CCR5 was used as well as the EcoRV PCR-RFLP designed to detect the CCR5-C927T polymorphism. The nucleotide sequence of the cloned PCR products were determined on both strands by the Dye Terminator Cycle Sequencing method using an automated fluorescent sequencer (Applied Biosystem 373). The nucleotide sequences were aligned using standard DNA sequencing alignment computer programs. Phylogenetic trees were constructed using the PAUP software package (Swofford, 1993). A dendrogram representative of an abridged and modified version of a phylogenetic tree generated was generated by computer algorithms. A haplotype analysis using only individuals who were compound homozygous for the CCR2 and CCR5 genetic markers (except for CCR5-Δ32) was conducted. The genotypic data required to derive the phase known haplotypes represents a subset of the data shown in Table 1.

4. CCR5 Surface Staining

20 CCR2-64I homozygote cases were matched with 39 controls (CCR2-64 V/64 V; approximately 2:1 matching) and their peripheral blood mononuclear cells (PBMCs) examined for CCR5 surface expression. The two groups were matched for CD4 count, race, age, gender and stage of disease, with no significant differences between these variables (P>0.20 Mann Whitney U). Frozen PBMCs were thawed rapidly in a 37° C. water bath, washed in phosphate buffered saline (PBS) and resuspended in 1% fetal calf serum (Summit, Ft. Collins, Colo.). The cells were stained at 4° C. for 30 minutes with the following conjugated antibodies: CCR5-FITC, CD4-PE, CD45RO-PE (Pharmingen, San Diego, Calif.). The stained cells were washed once in PBS, fixed in formaldehyde (final concentration 0.1%) and stored at 4° C. until analysis. Flow cytometry was performed using a FACS Calibur with Simulset analysis software (Becton Dickinson, San Jose, Calif.). In preliminary studies, it was determined that CCR5 expression levels on freshly isolated and stored PBMCs derived from the same donor were similar. PBMCs from normal donors were processed, and either immediately stained for CCR5 expression levels or stored for analysis at a later time point. CCR5 expression levels on freshly isolated and frozen PBMCs from the same individual varied by <5-10% (n=5).

5. Statistical Analysis

Time curves for progression to AIDS (1987 criteria) and survival were prepared by Kaplan-Meier method using SPSS for Windows version 7.0 (SPSS, Chicago, Ill.). Between-group analyses were accomplished using the log-rank test. Relative hazards were calculated in univariate Cox models, with wild type representing the reference category for genetic variables unless otherwise indicated. Prognostic models were developed with a forward and backward Cox proportional hazards model using improvement in likelihood ratio for entry. Continuous variables, including flow cytometry measurements, were compared with the Mann-Whitney U test.

mutation and, of the 116 individuals heterozygous for the CCR5-Δ32 mutation, only 12 lacked a CCR5-A29G polymorphism. 3) The CCR5-Δ32 and CCR2-64I polymorphisms occur on a CCR5 haplotype that includes a C-base at CCR5 position 627. 4) The allelic heterogeneity at the CCR5 locus appears to have arisen by a nested process, in that each new mutation arose within a given haplotype background, and some of its descendants' copies were, in turn, modified by subsequent mutations. Thus, the CCR5 sequences in a population probably constitute a hierarchically structured group of sequences, or alleles.

TABLE 1

Distribution and Relationship of CCR5-Δ32, CCR5-29G, CCR5-927T and CCR2-64I Alleles

|  | CCR5 | | CCR5 + 29 | | | CCR5 + 927 | | |
| --- | --- | --- | --- | --- | --- | --- | --- | --- |
|  | +/+ | +/Δ32 | A/A | A/G | G/G | C/C | C/T | T/T |
| CCR2-64 V/V | 732 | 106 | 673 | 157 | 9 | 790 | 46 | 1 |
| CCR2-64 V/I | 210 | 9 | 204 | 15 | 0 | 5 | 207 | 7 |
| CCR2-64 I/I | 20 | 0 | 20 | 0 | 0 | 0 | 0 | 20 |
| CCR5 +/+ |  |  | 887 | 76 | 1 | 691 | 244 | 28 |
| CCR5 +/Δ32 |  |  | 12 | 96 | 8 | 105 | 9 | 0 |

Proportions were compared with Chi-square test. "CI" indicates 95% confidence interval limits and "RH" denotes relative hazard.

C. Results

1. Evolutionary Relationships of Phenotypically Important CCR5 Alleles

To examine the relationship between polymorphic CCR5 regulatory sequences and the CCR2-V64I (CCR2-64I allele) or the CCR5-Δ32 polymorphism, CCR5 alleles derived from individuals with the CCR5/CCR5, CCR5/CCR5-Δ32, CCR2/CCR2 and 64I/64I genotypes were sequenced. CCR5 numbering is based on GenBank Accession numbers AF031236 and AF031237. Sequence analysis revealed several novel polymorphisms in the 5'-flanking regions, including a possible association between CCR5-A29G and CCR5-C927T and the CCR5-Δ32 and CCR2-64I alleles, respectively. These four polymorphisms appeared to be associated with CCR5-627C.

To extend these results, and to categorize the CCR5 alleles into specific haplotypes, PCR and PCR/RFLP assays were used to examine the frequency of these five genetic markers in this cohort. The genotyping data (Table 1) allowed the creation of a hypothetical evolutionary tree of the CCR5 locus as well as a dendrogram with CCR5-927 as the node, and together they highlight the following structural and evolutionary relationships among the different CCR2 and CCR5 alleles. 1) The CCR2-64I allele and the CCR5-C927T polymorphisms co-segregate. However, in contrast to a recent report (Kostrikis et al., 1998), the association between CCR5-927T and the CCR2-64I allele was not absolute: CCR5-927T-bearing alleles are associated with wild type (wt) CCR2 as well as CCR2-64I, and conversely, five CCR2-64I bearing alleles lacked the CCR5-C927T polymorphism. 2) The CCR5-Δ32 polymorphism is tightly linked to a mutation in the CCR5 promoter (A29G). The CCR5-29G allele may have evolutionarily antedated the phenotypically important Δ32 defect since the prevalence of the CCR5-29G allele is greater than that for the CCR5-Δ32 allele; eight of the nine individuals homozygous for the CCR5-29G allele also carried the Δ32

2. The CCR5-29G and CCR5-927T Alleles are Characterized by an Invariant Constellation of Regulatory Sequences As the CCR5 promoter is highly polymorphic, the dendrogram might not accurately reflect the genetic diversity in CCR5 regulatory regions, which would limit the ability to investigate the influence of CCR5 promoter variations on the clinical course of HIV-1. Therefore, an extensive inventory of CCR5 5'-flanking sequences derived from alleles representative of the major branches of this dendrogram was generated. In the region spanning CCR5 +1 to +981 six highly variable positions were identified. Additional nucleotide variations were evident among the alleles in this and other 5'-flanking regions. Nevertheless, by focusing on these six variable positions, the evolutionary relatedness among the alleles/haplotypes became apparent. At these six positions the CCR5-927C-bearing alleles exhibited extensive heterogeneity whereas the nucleotide sequences in all CCR5-927T and CCR5-29G alleles sequenced were invariant. Hence, despite the existence of a large assortment of CCR5 haplotypes, varying sometimes by a single or a few nucleotides, a phenotypically (HIV-1 disease-modifying) important CCR5 allele is likely to be embedded within a distinct haplotype that descended from a specific ancestral mutation. Thus, instead of investigating the disease-modifying effects of each CCR5 promoter polymorphism individually, the phenotypic effects of several CCR5 alleles that together share some mutations but are diverse for others were examined.

3. Racial Distribution of Evolutionarily-Related CCR5 Alleles

If CCR5 alleles have a hierarchical, or cladistic, history-dependent structure, then their racial distribution may reflect the specific evolutionary relationships and selective pressures among the observed alleles. To this end, the genotype frequencies of each of the polymorphisms studied were in Hardy-Weinberg equilibrium (P>0.05), and the allelic frequencies in the different racial groups for the CCR2-64I and CCR5-Δ32 alleles mirrored those of the CCR5-927T and CCR5-29G alleles, respectively (Table 2). The CCR5-29G and CCR5-Δ32 alleles were more prevalent in Caucasians (0.11 and 0.08) than in African Americans (0.06 and 0.02), or Hispanics (0.04 and 0.03). In contrast, the allelic frequencies of the CCR5-927T and CCR2-64I alleles were greater in African Americans (0.20 and 0.15) and Hispanics (0.17 and 0.14), than in Caucasians (0.10 and 0.09). The allelic frequencies of CCR2-64I and CCR5-Δ32 alleles are consistent with those of previous reports (Dean et al., 1996; Zimmerman et al., 1997; Huang et al., 1996; Smith et al., 1997).

TABLE 2

Racial Distribution of Different CCR2, CCR5 and SDF Genotypes

| Genotype | | Caucasian | Afr. Amer. | Hispanic | Other |
|---|---|---|---|---|---|
| CCR2-64 | V/V | 479 (82.7) | 288 (72.5) | 52 (74.3) | 20 (62.5) |
|  | V/I | 95 (16.4) | 96 (24.4) | 16 (22.9) | 12 (37.5) |
|  | I/I | 5 (0.86) | 13 (3.3) | 2 (2.9) | 0 |
| CCR5 + 29 | A/A | 459 (79) | 353 (88.5) | 64 (91.4) | 25 (78.1) |
|  | A/G | 113 (19.5) | 46 (11.5) | 6 (8.6) | 7 (21.9) |
|  | G/G | 9 (1.6) | 0 | 0 | 0 |
| CCR5 + 927 | C/C | 471 (81.4) | 261 (65.6) | 48 (68.8) | 18 (56.3) |
|  | C/T | 103 (17.8) | 116 (29.2) | 20 (28.6) | 14 (43.8) |
|  | T/T | 5 (0.86) | 21 (5.3) | 2 (2.9) | 0 |
| CCR5 | wt/wt | 490 (84.5) | 380 (95.5) | 66 (94.3) | 28 (87.5) |
|  | wt/D32 | 90 (15.5) | 18 (4.5) | 4 (5.7) | 4 (12.5) |
| SDF-1-3'A | G/G | 354 (61.1) | 338 (84.9) | 45 (64.3) | 17 (53.1) |
|  | G/A | 197 (34) | 58 (14.6) | 22 (31.4) | 13 (40.6) |
|  | A/A | 28 (4.8) | 2 (0.5) | 3 (4.3) | 2 (6.25) |

In each case, the differences in allelic frequencies between Caucasians and African Americans for these two sets of alleles were highly significant (P<0.0001), suggesting that the evolutionary history of CCR5-927T and CCR2-64I may be distinct from that of the CCR5-29G and CCR5-Δ32 alleles. Further support for this concept comes from the finding that only nine individuals in the entire cohort had both the CCR2-64I and CCR5-Δ32 alleles (Table 1), suggesting that these mutations occurred in the context of different chromosomal backgrounds.

4. Contrasting Effects of CCR5-927T Alleles Linked to CCR2-64I and wtCCR2

Whether the clinical course of HIV infection in individuals homozygous or heterozygous for the CCR5-927T allele, regardless of its CCR2 affiliation, differed from the course in those who were homozygous for CCR5-927C was evaluated. Kaplan-Meier (KM) analyses revealed that individuals possessing a CCR5-927T allele progressed to AIDS or death more slowly compared to individuals homozygous for the CCR5-927C allele. These trends were significant for prolongation of survival in the cohort as a whole (RH=0.76; 95% CI=0.60-0.97; P=0.03) and for AIDS-free survival in seroconverters (RH=0.62; 95% CI=0.39-0.98; P=0.039), and approached significance for survival in seroconverters (RH=0.56; 95% CI=0.31-1.0; P=0.058) and AIDS-free survival in the whole cohort (RH=0.80; 95% CI=0.64-1.0; P=0.056).

Next, the disease-modifying effects of the two haplotypes associated with the CCR5-927Tallele were examined. By inspection of the KM curves, relative to the CCR5-927Talleles that were associated with CCR2-64I, those linked to wtCCR2 appeared to be associated with an accelerated progression to AIDS and death. This dissociation in disease-modifying effects of the two CCR5-927T haplotypes was best highlighted by differences in the median AIDS-free survival. In the entire cohort, it was 10.3, 7.5, and 6.7 years in individuals with the CCR2-64I/CCR5-927T, wtCCR2/CCR5-927C, and wtCCR2/CCR5-927T haplotypes, respectively. In seroconverters, it was 10.1 and 7.8 years in individuals with the wtCCR2/CCR5-927C and wtCCR2/CCR5-927T haplotypes, respectively (median time point was not reached for individuals possessing a CCR2-64I/CCR5-927T haplotype). Furthermore, by the log-rank test, the difference between the two CCR5-927T haplotypes for AIDS-free survival was highly significant in the entire group (RH=1.9; 95% CI=1.2-3.0; P=0.004) as well as in the seroconvertors (RH=3.6, 95% CI=1.4-9.3; P=0.004).

To address directly the independent effects of the CCR5-927T allele versus the CCR2-64I allele these two variables were evaluated together for seroconvertors in a proportional hazards model for time to AIDS diagnosis. No arbitrary assumptions were made with respect to the importance of either CCR2 or CCR5 in HIV-1 pathogenesis, allowing for a more unbiased assessment of the disease-modifying effects of the CCR2-64I and CCR2-927T alleles. In this model, the only resulting independent factor associated with significant disease-altering effects was the CCR2-64I allele (RH=0.31; 95% CI: 0.12-0.83; P=0.02). Furthermore, when adjusted for the protective effects of the CCR2-64I allele, the CCR5-927T allele appeared to be associated with a slightly accelerated course to AIDS as well as death in seroconverters (RH=1.41; 95% CI: 0.47-4.26; P=0.54).

5. CCR5 Expression Levels in Individuals with the CCR2-64I/64I Genotype

To test the hypothesis that the CCR2-64I polymorphism linked to specific CCR5 promoter sequences results in lower CCR5 expression levels, a small case-control study was conducted. When examined at a single time point in their clinical course no differences in CCR5 expression levels on CD45RO+ or CD4+ cells were observed between 20 CCR2-64I homozygotes and 39 wt/wt homozygotes (median values: CD45RO+ cells =14.5%; CD4+ cells 5%).

6. Effects of the CCR2-64I Allele is Most Prominent in African Americans

The CCR2-64I allele is associated with strong disease-retarding effects. Since there were balanced numbers of Caucasians and African Americans who possessed a CCR2-64I allele in this cohort (Table 2), the comparative protective effect of this allele in these two racial groups was examined. For African Americans, the KM curves for individuals who either possessed or lacked the CCR2-64I allele were significantly divergent. In Caucasians, in contrast, the KM curves for time to AIDS diagnosis (RH=0.67; 95% CI=0.65-1.27; P=0.91) and survival (RH=1.0; 95% CI=0.70-1.42; P=1.0) were virtually superimposable, indicating no demonstrable disease-retarding effect of the CCR2-64I allele in this racial group.

This unexpected result prompted the question of whether African American individuals homozygous for wtCCR2 have a different clinical course compared to Caucasians who are also homozygous for wtCCR2. By KM estimates, the AIDS-free and survival curves for individuals with the CCR2/CCR2 genotype revealed no differences when factored by race. In contrast, Caucasians and African Americans possessing a CCR2-64I allele had markedly different outcomes for both development of AIDS diagnosis and for survival.

The interaction effect of the CCR2-64I allele and race demonstrates a unique advantage in the allele-possessing African Americans relative to other groups. Similarly, in a univariate Cox model using an interaction variable for race and 64I allele possession, a difference between CCR2-64I allele-bearing African Americans versus all Caucasians (wt/wt and wt/64I) and African-American with the wt/wt genotype was apparent. In seroconvertors, the African-American CCR2-64I allele-bearing group had a relative hazard of 0.33 (95% CI: 0.13-0.80) for reaching an AIDS diagnosis, and 0.21 (95% CI: 0.05-0.84) for survival compared to the group comprised of African Americans possessing the CCR2/CCR2 genotype and all Caucasians.

7. Role of the CCR5-Δ32 and the Related CCR5-29G Allele in HIV-1 Disease

The time to AIDS or death in seroconverters or the cohort as a whole was similar between individuals heterozygous for the CCR5-Δ32 allele and those with the CCR5/CCR5 genotype. Comparable results were obtained for the CCR5-29G allele: the time to AIDS or death in seroconverters or the cohort as a whole was similar between individuals homozygous or heterozygous for the CCR5-29G allele and those with the CCR5-29A/CCR5-29A genotype. Since the CCR5-Δ32 allele is more prevalent in Caucasians, the KM curves of time to death or AIDS in this racial group were examined. Again, a protective role for this allele in delaying either of the two endpoints was not demonstrable.

Rates of change of CD4+ T lymphocyte counts were calculated by fitting a least-squares line through each patient's serial CD4 measurements. No significant difference in CD4 slope was evident between individuals with the CCR5/CCR5 and CCR5/Δ32 genotypes (P=0.89 for whole cohort, P=0.083 for seroconvertors; Mann Whitney U), nor were there differences in proportion of heterozygotes in CD4 slope quartiles (P=0.44, Chi-square) or deciles (P=0.17).

Inspection of the KM curves for time to AIDS in the cohort as a whole with the CCR5/Δ32 genotype suggests that there may be a small divergence during the first seven years of follow-up. Since, in three previous studies the effect of CCR5-Δ32 heterozygosity was transient (Meyer et al., 1997; Katzenstein et al., 1997; Eugen-Olsen et al., 1997), restricted to the initial few years after seroconversion, analyses were repeated with right-censoring of the data at 5, 7 and 9 years. However, no significant effect could be demonstrated either by log-rank, Breslow or Tarone-Ware tests. It is possible that a weak disease-retarding effect for the CCR5-29G and CCR5-Δ32 allele was masked by the strong protective effects of the CCR2-64I allele. When adjusted for the effects of the CCR2-64I allele, a weak protective effect of the CCR5-Δ32 as well as the CCR5-29G allele was demonstrable.

8. Homozygosity for the Mutant SDF Allele and Accelerated Disease Progression

The frequency of homozygosity for the SDF1-3'A allele was 3.2%, with higher rates in Caucasians (4.8%) than in African Americans (0.5%; p<0.0001; Table 2). These frequencies are in agreement with those of a recent report (Winkler et al., 1998). Clinical outcomes for wild type homozygotes and for heterozygotes were essentially identical, so these groups were combined for analysis. Individuals homozygous for the SDF1-3'A allele progressed to death significantly more rapidly compared to those who either lack this allele or are heterozygous for this allele. A similar trend that did not reach statistical significance was seen for the clinical endpoint of AIDS diagnosis. The median survival times in the total cohort for individuals with the SDF1 genotypes wt/wt, wt/3'A and 3'A/3'A were 9.1, 9.5 and 6.8 years, respectively. Similarly, individuals with 3'A/3'A genotype progressed to AIDS more rapidly, with median times of 8.0, 7.4 and 6.1 years, respectively. Stratification by race or by presence of a CCR2-64I allele or adjustment for the CCR2-64I allele showed similar results for both clinical outcomes.

9. Independence of Genotypic Variants in Predicting Outcome

The two genetic mutations with significant value in univariate tests, namely CCR2-64I and SDF1-3'A, were considered for entry into forward and backward stepwise models along with baseline CD4 count, CD4 rate-of change or slope, patient age at diagnosis, and gender. Separate analyses were performed with the whole cohort and with the seroconverting subset. While all of the models included baseline CD4 count, this analysis revealed that genotypic variants at the CCR2 and SDF loci were additive and significant in predicting clinical endpoints (Table 3). These genetic markers often forced other strong univariate predictors such as CD4 slope and age out of the model. These findings suggest that genetic variants allow for prognostication at an early stage of the disease.

TABLE 3

Multivariate Analysis of Factors Predicting Clinical Endpoints in HIV Infection

| Endpoint | Factor | RH[a] | CI[b] | Wald[c] | P |
|---|---|---|---|---|---|
| Survival-all | CD4 count | 0.9974 | 0.9969-0.9979 | 96.5 | <.0001 |
| | Age | 1.0409 | 1.0251-1.0569 | 26.3 | <.0001 |
| | SDF-3'A/3'A | 2.4373 | 1.4465-4.1070 | 11.2 | 0.0008 |
| Survival-sero-converters | CD4 count | 0.9984 | 0.9974-0.9994 | 9.8 | 0.0017 |
| | CD4 slope | 0.9987 | 0.9977-0.9996 | 7.1 | 0.0075 |
| | SDF | 3.7207 | 1.3260-10.4405 | 6.2 | 0.0126 |
| | CCR2-64I | 0.5006 | 0.2554-0.9812 | 4.1 | 0.0439 |
| AIDS-all | CD4 count | 0.9976 | 0.9971-0.9981 | 103.4 | <.0001 |
| | SDF | 1.9577 | 1.1661-3.2867 | 6.5 | 0.011 |
| | CCR2-64I | 0.7403 | 0.5755-0.9523 | 5.5 | 0.0192 |
| AIDS-sero-converters | CD4 count | 0.9982 | 0.9973-0.9990 | 19.2 | <.0001 |
| | CD4 slope | 0.9985 | 0.9978-0.9992 | 17.0 | <.0001 |
| | CCR2-64I | 0.5579 | 0.3316-0.9385 | 4.8 | 0.0279 |

[a]Relative Hazard
[b]95% Confidence Interval Limits
[c]Wald statistic for the Cox proportional hazards model D. Discussion An extinct (or as yet unidentified) microbe or other environmental pressures may have modified the human genome by selecting for genetic variants of the chemokine system. The extensive genetic diversity of the CCR2/CCR5 locus illustrated here is very reminiscent of the adaptation to malaria (Weatherall et al., 1997). In both cases phenotypic convergence (e.g., red cell distortion in malaria resistance or altered chemokine receptor levels in HIV-1 resistance) may be the result of genotypic divergence (e.g., diverse β-globin mutations, and CCR5-Δ32 and promoter polymorphisms). It is intriguing that analogous to the selection of specific globin alleles in malaria, the phenotypically important CCR2-64I mutation as well as the CCR5-Δ32 polymorphism occur predominantly on a CCR5-627C bearing allele.

This study also highlights that genotype-phenotype relationships of the chemokine system gene variants can be complex. Some of the genotype-phenotype relationships observed in this cohort are not in complete concordance with those described in several recent reports (Dean et al., 1996; Zimmermann et al., 1997; De Roda Husman et al., 1997; Michael et al., 1997a; Meyer et al., 1997; Katzenstein et al., 1997; Eugen-Olsen et al., 1997; Smith et al., 1997; Kostrikis et al., 1998; Winkler et al., 1998). One explanation to reconcile these differences is that the outcome of HIV is multifactorial and that the effect of a given disease-retarding/promoting gene variant will be modulated, depending on the overall constellation of genetic, viral and environmental factors operative in a particular individual at a particular point during HIV disease. Given the difficulty of accounting for the influence of many of these confounding factors, the magnitude of effect of a particular chemokine system gene variant in a complex infection such as HIV will often be modest, sometimes indistinguishable from background noise.

This study design incorporates several features that reduce the noise surrounding the signal (effect) of chemokine/coreceptor gene variants in HIV disease progression. (1) The sample size is large, and based at a single center. (2) Relative homogeneity of the cohort with regard to health status before seroconversion, general socioeconomic status, access to free health care and relatively uniform treatment patterns may contribute to reduction in confounding environmental variables. (3) Several allelic markers were tested, some of which demonstrated a significant disease-modifying effect, whereas others did not. Taken together, the very features that make these data robust, namely their derivation from a cohort whose characteristics may help mitigate gene-environment interactions, impose limitations regarding the applicability of these findings to certain specialized patient subsets. The inability to replicate the positive associations reported by others may reflect differences in cohort characteristics. It should also be noted that since the cohort is composed mainly of male subjects, these findings may not be generalizable to women with HIV infection.

Unexpectedly, in this cohort the disease-retarding effect of the CCR2-64I was apparent in African Americans, but not in Caucasians. This effect is pronounced since it accounts for the observed protective effect of this allele in the cohort as a whole, and when stratified by race. There is only one other study that has investigated the role of the CCR2-64I allele in African Americans (Smith et al., 1997). However, in contrast to these results, a protective role for the CCR2-64I allele in this multi-cohort study was not found in the cohort that contained the largest number of African Americans (Smith et al., 1997). Since this cohort had a short follow-up, conceivably with time a protective effect of the CCR2-64I allele may become apparent.

Given the prominent protective effect conferred by the CCR2-64I allele in African Americans, the absence of a demonstrable effect in Caucasians is puzzling. However, this observation must be viewed with great caution. Gene-gene and gene-environment interactions, unrecognized confounders, chance, and selection bias must be viewed as possible alternative explanations. Selection bias or chance seem unlikely to explain the null results. First, these data are derived from a prospective cohort of initially healthy individuals detected in a screening program, and second, the cohort includes similar numbers of CCR2-64I allele-bearing Caucasians and African Americans, potentially providing equal statistical power in both sub-groups (Table 2). Nevertheless, as with all studies that fail to reject the null hypothesis, it is always possible that in a cohort with a larger Caucasian sample size and/or a longer follow-up period a protective effect may become apparent.

Since the CCR2-V64I polymorphism represents a conservative change, it has been postulated that it is simply a marker for polymorphisms in other co-receptors such as CCR5. These data indicate that the CCR2-64I and CCR5-C927T polymorphisms are in disequilibrium. However, both KM and multivariate analysis indicate that CCR5-C927T is an imperfect marker for the protective effect of the CCR2-64I allele. Furthermore, despite the invariant nature of the regulatory sequences in the CCR5-927T allele, additional determinants either in CCR5 or other closely linked genes or in CCR2 itself, are required to explain the dissociation between the HIV-1 disease-modifying effects of the CCR2-64I/CCR5-927T and wtCCR2/CCR5-927T haplotypes. A valine to isoleucine substitution (or vice versa) is considered a conservative change and a priori would not be expected to substantially alter the properties of the protein. However, there are several examples in which this substitution can markedly alter the bioactivity of proteins (Dawson et al., 1996; Kurumbail et al., 1996) or even HIV (Wang et al., 1996). Whether deletion of a methylene group at position 64 in CCR2 also results in differences in HIV-receptor interactions in vivo is not known.

There is controversy as to the disease-modifying role of CCR5-Δ32 heterozygosity. In this study an association of prolonged AIDS-free survival and CCR5-Δ32 heterozygosity was not detected. The CCR5-Δ32 allele was shown to be tightly linked to a mutation in the CCR5 promoter (A29G). Despite this linkage and a higher allelic frequency than the CCR5-Δ32 allele, the CCR5-29G allele did not confer protection. However, after adjusting for the effects of the CCR2-64I allele, a statistically significant disease-retarding role for the CCR5-29G allele, and a weak role for the CCR5-Δ32 allele was demonstrable. A limited protective role of CCR5-Δ32 has also been observed in several other cohorts (Meyer et al., 1997; Katzenstein et al., 1997; Eugen-Olsen et al., 1997; Morawetz et al., 1997; Huang et al., 1996). Whether adjusting for the effect of the CCR2-64I allele will reveal a more prominent role for the CCR5-Δ32 allele in these cohorts is not known.

It has been postulated that since SDF-1 can inhibit CXCR4-HIV interactions (Bleul et al., 1996; Oberlin et al., 1996), a genetic basis for significant differences in SDF-1 protein levels could lead to differences in disease progression. In this cohort, contrary to a recent report (Winkler et al., 1998), the SDF1-3'A/3'A genotype was associated with an accelerated progression to death in both seroconverters and the cohort as a whole.

Example 5

CCR5 Evolution and Regulation in Primates

Implications for the Pathogenesis of HIV-1

Polymorphisms in CC chemokine receptor 5 (CCR5), the major co-receptor of HIV-1 and SIV, have a major influence on HIV-1 transmission and disease progression. The effects of these polymorphisms may, in part, account for the differential pathogenesis of HIV-1 (immunosuppression) and SIV (natural resistance) in humans and non-human primates, respectively. Thus, understanding the genetic basis underlying species-specific responses to HIV-1 and SIV could reveal new anti-HIV-1 therapeutic strategies for humans. To this end, the inventors compared CCR5 structure/evolution and regulation among humans, Apes, Old World Monkeys, and New World Monkeys. Phylogenetic analysis suggests that the rate of evolution differs between the CCR5 cis-regulatory region and the coding region. CCR5 cis-regulatory region sequence variation in humans was substantially higher than anticipated. This variation could be organized into seven evolutionarily distinct human haplogroups (HH) designated HHA, -B, -C, -D, -E, -F, and -G. HHA haplotypes were defined as ancestral to all other haplotypes by comparison to the CCR5 alleles of non-human primates. Different human and non-human CCR5 haplotypes were associated with differential transcriptional regulation, and various polymorphisms resulted in modified DNA-nuclear protein interactions. In some primates, mutations at exon-intron boundaries caused loss of expression of selected CCR5 mRNA isoforms or production of novel mRNA isoforms. These findings suggest that the human response to HIV-1 infection may have been driven, in part, by evolution of the elements controlling CCR5 transcription and translation.

A. Introduction

Simian immunodeficiency viruses (SIVs) comprise a large and genetically diverse group of lentiviruses that originated in sub-Saharan Africa (Allan, 1992; Hirsch et al., 1999; Gojobori et al., 1990). SIVs isolated from chimpanzees and mangabeys are very similar to human immunodeficiency virus (HIV)-1 and HIV-2, respectively (Gojobori et al., 1990; Gao et al., 1999; Hirsch et al., 1989; Li et al., 1989). This suggests that HIVs arose via cross-species transmission from non-human primate viral reservoirs. Yet, despite their common ancestry and close similarity, HIVs and SIVs differ significantly with regard to clinical disease and pathogenesis. Human infection with HIVs results in a progressive immunodeficiency syndrome, while African apes and monkeys infected with SIV exhibit no evidence of disease (Allan et al., 1990; Gardner and Luciw, 1989; Jolly et al., 1996). These differences in pathogenicity may be due, in part, to primate species-specific variation in the genes controlling the host response or expression of host HIV/SIV entry factors (Unutmaz et al., 1998). Thus, understanding the evolution of these genes in primates will be an important step towards identifying the molecular mechanisms underlying the response of primates to infections with SIVs and HIVs. In turn, this may illuminate potential strategies that could be used to mitigate or prevent infection with HIV-1.

Host genetic determinants of HIV-1 pathogenesis include polymorphisms in the open reading frame (ORF) and cis-regulatory region of CC chemokine receptor 5 (CCR5), a major co-receptor for the entry of HIV and SIV (Unutmaz et al., 1998), which may influence cell surface density of CCR5. For example, homozygosity for a 32-bp deletion in CCR5 ORF leads to loss of surface expression and profound resistance against HIV-1 infection (Liu et al., 1996). Similarly, a 24-bp deletion in the CCR5 ORF that was discovered in non-human primates might influence SIV pathogenesis (Chen et al., 1998). Thus, due to this close interaction with lentiviral lifecycle, CCR5 is an excellent candidate for exploring the genetic basis of differential pathogenesis of HIV and SIV.

The gene and RNA structure of CCR5 is complex. The inventors have demonstrated that alternative splicing in the 5'-untranslated regions (UTR) of CCR5 generates several distinct mRNA isoforms that are under the control of at least two distinct promoters (Example 3). Furthermore, the 5'-UTR of CCR5 is encompassed within the downstream CCR5 promoter that contains several polymorphisms that are associated with altered rates of HIV-1 disease progression (Example 4; McDermott et al., 1998; Martin et al., 1998). Thus, polymorphisms in the non-coding region of CCR5 could influence not only cis-trans interactions that impact on gene expression but also CCR5 mRNA stability and/or the efficiency of translation. The important role of CCR5 in HIV-1 and SIV pathogenesis and the influence of CCR5 polymorphisms on HIV-1 transmission and disease progression underlies the strategy to understand the genetic basis of differences in the pathogenesis of HIV-1 and SIVs.

Given the multiple levels at which CCR5 expression could be regulated, a comprehensive analysis was performed of the ORF, RNA structure and transcriptional regulatory units of CCR5 relative to four important events in human evolution (Goodman, 1999): the divergence of humans from great apes (chimpanzees and gorillas) at 6 Ma, from the orangutan lineage at 15 Ma, from the cercopithecoids [Old World monkeys (OWM)] at ~35 Ma, and from New World Monkey (NWM) at 50 Ma. Results from these analyses enabled the evolutionary framework needed to define the relationships among human CCR5 haplotypes that influence HIV-1 pathogenesis to be built. Additionally, the hypothesis that polymorphisms in the human and non-human primate CCR5 cis-regulatory region confer differences in transcriptional efficiencies and/or interact with different trans-acting factors was directly tested.

B. Materials and Methods

1. Primate CCR5 ORFs

The CCR5 ORF was PCR amplified with primers that flanked the human CCR5 ORF (5' GCGGCCGCTTATGCA-CAGGGTGGAACAAG 3' (forward; SEQ ID NO:44) and 5' TCTAGACCACTTGAGTCCGTGTCA 3' (reverse; SEQ ID NO:45)), cloned and sequenced on both strands from the following species: *Pongo pygmaeus* (orangutan), *Macaca fascicularis* (cynomolgus; crab-eating macaque), *Chlorocebus (Cercopithecus) aethiops sabaeus* (sabaeus) and *Lagothrix lagothricha* (woolly monkey). In addition, the following sequences (GenBank accession numbers in parenthesis) were available in GenBank and were used to construct the CCR5 ORF network: *Homo sapiens* (human; X91492), *Pan troglodytes* (chimpanzee; AF005663 and U89797); *Gorilla gorilla* AF005659); *Cercocebus torquatus atys* (sooty mangabey; AF051905); *M. fascicularis* (AF005660); *M. mulatta* (rhesus monkey; AF005662); *M. mulatta* (U96762); *Papio hamadryas hamadryas* (baboon; AF005658); and *P. hamadryas anubis* (AF023452).

2. Primate CCR5 Cis-Regulatory Region

CCR5 numbering is based on GenBank Accession numbers AF031236 and AF031237 (Example 3). The region corresponding to human CCR5 +1 to +927 was PCR amplified, cloned and sequenced on both strands from the following primates: *P. troglodytes* (n=4); *G. gorilla; P. pygmaeus; P. hamadryas anubis* (n=3); *M. mulatta* (n=2); *M. fascicularis; M. nemestrina* (pig-tailed macaque); *Cercocebus torquatus torquatus* (red-capped mangabey); *C. galeritus chrysogaster* (gold-bellied mangabey); *Colobus guereza kikuyuensis* (black & white colobus); *C. guereza kikuyuensis* (kikuyu colobus); *Cercopithecus petaurista* (spot-nosed guenon); *C. neglectus* (DeBrazza's monkey); *C. diana* (Diana guenon); *C. L'hoesti* (L'Hoest's monkey); *C. (Miopithecus) talapoin* (Talapoin); *C. (Erythrocebus) patas* (patas monkey); *Chlorocebus aethiops* (grivet; n=3); *C. sabaeus* (sabaeus; n=8); *C. pygerythrus* (vervet; n=3); *Presbytis (Trachypithecus) francoisi* (Francois langur); *Saguinus oedipus* (cotton-topped tamarin); *Callithrix jacchus* (marmoset); *Aotes trivirgalus* (owl monkey); *Ateles geoffroyi* (black-handed spider monkey); and *L. lagothricha*. A single allele per non-human primate was sequenced. In parenthesis is the number of different members of the given non-human species that were sequenced. For *Homo sapiens*, 60 alleles derived from individuals who were homozygous or heterozygous for 29A or 29G, 927T or 927C, 627C or 627T (Example 4) were sequenced. CCR5 promoter region from non-human primates was PCR amplified using the following primers: 5' CATAAA-GAACCTGAACTTGACC 3' (forward; SEQ ID NO:46) and 5' TAGAA TTTCTAATATAAAATTCTATTAACAT-ACTCGTGAACCACAAACGGTCTA 3' (reverse; SEQ ID NO:47). All sequence alignments are available at the web site http://ahujalab.uthscsa.edu.

3. Genotype Analysis of Non-Human Primates

Genotyping methods for CCR5-29A/G and CCR5-927C/T were as described above (Example 4). The genotyping at CCR5-208G/T was by the PCR-RFLP method (a BsmA1 site was introduced in one of the PCR primers). CCR5-303G/A position was genotyped by the presence or absence of a naturally-occurring Bsp1286I restriction site after PCR amplification. CCR5-627C/T was genotyped by PCR-RFLP (a HindIII site was introduced in one of the PCR primers). Detailed genotyping methods are provided below (Example 7).

4. 5'-RACE and Reverse Transcription and PCR (RT-PCR)

Total RNA from human and non-human primate peripheral blood mononuclear cells (PBMC) and human leukocyte subsets was extracted using Trizol reagent. 5' RACE was performed on a human leukocyte cDNA library (Clontech) using an exon 3 specific primer (5' GGGAACGGATGTCT-CAGCTCTTCT 3'; SEQ ID NO:48) according to the manufacturer's protocols. For RT-PCR, RNA was reverse transcribed using a CCR5 exon 4 specific oligonucleotide (5' ACCAAAGATGAAC ACCAGTGAGTAGAG 3'; SEQ ID NO:49) and the resulting cDNA was amplified using a forward primer derived from newly identified sequence of exon 1 (5' TGTCTTCTCAGCTCTGCTGAC 3'; SEQ ID NO:50) and a reverse primer derived from exon 4 (5' GCTCCGATG-TATAATAATTGATGT 3'; SEQ ID NO:51). The specificity of the products obtained from the PCR was further confirmed by performing a nested PCR. The sequences of the primers used in the nested PCR were 5' AATACTTGAGATTTTCA-GATG 3' (forward; SEQ ID NO:52) and 5' AGATTGG ACT-TGACACTTGATAATCCAT 3' (reverse; SEQ ID NO:53). All the RT-PCR reactions were run with a negative control that did not include any cDNA template.

5. Promoter Analysis

To study the differences between the CCR5 promoter activity of sabaeus monkey and that of humans, a series of chimeric firefly luciferase-CCR5 promoter constructs were constructed, from sabaeus (S1 to S5) and humans (H1-H5), in the promoterless pGL3Basic vector (Promega). A single sabaeus allele and an allele representative of CCR5 HHA were used to construct the reporter plasmids. The constructs were transfected into human embryonic kidney (HEK), human erythroleukemia (K562), and COS (African Green Monkey (AGM) kidney cells) cell lines and tested for luciferase reporter activity as described above (Example 3). To study differences in promoter activity exhibited by the cis-regulatory regions of human CCR5 haplotypes, the genomic region spanning +1 to +948 was PCR-amplified from alleles corresponding to HHA, HHC, HHE, HHF or HHG haplogroups and cloned into the pGL3Basic vector. Transfection into K562 and Jurkat cell lines, and the Dual Luciferase Assays were as described above (Example 3). For all promoter analysis, at least two different plasmid preparations were used, and the DNA in each plasmid preparation was quantified spectrophotometrically twice. The Wilcoxon signed-ranks test was used to compare the mean luciferase activity between homologous sabaeus and human promoter constructs. Statistical analysis to determine the differences in the mean luciferase activity among human CCR5 promoter alleles was by one-way ANOVA followed by the Scheffe's post-hoc test.

6. Electrophoretic Mobility Shift Assay (EMSA)

All cell lines were obtained from ATCC. Nuclear extracts were prepared from K562, THP-1 (human monocyte), Jurkat (human T-cells), COS cell lines according to standard protocols. EMSAs were with labeled double-stranded oligonucleotides that overlap the second gap (5' GTTTTCGTTTACG-GAGTAATATTG 3' (SEQ ID NO:54) for the sabaeus monkey and 5' GTTTCCGTTTACAGAGAACAATAAT ATTG 3' (SEQ ID NO:55) for human) and third gap (5' GTTCATGT-GTATGGGGAGTGGGATAGG 3' (SEQ ID NO:56) in sabaeus and 5' GCATCTGTGTGGGGGTTGGGGTGG-GATAGG 3' (SEQ ID NO:57) in humans). For competition experiments, unlabeled competitor oligonucleotides were incubated with the nuclear extracts for ten minutes on ice prior to addition of the labeled probe. The specificity of the binding reactions was confirmed by using non-specific double-stranded oligonucleotide competitors. To determine if the adenine to guanine polymorphism at human CCR5 position 29 or the cytosine to thymidine polymorphism at human CCR5-927 affects nuclear protein binding activity, sets of sense and antisense oligonucleotides (corresponding to human CCR5 +16 to +39 or CCR5 +911 to +940) were annealed, radiolabeled and tested in EMSAs. The sequences of the sense oligonucleotides used in EMSA were 5' ATCTG-GAGTGAAG(A/G)ATCCTGCCAC 3' (for human CCR5 29; SEQ ID NO:58) and 5' GGAAACCCATAGAAGA(C/T) ATTTGGCAAACAC 3' (for human CCR5 927; SEQ ID NO:59). A similar strategy was used to determine the nuclear factor binding properties conferred by the polymorphisms at human CCR5 208, 303, 627, 630, or 676. The sequences of the oligonucleotides that were used in gel mobility shift assays were 5' TTTAGACAACAGGTT(G/T)TTTCCGTT-TACAGAG 3' (for CCR5 208G/T; SEQ ID NO:60), 5' GTG-GAGAAAAAGGGG(G/A)CACAGGGTTAATGTG-3' (for CCR5 303G/A; SEQ ID NO:61), 5' AGCCCGTAAATAAAC (C/T)TT(C/T)AGACCAGAGAT CTAT 3' (for CCR5 627C/T and CCR5 630C/T; SEQ ID NO:62) and 5' AAGCT-CAA CTTAAAA(A/G)GAAGAACTGTTCTCT 3' (for CCR5 676A/G; SEQ ID NO:63).

7. Phylogenetic Analysis

Sequences were aligned using SEQUENCHER software package. Descriptive statistics were obtained using ARLE-QUIN software (Schneider et al., 1997). Mean nucleotide diversity within populations was estimated using the equation, $\pi=(n/n-1) x_i x_j \pi_{ij}$, where n is the number of DNA sequences examined, $x_i$ and $x_j$ are the population frequencies of the ith and jth type of DNA sequences, and $\pi_{ij}$ is the proportion nucleotides which differ between the ith and jth types of DNA sequence. Genetic distances between sequences were estimated using DNADIST of the PHYLIP software package (Felsenstein J. PHYLIP (phylogeny inference package), version 3.5c. Distributed by the author. Department of Genetics. University of Washington, Seattle (1993)) using Kimura's two-parameter model. The transition to transversion ratio was varied from 2:1 to 10,000:1, but had no substantial impact on the results. Distances between populations were estimated from distances between individuals using NEIDIST (Jorde et al., 1995). Relationships between lineages and/or populations were depicted as neighbor-joining networks (Saitou and Nei, 1987), using NEIGHBOR. Inferred branch lengths with negative values were converted to branches of length zero. The robustness of branches was assessed by using bootstrap data sets obtained using SEQ-BOOT. Parsimony networks were constructed using DNA-PARS. Neighbor-joining and parsimony trees were condensed using CONSENSE. Networks were visualized using TREETOOL. Estimates of the rates of nonsynonymous (dN) and synonymous (dS) substitutions for all pairwise comparisons were calculated using the method of Nei and Gojobori (1986) as implemented in the PAML package (Yang, 1997).

C. Results

1. Molecular Evolution of the CCR5 ORF in Primates

Comparison of the complete CCR5 ORF from 15 different primates revealed that the nucleotide sequence and amino acid identity of CCR5 were highly conserved (species list in Materials and Methods section). Of the variable sites, 110 were single nucleotide polymorphisms (SNPs) including 91 transitions and 28 transversions. No insertion or deletion variants were found. Chimpanzee and human CCR5 ORFs differed at 5 sites, one of which produces a non-synonymous substitution. Levels of total nucleotide diversity substantially differed among hominoids, OWM, and NWM. For all primates, the mean nucleotide diversity of the CCR5 ORF was 0.014 (~1 variant in every 70 bp). Nucleotide diversity in hominoids (0.007) and OWM (0.006) was approximately half of that found within the total primate group.

In coding regions, mutation and selection are expected to have different effects on nonsynonymous (dN) and synonymous (dS) nucleotide substitutions. Consequently, comparisons of the rate of nonsynonymous to synonymous substitutions (dN/dS) can be utilized to explore molecular sequence evolution (Yang and Nielsen, 1998). Neutral theory predicts that despite varying mutation rates between lineages, dN/dS should remain constant among lineages. Thus, variation of dN/dS among lineages is considered evidence against neutrality, and dN/dS ratios >1.0 are strong evidence for positive selection (Messier and Stewart, 1997).

Pairwise maximum likelihood estimates of dN/dS among primate CCR5 ORFs were consistently <1.0. However, estimation of dN/dS for each of the functional domains of CCR5 (i.e., $NH_2$-terminus, extra-cellular loops, intracellular tail) revealed an interesting trend. Pairwise estimates of dN/dS among hominoids and NWM, for the sequence encoding the $NH_2$-terminus and second extra-cellular loop, were consistently >1.0. These findings suggested that the effects of natural selection might vary among specific domains of CCR5. Moreover, these results indicated that substitutions in the $NH_2$-terminus and second extra-cellular loop may underlie a selective response to the pathogens after the NWM and Catarrhines split. This was consistent with the finding that the bulk of polymorphisms in the human CCR5 ORF have been found in the $NH_2$-terminus and the only known naturally occurring amino acid substitution in an extracellular loop occurs in the second extracellular loop (Carrington et al., 1997).

Phylogenetic reconstruction of the genetic affinities among hominoids, OWM, and NWM demonstrated that NWM were substantially more divergent from either hominoids or OWM. That is, the genetic distance between NWM and hominoids (0.068) or NWM and OWM (0.073) was more than 4 times the genetic distance between hominoids and OWM (0.016). These findings were consistent with estimates of genetic divergence among these groups based upon analysis of morphological and neutral genetic markers (Goodman et al., 1998). Thus, despite the different roles that CCR5 may have played in mediating responses to pathogens (e.g., SIV and HIV-1) among OWM and hominoids, sequence encoding the structural region of CCR5 has been conserved since their divergence more than 50 million years ago (Takahata and Satta, 1997). Overall these data suggest that the expression of CCR5 among OWM and hominoids is more likely to be controlled by factors that regulate CCR5 transcription, mRNA processing, and/or translation. For this reason, the nature of variation in the mRNA structure and cis-regulatory region of CCR5 in NWM, OWM, and hominoids was studied.

2. CCR5 mRNA Splicing Patterns in Primates

Two full-length CCR5 mRNA transcripts (CCR5A and CCR5B) arise by alternative splicing of four exons. Several truncated transcripts can also originate in either exon 2 or exon 3 of CCR5. Using 5'-RACE on a human leukocyte cDNA library, the known CCR5 mRNA sequence was extended by 141 additional nucleotides. This new exon 1 sequence was subsequently found in different human leukocyte subsets as well as in mononuclear cells of several non-human primate species.

Comparison of the genomic DNA sequence extending from exon 1 through exon 3 among non-human primates and RNA transcripts in mononuclear cells derived from chimpanzees, rhesus macaque, cynomolgus macaque, and African Green monkey (AGM sabaeus) revealed the following. First, the exon-intron splice donor and acceptor sites were conserved between humans and orangutan, gorilla, langur and NWM. Second, the CCR5 mRNA structure in primates was highly dependent on the nature of the sequences that flank the exon-intron boundaries. For example, mutations in the exon-intron splice acceptor donor sites lead to loss of expression of selective CCR5 mRNA isoforms in different non-human primates. Alternatively, usage of a non-canonical splice donor site in exon 1 of sabaeus resulted in the expression of a novel mRNA isoform.

Despite these differences, it appears that the overall mRNA structure of CCR5 has been conserved for at least 35 million years, suggesting that the retention of this complicated RNA organization may have afforded a selective advantage.

3. Evolution of the Cis-Regulatory Region of CCR5 in Non-Human Primates

The region corresponding to human CCR5 +1 to +927 was sequenced from 60 humans and 43 non-human primates. The sequence of an allele corresponding to CCR5 human haplogroup A (HHA) was used for reference and the numbering was based on GenBank Accession numbers AF031236 and AF031237 (Example 3). Seven common polymorphic nucleotides identified in the CCR5 cis-regulatory region spanning from +1 to +927 were determined ("human polymorphisms:" +29, +208, +303, +627, +630, +676, +927).

Alignment of the nucleotide sequence of the cis-regulatory regions of CCR5 from non-human primates revealed high sequence conservation. Nevertheless, substantial intra- and inter-species sequence variation was observed. Compared to the human sequence one gap was required to align the sequence of the chimpanzee CCR5 cis-regulatory region and 6 gaps were inserted to align the OWM sequences; no gaps were required to align the gorilla and orangutan CCR5 promoter sequences.

Compared to the CCR5 ORF, the cis-regulatory region of CCR5 demonstrated substantially higher nucleotide sequence diversity. Of the polymorphic sites, 237 were SNPs including 177 transitions and 68 transversions. For all primates, the mean nucleotide diversity of the cis-regulatory region of CCR5 is 0.022, which is approximately 1 variant in every 45 bp. Mean nucleotide diversity is 0.007, 0.007, and 0.028 in hominoids, OWM, and NWM, respectively. The cis-regulatory regions of CCR5 in chimpanzee and human differed at 41 sites, including 8 fixed sites and 33 variable sites.

Genetic distances estimated from the cis-regulatory region of CCR5 of hominoids, OWM, and NWM indicated that hominoids were nearly equally divergent from OWM and NWM. That is, the genetic distance between hominoids and OWM (0.058) was comparable to the genetic distance between hominoids and NWM (0.067). This was in contrast to the closer affinity of hominoids and OWM as estimated from analysis of the CCR5 ORF. In other words, the genetic distance between OWM and NWM was similar regardless of whether the CCR5 ORF or CCR5 cis-regulatory regions were compared. These data suggested that the CCR5 cis-regulatory region of hominoids was substantially more divergent from OWM than is the CCR5 ORF. This underscores the potential role that natural selection may have played in shaping the genetic variation of the cis-regulatory region of hominoid CCR5.

4. Functional Effects of Variation in the CCR5 cis-Regulatory Region

The region encompassing human CCR5 +1 and +828 confers strong promoter activity in different cellular environments (Example 3; Guignard et al., 1998; Moriuchi et al., 1997; Liu et al., 1998). To determine if the homologous genomic region in AGM conferred similar or different promoter activities, the promoter strengths of various human and AGM constructs were tested in HEK, K562, and COS cell lines. Constructs that originated at +1, +192 and +487 had the highest transcriptional efficiency. Relative to human construct H2, the homologous cis-regulatory region in sabaeus (S2) had higher promoter activity in all three cellular environments tested, and S1 and S3 had higher promoter activity than H1 and H3, respectively, in COS cells.

To determine whether the gaps in AGM sequence (relative to humans) influence cis-trans interactions, the nuclear protein binding activity of radiolabeled double-stranded oligonucleotide probes that correspond to (1) human CCR5 sequences spanning the second and third gaps (oligonucleotides G2H and G3H respectively) and (2) the cognate sabaeus sequences (labeled G2S and G3S) were compared. An oligonucleotide corresponding to the human sequence spanning the second gap (G2H) bound two nuclear proteins, NF1 and NF2, in K562 and COS cells. In contrast, an oligonucleotide (G2S) corresponding to the homologous region in sabaeus did not bind to any nuclear proteins in K562 cells and bound only NF1 in COS cells. Competition assays performed in K562 cells demonstrated that the binding of NF1 and NF2 to G2H was specific. A similar result was observed with oligonucleotides that span the third gap (G3H and G3S). G3H bound specifically to a protein designated as NF3 in both K562 and COS cells. In contrast, the oligonucleotide corresponding to the AGM sequences (G3S) bound very weakly to NF3 in nuclear extracts from K562 cells but not COS cells.

5. Evolution of the Cis-Regulatory Region of CCR5 in Humans

Figure 1B:
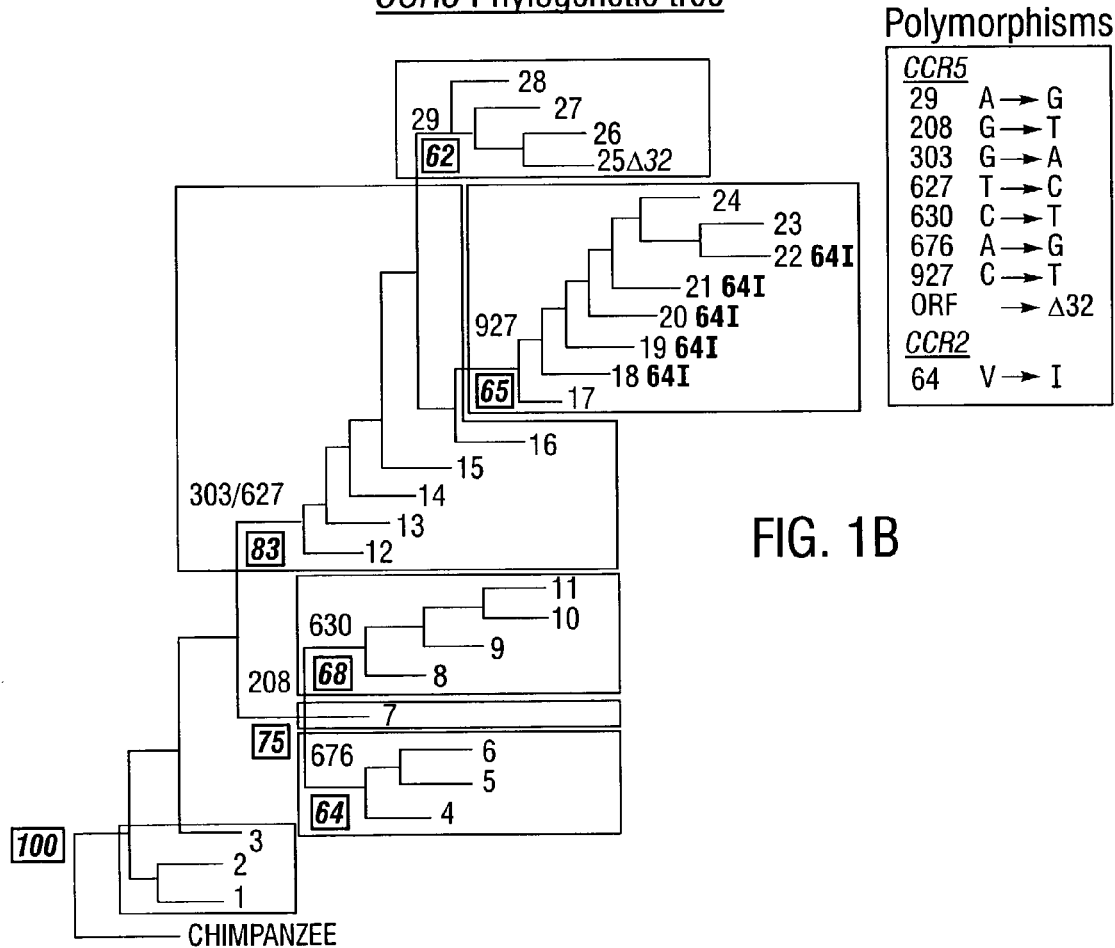

Sequence analysis of the cis-regulatory region (+1 to +927) of 60 human CCR5 alleles revealed a total of 32 variable sites that define 27 unique human haplotypes (FIG. 1A, FIG. 1B, FIG. 1C, FIG. 1D, FIG. 1E). An additional unique CCR5 haplotype was found by sequencing a genomic clone (GenBank Accession number AF009962). Sequencing of the homologous region from the 43 non-human primates and genotypic data from 40 additional non-human primates, including 23 chimpanzees enabled the CCR5 haplotype ancestral to humans to be defined. That is, the polarity (the ancestral-descendant relationship) of each nucleotide variant in the cis-regulatory region of human CCR5 was determined. In previous studies, seven common polymorphic sites were found in the region between CCR5 +1 to +927 (FIG. 1A; Examples 3 and 4). 29A, 208G, 303G, 627T, 630C, 676A, and 927C represented the ancestral state for these variable sites in human CCR5 (FIG. 1B and FIG. 1C). The nucleotide identity at each of these positions was invariant among Great Apes (except Gorilla which had a CCR5-630T), and OWM. This ancestral CCR5 haplotype was used to root a phylogenetic network depicting the evolutionary relationships among unique human CCR5 haplotypes (FIG. 1B).

Figure 1E:
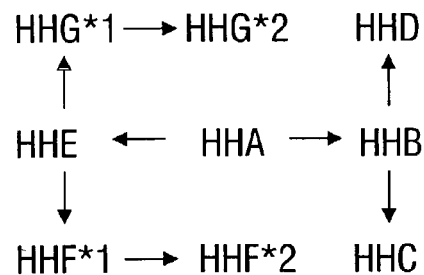

A phylogenetic network of unique CCR5 haplotypes provided the evolutionary framework for defining seven biologically distinct clusters of haplotypes that were designated as CCR5 human haplogroups (HH)-A, -B, -C, -D, -E, -F, and -G (FIG. 1D). HHA represented the ancestral CCR5 haplogroup. The haplogroups, HHC through HHG, were defined by at least one SNP. That is, SNPs 676G, 630T, 927T and 29G distinguish CCR5 HHC, HHD, HHF, and HHG, respectively. HHB haplotypes had a 208T mutation but lacked the 630T and 676G SNPs. An HHB haplotype is likely to be ancestral to HHC and HHD (FIG. 1E). SNPs 303A and 627C were in complete linkage disequilibrium. Alleles with 303A and 627C but lacking 29G or 927T defined HHE. The polymorphisms CCR5 29G, Δ32, 927T, and CCR2-64I defined the haplotypes that are descendants of ancestral haplotypes in HHE (FIG. 1E). The CCR2-64I and CCR5-Δ32 polymorphisms were found only on CCR5 haplotypes in haplogroups F (HHF*2) and G (HHG*2), respectively. To assess the robustness of each of the branches that define, in part, human CCR5 haplogroups, a bootstrap analysis was performed. Bootstrapping is a commonly used procedure for estimating the statistical significance of individual branches within a network. Each branch was observed in 60% or more of the networks generated (FIG. 1B). Collectively, these findings demonstrate that SNPs in CCR5 may have arisen by a nested mutational process and that this locus represents a complex multi-allelic system.

6. Functional Effects of Variation in a Cis-Regulatory Region of Human CCR5

Polymorphisms in the cis-regulatory region of humans substantially altered promoter and nuclear protein binding activity. That is, there was a significant difference among the luciferase activity of the five haplotype-specific promoter constructs tested, with the HHA-specific promoter construct demonstrating the least promoter activity. Next, it was determined whether SNPs at 29, 208, 303, 627, 630, 676 or 927 result in differential nuclear factor binding. Radiolabeled 29G oligonucleotide bound specifically to a nuclear factor designated as NF4 in nuclear extracts from K562, THP-1, and Jurkat cells. In contrast, the 29A oligonucleotide did not bind to NF4. Binding of NF4 to the radiolabeled 29G oligonucleotide was competitively blocked by increasing concentrations of unlabeled 29G and 29A oligonucleotide (29G>>>29A), but not by two non-specific (NS) oligonucleotides.

Radiolabeled 927C oligonucleotide bound specifically to two nuclear factors (NF5 and NF6). The 927T oligonucleotide did not bind to NF6 but could bind to NF5. Increasing concentrations of unlabeled 927C oligonucleotide competed for the binding of NF5 and NF6 to the radiolabeled 927C probe. In contrast, increasing concentrations of the 927T oligonucleotide competed for the binding of NF5, but not NF6 to the radiolabeled 927C oligonucleotide. Two non-homologous unlabeled oligonucleotides also failed to disrupt the interactions between radiolabeled 927C oligonucleotide and NF5 and NF6. Collectively these findings demonstrated that SNPs in CCR5 might result in the loss of binding of a nuclear protein(s) or the binding of novel nuclear factors to polymorphic SNPs. In nuclear extracts derived from K562, differential nuclear factor binding patterns were not observed with oligonucleotides spanning the 208, 303, 627, 630 or 676 SNPs. It is conceivable that nuclear extracts derived from other cellular environments or different oligonucleotides spanning these SNPs may reveal evidence of differential nuclear factor binding patterns or altered affinity to trans-acting factors (Bream et al., 1999).

7. Comparative Genomics and Evolution of Primate CCR5

There has been substantial effort to understand the evolution of HIV and SIV. However, there is little information about the evolution or even inter-species variation of the host determinants of HIV-1 and SIV pathogenicity. It has been demonstrated that polymorphisms in the ORF and 5' cis-regulatory region of CCR5 are associated with inter-individual and inter-population differences in susceptibility to HIV-1 and rate of disease progression (Examples 4 and 7; McDermott et al., 1998; Martin et al., 1998; Dean et al., 1996; Huang et al., 1996; Michael et al., 1997a; 1997b; Zimmerman et al., 1997; Kostrikis et al., 1998). These polymorphisms regulate, in part, the expression of CCR5. Yet, it has been unclear whether the varied regulation of CCR5 transcription and translation is a novel human response or a general strategy of many primates to infection with SIVs. Specifically, could unique polymorphisms in non-human primate CCR5 be responsible for the diminished pathogenicity of SIVs. If so, could these polymorphisms highlight potentially effective molecular strategies by which HIV-1 infections in humans could be prevented or attenuated.

The ORF and the cis-regulatory region of human CCR5 exhibited a higher nucleotide variability than average reported values (Li and Sadler, 1991) and variation in CCR5 was clearly higher than has been commonly appreciated (McDermott et al., 1998; Martin et al., 1998). Moreover, the ascertainment bias introduced by the initial sampling of individuals homozygous for different CCR5 SNPs suggested that the estimate of sequence diversity is conservative. Inter-species CCR5 sequence differences can be used to estimate the affinities of different primates to one another. The genetic distance between OWM and hominoids estimated from the CCR5 cis-regulatory region was more than 4 times larger than the distance estimated from the CCR5 ORF. This may be the consequence of relaxed selection on a non-coding region of CCR5 versus the CCR5 ORF. Alternatively, this pattern may be due to selection for different polymorphisms in the CCR5 cis-regulatory region among OWM and hominoids. If the former is true, estimates of the genetic affinities among primate groups from the cis-regulatory region of CCR5 and the CCR5 ORF should be comparable. Only the genetic distance between OWM and hominoids should be different if the latter is true. Thus the results suggest that selection may be responsible, in part, for the variation observed in the cis-regulatory region of hominoid CCR5. These polymorphisms may have affected the transcriptional/translational activity of CCR5 permitting OWM and hominoids to modulate responses to different repertoires of pathogens.

Many of the non-synonymous substitutions in the CCR5 ORF were clustered in the region encoding the $NH_2$-terminus of CCR5. HIV-1 appears to interact via gp120 with the ligand-binding site of CCR5 and the $NH_2$-terminus of CCR5 determines, in part, the specificity of this binding (Dragic et al., 1998). A dN/dS of >1.0 for the $NH_2$-terminus of CCR5 suggested that positive selection may have had an important role in generating variation in this region of the CCR5 ORF in hominoids. Thus, certain amino acid substitutions in the $NH_2$-terminus of CCR5 may represent selection of variant phenotypes (and, hence genotypes) following interaction of hominoid ancestors with members of the lentivirus family. More importantly, these results indicate that the $NH_2$-terminus of CCR5 may be a preferred target for interventions to prevent HIV-1 entry into human macrophages. Nevertheless, the bulk of polymorphisms in CCR5 were found in the cis-regulatory regions. Thus, it is important that this variation be organized in such a manner as to be useful for understanding the effect of these polymorphisms on the pathogenesis of HIV-1. This was the logic behind organizing CCR5 cis-regulatory region haplotypes into a rooted phylogenetic network.

A limitation of previous attempts to understand the organization of human CCR5 haplotypes has been a lack of an appropriate outgroup to root the ancestral CCR5 haplotype. Here, the ancestral CCR5 haplotype was established, and this information was used to create a framework for a biologically based classification and nomenclature of human CCR5 haplotypes. The organization of the complex patterns of CCR5 polymorphisms into evolutionarily meaningful relationships has at least three merits. First, it provides a framework for understanding the association between different CCR5 haplotypes and HIV-1 disease progression or transmission. Because of extensive sequence variation, comprehensive genotyping of each individual for every CCR5 polymorphism would be costly, labor-intensive, and inefficient. In contrast, a phylogenetic network of CCR5 haplotypes forms a basis for grouping CCR5 haplotypes whose relationships to each other can be defined unambiguously by a single or few polymorphisms. This forms the rationale for grouping CCR5 haplotypes that are closely related to each other (e.g., all descendants of a shared ancestral haplotype). For example, all alleles that are characterized by the 29G polymorphism but lack the CCR5 Δ32 mutation can be grouped into HHG*1. Although CCR2-64I is nearly always in linkage disequilibrium with CCR5 927T, the converse is not always true (FIG. 1A, FIG. 1B, FIG. 1C, FIG. 1D, FIG. 1E; Examples 4 and 7). FIG. 1A, FIG. 1B, FIG. 1C, FIG. 1D and FIG. 1E show that a small subset of CCR5 927T-bearing alleles lack CCR2-64I and are classified as HHF*1. By extensive genotyping of human subjects, the prevalence of HHF*1 alleles in world-wide populations was found to vary from ~1-12% (Examples 4 and 7). Martin et al have confirmed the existence of CCR5 alleles that lacked the CCR2 64I polymorphism but that had the CCR5 927T polymorphism, i.e., presumably HHF*1 alleles and found that the prevalence of this allele to be approximately 7% (Martin et al. 1998).

The phylogenetic network of CCR5 haplotypes also helps to lessen haplogroup misclassification and facilitates genotype-phenotype analyses. For example, McDermott et al reported recently that the 303A allele was associated with higher transcriptional efficiency, and that homozygosity for this allele was associated with accelerated disease progression (McDermott et al., 1998). Similarly, homozygosity for another allele designated as the P1 allele was also shown to be associated with disease progression (Martin et al., 1998). However, the data presented in this Example demonstrate that these two alleles (P1 or 303A) are a mixture of at least three haplogroups that share 303A and 627C(HHE, HHF*1, and HHG*1). Based on sequence data from +208 to +811, Martin et al described 9 additional CCR5 alleles designated as P2-P10 (Martin et al., 1998). The data presented in this Example suggests that P2, P3, and P4 represent alleles that correspond to alleles within HHA, HHD, and HHC, respectively, and that alleles labeled as P5-P10 are likely to correspond to alleles within HHA, HHC or HHD. Thus, the organization of CCR5 haplotypes into an evolutionary framework minimizes the confounding that occurs by mixing SNPs and/or haplotypes with different evolutionary and phenotypic effects.

Second, this classification enabled the study of the basis for the distribution of CCR5 haplotypes among contemporary human populations. For example, the allele frequency of the ancestral CCR5 haplotype (HHA) is higher in individuals of African descent (>0.20) than Caucasians (~0.09), and peaks in African Pygmies (0.71) in whom the prevalence of HIV-1 infection appears to be very low (Example 7). Although no evidence was found that HHA affords resistance to infection, this haplotype was associated with HIV-1 disease-retardation in African Americans but not in Caucasians. Determining the biological basis for the varied frequencies of CCR5 haplotypes among populations is important in evaluating differences in susceptibility and disease progression among these groups. It should be noted that the phylogenetic network presented in this study is a relatively robust and objective depiction of the relationships among the polymorphisms in an important cis-regulatory region of CCR5. As more sequence data is incorporated, the topology of some of the branches is likely to change, and these changes can be easily incorporated into this network.

The distribution and placement of CCR5 polymorphisms relative to one another in the network of haplotypes also facilitates investigation of the evolutionary forces that have driven these haplotypes to varying frequencies among different human populations. For example, population-specific deleterious or protective mutations (e.g., Δ32) that were found near the tips of branches may have arisen more recently than polymorphisms embedded deeper in the network. This suggests that: (1) SNPs at 29, 208, 303, 627, and 927 are older than the Δ32, 630T, 676G, and CCR2-V64I polymorphisms; (2) that CCR2-V64I predates the Δ32 mutation; and (3) contrary to previous assertions it is more likely that the ancestral state of the 303 residue is guanine and not adenine (McDermott et al., 1998).

The third advantage of organizing CCR5 variation into a phylogenetic network is that it increases the efficiency of identifying specific sequence motifs in the cis-regulatory region of CCR5 that might produce different effects in vitro. It is demonstrated herein that some of the mechanisms underlying the effects of different CCR5 haplotypes might include unique species-specific cis-trans interactions, differential transcriptional efficiency, and varied nuclear factor binding. Yet, it would be more difficult to interpret these findings if the ancestor-descendant relationships between polymorphisms were unknown. Promoter analysis of constructs spanning the major SNPs that distinguish CCR5 haplogroups demonstrate that nucleotide substitutions in the cis-regulatory regions of CCR5 produce differences in transcriptional activity. For example, in K562 cells, the ancestral HHA haplotype-promoter construct consistently demonstrated the lowest transcriptional activity while the transcriptional activity of HHF haplotypes was the highest of the haplogroup-specific constructs tested. Analysis of the association of CCR5 haplogroups and HIV-1 disease progression suggests that HHA and HHF*2 haplotypes are both associated with HIV-1 disease retardation (Example 7). This suggests that correlating in vitro findings of differences in haplotype-specific transcriptional efficiencies to differences in the surface expression of CCR5 and/or the disease-modifying effects of CCR5 haplotypes may be difficult.

The present findings also indicate that the interaction between trans-acting factors and disease-modifying cis-acting mutations may influence HIV-1 disease susceptibility. Differences in DNA-protein interactions at polymorphic nucleotide sites have been previously suggested to influence other infectious disease states. For example, Knight et al demonstrated recently that a polymorphism that affects OCT-1 binding to the tumor necrosis factor promoter region is associated with severe malaria (Knight et al., 1999). Thus, identification of the nuclear factors that bind to polymorphic CCR5 cis-acting sites may aid in understanding the mechanisms underlying HIV-1 pathogenesis.

Novel human CCR5 mRNA sequences have been identified herein, and these sequences and the complex RNA structure of human CCR5 wee shown to be conserved in OWMs and apes. These findings support the hypothesis that both different CCR5 mRNA isoforms and polymorphisms in the distinct 5'-UTRs that compose these RNA species might influence CCR5 cell surface expression by regulating gene expression at a post-transcriptional level. Alternatively, distinct secondary structures such as stem loops could increase or decrease the levels of coding mRNA, leading to the modulation of subclasses of CCR5 RNA isoforms.

Simian immunodeficiency viruses in their natural host African primate have most likely arisen through co-evolution with their respective host suggesting a long period of adaptive evolution (Allan et al., 1991; Fomsgaard et al., 1991). For sooty mangabeys and AGMs including sabaeus monkeys, a lack of pathogenicity has been associated with an overall lower viral burden in peripheral blood cells as compared to HIV infected humans (Rey-Cuille et al., 1998). However, high plasma viremias are maintained in these monkeys in spite of significantly fewer infected cells suggesting fundamental differences in host virus dynamics. In part, these differences may result from subtle differences in the levels of expression of co-receptors including CCR5. While CCR5 appears to be the main co-receptor used by a variety of SIVs and HIV, other co-receptor usage could also be modulated in the natural host (Edinger et al., 1998; Deng et al., 1997). The present data would support the notion that differences in mRNA isoforms and importantly differences in regulatory regions might result in subtle differences in expression and possibly tissue tropism for SIVs, leading to overall fewer infected cells and hence a non-pathogenic state. Furthermore, the present data also emphasize an important role for generating and maintaining polymorphisms in the regulatory regions and 5'-UTR of CCR5. These polymorphisms and the trans-acting nuclear factors that bind them are likely to be important determinants in HIV and SIV pathogenesis.

Example 6

CCR5 Haplotypes Associated with Altered Rates of Mother-to-Child Transmission of HIV-1 and Progression to Disease in Infected Children Genetic variation in CC chemokine receptor 5 (CCR5), the major co-receptor for HIV-1 cell entry, has been associated with differences in susceptibility to infection by HIV-1 as well as progression to disease in adults. However, it has been difficult to generalize these results among different populations, in part, because it is challenging to find genetically well-defined and matched control subjects with comparable levels of risk exposure, or infected cohorts with similar modes of transmission and well-defined estimates of time of transmission. Comparison of CCR5 haplotype frequencies between perinatally-exposed infected and uninfected children overcomes these challenges and thus may be a better model for studying the genetic determinants of HIV-1 transmission and pathogenesis. Using an evolutionary-based classification of CCR5 haplotypes that stratifies CCR5 haplotypes into 7 human haplogroups (i.e., HHA→HHG), the inventors genotyped 649 Argentinean children exposed perinatally to HIV-1. Possession of an HHE allele was associated with a significantly higher risk of acquiring HIV-1 from an infected mother as well as progressing to AIDS. Five haplotype pairs influenced the risk of vertical transmission, including three HHE-containing haplotype pairs that were associated with increased susceptibility. Pairing of the CCR5-Δ32 allele (HHG*2) with HHC was associated with a reduced risk of transmission whereas the haplotype pair HHE/HHG*2 was associated with a nearly 6-fold higher likelihood of acquiring HIV-1, highlighting the importance of CCR5 allele-allele interactions. A subset of the haplotype pairs associated with altered rates of transmission and course of disease in children was similar to those that influenced disease progression in HIV-1 infected adults. Thus, genetic variation in CCR5 is a powerful determinant of susceptibility to HIV-1 infection, and a common CD4/CCR5-dependent mechanism influences both HIV-1 transmission and progression to disease.

A. Introduction

There is growing appreciation that inter-individual and inter-population variation in the host response to infectious diseases is, in part, genetically determined (Shearer and Clerici, 1996). For example, all individuals are not equally susceptible to infection with HIV-1: occasional hosts resist HIV-1 infection, and after infection has occurred, there is substantial variation in the rate of progression to AIDS even in individuals receiving the same contaminated blood products (Shearer and Clerici, 1996; Fowke et al., 1996; Liu et al., 1997; Dragic et al., 1996; Zimmerman et al., 1997; Dean et al., 1996; Zagury et al., 1998). The precise contribution of most host genetic factors to the variability of HIV-1 transmission rates and/or disease progression is unknown, but a better understanding could provide novel approaches for prevention and treatment, and an improved understanding of HIV pathogenesis.

Recent studies in adults infected with HIV-1 indicate that genetic variation in CC chemokine receptor 5 (CCR5), the major co-receptor for HIV-1 entry, is associated with inter-individual and inter-population differences in HIV-1 transmission and disease progression (Examples 4 and 7; Zimmerman et al., 1997; Dean et al., 1996; McDermott et al., 1998; Martin et al., 1998; van Rij et al., 1998; Huang et al., 1996; Michael et al., 1997; Smith et al., 1997; Kostrikis et al., 1998; Rizzardi et al., 1998; Samson et al., 1996; Garred, 1998). For example, homozygosity for a 32-bp deletion in the coding region of CCR5 is the only known genotype to confer protection against HIV-1 infection. Heterozygosity for the CCR5-32 bp deletion (CCR5 Δ32) and the CCR2-64I polymorphism that is linked to the CCR5 927T allele have been associated with disease retardation. As described herein, using an evolutionary-based classification of CCR5 haplotypes, a large U.S. cohort composed of infected adults was genotyped, and several CCR5 haplotype pairs associated with altered rates of disease progression were identified (Example 7). In contrast, studies examining the association of CCR5 variation and vertical transmission or disease progression in infected children are few, and are limited to the effect of CCR5-Δ32 (Misrahi et al., 1998; Rousseau et al., 1997; Shearer et al., 1998; Mangano et al., 1998; Mandl et al., 1998; Philpott et al., 1999; Esposito et al., 1998).

Perinatally acquired HIV-1 infection (Peckham and Gibb, 1995) is an unfortunate, yet exceptionally valuable model to determine the host determinants of HIV-1 transmission and progression to disease. First, HIV-1 is transmitted to 13 to 48% of children born to infected mothers (The Working Group on Mother-To-Child Transmission of HIV, 1995), and thus the risk of mother-to-child transmission is very high. In contrast, the risk of HIV-1 transmission after a single sexual exposure, the most common mode of acquiring HIV-1, is significantly lower (~1.0 to 1%) (Royce et al., 1997). Second, the uninfected children of HIV-infected mothers who did not receive zidovudine (ZDV), a anti-retroviral drug known to reduce mother-to-child transmission (Sperling et al., 1996), are an ideal control population of high-risk exposed yet uninfected individuals, against which the infected HIV-1 infected cohort can be compared. Third, it is possible to make relatively precise estimates of the time of HIV-1 transmission, even in comparison to adult seroconverting cohorts. Finally, the course of disease in infected children is well studied: ~20% of the children progress rapidly to AIDS and die between the ages of 2 to 4, whereas, the majority progress more slowly, with a median survival time of 8 years (Blanche et al., 1997).

The susceptible cell types that HIV-1 uses during transmission from the mother to fetus/infant are not known although epithelial cells such as M cells and/or enterocytes have been suggested as plausible candidates (Van de Perre, 1999). In contrast, dendritic cells are generally involved in sexual and blood-borne transmission of HIV-1 (Royce et al., 1997). The inventors postulated that if there is a pathophysiological relationship that explains the association between CCR5 haplotypes and HIV-1 susceptibility, then the following two conditions should exist. First, the CCR5 haplotypes/haplotype pairs that influence mother-to-child transmission of HIV should be similar to those that affect progression to disease in perinatally infected children. Second, CCR5 haplotypes/haplotype pairs that influence HIV transmission and disease progression in children should be similar to those that are associated with altered rates of disease progression in adults. If both of these conditions were found to exist, it would suggest that the CCR5 haplotypes that influence transmission of HIV and progression to disease operate through interrelated mechanisms.

B. Methods

1. Patients

DNA was available from 649 children perinatally exposed to HIV-1 between 1986 and 1998 and prospectively followed at the Hospital de Pediatria "J. P. Garrahan" of Buenos Aires, Argentina. Of these, 347 were infected and 302 remained uninfected. HIV-1 infection status, AIDS definition and stage of immune suppression were established according to the 1994 criteria of the Centers for Disease Control and Prevention (CDC) classification for children (*MMWR Morb. Mortal Wkly Rep.,* 1994). The ZDV prophylaxis to mother-infant pairs was according to the ACTG 076 protocol (Sperling et al., 1996) and was considered complete in 110 (92 uninfected and 18 infected children), partial (mother or child) in 17 (2 uninfected and 15 infected) and absent in 466 (160 uninfected and 306 infected). For statistical analysis mother-infant pairs that received complete or partial therapy were pooled. Information regarding ZDV prophylaxis was unavailable in 56 mother-children pairs (48 uninfected and 8 infected). Since 1992, all infected children received anti-retroviral therapy according to the recommended guidelines (Center for Disease Control and Prevention, 1998). The median follow-up was 4.08 years. 55.6% of this cohort progressed to AIDS and 7.2% died during the study period which ended Jan. 1, 1999. Informed written consent was obtained from the parents or legal guardians for the study. It should be noted that the demographic history of Argentineans as a whole is different from other Latin American countries. The vast majority of Argentineans are descendants of individuals from southern Europe, primarily from Spain and Italy. There is little admixture of Amerindians and there is no black population.

Genotype-phenotype comparisons were made between the aforementioned pediatric cohort and adult patients with HIV-1 participating in the US Air Force portion of the Tri-Service HIV Natural History Study. The voluntary, fully informed consent of the subjects used in this research was obtained as required by Air Force Regulation (AFR) 169-9. A total of 1151 patients were evaluated, including 528 seroconvertors and 623 seroprevalent individuals. The demographic background of this cohort is 54% Caucasian, 37% African American, 6% Hispanic and 3% "other." Additional features of this cohort are described herein (Examples 4 and 7). In this study, only the disease-modifying effects of HHE were determined, and the disease modifying effects of the other alleles were determined as described herein below (Example 7).

2. Genotyping Analysis

CCR5 numbering is based on GenBank Accession numbers AF031236 and AF031237 (Example 3). The cohorts were genotyped for polymorphisms in the CCR2 ORF (position 190; CCR2-64I), the CCR5 cis-regulatory SNPs at 29, 208, 303 (only adult cohort), 627, 630, 676, 927 and the CCR5 ORF (Δ32) by a combination of PCR-restriction fragment length polymorphism (RFLP) and molecular beacon genotyping techniques as described herein (Example 7). In 1138 individuals, the 303G and 303A SNPs was found to be in nearly complete linkage disequilibrium with 627T and 627C, respectively (Example 7). For this reason, the haplotype analysis reported for the pediatric cohort was restricted to analysis of SNPs at CCR2-190, CCR5 29, 208, 627, 630, 676, 927, and the Δ32 polymorphism. The CCR5 haplotype classification, and the methods used for haplotype assignment and genotyping, were as described herein (Examples 5 and 7). In this classification system, CCR5 alleles are grouped into one of 7 human haplogroups (HH)-A, -B, -C, -D, -E, -F (F*1 and F*2), -G (G*1 and G*2). The genotypic characteristics of these haplogroups at the polymorphic positions CCR2-64I, and CCR5A29G, G208T, G303A, T627C, C630T, A676G, C927T and Δ32 [presence (+) or absence (−)] is as follows. For the ancestral CCR5 haplotype HHA it is: 64V, 29A, 208G, 303G, 627T, 630C, 676A, 927C, and −Δ32. Changes relative to HHA are in bold letters. For HHB: 64V, 29A, 208T, 303G, 627T, 630C, 676A, 927C, and −Δ32. For HHC: 64V, 29A, 208T, 303G, 627T, 630C, 676G, 927C, and −Δ32. For HHD: 64V, 29A, 208T, 303G, 627T, 630T, 676A, 927C, and −Δ32. For HHE: 64V, 29A, 208G, 303A, 627C, 630C, 676A, 927C, and −Δ32. For HHF*1: 64V, 29A, 208G, 303A, 627C, 630C, 676A, 927T, and −Δ32. For HHF*2: 64I, 29A, 208G, 303A, 627C, 630C, 676A, 927T, and −Δ32. For HHG*1: 64V, 29G, 208G, 303A, 627C, 630C, 676A, 927C, and −Δ32. For HHG*2: 64V, 29G, 208G, 303A, 627C, 630C, 676A, 927C, and +Δ32.

3. Statistical Analysis

Time curves for progression to AIDS (1994 criterion for children and 1987 criterion for adults) and survival was prepared by the Kaplan-Meier method using SAS. Between-group analyses were completed using the log-rank test. Relative hazards were calculated using univariate and multivariate Cox-proportional hazard models. CI indicates 95% confidence interval limits and RH denotes relative hazard. Logistic regression models were used to evaluate altered risk of transmission. The test of equivalence used was the Cochrane-Mantel-Haenzel test of association (Fleiss, 1981). This test evaluated the association of possession of HHE and progression to AIDS, after controlling for child/adult Hispanic American status.

C. Results

1. CCR5 Haplotypes in HIV-1 Transmission

In an adult cohort of HIV-1 seropositive individuals, 52 human CCR5 haplotype pairs were identified (Example 7). Of these, 33 CCR5 haplotype pairs were found in the children perinatally-exposed to HIV-1 (Table 4). Similar to Caucasians, but in contrast to African Americans (Example 7), the haplotype pairs HHC/HHE, HHC/HHC, and HHE/HHE were the three most common haplotype pairs found in uninfected and infected children, accounting for nearly 40% of all haplotype pairs (Table 4). The CCR5 alleles among the infected or uninfected groups remained the same regardless of prophylactic therapy with ZDV (Table 5). However, in the HIV-infected children, the allele frequency of HHE was significantly higher than in the uninfected children (P=0.003; Table 5), and possession of one or two HHE alleles was associated with up to a 2-fold increased risk of acquiring HIV-1 (P=0.007; Table 6).

TABLE 4

CCR5 Genotypes in Children Perinatally Exposed to HIV-1

| Genotype | Total | | No Prophylaxis[3] | | Prophylaxis[4] | |
|---|---|---|---|---|---|---|
| | I[1] | U[2] | I | U | I | U |
| A/A | 0 | 3 | 0 | 0 | 0 | 2 |
| A/B | 0 | 0 | 0 | 0 | 0 | 0 |
| A/C | 15 | 19 | 12 | 12 | 2 | 6 |
| A/D | 0 | 0 | 0 | 0 | 0 | 0 |
| A/E | 8 | 7 | 7 | 4 | 1 | 2 |
| A/F*1 | 2 | 4 | 2 | 1 | 0 | 2 |
| A/F*2 | 9 | 6 | 5 | 3 | 3 | 2 |
| A/G*1 | 2 | 2 | 2 | 2 | 0 | 0 |
| A/G*2 | 2 | 1 | 2 | 0 | 0 | 1 |
| B/C | 1 | 1 | 1 | 0 | 0 | 1 |
| B/D | 0 | 0 | 0 | 0 | 0 | 0 |
| B/E | 0 | 1 | 0 | 0 | 0 | 0 |
| C/C | 35 | 44 | 30 | 25 | 5 | 11 |
| C/D | 3 | 0 | 3 | 0 | 0 | 0 |
| C/E | 92 | 57 | 87 | 28 | 3 | 18 |
| C/F*1 | 12 | 4 | 9 | 3 | 3 | 1 |
| C/F*2 | 30 | 27 | 27 | 17 | 3 | 6 |
| C/G*1 | 11 | 17 | 9 | 9 | 2 | 6 |
| C/G*2 | 3 | 9 | 3 | 6 | 0 | 3 |
| D/D | 0 | 0 | 0 | 0 | 0 | 0 |
| D/E | 1 | 1 | 1 | 1 | 0 | 0 |
| D/F*1 | 0 | 0 | 0 | 0 | 0 | 0 |
| D/F*2 | 3 | 0 | 3 | 0 | 0 | 0 |
| D/G*1 | 0 | 0 | 0 | 0 | 0 | 0 |
| D/G*2 | 0 | 0 | 0 | 0 | 0 | 0 |
| E/E | 41 | 25 | 33 | 10 | 6 | 10 |
| E/F*1 | 8 | 9 | 6 | 6 | 0 | 3 |
| E/F*2 | 23 | 27 | 21 | 15 | 2 | 7 |
| E/G*1 | 14 | 8 | 14 | 3 | 0 | 5 |
| E/G*2 | 13 | 3 | 11 | 1 | 2 | 2 |
| F*1/F*1 | 0 | 1 | 0 | 1 | 0 | 0 |
| F*1/F*2 | 0 | 1 | 0 | 0 | 0 | 1 |
| F*1/G*1 | 0 | 2 | 0 | 0 | 0 | 1 |
| F*1/G*2 | 2 | 0 | 2 | 0 | 0 | 0 |
| F*2/F*2 | 8 | 12 | 8 | 6 | 0 | 2 |
| F*2/G*1 | 4 | 4 | 4 | 2 | 0 | 1 |
| F*2/G*2 | 1 | 4 | 1 | 2 | 0 | 1 |
| G*1/G*1 | 0 | 1 | 0 | 1 | 0 | 0 |
| G*1/G*2 | 4 | 1 | 3 | 1 | 1 | 0 |
| G*2/G*2 | 0 | 1 | 0 | 1 | 0 | 0 |
| Total | 347 | 302 | 306 | 160 | 33 | 94 |

I: Infected, U: Uninfected;
I[1]: Infected total includes 8 patients without treatment data
U[2]: Uninfected total includes 48 patients without treatment data
No Prophylaxis[3]: Mother-child pairs without ZDV treatment
Prophylaxis[4]: Full or partial ZDV treatment

TABLE 5

Allele Frequency of CCR5 Human Haplogroups in Children Perinatally Exposed to HIV-1

| CCR5 Haplogroup | All | | | | No Prophylaxis[1] | | | |
|---|---|---|---|---|---|---|---|---|
| | Infected | | Uninfected | | Infected | | Uninfected | |
| | n | % | n | % | n | % | n | % |
| A | 38 | 5.5 | 45 | 7.5 | 30 | 4.9 | 22 | 6.9 |
| B | 1 | 0.1 | 2 | 0.3 | 1 | 0.2 | 0 | 0 |
| C | 237 | 34.1 | 222 | 36.8 | 211 | 34.5 | 125 | 39.1 |
| D | 7 | 1.0 | 1 | 0.2 | 7 | 1.1 | 1 | 0.3 |
| E | 241 | 34.7 | 163 | 27** | 213 | 34.8 | 78 | 24.4** |
| F*1 | 24 | 3.5 | 22 | 3.6 | 19 | 3.1 | 12 | 3.8 |
| F*2 | 86 | 12.4 | 93 | 15.4 | 77 | 12.6 | 51 | 15.9 |

TABLE 5-continued

Allele Frequency of CCR5 Human Haplogroups in Children Perinatally Exposed to HIV-1

| CCR5 Haplogroup | All | | | | No Prophylaxis[1] | | | |
|---|---|---|---|---|---|---|---|---|
| | Infected | | Uninfected | | Infected | | Uninfected | |
| | n | % | n | % | n | % | n | % |
| G*1 | 35 | 5.0 | 36 | 6.0 | 32 | 5.2 | 19 | 5.9 |
| G*2 | 25 | 3.6 | 20 | 3.3 | 22 | 3.6 | 12 | 3.8 |

[1]No prophylaxis refers to mother-child pairs that did not receive ZDV prophylaxis
**P = 0.001, difference between infected and uninfected, P > 0.05 for all others

TABLE 6

Accelerated Risk of Mother-to-child Transmission of HIV-1 Associated with Possession of an HHE Allele

| Allele | All Adjusted for ZDV prophylaxis | | | No prophylaxis[1] | | |
|---|---|---|---|---|---|---|
| | P | RH | CI | P | RH | CI |
| HHA | 0.333 | 0.77 | 0.46-1.30 | 0.201 | 0.68 | 0.38-1.23 |
| HHB[2] | | | | | | |
| HHC | 0.507 | 0.89 | 0.62-1.26 | 0.483 | 0.87 | 0.59-1.29 |
| HHD | 0.221 | 3.72 | 0.45-30.52 | 0.221 | 3.72 | 0.45-30.52 |
| HHE | 0.007 | 1.61 | 1.14-2.28 | 0.001 | 1.93 | 1.31-2.85 |
| HHF*1 | 0.846 | 0.94 | 0.47-1.85 | 0.781 | 0.90 | 0.42-1.93 |
| HHF*2 | 0.291 | 0.81 | 0.54-1.20 | 0.184 | 0.74 | 0.48-1.15 |
| HHG*1 | 0.578 | 0.86 | 0.50-1.48 | 0.793 | 0.92 | 0.50-1.70 |
| HHG*2 | 0.810 | 1.09 | 0.56-2.13 | 0.900 | 1.05 | 0.50-2.22 |

RH = Relative Hazard; CI = 95% Confidence Interval limit
[1]No prophylaxis refers to mother-child pairs that did not receive ZDV prophylaxis
[2]Not determinable due to limited sample size In adult European- and African-American seropositive individuals, 11 haplotype pairs were identified that were associated with altered rates of disease progression, although the haplotype pairs that influenced disease progression in these two races were different (Example 7). By univariate analysis, the association of these 11 haplotype pairs with HIV-1 transmission was determined (Table 7). 5 of these 11 haplotype pairs were associated with altered rates of mother-to-child transmission of HIV-1 (Table 7). Concordant results were obtained whether the analysis was conducted on mother-infant pairs that did not receive any ZDV therapy, or when the entire cohort was evaluated and the analysis was adjusted for preventive therapy with ZDV (Table 7). When the analysis was extended to include all the CCR5 haplotype pairs found in the cohort, no additional haplotype pairs were found to be significantly associated with altered susceptibility to transmission of virus.

TABLE 7

Univariate Analysis of the Risk of Mother-to-child Transmission of HIV-1 Associated with CCR5 Haplotype Pairs

| Genotype | All Adjusted for ZDV prophylaxis | | | No prophylaxis[1] | | |
|---|---|---|---|---|---|---|
| | P | RH | CI | P | RH | CI |
| HHC/HHE | 0.060 | 1.50 | 0.98-2.28 | 0.010 | 1.87 | 1.16-3.02 |
| HHE/HHE | 0.053 | 1.83 | 0.99-3.38 | 0.113 | 1.81 | 0.87-3.78 |
| HHE/HHG*2 | 0.035 | 4.26 | 1.10-16.42 | 0.089 | 5.93 | 0.79-46.34 |
| HHC/HHG*2 | 0.032 | 0.23 | 0.06-0.88 | 0.055 | 0.25 | 0.06-1.03 |
| HHC/HHC | 0.155 | 0.68 | 0.41-1.15 | 0.067 | 0.59 | 0.33-1.04 |

Figure 4A:
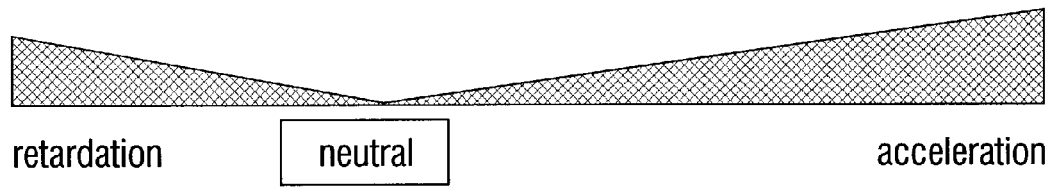
FIG. 4A and FIG. 4B. CCR5 haplotype pairs associated with increased or decreased rates of mother-to-child transmission (FIG. 4A) or disease progression (FIG. 4B) in a cohort of children exposed perinatally to HIV-1 infection.

RH = Relative Hazard; CI = 95% Confidence Interval limit
[1]No prophylaxis refers to mother-child pairs that did not receive ZDV prophylaxis Homozygosity for HHA (n=3), HHF*1 (n=1), HHG*1 (n=1), and HHG*2 (n=1), and the haplotype pairs HHB/HHE (n=1) and HHF*1/HHG*1 (n=2) were found only among the uninfected children. In contrast, the haplotype pairs HHF*1/HHG*2 (n=2), HHD/HHF*2(n=3) and HHC/HHD (n=3) were found only in the infected children. FIG. 4A shows the CCR5 haplotype pairs that influence mother-to-child transmission in children exposed perinatally to HIV-1 infection.

2. CCR5 Haplotypes in HIV-1 Disease Progression

Homozygosity and heterozygosity for HHE was associated with an accelerated progression to AIDS; homozygosity for HHE was also associated with a more rapid progression to death (P 0.05; RH=3.12; 95% CI=1.0-9.93). The disease course in infected Argentinean children who possessed an HHE allele was very similar to that observed in adult Hispanic Americans. In both Argentinean children (P=0.01; RH=1.474; 95% CI=1.09-2.0) and adult Hispanic Americans (P=0.08; RH=2.66; 95% CI=0.90-5.05), possession of an HHE allele was associated with accelerated progression to AIDS. In adult Hispanic-Americans, possession of an HHE allele was also associated with accelerated progression to death (P=0.06; RH=2.23; 95% CI=0.95-5.27). In adult Hispanic Americans, 36% of those who lacked an HHE allele progressed to AIDS whereas 64% who possessed an HHE allele progressed to AIDS. In children these percentages were similar, and a test of equivalence (Fleiss, 1981 and see Methods) suggested that the pattern of association between possession of HHE and progression to disease is the same in Argentinean children and adult Hispanic-Americans (P=0.004).

The infected children that possessed an HHE allele were stratified into 4 groups, with each group comprised of different haplotype combinations. A disease-accelerating effect was observed for the haplotype pairs HHE/HHE, HHC/HHE, and HHE/HHG*2 and for the pooled analysis of the haplotype combinations of HHE paired with HHA, HHD, HHF*1 or HHG*1. In contrast, if a HHE haplotype is paired with HHF*2 (CCR2-64I), a haplotype that is associated with demonstrable protection, the disease-accelerating effects of the HHE haplotype were negated.

Among all HHF*2 containing haplotype pairs, the most common haplotype pairs were HHC/HHF*2 and HHE/HHF*2 (Table 4). To examine the disease-modifying effect associated with these two haplotype pairs, the patients that possessed an HHF*2 allele were stratified into 3 groups, with each group comprised of different haplotype combinations of HHF*2. The maximum disease-retarding effect was observed for the haplotype pair HHC/HHF*2. The clinical course of those who possessed the haplotype pair HHE/HHF*2 and those who lacked an HHF*2 allele was similar (P=0.20;

RH=0.66; CI=0.35-1.26). Possession of HHF*2 was also associated with a delay in progression to death (P=0.06; RH=0.15; CI=0.02-1.11).

Figure 4B:
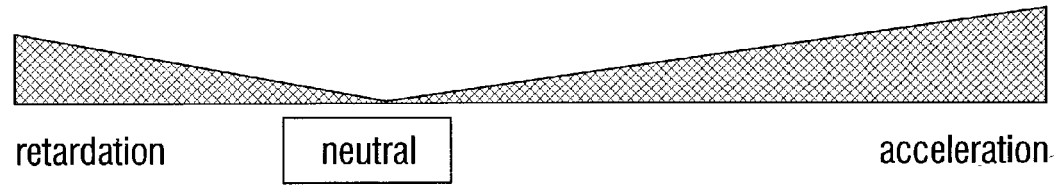

By Cox proportional hazard models, possession of an HHA, HHD, HHG*1 or HHG*2 haplotype was not associated with an altered disease-modifying effect, and the number of individuals who possessed the haplotype pair HHC/HHG*2 were too few to conduct time-to-event analysis. The spectrum of haplotype pairs that influence progression to disease in perinatally-infected Argentinean children is shown in FIG. 4B, wherein X=HHA or HHD or HHF*1.

D. CCR5 Variation and Host Susceptibility to HIV-1 Infection

Comparison of CCR5 haplotype frequencies between perinatally-exposed infected and uninfected children may provide greater insights into the CCR5 determinants that influence viral transmission than a similar comparison between infected adult cohorts and the general population. This is because large cohorts of uninfected adults from a single ethnic background with little admixture, who are highly exposed to HIV-1 through sexual or blood contact, are generally unavailable. Additionally, the per-contact probability of HIV-1 transmission following a single sexual contact is low, and the quantification of the exposure risk in multiply exposed individuals is difficult.

Five CCR5 haplotype pairs were identified that promote or retard transmission of HIV-1 from mother-to-child. Possession of an HHE allele was associated with increased susceptibility to infection, and of the 5 haplotype pairs associated with altered risk of transmission, only the HHE-containing haplotype pairs (HHE/HHE, HHC/HHE and HHE/HHG*2) were associated with enhanced susceptibility. In contrast, the two non-HHE containing haplotype pairs, HHC/HHG*2 and HHC/HHC, were associated with reduced susceptibility to infection. Possession of an HHE was also associated with an accelerated disease course, and notably, the three HHE-containing haplotype pairs that promoted transmission were also associated with an accelerated progression to disease in children (Table 8). Thus, possession of an HHE allele was demonstrated to be adversely associated with two distinct facets of HIV infection in Argentinean children perinatally-exposed to HIV-1: transmission and disease progression.

The spectrum of CCR5 haplotypes that influenced transmission or disease progression in children perinatally-exposed to HIV-1 overlapped but was not identical to the spectrum of haplotypes that influenced disease progression in adult European-, Hispanic- and African Americans (Table 8) (Example 7). This is not completely unanticipated because CCR5 haplotypes may have different effects on vertically transmitted HIV versus horizontally transmitted HIV and/or disease progression in children versus adults. Nevertheless similar to the increased and reduced susceptibility of mother-to-child transmission of HIV-1 afforded by HHE/HHE and HHC/HHG*2, respectively, these haplotype pairs afforded maximal disease acceleration and retardation, respectively in European American adults (Table 8) (Example 7). In Argentinean children and Hispanic-Americans, either homozygosity or heterozygosity for HHE was associated with rapid disease progression. In contrast, only homozygosity for HHE was associated with accelerated disease progression in European Americans (Example 7). In Argentinean children the maximum disease-retarding effect was associated with the HHC/HHF*2 haplotype pair, whereas in African-American adults, the maximum disease-retarding effect was associated with the HHA/HHF*2 haplotype pair (Example 7).

The observation that the CCR5 haplotypes associated with altered rates of HIV-1 transmission or progression to disease overlap but are not identical in different populations should not be surprising. First, the prevalence of different CCR5 haplotypes varies widely among different populations (Examples 4 and 7; Dean et al., 1996; McDermott et al., 1998; Martin et al., 1998; Smith et al., 1997), and this may produce differences in disease susceptibility among populations. Second, the same CCR5 haplotype may be associated with different phenotypic effects among populations (Example 7). Last and most importantly, different pair-wise combinations of CCR5 haplotypes may be associated with very different phenotypes, and the same haplotype pair may have different effects in different populations (Example 7). For example, it is generally believed that possession of a CCR5-Δ32 bearing allele (i.e., HHG*2) is associated with disease protection. However, analysis of the haplotype pairs containing an HHG*2 allele proved very different.

The studies in this Example demonstrate that the phenotype associated with HHG*2 is highly dependent on the other CCR5 allele such that it can be associated with either enhanced (HHE/HHG*2) or reduced (HHC/HHG*2) susceptibility to transmission. Because of the genetic heterogeneity of populations that are often called Caucasian, the prevalence of HHC, HHE and HHG*2 may vary substantially from cohort to cohort. In turn, this will affect the prevalence of HHC/HHG*2 and HHE/HHG*2 among all HHG*2-bearing haplotype pairs in a cohort. This may have been the case in previous analyses restricted to CCR5-Δ32 heterozygotes in which no association was found between HHG*2 and mother-to-child transmission of HIV-1 (Misrahi et al., 1998; Rousseau et al., 1997; Shearer et al., 1998; Mangano et al., 1998; Mandl et al., 1998; Philpott et al., 1999; Esposito et al., 1998). These findings might also explain the highly discordant results regarding the role of CCR5-Δ32 heterozygosity in sexual transmission in Caucasian adults (Zimmerman et al., 1997; Dean et al., 1996; Huang et al., 1996; Samson et al., 1996). For example, Samson et al. found that in adult Caucasian cohorts that included HIV-1 seropositive and seronegative individuals from a similar geographic region and with European patronymes there was a lower frequency of CCR5-Δ32 heterozygotes in seropositive patients, indicating partial resistance (Samson et al., 1996). However, this finding has not been replicated in less well-defined Caucasian cohorts.

TABLE 8

Overlap Between CCR5 Haplotype/Haplotype Pairs that Influence Mother-to-child Transmission of HIV-1 and Disease Progression in Infected Children and Adults

| | Argentinean Children | | American Adults[1] | | |
| --- | --- | --- | --- | --- | --- |
| | Trans- | | Disease Progression | | |
| | mission | Progression | African | Caucasian | Hispanic |
| Haplotype | | | | | |
| HHE | A | A | N | N | A |
| HHF*2 | N | R | R | N | ND |
| Genotype | | | | | |
| HHC/HHC | R | N | A | ** | ND |
| HHC/HHE | A | A | A | ** | ND |
| HHC/HHG*2 | R | ND | ND | R | ND |
| HHE/HHE | A | A | ND | A | ND |
| HHE/HHG*2 | A | A | ND | NT | ND |

A = Acceleration; R = Retardation; N = No Difference; NT = Not Tested
ND = Not determinable due to limited sample size and/or events
[1]Data derived from Example 4, and this study for HHE in adult Hispanic Americans
**Combined analysis of homozygosity and heterozygosity for HHC is associated with a delay of disease progression These findings suggest that genotype-phenotype studies that fail to consider the prevalence of different CCR5 haplotype pairs may miss the effects of interactions between a given CCR5 haplotype such as HHG*2 and other CCR5 alleles. This demonstrates that it is important (1) to understand the spectrum of CCR5 haplotype variation within a population, (2) stratify CCR5 haplotypes according to a biologically-based classification system, and (3) consider CCR5 haplotype interactions on HIV-1 transmission and disease progression. In practice, it will be important to consider these points when designing public health initiatives to develop better prevention and intervention strategies. It also suggests that it may be difficult to interpret the results of studies that pool data across cohorts (e.g., meta-analysis) (Ioannidis et al., 1998).

CCR5 haplotype pairs associated with altered susceptibility to mother-to-child transmission of HIV and progression to disease have been identified in this Example, and a subset of these haplotype pairs also influence HIV disease in adults. Despite disparate front-line cells encountered by HIV-1 during perinatal and sexual transmission, these findings provide indirect evidence that CD4/CCR5-bearing cells are used for HIV cell entry in both instances. These findings also highlight the inter-racial heterogeneity of CCR5 resistance or susceptibility alleles and intra-locus allele interactions. Thus, genotype-phenotype association data derived from one population may not be generalizable to other populations. Concordance between the CCR5 haplotypes associated with an altered risk of transmission and the course of disease favors a unifying CD4/CCR5-dependent mechanism that influences both facets of HIV infection.

Example 7

Race-Specific HIV-1 Disease-Modifying Effects of CCR5 Haplotypes

Genetic variation in CC chemokine receptor 5 (CCR5), the major HIV-1 co-receptor, has been shown to influence HIV-1 transmission and disease progression. However, it is generally assumed that the same CCR5 genotype (or haplotype) has similar phenotypic effects in different populations. An evolutionary-based classification of CCR5 haplotypes was used to determine their associated HIV-1 disease modifying effects in a large, well-characterized racially mixed cohort of HIV-1 seropositive individuals. The studies in this Example demonstrate that the spectrum of CCR5 haplotypes associated with disease acceleration or retardation differs between African Americans and Caucasians. Also, there is a strong interactive effect between CCR5 alleles with different evolutionary histories. The striking population-specific phenotypic effects associated with CCR5 haplotypes emphasize the importance of understanding the evolutionary context in which disease susceptibility genes are expressed.

A. Introduction

Human populations have varied evolutionary histories and more importantly, have co-evolved with different combinations of microbes. Hence, the repertoire of alleles that afford resistance or susceptibility to pathogens (e.g., malaria) may vary in different populations (Hill et al., 1998). Evolutionary forces may have had similar effects on the genes encoding proteins that affect susceptibility to HIV-1, especially in African populations where cross-species transmission of HIV-like retroviruses likely first occurred (Gao et al., 1999).

CC chemokine receptor 5 (CCR5) serves as the major portal of entry for HIV-1, and it has been hypothesized that polymorphisms in the coding and/or cis-regulatory regions may influence cell-surface expression, and consequently could influence an individual's susceptibility to HIV-1 (Moore et al., 1997; Cohen et al., 1997). Thus, significant attention has been focused on understanding the HIV-1 disease-modifying effects of CCR5 polymorphisms (Dean et al., 1996; Huang et al., 1996; Michael et al., 1997; Smith et al., 1997; Zimmerman et al., 1997; Winkler et al., 1998; Kostrikis et al., 1998; Rizzardi et al., 1998; Martin et al. 1998; McDermott et al., 1998). For example, the CCR5-Δ32 allele and a CCR5 allele in linkage disequilibrium with the CCR2-64I polymorphism has been associated with disease retardation. These associations were found in cohorts composed of predominantly homosexual Caucasian men. Whether the results of these association studies can be generalized to other ethnic/population groups is unclear.

In the U.S., AIDS is evolving from a disease that once predominately affected homosexual Caucasian men to one that now largely strikes minority groups (Center for Disease Control and Prevention, 1998). This changing epidemiology of HIV-1 makes stratification for population-specific disease-modifying genetic determinants compelling. The variability in HIV-1 disease progression according to CCR5 haplotype and ethnicity was studied in a large, well characterized, racially mixed cohort of HIV-1 seropositive individuals. This cohort has several epidemiologic features that make it ideally suited for dissecting the population-specific genetic determinants of HIV-1 infection (Example 4). In this cohort, the inventors showed that the CCR2-64I allele was associated with a delay in disease progression in African Americans but not in Caucasians (Example 4). To determine whether the population-specific risk of HIV-1 infection varied according to CCR5 haplotype, the genotype of 1151 individuals from this cohort was compared to that of 1199 uninfected individuals representing ethnic groups living in Africa, Asia, and Europe.

B. Materials and Methods

1. Subjects

Patients with HIV-1 participating in the US Air Force portion of the Tri-Service HIV Natural History Project contributed samples for this study. Wilford Hall Medical Center (WHMC) is the referral hospital for all Air Force personnel who develop infection with HIV. The voluntary, fully informed consent of the subjects used in this research was obtained as required by Air Force Regulation 169-9. A total of 1151 patients were evaluated, including 528 seroconvertors and 623 seroprevalent individuals. The demographic background of this cohort is 54% Caucasian, 37% African American, 6% Hispanic and 3% "other." The median age at the time of diagnosis is 28 years (range, 18 to 70 years), and 94% of the subjects are male. The median follow-up time was 5.9 years for the entire cohort. It was 6.3 years for the seroconvertors, using as the initial time-point the estimated seroconversion date (the midpoint between the last negative and first positive HIV test). The median time from the last negative HIV test to estimated seroconversion was 10.4 months. 38% of this cohort progressed to AIDS (1987 criteria) and 34% died during the study period. Additional epidemiological features of the WHMC cohort, and the different ethnic populations analyzed are described below.

2. HIV-1 Seropositive Subjects

Several factors serve to reduce confounding effects for genetic analysis of this cohort (Dolan et al., 1993, 1995; Blatt et al., 1993, 1995). First, recruitment to the WHMC cohort was not based on a single HIV risk factor. Second, recruitment was not biased toward a specific race, ethnic group, or geographic region. The cohort was drawn from a mixed North American population and then stratified by race. Third, recruitment was from a pool of individuals who were otherwise healthy, thus reducing the effects of co-morbid illnesses (e.g., hemophilia). Fourth, the age and gender (predominantly male) distributions of African Americans and Caucasians in the cohort were comparable. Fifth, all cohort members had equal and ready access to health care and anti-retroviral therapy, and were prospectively followed at a single medical center. Sixth, the concordance of CCR5 haplotype frequencies was checked by comparing the distribution of CCR5 haplotypes of African Americans and Caucasians in the cohort to the CCR5 haplotype distributions of uninfected Africans and Europeans, respectively. Last, CCR5 haplotypes were organized in an evolutionary framework to minimize the confounding that might occur by mixing SNPs and/or haplotypes with different evolutionary and phenotypic effects.

3. Ethnic Populations

The ethnic groups (number of individuals) from Africa included: Alur (10); Kenyan (24); Nande (15); Nigerian (59); African !Kung (15); Pedi (11); Biaka and Mbuti Pygmies (40); and assorted sub-Saharan groups (34). Individuals of European origin were a group classified as Caucasian (127); Finnish (50); Polish (10); and the CEPH cohort (126). Ethnic groups from Asia include Chinese (11); Cambodian (11); Japanese (8); Malaysian (6); Vietnamese (5); South Indian (647); assorted Southeast Asians (40). 200 Caucasians and 221 African Americans from North America were also included. The characteristics of these ethnic groups were as described previously (Yu et al., 1998; Jorde et al., 1998; Dausset et al., 1990; Bamshad et al., 1998).

4. Genotype Analysis

PCR-restriction fragment length polymorphism (RFLP) based assays were used to genotype the WHMC cohort and ethnic populations at a single nucleotide polymorphism (SNP) in the CCR2 coding region (G190A; CCR2-V64I), the SNPs in a CCR5 cis-regulatory region (A29G, G208T, G303A (only WHMC cohort), T627C, C630T, A676G, C927T) and the CCR5-Δ32 mutation (Examples 3 and 4). Molecular beacon-based genotyping methods were used to confirm the genotype at CCR5 627 and 676 in the WHMC cohort. Detailed protocols follow and are also provided in the description of the drawings in U.S. provisional application Ser. No. 60/159,137, filed Oct. 12, 1999, and are thus specifically incorporated herein by reference.

PCR methods and restriction endonuclease digestion were used for the PCR-RFLP genotyping assays. The HIV-1 seropositive cohort was genotyped for the 9 polymorphic sites. The uninfected ethnic populations were not genotyped for the SNP at CCR5 303 since, in the HIV-1 seropositive cohort it was found that the SNPs at CCR5 303 and 627 were in nearly complete linkage disequilibrium (Table 9). There was complete concordance between the genotype determined by PCR-RFLP methods and direct sequencing. Additional details regarding the genotyping of these 9 polymorphisms, including primer sequences are provided below.

CCR5 numbering is based on GenBank Accession numbers AF031236 and AF031237 (Example 3). Certain of the methods used were as described above (Example 4). The CCR5 T627C SNP was genotyped as a HindIII PCR-restriction fragment length polymorphism (RFLP). The restriction endonuclease site HindIII is created by changing a C>G at position 626 in the sense primer (change is underlined). The enzyme digests the amplicons that contain 627C. Two sense primers were designed: S1 (5' GTGGGATGAGCAGAGAA-CAAAAACAAAATAATCCAGT-GAGAAAAGCCCGTAAA TAAAG 3'; SEQ ID NO:1) and S2 (5' CAGAGAACAAAAACAAAAT AATCCAGT-GAGAAAAGCCGTAAATAAAG 3'; SEQ ID NO:2), and one antisense primer (5' GATAATTGTATGAGCACTTG-GTG 3'; SEQ ID NO:3). In some samples, the PCR efficiency was better with S2 than with S1. The sense primer does not include the CCR5 630 position. The HindIII restriction site introduced is independent of the SNP at CCR5 630.

The genotype at CCR5 627 in the entire HIV seropositive cohort was confirmed by using a molecular beacon-based genotyping assay. There was complete concordance in the genotype obtained by PCR-RFLP and molecular beacon assays. The molecular beacon assay data was used only when there is a CCR5 630C. The CCR5 G208T SNP was genotyped as a BsmAI PCR-RFLP. The restriction site BsmAI is created by changing an A>G at position 210 in the antisense primer (change is underlined). The sense primer is 5' TTGCCTTCT-TAGAGATCACAAGCCAAAGCT 3' (SEQ ID NO:4) and the antisense primer is 5' CCCACACAGATGCTCACCAC-CCAATATTATTGTTCTCT GTAAACGGAGA 3' (SEQ ID NO:5). The enzyme digests the amplicons that contain 208G.

The CCR5 C630T SNP was genotyped as a DraI PCR-RFLP. The restriction site DraI is created by changing a C>T at position 632 in the antisense primer (5' AACAGTTCT-TCTTTTTAAGTTGAGCTTAAAATAAGCTAGAGAAT AGATCTCTGGTTT 3' (SEQ ID NO:6); change is underlined). The sense primer is 5' GGTTAATGTGAAGTCCAG-GATCC 3' (SEQ ID NO:7). The enzyme digests the amplicons that contain 630T. The anti-sense primer does not include the position CCR5 627, and the DraI restriction site introduced is independent of the SNP at CCR5 627.

The CCR5 A676G SNP was genotyped as either an AlwI or DraI PCR-RFLP. All samples were initially genotyped using the AlwI PCR-RFLP assay. Those samples that were negative or where the results were not clear the DraI PCR-RFLP assay was used. Note the genotype at CCR5 676 in the entire HIV-1 seropositive cohort was confirmed by using a molecular beacon-based genotyping assays. There was complete 100% concordance in the genotype obtained by PCR-RFLP and molecular beacon assays. The primers for CCR5 A676G AlwI PCR-RFLP assay were sense (5' GGTTAATGTGAAGTC-CAGGATCC 3'; SEQ ID NO:8) and antisense (5' CAT-TAAGTGTATTGAAGGCGAAAAGAATCA-GAGAACAGTTGATC 3'; SEQ ID NO:9). The restriction site Alw I is created by changing CT>GA at positions 680 and 679, respectively in the antisense primer (changes underlined). The enzyme digests the amplicons that contain 676G. The primers for CCR5 A676G DraI PCR-RFLP assay were sense (5' GTAAATAAACCTTCAGACCAGAGATC TAT-TCTCCAGCTTATTTTAAGCTCAACTTTTAA3'; SEQ ID NO:10) and antisense (5' GATAATTGTATGAGCACTTG-GTGTTTGCC 3'; SEQ ID NO:11). The restriction site DraI is created by changing AA>TT at positions 672 and 673, respectively, in the sense primer (changes are underlined). The enzyme digests the amplicons that contain 676A.

The CCR5 C927T SNP was genotyped as a EcoRV PCR-RFLP. The restriction site EcoRV is created by changing an A>G at position 930 in the antisense primer (5' ATCTTAAA-GATTATATTTTAAGATAATTGTAT GAGCACTTGGT-GTTTGCCAGAT 3' (SEQ ID NO:12); change is underlined). The sense primer is 5' GTTGGTTTAAGTTGGCTT 3' (SEQ ID NO:13). The enzyme digests the amplicons that contain 927T.

The CCR2 G190A (CCR2 V64I) polymorphism was genotyped as a BsaBI PCR-RFLP. The restriction site Bsa BI is created by changing a C>A at position 184 in the sense primer (5' CTCCGCTCTACTCGCTGGTGT- TCATCTTTGGTTTTGTGGGCAACATGAT GG 3' (SEQ ID NO:14); change is underlined). The antisense primer is 5' AGTTGACTGGTGCTTTCA 3' (SEQ ID NO:15). The enzyme digests the amplicons that contain 190A. A natural BamHI restriction site is created by the CCR5 A29G polymorphism. The sense primer is 5' GAGCCAAGGTCACG-GAAGCCC 3' (SEQ ID NO:16), and the antisense primer is 5' GGACCCAGGATCTTAGTG 3' (SEQ ID NO:17).

The CCR5 Δ32 polymorphism was genotyped by detecting size differences in the amplicons. The sense primer is 5' CAAAAAGAAGGTCTTCATT ACACC 3' (SEQ ID NO:18) and the antisense primer is 5' TCACAAGCCCACAGAT ATTTCCTG 3' (SEQ ID NO:19). The CCR5 G303A SNP was genotyped by the presence (303G) or absence (303A) of a Bsp1286I restriction site. A natural restriction site Bsp1286I is created by the 303G polymorphism. Two different primer pairs were used. In some assays the first primer set (S1: 5' GATGGGAAACCTGTT TAGCTCACCCGTGAGC 3' (SEQ ID NO:20) and A1: 5' CATCCCACTACACAGA ATCTGTTAG 3' (SEQ ID NO:21)) worked better, and in other samples the second set gave better results (S2: 5' CCCGTGAGCCCATAGTTAAAACTC 3' (SEQ ID NO:22) and A2: 5' TCACAGGGCTTTTCAACAGTAAGG 3' (SEQ ID NO:23); these primers correspond to those described by McDermott et al. (1998). The only special consideration to note is that despite adding extra restriction endonuclease and extending the total duration of digestion, a faint upper band was observed for the 303G/303G genotype.

Ethidium bromide stained agarose gels showed the results of the PCR-RFLP genotyping assay for CCR5 T627C, CCR5 G208T, CCR5 C630T, CCR5 A676G; AlwI PCR-RFLP), CCR5 C927T, CCR2 G190A, CCR5 A29G, CCR5 Δ32 and CCR5 G303A. In many instances, the CCR5 303G/303G genotype gave an incomplete digestion pattern that results in a light upper band.

Methods for molecular beacon-based genotyping assays (Tyagi et al., 1998; Kostrikis et al., 1998) were used for genotyping CCR5 T627C and A676G. An example for real-time monitoring of PCR for genotyping of CCR5 627 (C/T) was developed. Real-time measurements of CCR5 amplicon synthesis from DNA samples that are homozygous C/C (red), homozygous T/T (green) or heterozygous C/T (blue) were observed. DNA samples were amplified and detected as either molecular beacons complementary to CCR5 627C labeled with fluorescein or to CCR5 627T labeled with tetrachlorofluorescein (TET). The molecular beacon assay method was as described (Tyagi et al., 1998). PCR amplifications were performed in a 7700 Prism spectrofluorometric thermal cycler (Perkin-Elmer) for 45 cycles with the following conditions: 95 C for 30 s, 55 C (CCR5 627) or 50 C (CCR5 676) annealing for 60 s, and 72 C for 30 s. Fluorescence was measured during the 60 s annealing step in each thermal cycle.

For genotyping CCR5 T627C the PCR primers used were 5' AGATGAATGTAAATGTTCTTCTAG 3' (forward; SEQ ID NO:24) and 5' CTTTTTAAGTTGAGCTTAAAATAAGC 3' (reverse; SEQ ID NO:25). The molecular beacon used to type CCR5 627C was fluorescein-5' CGCACCTCTGGTCTGAAGGTTTATGGTGCG 3'-DABCYL (SEQ ID NO:26), and to type CCR5 627T was TET-5' CGCACCTCTGGTCTGAAGTT TATTGGTGCG 3'-DABCYL (SEQ ID NO:27). The arm sequences in the molecular beacons are underlined. Knowledge of the SNP at position 630 (as determined by PCR-RFLP genotyping) was used to guide results.

Since the molecular beacon probe used for genotyping CCR5 T627C is designed to be complementary to CCR5 630C, the following genotypes could be assayed for unambiguously: (1) CCR5 627C/627C, since in this genotype CCR5 630 is 630C/630C (n=270); (2) CCR5 627C/627T when CCR5 627T is in linkage disequilibrium with CCR5 630C(HHA, HHB or HHC; n=525); data obtained by the molecular beacon assay for position CCR5 627 is ignored when CCR5 630 is a 630T (i.e., when CCR5 627T is in linkage disequilibrium with CCR % 630T (HHD); n=166); or (3) CCR5 627T/627T when the CCR5 627T is in linkage disequilibrium with CCR5 630C (n=190).

For genotyping CCR5 A676G the PCR primers used were 5' AGACCAGAGATCTATTCTCC AGCT 3' (forward: SEQ ID NO:28) and 5' TATTGAAGGCGAAAAGAATCAG 3' (reverse; SEQ ID NO:29). The molecular beacon used to type CCR5 676A was fluorescein-5' CCGGTCAACTTAAAAAGAAGAACTGGACCGG 3'-DABCYL (SEQ ID NO:30), and to type CCR5 676G was TET-5' CCGGTCAACTTAAAAGG AAGAACTG GACCGG 3'-DABCYL (SEQ ID NO:31). The arm sequences in the molecular beacons are underlined. There was complete concordance between the genotype determined by molecular beacon and PCR-RFLP genotyping assays.

Illustration of the ability of molecular beacon assays to unambiguously discriminate for CCR5 627C and 627T whenever CCR5 630 is 630C. Data from this assay was not used when the CCR5 630 position is 630T. The CCR5 630SNP was determined by a PCR-RFLP genotyping assay. Fluorescein fluorescence at the $35^{th}$ cycle was plotted against tetrafluorescein (TET) fluorescence. Representative data from the WHMC cohort was presented in U.S. provisional application Ser. No. 60/159,137. Each sample falls into one of the four easily distinguishable categories: (1) high fluorescein fluorescence and low TET fluorescence (green); (2) low fluorescein fluorescence and high TET fluorescence (red); (3) high fluorescein fluorescence and high TET fluorescence (orange); and (4) low fluorescein fluorescence and low TET fluorescence (negative controls; blue). The entire fluorescence vs. cycle profiles were analyzed for the samples that produced little fluorescence signal at the $35^{th}$ cycle.

Using the foregoing methods, the relationship between CCR5 C927T and CCR2 V64I, CCR5 G303A and CCR5 T627C, and CCR5 A29G and CCR5 Δ32 was defined, and is described in Tables 10, 11 and 12. In 1138 individuals from the WHMC cohort, CCR5 303G and 303A were found to be in nearly complete linkage disequilibrium with 627T and 627C, respectively (Table 11). For this reason, the haplotype reported was restricted to the genotype analysis of SNPs at CCR2190, CCR5 29, 208, 627, 630, 676, 927, and the Δ32 polymorphism.

Methods for CCR5 haplotype assignment and the frequency of the different haplotype pairs/genotypes found in the WHMC cohort are based on the following. The relationships between CCR5 C927T and CCR2 V64I, CCR5 T627C and CCR5 G303A, and CCR5 A29G and CCR5 Δ32 are shown in Tables 10, 11 and 12. Since 303G and 627T, and 303A and 627C polymorphisms were in nearly complete linkage disequilibrium, the genotype at CCR5 627 was used for haplotype assignment. The CCR5 haplotype classification system used organizes CCR5 alleles with common genotypic features (i.e., distinct constellations of SNPs) into 7 evolutionarily-related human haplogroups. Thus, by genotyping for 8 polymorphic sites, the two alleles in a genomic DNA sample can be assigned to one of 7 CCR5 haplogroups. The genotype at each polymorphic site was assigned a number: 0, wild type; 1, heterozygous; 2, homozygous mutated.

Haplotype assignment for ~99% of the WHMC cohort could be made (39 haplotype pairs). In the remaining 1% of the cohort, the haplotype pairs contained at least one allele that appeared to be the product of recombination or other mutational events. These individuals were not included in the statistical analysis. Examples of haplotype assignment are as follows. Wild type at all SNPs is representative of homozygosity for the ancestral CCR5 haplogroup, designated as human haplogroup A (HHA/HHA). Homozygosity for CCR5 627C (or 303A; T627C=2) but wild type at the other SNPs is consistent with the genotype HHE/HHE. Since CCR5 Δ32 and CCR2 64I both occur on a genetic background of CCR5 627C but on different alleles, it would be expected then that a genomic DNA sample that contains both of these alleles will be homozygous for CCR5 627C and heterozygous for CCR2 64I and CCR5 Δ32 (T627C 2, G190A=1, Δ32=1). However, since CCR2 64I allele usually occurs on the background of 927T, heterozygosity for CCR5 927T would be also be expected (C927T=1). Furthermore, since CCR5 Δ32 usually occurs on the genetic background of CCR5 29G, heterozygosity for CCR5 29G would also be expected (A29G=1). It is inferred that the CCR2 64I/CCR5 927T-bearing allele occurs on an allele that is CCR5 29A that also lacks the Δ32 mutation. Conversely, the CCR5 29G/CCR5 Δ32 allele occurs on the background of CCR5 927C and CCR2 64V.

The CCR5 haplotype classification system/genotyping method adopted minimized haplotype misclassification and requires a cross-check of the genotype of several SNPs. Two examples are provided to illustrate this. In the first, the CCR5 29G occurs on the background of CCR5 627C. Thus, if genotyping suggested the presence of a CCR5 29G polymorphism but not a CCR5 627C, then in this case the assays would be repeated for these two SNPs. In the second, the CCR5 630T occurs on the background of 627T and 208T. Thus, if an allele was found that corresponds to CCR5 630T and CCR5 627T but a CCR5 208G the assay would be repeated for the SNP at CCR5 208. Hence, based on an understanding of the different patterns of linkage disequilibrium between the CCR2/CCR5 SNPs permitted the accurate genotyping across several SNPs. To make an error in haplotype assignment would mean that several SNP positions would have to be incorrectly genotyped.

5. Statistical Analysis

Time curves for progression to AIDS (1987 criteria) and survival were prepared by Kaplan-Meier (KM) method using SAS. Between-group analyses were completed using the log-rank test. Relative hazards (RH) were calculated using univariate and multivariate Cox-proportional hazard models. The reference group for each of the analyses is indicated in the figure legends. In seventeen individuals one CCR5 allele appeared to be the product of a recombination event, and these patients were excluded from analysis. CI indicates 95% confidence interval limits. Because of the disease-modifying effects associated with HHF*2 (CCR2-64I) and HHG*2 (CCR5 Δ32) (Example 4), adjustments were made for their protective effects in African Americans and Caucasians, respectively; in survival analysis for the entire cohort, adjustments were made for these two haplogroups.

C. Results

1. Spectrum of CCR5 Haplotypes in World-Wide Populations

CCR5 haplotypes were grouped into seven phylogenetically distinct clusters designated CCR5 human haplogroups (HH)-A, -B, -C, -D, -E, -F, and -G, with HHA representing the ancestral CCR5 haplogroup (Example 5). HHA haplotypes were defined as ancestral to all other haplotypes by comparison to the CCR5 alleles of Great Apes, Old and New World monkeys. CCR5 haplogroup frequencies were similar between HIV-infected and uninfected Caucasians and African Americans (Table 9). Among uninfected populations CCR5 haplogroup frequencies varied substantially among races and ethnic groups (Table 9). Overall, haplotype diversity was highest in Africans, and only a subset of these haplotypes was found in non-African populations.

TABLE 9

CCR5 Haplotype Frequencies in Different Racial and Ethnic Groups

| | African | | African Americans | |
| --- | --- | --- | --- | --- |
| Haplogroup | Pygmies | Non-pygmies | Uninfected | HIV-1 Infected |
| HHA | 70.6 (34) | 26.5 (49) | 22 (209) | 20.1 (410) |
| HHC | 2.0 (25) | 10.6 (71) | 15.6 (212) | 14.8 (410) |
| HHD | 0 (37) | 20.1 (82) | 18.4 (212) | 20.1 (410) |
| HHE | 11.8 (38) | 20.7 (58) | 18.4 (193) | 18.7 (410) |
| HHF*1 | 6.3 (40) | 11.8 (68) | 4.1 (195) | 5.0 (410) |
| HHF*2 | 6.3 (40) | 14.7 (68) | 14.1 (195) | 14.9 (410) |
| HHG*1 | 2.5 (40) | 0.7 (71) | 4.5 (210) | 3.7 (410) |
| HHG*2 | 0 (40) | 0 (71) | 2.6 (210) | 2.3 (410) |

| | Asian Uninfected | Caucasian | | Hispanic Am. |
| --- | --- | --- | --- | --- |
| Haplogroup | | Uninfected | HIV-1 Infected | HIV-1 Infected |
| HHA | 16.8 (158) | 10.7 (248) | 9.3 (618) | 9.5 (74) |
| HHC | 36.5 (163) | 37.1 (206) | 36.3 (618) | 34.5 (74) |
| HHD | 4.4 (34) | 0 (429) | 1.0 (618) | 3.4 (74) |
| HHE | 25 (376) | 31.8 (140) | 31.9 (618) | 30.4 (74) |
| HHF*1 | 1.6 (478) | 2.0 (154) | 0.8 (618) | 2.7 (74) |
| HHF*2 | 12.8 (478) | 5.5 (154) | 8.6 (618) | 14.2 (74) |
| HHG*1 | 0.8 (518) | 3.3 (151) | 4.4 (618) | 2.0 (74) |
| HHG*2 | 0.1 (518) | 5.6 (151) | 7.7 (618) | 3.4 (74) |

The number in parentheses denotes the number of individuals from whom the haplotype frequency (%) was derived. HHB haplotypes are rare. Because of failure to amplify by PCR all CCR5 polymorphisms and/or limited DNA quantities, the number of non-infected individuals for whom complete haplotype frequency data are available varies. For these two reasons the frequencies approximate but do not total to 100%. Individuals in whom a CCR5 haplotype appeared to be a product of a recombination event were excluded from analysis.

The distribution of haplotype pairs between African Americans and Caucasians was also different. Fifty-two different haplotype pairs were found in the HIV-1 positive cohort, and 99% of individuals in the cohort had one of 39 of these pairs. In Caucasians, most individuals had one of only a few different haplotype pairs, and the three most common haplotype pairs were HHC/HHE (25%), HHC/HHC (~11%), and HHE/HHE (~10%). In contrast, no single haplotype pair was common in Africans, and the prevalence of each haplotype pair was less than 10%. This heterogeneous distribution of haplotype pairs suggested that the spectrum of CCR5 haplotype pairs associated with differences in HIV-1 disease progression might differ between Caucasians and African Americans.

2. Varied Disease-Modifying Effects of CCR5 Haplotypes

There was a delay in progression to AIDS and death in Caucasians for those with the HHG*2 haplotypes (CCR5 Δ32) compared to those without it. Although both HHG*1 (CCR5 29G without CCR5 Δ32) and HHG*2 were found on a haplotype background with CCR5 29G (Table 12), only haplotypes with the CCR5 Δ32 mutation were associated with disease retardation in comparison to the population not possessing any HHG haplotypes. The disease-modifying effects of the HHG*1 and HHG*2 haplotypes differed with respect to each other for both progression to AIDS (P=0.07) and death (P=0.02).

TABLE 10

The CCR5 927T Polymorphism is not in Complete Disequilibrium with CCR2 64I, Whereas the CCR2 64I Polymorphism is in Nearly Complete Linkage Disequilibrium With CCR5 927T

| | CCR5 927 | | |
|---|---|---|---|
| | C/C | C/T | T/T |
| CCR2 64V/V | 851 | 49 | 1 |
| CCR2 64V/I | 5 | 217 | 7 |
| CCR2 64I/I | 0 | 0 | 21 |

Data are from 1151 individuals from the WHMC cohort. Of the 316 alleles that carry a 927T polymorphism, 266 also contain the CCR2 64I polymorphism, i.e., 16% of 927T alleles are not in linkage disequilibrium with CCR2 64I (HHF*1 allele). Of the 271 alleles that carry a CCR2 64I polymorphism, 266 alleles also contain the CCR5 927T polymorphism, i.e., 98% of CCR2 64I alleles are in linkage disequilibrium with CCR5 927T.

TABLE 11

The CCR5 303A and 627C, and 303G and 627T Are in Nearly Complete Linkage Disequilibrium

| | CCR5 303 | | |
|---|---|---|---|
| | G/G | G/A | A/A |
| CCR5 627T/T | 270 | 0 | 1 |
| CCR5 627C/T | 7 | 585 | 3 |
| CCR5 627C/C | 0 | 0 | 272 |

Data is from 1138 individuals from the WHMC cohort. Of the 1139 alleles that contain a CCR5 627C, 1132 also have the CCR5 303A polymorphism, i.e., 99.4% of 627C alleles are in linkage disequilibrium with the 303A polymorphism. Of the 1137 CCR5 303A bearing alleles, 1132 also contain the CCR5 627C polymorphism, i.e., 99.6% of CCR5 303A alleles are in linkage disequilibrium with the CCR5 627C polymorphism.

TABLE 12

CCR5 29G is Not in Complete Linkage Disequilibrium With the CCR5 Δ32 Mutation, Whereas the CCR5 Δ32 Mutation is in Nearly Complete Linkage Disequilibrium With CCR5 29G

| | CCR5 29 | | |
|---|---|---|---|
| | A/A | A/G | G/G |
| CCR5 +/+ | 945 | 81 | 1 |
| CCR5 +/Δ32 | 0 | 116 | 8 |

Data is from the WHMC cohort. All 124 alleles that contain the CCR5 Δ32 mutation are in linkage disequilibrium with CCR5 29G. However, of the 215 CCR5 29G alleles, only 124 also carry the CCR5 Δ32 mutation. In other words, 42% of CCR5 29G alleles are not in linkage disequilibrium with CCR5 Δ32 (HHG*1 alleles).

Haplotypes in linkage disequilibrium with SNP 927T were associated with different disease-modifying effects. HHF*2 haplotypes (combining homozygotes (+/+) and heterozygotes (+/−)) were associated with a delay in progression to AIDS (P=0.01; RH=0.58; CI=0.38-0.88) and death (P=0.005; RH=0.50; CI=0.31-0.81) in African Americans but not in Caucasians ((for AIDS, P=0.77; RH=0.95; CI=0.68-1.33) (for death, P=0.84; RH=1.04; CI=0.74-1.46)). In contrast, HHF*1 haplotypes (+/+ and +/−) were associated with an acceleration to AIDS in the entire cohort Americans (P=0.05; RH=1.47; CI=1.0-2.16) and in African Americans (P=0.04; RH=1.64; CI=1.01-2.66).

In the entire cohort, HHA haplotypes (combining +/+ and +/−) were associated with a delay in progression to AIDS (adjusted for HHF*2 and HHG*2, P=0.04; RH=0.77; CI=0.60-0.99) and death (adjusted P=0.04; RH=0.79; CI=0.62-0.99). This association was demonstrable in African Americans but not Caucasians (for AIDS, adjusted for HHG*2, P=0.71; for death, adjusted P=0.94). These findings suggested that HHA haplotypes in African Americans were associated with disease retardation, and that this association was independent of the effect of HHF*2. However, the findings did not exclude the possibility of an additive and/or interactive effect between HHA and HHF*2 haplotypes. Thus, the African American and Caucasian patients were stratified into 4 groups, with each group composed of a different pairwise haplotype combination. For African Americans, the three groups that contain an HHA and/or HHF*2 haplotype were each associated with a delay in progression to AIDS and death, with the combination of HHA and HHF*2 providing the greatest advantage. In Caucasians there were no demonstrable differences between various combinations of these two haplotypes.

In the overall cohort, there was no difference in clinical outcomes for groups possessing zero, one or two HHC haplotypes. If the cohort was stratified by race, the effect of HHC haplotypes on HIV-1 disease differed between African-Americans, Caucasians, and Hispanics. In Caucasians and Hispanics HHC haplotypes were associated with disease-retardation, particularly a delayed progression to death. In contrast, for African-Americans, possession of HHC haplotypes was associated with disease acceleration.

HHE homozygosity was associated with acceleration to AIDS (adjusted for both HHC and HHF*2, P=0.02; RH=1.55; CI=1.09-2.20) and death (adjusted P=0.003; RH=1.72; CI=1.20-2.46) in the entire cohort, while HHE heterozygotes had similar outcomes to non-HHE bearing individuals. For, Caucasians HHE homozygosity (but not HHE heterozygosity) was associated with disease acceleration, particularly an accelerated progression to death. HHE homozygosity was not associated with disease-modifying effects in the African Americans.

3. CCR5 Haplotype Interactions in African Americans

Figure 3:
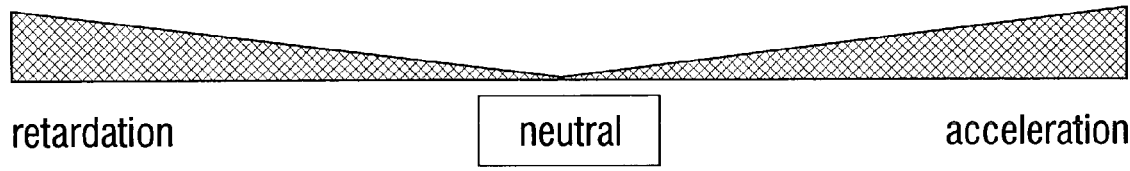
FIG. 3. HHC-associated allele-allele interactions in African Americans and the disease-modifying role of HHD haplotypes. KM curves comparing the clinical course of African Americans who possess or lack various haplotype were determined. Appropriate reference groups for the statistical analyses were used. Data was generated for the combination of the seroconverting and seroprevalent populations. HHF*2-unadjusted and -adjusted relative risk of AIDS and death associated with three HHC-containing haplotype pairs in African Americans were calculated. The reference group for the log-rank test is for African Americans who lack these haplotype pairs. The foregoing analyses provide the data of FIG. 3: CCR5 haplotypes in African Americans that are associated with different HIV-1 disease progression rates.

Since the distribution of haplotypes is known to differ between Caucasians and African Americans, the potential partner alleles for a single HHC allele also differs. Therefore, the effect of HHC allele pairs on disease progression was studied (FIG. 3). For African Americans, the pairing of an HHC haplotype with an HHD or HHE haplotype was associated with accelerated disease. This phenotype was similar to that observed in HHC homozygotes. For African Americans who possessed one of the haplotype pairs HHC/HHC, HHC/HHD or HHC/HHE the combined median time to AIDS and death was 5.21 and 6.34 years, respectively. In contrast, the median time to AIDS was 9.37 years in African Americans lacking an HHC haplotype. The median time to death had not been reached in African Americans lacking an HHC haplotype but a calculated estimate was greater than 12 years. A disease-accelerating effect was also observed for the haplotype pair, HHC/HHF*1. In contrast, if an HHC haplotype was paired with one of the haplotypes that was associated with protection in African Americans (HHA or HHF*2 (CCR2-64I)) the disease-accelerating effects of the HHC haplotype were negated.

To test the disease-modifying effects of the HHD haplotype independent of its association with HHC, African Americans were stratified into four groups of haplotype pairs. The disease course of individuals who possess both an HHD and HHC haplotype was significantly more rapid than in those who have an HHD haplotype paired with a non-HHC haplotype (for AIDS, P=0.005; for death P=0.02). These findings suggest that in African Americans, the detrimental phenotypic effect associated with the HHC haplotype was evident when combined with HHD or HHE, but not with HHA or HHF*2 haplotypes. Collectively, these findings permitted the identification of CCR5 haplotype pairs that were associated with a broad spectrum of effects on HIV-1 disease in African Americans (FIG. 3). Notably, HHC/HHC and HHC/HHD, the haplotype pairs associated with maximal disease progression in African Americans represent individuals who are homozygous for the CCR5 208T SNP.

4. CCR5 Haplotype Interactions in Caucasians

In Caucasians, the KM curves for haplotype pairs that contained at least one HHC haplotype were above or superimposed on the KM curve of haplotype pairs that did not contain a HHC haplotype. Together, these haplotype pairs accounted for ~50% of all Caucasians. HHC/HHC and HHC/HHE accounted for nearly 34% of Caucasian haplotype pairs, but they represented only a small proportion of African American haplotype pairs. Yet, there were sharply contrasting disease-modifying effects between African Americans and Caucasians for HHC/HHC and HHC/HHE. Furthermore, after adjustment for the protective effects of HHG*2, the haplotype pair HHC/HHE was associated with a delay in time to death in Caucasians (adjusted P=0.04; RH=0.70; CI=0.50-0.98) in contrast to the accelerated progression seen in HHE/HHE homozygotes.

The haplotype pair HHC/HHG*2 was also associated with a trend towards a delay in progression to AIDS (P=0.08, RH=0.59; CI=0.34-1.05) and death (P=0.08; RH=0.59; CI=0.32-1.06). Since the strength of this association was similar to that for all HHG*2 alleles, the effects of HHC/HHG*2 were compared versus all haplotype pairs that contained an HHG*2 (Δ32 mutation) haplotype and a non-HHC haplotype. Although an HHG*2 haplotype was most commonly found in association with an HHA, HHC or HHE haplotype, the pairing of HHG*2 with HHC accounts for most of HHG*2's beneficial effect. These findings suggest that the phenotypic effects associated with CCR5 Δ32 depend, in large part, on the identity of its partner allele.

5. Population-Specific Effects of CCR5 Haplotypes

Figure 2:
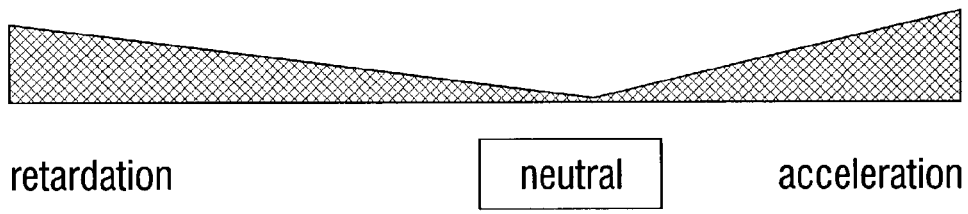
FIG. 2. Disease-modifying effects of CCR5 haplotypes in Caucasians. CCR5 HHG*1 and HHG*2 haplotypes are associated with different HIV-1 disease-modifying effects in Caucasians. The KM curves of the development of AIDS (1987 criteria) or death for Caucasians who possessed at least one HHG*1 or HHG*2 allele were determined. The reference group for the survival analyses was Caucasians that did not possess either of these two alleles (–HHG*1/–HHG*2). For statistical analysis comparing HHG*2 to non-HHG bearing patients, individuals who were homozygous for HHG*1 and also had a Δ32 mutation (HHG*2) on one these alleles were considered as part of HHG*2. They were excluded from the comparison of HUG*1 and HHG*2. P and RH values were determined to indicate the significance value by log-rank test and the relative hazard with respect to the reference group, respectively. Data was developed for the combination of the seroconverting and seroprevalent Caucasians. KM curves comparing the clinical course of Caucasians lacking an HHE haplotype (0), or possessing one (1), or two HHE haplotypes (2) were determined. The reference group for the survival analyses is Caucasians that do not possess HHE haplotypes. The unadjusted P and RH values were determined, as were the values adjusted for the protective effects of HHG*2. KM curves comparing the clinical course of Caucasians who possess or lack various haplotype pairs were also determined. The KM curves of the development of AIDS or death in Caucasians with the following haplotype pairs (presence (+) and absence (–)): +HHC/+HHG*2; –HHC/+HHG*2; –HHG*2/–HHG*2 were determined. The reference group for the statistical analyses were Caucasians who are –HHG*2/–HHG*2. The foregoing analyses provide the data of FIG. 2: CCR5 haplotypes in Caucasians associated with different outcomes of HIV-1 disease. The haplotype pairs associated with no statistically significant disease-modifying effects are designated as being neutral.

Collectively, these findings indicate that the CCR5 haplotypes associated with altered rates of HIV-1 disease progression in Caucasians were different from those in African Americans (compare FIG. 2 and FIG. 3). These studies also highlight the importance of understanding the interactions between CCR5 haplotypes, and emphasize that analysis of a single mutation or haplotype in isolation may obscure the complexity underlying CCR5 genotype-phenotype relationships. HHA and HHF*2 haplotypes have significantly higher frequencies in African Americans than in Caucasians, and in the WHMC cohort their effect was dominant (i.e., even a single allele confers disease retardation). However, this phenotypic effect was demonstrable only in African Americans, not Caucasians. Conversely, HHC haplotypes have significantly higher frequencies in Caucasians than in African Americans. In African Americans, HHC haplotypes were associated with a detrimental effect that was mitigated when paired with haplotypes associated with protective effects (i.e., HHA or HHF*2). These race-specific CCR5 haplotype-pair associations may be the consequence of the evolution of different combinations of alleles encoding mediators of the immune response in Africans versus Caucasians. Such combinations of alleles may have offered selective advantages to ancestral Caucasian and African populations that were exposed to different spectrums of pathogens. These findings also suggest that disruption of combinations of alleles that may have been previously favored by selection might result in deleterious effects in very specific circumstances.

The heterogeneous distribution of CCR5 haplotypes in Africans and Caucasians may influence the results of genotype-phenotype association studies. For example, among all Caucasians who possess a CCR5-Δ32-bearing haplotype (HHG*2), the haplotype pair, HHC/HHG*2, affords the strongest protective effects. Thus, the frequencies of HHC and HHG*2 haplotypes in Caucasians will determine the frequency of HHC/HHG*2 haplotype pairs, and therefore, the likelihood of associating a CCR5-Δ32-bearing haplotype with a protective phenotype. Varying frequencies of both HHC and HHG*2 haplotypes in cohorts could therefore explain some of the inter-cohort outcome differences reported for the CCR5 Δ32 mutation (Garred, 1998). This suggests that it may be more appropriate to estimate whether haplotype pairs, rather than individual haplotypes, are associated with particular disease-modifying phenotypes.

It is noteworthy that despite presumably intimate contact with a SIVcpz/HIV-1 reservoir for thousands of years, the frequency of zoonotic transmission of SIVcpz/HIV-1 to pygmies appears to be very low (Gao et al., 1999; Kowo et al., 1995; Ndumbe et al., 1993; Brun-Vezinet et al., 1986; Gonzalez et al., 1987). Yet, among these secluded ethnic populations, there is a high prevalence of other blood-borne infections such as HBV, HCV and HTLV-1 (Kowo et al., 1995; Ndumbe et al., 1993). The very close relationships among some STLV-1 strains from chimpanzees and HTLV-1 subtype B strains present in pygmies (Koralnik et al., 1994; Saksena et al., 1994) reinforces the possibility of zoonotic transmission of other primary lentiviruses such as SIVcpz from chimpanzees to this ethnic group. These results indicate that HHA haplotypes are associated with a delay in disease progression in individuals of African descent, although there is no evidence that HHA haplotypes are associated with a reduction in transmission risk. Nonetheless, the highest prevalence of ancestral HHA haplotypes was in individuals of African descent ($\geq 0.22$), reaching its maximum in Mbuti and Biaka pygmies (0.71; Table 9). Whether protection against HIV-1 infection in pygmies could have been afforded, in part, by HHA haplotypes is unclear.

To lessen the potential of conflating protective and non-protective CCR5 haplotypes, the complex patterns of human CCR5 SNPs/polymorphisms were organized into evolutionarily meaningful relationships (Example 5) that provided the framework necessary for defining the effects of interactions between CCR5 haplotypes. This organization/classification of CCR5 haplotypes differs from than that reported recently (Martin et al., 1998). Based on genotypic data from a region of CCR5 spanning +208 to +811, ten CCR5 promoter alleles have been described (i.e., P1-P10). These CCR5 alleles represent only a subset of the haplotypes observed in world-wide populations in the studies described herein (Example 5). P2, P3, and P4 correspond to HHA, HHD, and HHC, respectively. The additional alleles defined by P5-P10 likely are members of haplogroup A, B, C or D. In this study, possession of HHD alleles were found to be restricted primarily to individuals of African descent, whereas the previously reported allelic frequency was 0.14 for this allele in Caucasians (Martin et al., 1998).

Homozygosity for the P1 (Martin et al., 1998) or 303A (McDermott et al., 1998) allele has been associated with disease acceleration. However, the present invention shows that the P1/303A allele is a composite of at least three haplogroups that share 303A and 627C(HHE, HHF*1, and HHG*1). The reason for this is that although the CCR2-64I allele is in nearly complete linkage disequilibrium with CCR5 927T, the converse is not true. In the WHMC cohort, 16% of CCR5 927T alleles were linked to CCR2-64V (HHG*1 allele; Table 10). Similarly, although the CCR5 Δ32 mutation is in nearly complete disequilibrium with CCR5 29G, 42% of CCR5 29G alleles are not linked to the Δ32 mutation (HHG*1 allele; Table 12). Thus, HHE is composed of P1/303A alleles lacking CCR5 29G and 927T. Inclusion of HHG*1 (neutral phenotype) and HHF*1 (disease-accelerating phenotype) haplotypes into HHE in the WHMC cohort would have increased the number of HHE homozygotes by 45% and this would have altered the significance of the phenotypic effects of this genotype. Thus, the P1/303A allele is a conflation of three alleles with different evolutionary histories and HIV-1 disease-modifying phenotypic effects.

The mechanistic basis for the HIV-1 disease-modifying effects of genetic variation in CCR5 is unclear and may, in part be attributable to differences in haplotype-specific transcriptional efficiency and/or differential nuclear factor binding to polymorphic CCR5 cis-regulatory sites (Example 5). However, the translation of in vitro data on differences transcriptional efficiency and/or DNA-protein interactions to differences in CCR5 surface expression, much less differences in disease progression, may be challenging.

In summary, the findings of this study suggest that CCR5 haplotypes are associated with powerful, population-specific HIV-1 disease-modifying effects. This highlights the importance of understanding the evolutionary context in which disease-associated haplotypes are found, and underscores the impact of allele-allele interactions, especially between alleles with different evolutionary histories.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

In addition to the U.S., PCT and European patents and patent applications referenced in the present text, the following references, to the extent that they provide exemplary procedural or other details supplementary to those set forth herein, are specifically incorporated herein by reference.

Abel and Dessein, "The impact of host genetics on susceptibility to human infectious diseases," *Curr. Opin. Immunol.*, 9:509-516, 1997.

Achord et al., "HIV-1 disease association with HLA-DQ antigens in African Americans and Caucasians," *Pathobiology*, 64:204-208, 1996.

Ahuja and Murphy, "Molecular piracy of mammalian interleukin-8 receptor type B by herpesvirus saimiri," *J. Biol. Chem.*, 268(28):20691-20694, 1993.

Ahuja and Murphy, "The CXC chemokines growth-regulated oncogene (GRO) alpha, GRObeta, GROgamma, neutrophil-activating peptide-2, and epithelial cell-derived neutrophil-activating peptide-78 are potentagonists for the type B, but not the type A, human interleukin-8 receptor," *J. Biol. Chem.*, 271(34):20545-20550, 1996.

Ahuja et al., "Molecular evolution of the human interleukin-8 receptor gene cluster," *Nat. Genet.*, 2(1):31-36, 1992.

Ahuja et al., "Chemokine receptors and molecular mimicry," *Immunol. Today*, 15(6):281-287, 1994.

Ahuja et al., "Comparison of the genomic organization and promoter function for human interleukin-8 receptors A and B," *J. Biol. Chem.*, 269(42):26381-26389, 1994a.

Ahuja et al., "Characterization of the promoters of human IL-8 receptors A and B in myeloid and lymphoid cell lines, and CD34+ peripheral blood hematopoietic progenitor cells," *Mol. Biol. Cell*, 5:122A, 1994b.

Ahuja et al., "Autocrine activation of hemopoietic progenitor-derived myelo-monocytic cells by IFN-gamma gene transfer," *J. Immunol.*, 156(11):4345-4353, 1996.

Ahuja et al., "CXC chemokines bind to unique sets of selectivity determinants that can function independently and are broadly distributed on multiple domains of human interleukin-8 receptor B. Determinants of high affinity binding and receptor activation are distinct," *J. Biol. Chem.*, 271(1):225-232, 1996.

Alkhatib et al., "CC CKR5: a RANTES, MIP-1alpha, MIP-1beta receptor as a fusion cofactor for macrophage-tropic HIV-1," *Science*, 272(5270):1955-1958, 1996.

Alkhatib et al., "CC chemokine receptor 5-mediated signaling and HIV-1 Co-receptor activity share common structural determinants. Critical residues in the third extracellular loop support HIV-1 fusion," *J. Biol. Chem.*, 272(32): 19771-19776, 1997.

Alkhatib et al., "HIV-1 coreceptor activity of CCR5 and its inhibition by chemokines: independence from G protein signaling and importance of coreceptor downmodulation," *Virology*, 234(2):340-348, 1997.

Allan et al., *AIDS Res. Hum. Retroviruses*, 6(3):275-285, 1990.

Allan et al., *J. Virol.*, 65(6):2816-2828, 1991.

Allan, *NIH Res.*, 4:51-54, 1992.

Amara et al., "HIV co-receptor downregulation as antiviral principle: SDF-1alpha-dependent internalization of the chemokine receptor CXCR4 contributes to inhibition of HIV replication," *J. Exp. Med.*, 186:139-146, 1997.

Angotti et al., "A polymorphism (G→A transition) in the −78 position of the apolipoprotein A-I promoter increases transcription efficiency," *J. Biol. Chem.*, 269(26):17371-17374, 1994.

Ansari-Lari et al., "The extent of genetic variation in the CCR5 gene," *Nat. Genet.*, 16(3):221-222, 1997.

Anzala et al., "CCR2-64I allele and genotype association with delayed AIDS progression in African women," University of Nairobi Collaboration for HIV Research, *Lancet*, 351:1632-1633, 1998.

Asano et al., "Naturally occurring mutations in the human 5-lipoxygenase gene promoter that modify transcription factor binding and reporter gene transcription," *J. Clin. Invest.*, 99(5):1130-1137, 1997.

Atchison et al., "Multiple extracellular elements of CCR5 and HIV-1 entry: dissociation from response to chemokines," Science, 274(5294):1924-1926, 1996.

Ayoubi and Van De Ven, FASEB J., 10:453-460, 1996.

Ball et al., J. Biol. Chem., 270:27272-27276, 1995.

Bamshad, Watkins, Dixon, Jorde, Rao, Naidu, Prasad, Rasanayagam and Hammer, Nature 395:651-652, 1998.

Bellamy and Hill, "Genetic susceptibility to mycobacteria and other infectious pathogens in humans," Curr. Opin. Immunol., 10:483-487, 1998.

Berger, "HIV entry and tropism: the chemokine receptor connection," AIDS, 11:S3-S16, 1997.

Berger et al., "A new classification for HIV-1," Nature, 391:240, 1998.

Biti R et al., "HIV-1 infection in an individual homozygous for the CCR5 deletion allele," Nat. Med., 3(3):252-253, 1997.

Bjorndal et al., "Co-receptor usage of primary human immunodeficiency virus type 1 isolates varies according to biological phenotype," J. Virol., 71:7478-7487, 1997.

Blanche et al., "Morbidity and mortality in European children vertically infected by HIV-1," The French Pediatric HIV Infection Study Group and European Collaborative Study. J. Acquir. Immune Defic. Syndr. Hum. Retrovirol., 14:442-450, 1997.

Blatt et al., "Total lymphocyte count as a predictor of absolute CD4+ count and CD4+ percentage in HIV-infected persons," JAMA, 269:622-626, 1993a.

Blatt et al., "Delayed-type hypersensitivity skin testing predicts progression to AIDS in HIV-infected patients," Ann. Intern. Med., 119:177-184, 1993b.

Blatt et al., "Multivariate models for predicting progression to AIDS and survival in human immunodeficiency virus-infected persons," J. Infect. Dis., 171:837-44, 1995.

Bleul et al., "The lymphocyte chemoattractant SDF-1 is a ligand for LESTR/fusin and blocks HIV-1 entry," Nature, 382(6594):829-833, 1996.

Bleul et al., "The HIV coreceptors CXCR4 and CCR5 are differentially expressed and regulated on human T lymphocytes," Proc. Natl. Acad. Sci. USA, 94(5):1925-1930, 1997.

Boucher et al., "Phase I evaluation of Zidovudine administered to infants exposed at birth to the human immunodeficiency virus," J. Pediatrics 122:137-144, 1993.

Bozon et al., "Comparison of HLA-A antigen typing by serology with two polymerase chain reaction based DNA typing methods: implications for proficiency testing," Tissue Antigens, 47:512-518, 1996.

Bozzette et al., "The care of HIV-infected adults in the United States," HIV Cost and Services Utilization Study Consortium, N. Engl. J. Med., 339:1897-1904, 1998.

Brackin et al., "Progression of HIV infection is associated with HLA-DQ antigens in Caucasians and African Americans," Pathobiology, 63:22-41, 1995.

Bream et al., Science, 284:223, 1999.

Brettle et al., "Progression of HIV: follow-up of Edinburgh injecting drug users with narrow seroconversion intervals in 1983-1985," Aids, 10:419-430, 1996.

Brun-Vezinet et al., "Lack of evidence for human or simian T-lymphotropic viruses type III infection in pygmies," Lancet, 1:854, 1986.

Buchacz et al., "Genetic and immunological host factors associated with susceptibility to HIV-1 infection," Aids, 12:S87-S94, 1998.

Bustin and McKay, "Transcription factors: targets for new designer drugs," Br. J. Biomed Sci., 51(2):147-157, 1994.

Cairns and D'Souza, "Chemokines and HIV-1 second receptors: the therapeutic connection," Nat. Med., 4:563-568, 1998.

Cameron et al., "Influence of C4 null genes on infection with human immunodeficiency virus," Br. Med. J. (Clin. Res. Ed), 296:1627-1628, 1988.

Cameron et al., "Major histocompatibility complex genes influence the outcome of HIV infection. Ancestral haplotypes with C4 null alleles explain diverse HLA associations," Hum. Immunol., 29:282-295, 1990.

Carrington et al., "Novel alleles of the chemokine-receptor gene CCR5," Am. J. Hum. Genet., 61(6):1261-1267, 1997.

Carrington et al., "HLA and HIV-1: heterozygote advantage and B*35-Cw*04 disadvantage," Science, 283:1748-1752, 1999.

Carroll et al., "Differential regulation of HIV-1 fusion cofactor expression by CD28 costimulation of CD4+ T cells," Science, 276(5310):273-276, 1997.

Center for Disease Control and Prevention, "Guidelines for the use of antiretroviral agents in pediatric HIV infection," MMWR Morb. Mortal Wkly Rep., 47:1-43, 1998.

Center for Disease Control and Prevention, "HIV/AIDS Surveillance Report," 10(1), 1998.

Chen et al., J. Exp. Med., 188(11):2057-2065, 1998.

Choe et al., "The beta-chemokine receptors CCR3 and CCR5 facilitate infection by primary HIV-1 isolates," Cell, 85(7):1135-1148, 1996.

Cocchi et al., "Identification of RANTES, MIP-1 alpha, and MIP-1 beta as the major HIV-suppressive factors produced by CD8+ T cells," Science, 270(5243):1811-1815, 1995.

Cohen et al., "Host factors in the pathogenesis of HIV disease," Immunol. Rev., 159:31-48, 1997.

Combadiere et al., "Cloning and functional expression of a human eosinophil CC chemokine receptor," J. Biol. Chem., 270(28):16491-16494, 1995; Published erratum J. Biol. Chem., 270(50):30235, 1995a.

Combadiere et al., "Monocyte chemoattractant protein-3 is a functional ligand for CC chemokine receptors 1 and 2B," J. Biol. Chem., 270(50):29671-29675, 1995b.

Combadiere et al., "Cloning, chromosomal localization, and RNA expression of a human beta chemokine receptor-like gene," DNA Cell Biol., 14(8):673-680, 1995c.

Combadiere et al., "Cloning and functional expression of CC CKR5, a human monocyte CC chemokine receptor selective for MIP-1(alpha), MIP-1(beta), and RANTES," J. Leukoc. Biol., 60(1):147-152, 1996.

Connor et al., "Change in coreceptor use correlates with disease progression in HIV-1-infected individuals," J. Exp. Med., 185(4):621-628, 1997.

Cook et al., "Developmentally regulated mRNAs in 3T3-adipocytes: analysis of transcriptional control," J. Cell Biol., 100(2):514-520, 1985.

Corzo et al., "Advances in HLA genetics," Exp. Clin. Immunogenet., 12:156-170, 1995.

Csink and Henikoff, "Something from nothing: the evolution and utility of satellite repeats," Trends Genet., 14:200-204, 1998.

Cunningham et al., "Comparison of health-related quality of life in clinical trial and nonclinical trial human immunodeficiency virus-infected cohorts," Med. Care, 33:AS15-AS25, 1995.

Curnow et al., Mol. Endocrinol., 9:1250-1262, 1995.

Dallinga-Thie et al., "Complex genetic contribution of the Apo AI-CIII-AIV gene cluster to familial combined hyperlipidemia. Identification of different susceptibility haplotypes," J. Clin. Invest., 99(5):953-961, 1997.

Dausset, "Le centre d'etude du polymorphisme humain," *Presse Med.*, 15(36):1801-1802, 1986.

Dausset, Cann, Cohen, Lathrop, Lalouel and White, *Genomics* 6:575-577, 1990.

Dawkins et al., "HIV-1-associated Kaposi's sarcoma in a predominantly black population at an inner city hospital," *South Med. J*, 91:546-549, 1998.

Dawson et al., "A single amino acid change converts an inhibitory transcription factor into an activator," *J. Biol. Chem.*, 271:11631-11633, 1996.

de Roda Husman et al., "Association between CCR5 genotype and the clinical course of HIV-1 infection," *Ann. Intern. Med.*, 127:882-890, 1997.

Dean et al., "Genetic restriction of HIV-1 infection and progression to AIDS by a deletion allele of the CKR5 structural gene," Hemophilia Growth and Development Study, Multicenter AIDS Cohort Study, Multicenter Hemophilia Cohort Study, San Francisco City Cohort, ALIVE Study, *Science*, 273:1856-1862, 1996 (Erratum published in *Science*, 274(5290):1069, 1996).

Deichmann et al., "Expression of the human immunodeficiency virus type-1 coreceptors CXCR-4 (fusin, LESTR) and CKR-5 in CD34+ hematopoietic progenitor cells," *Blood*, 89(10):3522-3528, 1997.

Deng et al., "Identification of a major co-receptor for primary isolates of HIV-1,". *Nature*, 381(6584):661-666, 1996.

Deng et al., "Expression cloning of new receptors used by simian and human immunodeficiency viruses," *Nature*, 388(6639):296-300, 1997.

Dillon et al., "The effect of distance on long-range chromatin interactions," *Mol. Cell*, 1:131-139, 1997.

Dolan et al., "Early markers of HIV infection and subclinical disease progression," *Vaccine*, 11:548-551, 1993.

Dolan et al., "In vitro T cell function, delayed-type hypersensitivity skin testing, and CD4+ T cell subset phenotyping independently predict survival time in patients infected with human immunodeficiency virus," *J. Infect. Dis.*, 172:79-87, 1995.

Donald et al., "Progression of HIV-related disease is associated with HLA DQ and DR alleles defined by restriction fragment length polymorphisms," *Tissue Antigens*, 39:241-248, 1992.

Doranz et al., "A dual-tropic primary HIV-1 isolate that uses fusin and the beta-chemokine receptors CKR-5, CKR-3, and CKR-2b as fusion cofactors," *Cell*, 85(7):1149-1158, 1996.

Dragic et al., "HIV-1 entry into CD4+ cells is mediated by the chemokine receptor CC-CKR-5," *Nature*, 381:667-673, 1996.

Dragic et al., *J. Virol.*, 72(1):279-285, 1998.

D'Souza and Harden, "Chemokines and HIV-1 second receptors. Confluence of two fields generates optimism in AIDS research," *Nat. Med.*, 2:1293-1300, 1996.

Edinger et al., *Virology*, 249(2):367-378, 1998.

Esposito et al., "Role of CCR5 chemokine receptor gene in vertical human immunodeficiency virus type 1 transmission and disease progression," *Pediatr. Infect. Dis. J.*, 17:847-849, 1998.

Eugen-Olsen et al., "Heterozygosity for a deletion in the CKR-5 gene leads to prolonged AIDS-free survival and slower CD4 T-cell decline in a cohort of HIV-seropositive individuals," *AIDS*, 11:305-310, 1997.

Eugen-Olsen et al., "Chemokine receptor CCR2b 64I polymorphism and its relation to CD4 T-cell counts and disease progression in a Danish cohort of HIV-infected individuals," Copenhagen AIDS cohort, *J. Acquir. Immune Defic. Syndr. Hum. Retrovirol.*, 18:110-116, 1998.

Fabio et al., "HLA-associated susceptibility to HIV-1 infection," *Clin. Exp. Immunol.*, 87:20-23, 1992.

Farzan et al., "HIV-1 entry and macrophage inflammatory protein-1beta-mediated signaling are independent functions of the chemokine receptor CCR5," *Biol. Chem.*, 272(11):6854-6857, 1997.

Fauci, "Host factors and the pathogenesis of HIV-induced disease," *Nature*, 384(6609):529-534, 1996.

Fauci, "Host factors in the pathogenesis of HIV disease," *Antibiot. Chemother.*, 48:4-12, 1996.

Feng et al., "HIV-1 entry cofactor: functional cDNA cloning of a seven-transmembrane, G protein-coupled receptor," *Science*, 272(5263):872-877, 1996.

Ferbas, "Perspectives on the role of CD8+ cell suppressor factors and cytotoxic T lymphocytes during HIV infection," *AIDS Res. Hum. Retroviruses*, 14(Suppl 2):S153-S160, 1998.

Fernandez-Reyes et al., "A high frequency African coding polymorphism in the N-terminal domain of ICAM-1 predisposing to cerebral malaria in Kenya," *Hum. Mol. Genet.*, 6:1357-1360, 1997.

Fischl et al., "The efficacy of azidothymidine (AZT) in the treatment of patients with AIDS and AIDS-related complex," *NEJM* 317:185-191, 1987.

Fischl et al., "A randomized controlled trial of a reduced daily dose of Zidovudine in patients with the acquired immunodeficiency syndrome," *NEJM* 323:1009-1014, 1990.

Fleiss, In: *Statistical Methods for Rates and Proportions*, 2nd ed., New York, John Wiley & Sons., pp. 174, 1981.

Fomsgaard et al., *Virology*, 182(1):397-402, 1991.

Fowke et al., "Resistance to HIV-1 infection among persistently seronegative prostitutes in Nairobi, Kenya," *Lancet*, 348:1347-1351, 1996.

Freimer and Slatkin, "Microsatellites: evolution and mutational processes," *Ciba Found. Symp.*, 197:51-67, 1996.

Frohman, In: "PCR Protocols: A Guide To Methods And Applications", Academic Press, N.Y., 1990.

Furci et al., "Antigen-driven C-C chemokine-mediated HIV-1 suppression by CD4(+) T cells from exposed uninfected individuals expressing the wild-type CCR-5 allele," *J. Exp. Med.*, 186:455-460, 1997.

Furci et al., "CD8+ T lymphocyte-derived chemokines and other HIV-suppressive factors: mini-review," *J. Chemother.*, 10: 146-149, 1998.

Furman et al., "Phosphorylation of 3'-azido-3'-deoxythymidine and selective interaction of the 5'-triphosphate with human immunodeficiency virus reverse transcriptase" *Proc. Natl. Acad. Sci. USA* 83:8333-8337, 1986.

Furman et al., "Spectrum of antiviral activity and mechanism of action of Zidovudine," *Am. J. Med.* 85:176-181, 1988.

Gao et al., "Origin of HIV-1 in the chimpanzee Pan troglodytes troglodytes," *Nature*, 397(6718):436-441, 1999.

Gardner and Luciw, *FASEB J.*, 3(14):2593-2606, 1989.

Garred et al., "Dual effect of CCR5 delta 32 gene deletion in HIV-1-infected patients," Copenhagen AIDS Study Group, *Lancet*, 349(9069):1884, 1997.

Garred, "Chemokine-receptor polymorphisms: clarity or confusion for HIV-1 prognosis?," *Lancet*, 351:2-3, 1998.

Garzino-Demo et al., "Beta-chemokines and protection from HIV type 1 disease," *AIDS Res. Hum. Retroviruses*, 14(Suppl 2):S177-S184, 1998.

Garzino-Demo et al., "Chemokine receptors and chemokines in HIV infection," *J. Clin. Immunol.*, 18:243-255, 1998.

Gerard et al., "Human chemotaxis receptor genes cluster at 19q13.3-13.4. Characterization of the human C5a receptor gene," *Biochemistry*, 32(5):1243-1250, 1993.

Glushakova et al., "Evidence for the HIV-1 phenotype switch as a causal factor in acquired immunodeficiency," Nat. Med., 4:346-349, 1998.

Gojobori et al., Proc. Natl. Acad. Sci. USA, 87(11):4108-4111, 1990.

Goldstein and Pollock, "Launching microsatellites: a review of mutation processes and methods of phylogenetic inference," J. Hered., 88:335-342, 1997.

Gonzalez et al., "True HIV-1 infection in a pygmy," Lancet, 1:1499, 1987.

Goodman et al., Mol. Phylogenet. Evol., 9(3):585-598, 1998.

Goodman, Am. J. Hum. Genet., 64(1):31-39, 1999.

Gosling et al., "Molecular uncoupling of C-C chemokine receptor 5-induced chemotaxis and signal transduction from HIV-1 coreceptor activity," Proc. Natl. Acad. Sci. USA, 94(10):5061-5066, 1997.

Granelli-Piperno et al., "Efficient interaction of HIV-1 with purified dendritic cells via multiple chemokine coreceptors," J. Exp. Med., 184(6):2433-2438, 1996.

Granja et al., "Population genetics and human leukocyte polymorphism," In: Transplantation Biology: Cellular and Molecular Aspects, Tilney et al., Eds., 311-324, 1996.

Graziosi et al., "Immunopathogenesis of HIV infection," AIDS Res. Hum. Retroviruses, 14(Suppl 2):S135-S142, 1998.

Guignard et al., J. Immunol., 160(2):985-992, 1998.

Haffner et al., "Hyperinsulinemia in a population at high risk for non-insulin-dependent diabetes mellitus," N. Engl. J. Med., 315(4):220-224, 1986.

Hendel et al., "Distinctive effects of CCR5, CCR2, and SDF1 genetic polymorphisms in AIDS progression," J. Acquir. Immune Defic. Syndr. Hum. Retrovirol., 19:381-386, 1998.

Hill, "HLA and infection," J. R. Coll. Physicians Lond., 26:11-16, 1992.

Hill, "Malaria resistance genes: a natural selection," Trans. R. Soc. Trop. Med. Hyg., 86:225-226, 232, 1992b.

Hill et al., "Human leukocyte antigens and natural selection by malaria," Philos. Trans. R. Soc. Lond. B. Biol. Sci., 346:379-385, 1994.

Hill, "Genetic susceptibility to malaria and other infectious diseases: from the MHC to the whole genome," Parasitology, 112:S75-S84, 1996.

Hill, "HIV and HLA: confusion or complexity?," Nat. Med., 2:395-396, 1996.

Hill et al., "Genetic analysis of host-parasite coevolution in human malaria," Philos. Trans. R. Soc Lond. B. Biol. Sci., 352:1317-1325, 1997.

Hill, "The immunogenetics of human infectious diseases," Annu. Rev. Immunol., 16:593-617, 1998.

Hirashima et al., "Nucleotide sequence of the third cytokine LD78 gene and mapping of all three LD78 gene loci to human chromosome 17," DNA Seq., 3:203-212, 1992.

Hirsch et al., Nature, 339(6223):389-392, 1989.

Hirsch et al., J. Virol., 73(2): 1036-1045, 1999.

HIV/AIDS Surveillance Report CDC, "U.S. HIV and AIDS cases reported through June 1988," 10(1), 1998.

Hovanessian et al., "Antiviral activity of Poly(A)·Poly(U) against HIV in vitro," Intl. Conf. AIDS 7:113 (abstract W.A.1084), 1991.

Hu et al., "How important is race/ethnicity as an indicator of risk for specific AIDS-defining conditions?," J Acquir. Immune Defic. Syndr. Hum. Retrovirol., 10:374-380, 1995.

Huang et al., "The role of a mutant CCR5 allele in HIV-1 transmission and disease progression," Nat. Med., 2(11):1240-1243, 1996.

Iannetti et al., "HLA antigens, epilepsy and cytomegalovirus infection," Brain Dev., 10:256-258, 1988.

Inoue et al., "A nucleotide substitution in the promoter of human angiotensinogen is associated with essential hypertension and affects basal transcription in vitro," J. Clin. Invest., 99(7):1786-1797, 1997.

Ioannidis et al., "Genetic effects on HIV disease progression," Nat. Med., 4:536, 1998.

Itescu et al., "HLA-B35 is associated with accelerated progression to AIDS," J. Acquir. Immune Defic. Syndr., 5:37-45, 1992.

Itescu et al., "Certain HLA-DR5 and -DR6 major histocompatibility complex class II alleles are associated with a CD8 lymphocytic host response to human immunodeficiency virus type 1 characterized by low lymphocyte viral strain heterogeneity and slow disease progression," Proc. Natl. Acad. Sci. USA, 91:11472-11476, 1994.

Itescu et al., "Grouping HLA-B locus serologic specificities according to shared structural motifs suggests that different peptide-anchoring pockets may have contrasting influences on the course of HIV-1 infection," Hum. Immunol., 42:81-89, 1995.

Iwamoto et al., "Genomic organization of the glycoprotein D gene: Duffy blood group Fya/Fyb alloantigen system is associated with a polymorphism at the 44-amino acid residue," Blood, 85(3):622-626, 1995.

Iwamoto et al., "Identification of a novel exon and spliced form of Duffy mRNA that is the predominant transcript in both erythroid and postcapillary venule endothelium," Blood, 87(1):378-385, 1996.

Izuta et al., "The 5'-triphosphates of 3'-azido-3'-deoxythymidine and 2',3'-dideoxynucleosides inhibit DNA polymerase γ by different mechanisms," Biochem. Biophys. Res. Comm. 179:776-783, 1991.

Jackson, Cell, 74:9-14, 1993.

Jolly et al., J. Med. Primatol., 25(2):78-83, 1996.

Jones et al., "Trends in AIDS-related opportunistic infections among men who have sex with men and among injecting drug users, 1991-1996,". J. Infect. Dis., 178:114-120, 1998.

Jorde et al., Am. J. Hum. Genet., 57(3):523-538, 1995.

Jorde et al., "Using mitochondrial and nuclear DNA markers to reconstruct human evolution," Bioessays, 20:126-136, 1998.

Joyce et al., "Variation in inpatient resource use in the treatment of HIV: do the privately insured receive more care?," Med. Care, 37:220-227, 1999.

Just et al., "Genetic risk factors for perinatally acquired HIV-1 infection," Paediair. Perinat. Epidemiol., 6:215-224, 1992.

Just et al., "Influence of host genotype on progression to acquired immunodeficiency syndrome among children infected with human immunodeficiency virus type 1," J. Pediatr., 127:544-549, 1995.

Just, "Genetic predisposition to HIV-1 infection and acquired immune deficiency virus syndrome: a review of the literature examining associations with HLA," [Erratum published in Hum. Immunol., 45(1):78, 1996, Hum. Immunol., 44:156-169, 1995.

Kaloterakis et al., "HLA in familial and nonfamilial Mediterranean Kaposi's sarcoma in Greece," Tissue Antigens, 45:117-119, 1995.

Kaplan et al., "HLA-associated susceptibility to acquired immune deficiency syndrome in HIV-1-seropositive subjects," Hum. Hered., 40:290-298, 1990.

Kaslow et al., "A1, Cw7, B8, DR3 HLA antigen combination associated with rapid decline of T-helper lymphocytes in HIV-1 infection," A report from the Multicenter AIDS Cohort Study, Lancet, 335:927-930, 1990.

Kaslow et al., "Influence of combinations of human major histocompatibility complex genes on the course of HIV-1 infection," *Nat. Med.*, 2:405-411, 1996.

Katzenstein et al. "HIV-infected individuals with the CCR delta32/CCR5 genotype have lower HIV RNA levels and higher CD4 cell counts in the early years of the infection than do patients with the wild type," Copenhagen AIDS Cohort Study Group, *J. Acquir. Immune Defic. Syndr. Hum. Retrovirol.*, 16:10-14, 1997.

Kazazian, "The Thalassemia syndromes: molecular basis and prenatal diagnosis in 1990," *Sem. Hematol.*, 27(3):209-228, 1990.

Keet et al., "The role of host genetics in the natural history of HIV-1 infection: the needles in the haystack," *Aids*, 10:S59-S67, 1996.

Klein et al., "Associations between HLA frequencies and pathogenic features of human immunodeficiency virus type 1 infection in seroconverters from the Amsterdam cohort of homosexual men," *J. Infect. Dis.*, 169:1244-1249, 1994.

Knight et al., *Nat. Genet.*, 22(2): 145-150, 1999.

Koralnik et al., "Phylogenetic associations of human and simian T-cell leukemia/lymphotropic virus type I strains: evidence for interspecies transmission," *J. Virol.*, 68:2693-2707, 1994.

Kostrikis et al., "A chemokine receptor CCR2 allele delays HIV-1 disease progression and is associated with a CCR5 promoter mutation," *Nat. Med.*, 4:350-353, 1998.

Kostrikis et al., "Spectral genotyping of human alleles," *Science*, 279:1228-1229, 1998.

Kowo et al., "Prevalence of hepatitis C virus and other blood-borne viruses in Pygmies and neighbouring Bantus in southern Cameroon," *Trans. R. Soc. Trop. Med. Hyg.*, 89:484-486, 1995.

Kozak, *Proc. Natl. Acad. Sci. USA*, 83:2850-2854, 1986.

Kozak, *J. Cell Biol.*, 108:229-241, 1989.

Kozak, *J. Cell Biol.*, 115:887-903, 1991.

Kurumbail et al., "Structural basis for selective inhibition of cyclooxygenase-2 by anti-inflammatory agents," *Nature*, 384:644-648, 1996.

Lacey et al., "Biochemical studies on the reverse transcriptase and RNase H activities from human immunodeficiency virus strains resistant to 3'-azido-3'-deoxythymidine," *J. Biol. Chem.* 267:15789-15794, 1992.

Lambert et al., "2',3'-dideoxyinosine (ddI) in patients with the acquired immunodeficiency syndrome or AIDS-related complex," *NEJM* 322:1333-1340, 1990.

Larder, "Inhibitors of HIV reverse transcriptase as antiviral agents and drug resistance." In Reverse Transcriptase (A. M. Skalka & S. P. Goff, ed.), Cold Spring Harbor Laboratory Press, Plainview, N.Y., pp. 205-222, 1993.

Leen et al., "Structural and functional analysis of HLA-DR beta-promoter polymorphism and isomorphism," *Hum. Immunol.*, 41(2):112-120, 1994.

Levis and Penman, "The metabolism of poly (A)+ and poly (A)-hnRNA in cultured *Drosophila* cells studied with a rapid uridine pulse-chase," *Cell*, 11(1):105-113, 1977.

Li et al., *J. Med. Primatol.*, 18(3-4):261-269, 1989.

Li and Sadler, *Genetics*, 129(2):513-523, 1991.

Li et al., "PU.1 is essential for p47phox promoter activity in myeloid cells," *J. Biol. Chem.*, 272(28): 17802-17809, 1997.

Libert et al., "The deltaccr5 mutation conferring protection against HIV-1 in Caucasian populations has a single and recent origin in Northeastern Europe," *Hum. Mol. Genet.*, 7:399-406, 1998.

Lifson et al., "Early viral replication dynamics predict clinical course in SIV infected macaques," *4th Conf Retro. and Opportun. Infect.*, 136, Abstract No. 390, Jan. 22-26, 1997.

Liu et al., "Homozygous defect in HIV-1 coreceptor accounts for resistance of some multiply-exposed individuals to HIV-1 infection," *Cell*, 86(3):367-377, 1996.

Liu et al., "Divergent patterns of progression to AIDS after infection from the same source: human immunodeficiency virus type 1 evolution and antiviral responses," *J. Virol.*, 71:4284-4295, 1997.

Liu et al., *AIDS Res. Hum. Retroviruses*, 14(17):1509-1519, 1998.

Liu et al., "Polymorphism in RANTES chemokine promoter affects HIV-1 disease progression," *Proc. Natl. Acad. Sci. USA*, 96:4581-4585, 1999.

Louie et al., "Influence of host genotype on progression to AIDS among HIV-infected men," J. Acquir. Immune Defic. Syndr., 4:814-818, 1991.

Lu et al., "Evolution of HIV-1 coreceptor usage through interactions with distinct CCR5 and CXCR4 domains," *Proc. Natl. Acad. Sci. USA*, 94(12):6426-6431, 1997.

Lucotte, "Frequencies of the CC chemokine receptor 5 delta 32 allele in various populations of defined racial background," *Biomed. Pharmacother.*, 51:469-473, 1997.

Ma et al., "New thymidine triphosphate analogue inhibitors of human immunodeficiency virus-1 reverse transcriptase," *J. Med. Chem.* 35:1938-1941, 1992.

Malnati et al., "Increased plasma levels of the C-C chemokine RANTES in patients with primary HIV-1 infection," *J. Biol. Regul. Homeost. Agents*, 11:40-42, 1997.

Mandl et al., "Possible influence of the mutant CCR5 Allele on vertical transmission of HIV-1," *J. Med. Virol.*, 55:51-55, 1998.

Mangano et al., "Distribution of CCR-5 delta32 allele in Argentinean children at risk of HIV-1 infection: its role in vertical transmission," *AIDS*, 12:109-110, 1998.

Mann et al., "HLA antigen frequencies in HIV-1-related Kaposi's sarcoma," *J. Acquir. Immune Defic. Syndr.*, 3:S51-S55, 1990.

Mann et al., "HLA phenotype is a factor in determining rate of disease progression and outcome in HIV-1-infected individuals," *AIDS Res. Hum. Retroviruses*, 8:1345-1346, 1992.

Mann et al., "Major histocompatibility complex genotype is associated with disease progression and virus load levels in a cohort of human immunodeficiency virus type 1-infected Caucasians and African Americans," *J. Infect. Dis.*, 178: 1799-1802, 1998.

Martin et al., "Genetic acceleration of AIDS progression by a promoter variant of CCR5," *Science*, 282(5395): 1907-1911, 1998.

Martinson et al., "Global distribution of the CCR5 gene 32-basepair deletion," *Nat. Genet.*, 16(1):100-103, 1997.

Masood et al., "Cellular pharmacology of the anti-HIV agent 2',3'-didehydro-2',3'-dideoxythymidine," *Proc. Amer. Assoc. Cancer Res.* 30:594 (abstract A2364), 1989.

McDermott et al., "CCR5 promoter polymorphism and HIV-1 disease progression," Multicenter AIDS Cohort Study (MACS), *Lancet*, 352(9131):866-870, 1998.

McGuire et al., "Variation in the TNF-alpha promoter region associated with susceptibility to cerebral malaria," *Nature*, 371(6497):508-510, 1994.

McKnight and Palmiter, "Transcriptional regulation of the ovalbumin and conalbumin genes by steroid hormones in chick oviduct," *J. Biol. Chem.*, 254(18):9050-9058, 1979.

McNeil et al., "Association of HLA types A1-B8-DR3 and B27 with rapid and slow progression of HIV disease," *QJM*, 89:177-185, 1996.

McNicholl et al., "Host genes and HIV: the role of the chemokine receptor gene CCR5 and its allele," Erratum published in *Emerg. Infect. Dis.*, 3(4):584, 1997, *Emerg. Infect. Dis.*, 3:261-271, 1997.

Mehra, "Role of HLA linked factors in governing susceptibility to leprosy and tuberculosis," *Trop. Med. Parasitol.*, 41:352-354, 1990.

Mellors et al., "Prognosis in HIV-1 infection predicted by the quantity of virus in plasma," erratum published in *Science*, 275(5296):14, 1997, *Science*, 272:1167-1170, 1996.

Mellors et al., "Plasma viral load and CD4+ lymphocytes as prognostic markers of HIV-1 infection," *Ann. Intern. Med.*, 126:946-954, 1997.

Meng et al., AIDS clinical trials group: Phase I/II study of combination 2',3'-dideoxycytidine and Zidovudine in patients with acquired immunodeficiency syndrome (AIDS) and advanced AIDS-related complex," *Am. J. Med.* 88:27 S-30S, 1990.

Messier and Stewart, *Nature*, 385(6612):151-154, 1997.

Meyer et al., "Early protective effect of CCR-5 delta 32 heterozygosity on HIV-1 disease progression: relationship with viral load," The SEROCO Study Group, *AIDS*, 11:F73-F78, 1997.

Michael et al., "The role of CCR5 and CCR2 polymorphisms in HIV-1 transmission and disease progression," *Nat. Med.*, 3(10): 1160-1162, 1997a.

Michael et al., "The role of viral phenotype and CCR-5 gene defects in HIV-1 transmission and disease progression," *Nat. Med.*, 3(3):338-340, 1997b.

Misrahi et al., "CCR5 chemokine receptor variant in HIV-1 mother-to-child transmission and disease progression in children," French Pediatric HIV Infection Study Group. *Jama*, 279:277-280, 1998.

Mitsuya et al., "3'-Azido-3'-deoxythymidine (BW A509U): An antiviral agent that inhibits the infectivity and cytopathic effect of human T-lymphotropic virus type III/lymphadenopathy-associated virus in vitro," *Proc. Natl. Acad. Sci. USA* 82:7096-7100, 1985.

*MMWR Morb. Mortal Wkly Rep.*, "Revised classification for HIV-1 infection in children," *MMWR Morb. Mortal Wkly Rep.* 43: 1-10, 1994.

Moore et al., "Co-receptors for HIV-1 entry," *Curr. Opin. Immunol.*, 9:551-562, 1997.

Moore, "Coreceptors: implications for HIV pathogenesis and therapy," *Science*, 276:51-52, 1997.

Morawetz et al., "Genetic polymorphism of CCR5 gene and HIV disease: the heterozygous (CCR5/delta ccr5) genotype is neither essential nor sufficient for protection against disease progression," Swiss HIV Cohort, *Eur. J. Immunol.*, 27:3223-3227, 1997.

Moriuchi et al., "CD8+ T-cell-derived soluble factor(s), but not beta-chemokines RANTES, MIP-1 alpha, and MIP-1 beta, suppress HIV-1 replication in monocyte/macrophages," *Proc. Natl. Acad. Sci. USA*, 93:15341-15345, 1996.

Moriuchi et al., "Nuclear factor-kappa B potently up-regulates the promoter activity of RANTES, a chemokine that blocks HIV infection," *J. Immunol.*, 158:3483-3491, 1997.

Moriuchi et al., *J. Immunol.*, 159(11):5441-5449, 1997.

Murphy et al., "Sequence and organization of the human N-formyl peptide receptor-encoding gene," *Gene*, 133(2): 285-290, 1993.

Murphy, "Chemokine receptors: structure, function and role in microbial pathogenesis," *Cytokine Growth Factor Rev.*, 7(1):47-64, 1996.

Murphy, *Annu. Rev. Immunol.*, 12:593-633, 1994.

Mutoh et al., "Two different promoters direct expression of two distinct forms of mRNAs of human platelet-activating factor receptor," *FEBS Lett.*, 322(2): 129-134, 1993.

Naganawa et al., "Intestinal transcription and synthesis of apolipoprotein AI is regulated by five natural polymorphisms upstream of the apolipoprotein CIII gene," *J. Clin. Invest.*, 99(8):1958-1965, 1997.

Nakao et al., "Structures of human genes coding for cytokine LD78 and their expression," *Mol. Cell Biol*, 10:3646-3658, 1990.

Ndumbe et al., "Infections among pygmies in the Eastern Province of Cameroon," *Med. Microbiol. Immunol.*, 182: 281-284, 1993.

Nei and Gojobori, *Mol. Biol. Evol.*, 3(5):418-426, 1986.

Nelson et alt, "Genomic organization and transcriptional regulation of the RANTES chemokine gene," *J. Immunol.*, 151:2601-2612, 1993.

Nelson et al., "Frequency of HLA allele-specific peptide motifs in HIV-1 proteins correlates with the allele's association with relative rates of disease progression after HIV-1 infection," *Proc. Natl. Acad. Sci. USA*, 94:9802-9807, 1997.

Nibbs et al., *J. Biol. Chem.*, 272:12495-12504, 1997.

Nomiyama et al., "Characterization of cytokine LD78 gene promoters: positive and negative transcriptional factors bind to a negative regulatory element common to LD78, interleukin-3, and granulocyte-macrophage colony-stimulating factor gene promoters," *Mol. Cell. Biol.*, 13:2787-2801, 1993.

Oberlin et al., "The CXC chemokine SDF-1 is the ligand for LESTR/fusin and prevents infection by T-cell-line-adapted HIV-1," *Nature*, 382(6594):833-835, 1996 (Erratum published in *Nature*, 384(6606):288, 1996).

O'Brien et al., "HIV-1 infection in a man homozygous for CCR5 delta 32," *Lancet*, 349(9060):1219, 1997.

Oliveira and McCarthy, *J. Biol. Chem.*, 270:8936-8943, 1995.

Olsen et al., "Interaction of HIV1-RT with azidothymidine triphosphate and the nonnucleoside inhibitor L-697, 661," *Int. Conf. AIDS* 7:A45 (abstract PoA 2255), 1992.

Oravecz et al., "Beta-chemokine inhibition of monocytotropic HIV-1 infection. Interference with a postbinding fusion step," *J. Immunol.*, 157:1329-1332, 1996.

Orkin, "Transcription factors and hematopoietic development," *J. Biol. Chem.*, 270(10):4955-4958, 1995.

Pang et al., "Functional characterization of the promoter region of the platelet-activating factor receptor gene. Identification of an initiator element essential for gene expression in myeloid cells," *J. Biol. Chem.*, 270(23):14123-14129, 1995.

Papasteriades et al., "Histocompatibility antigens HLA-A, -B, -DR in Greek patients with Kaposi's sarcoma," *Tissue Antigens*, 24:313-315, 1984.

Parker et al., "Inhibition of human DNA polymerases and human immunodeficiency virus (HIV) reverse transcriptase by a novel class of compounds, galloylquinic acids," *Proc. Amer. Assoc. Cancer Res.* 30:578 (abstract 2301), 1989.

Parker et al., "Mechanism of inhibition of human immunodeficiency virus type 1 reverse transcriptase and human DNA polymerases $\alpha$, $\beta$, and $\gamma$ by the 5'-triphosphates of Carbovir, 3'-azido-3'-deoxythymidine, 2',3'-dideoxyguanosine, and 3'-deoxythymidine," *J. Biol. Chem.* 266:1754-1762, 1991.

Parola and Kobilka, *J. Biol. Chem.*, 269:4497-4505, 1994.

Paxton et al., "Relative resistance to HIV-1 infection of CD4 lymphocytes from persons who remain uninfected despite multiple high-risk sexual exposure," *Nat. Med.*, 2:412-417, 1996a.

Paxton et al., "The beta-chemokines, HIV type 1 second receptors, and exposed uninfected persons," *AIDS Res. Hum. Retroviruses*, 12:1203-1207, 1996b.

Paxton and Koup, "Mechanisms of resistance to HIV infection," *Springer Semin. Immunopathol.*, 18:323-340, 1997.

Paxton et al., "Reduced HIV-1 infectability of CD4+ lymphocytes from exposed-uninfected individuals: association with low expression of CCR5 and high production of beta-chemokines," *Virology*, 244:66-73, 1998.

Paxton et al., "The HIV type 1 coreceptor CCR5 and its role in viral transmission and disease progression," *AIDS Res. Hum. Retroviruses*, 14(Suppl 1):S89-S92, 1998.

Peckham and Gibb, "Mother-to-child transmission of the human immunodeficiency virus" *N. Engl. J. Med.*, 333:298-302, 1995.

Pei-Zhen et al., "An in vitro EIAV RT model for screening of anti-HIV agents", *Intl. Conf. AIDS* 5:501 (abstract B.626), 1989.

Peterson and Baichwal, "Transcription factor based therapeutics: drugs of the future?," *Trends Biotechnol.*, 11(1):11-18, 1993.

Philpott et al., "0CCR5 genotype and resistance to vertical transmission of HIV-1," *J. Acquir. Immune Defic. Syndr.*, 21:189-193, 1999.

Piatek et al., "Molecular beacon sequence analysis for detecting drug resistance in *Mycobacterium tuberculosis*," *Nat. Biolechnol.*, 16:359-363, 1998.

Picchio et al., "Chemokine receptor CCR5 genotype influences the kinetics of human immunodeficiency virus type 1 infection in human PBL-SCID mice," *J. Virol.*, 71(9):7124-7127, 1997.

Prestridge, *CABIOS*, 7:203-206, 1991.

Puppo et al., "Major histocompatibility gene products and human immunodeficiency virus infection," *J. Lab. Clin. Med.*, 117:91-100, 1991.

Quandt et al., *Nucl. Acids Res.*, 23:4878-4884, 1995.

Quillent et al., "HIV-1-resistance phenotype conferred by combination of two separate inherited mutations of CCR5 gene," *Lancet*, 351:14-18, 1998.

Raport et al., "Molecular cloning and functional characterization of a novel human CC chemokine receptor (CCR5) for RANTES, MIP-1beta, and MIP-1alpha," *J. Biol. Chem.*, 271(29):17161-17166, 1996.

Reardon, "Human immunodeficiency virus reverse transcriptase; Steady-state and pre-steady-state kinetics of nucleotide incorporation," *Biochemistry* 31:4473-4479, 1992.

*Remington's Pharmaceutical Sciences*, 15th Ed., Mack Publishing Company, 1975.

Ressing et al., "Immunotherapy of cancer by peptide-based vaccines for the induction of tumor-specific T cell immunity," *Immunotechnology*, 2:241-251, 1996a.

Ressing et al., "Occasional memory cytotoxic T-cell responses of patients with human papillomavirus type 16-positive cervical lesions against a human leukocyte antigen-A *0201-restricted E7-encoded epitope," *Cancer Res.*, 56:582-588, 1996b.

Rey-Cuille et al., *J. Virol.*, 72(5):3872-3886, 1998.

Rizzardi et al., "CCR2 polymorphism and HIV disease," Swiss HIV Cohort. *Nat. Med.*, 4:252-253, 1998.

Rodgers et al., "Measurement of mRNA concentration and mRNA half-life as a function of hormonal treatment," *Methods Enzymol.*, 109:572-592, 1985.

Roger, "Influence of host genes on HIV-1 disease progression," *FASEB J.*, 12:625-632, 1998.

Rosenberg and Walker, "HIV type 1-specific helper T cells: a critical host defense," *AIDS Res. Hum. Retroviruses*, 14(Suppl 2):S143-S147, 1998.

Rousseau et al., "CCR5del32 in perinatal HIV-1 infection," *J. Acquir. Immune Defic. Syndr. Hum. Retrovirol*, 16:239-242, 1997.

Rowland-Jones et al., "HIV-specific cytotoxic T-cells in HIV-exposed but uninfected Gambian women," Erratum published in *Nat. Med.*, 1(6):598, 1995, *Nat. Med.*, 1:59-64, 1995.

Royce et al., "Sexual transmission of HIV," *N. Engl. J. Med.*, 336:1072-1078, 1997.

Rucker et al., "Regions in beta-chemokine receptors CCR5 and CCR2b that determine HIV-1 cofactor specificity," *Cell*, 87(3):437-446, 1996.

Saah et al., "Association of HLA profiles with early plasma viral load, CD4+ cell count and rate of progression to AIDS following acute HIV-1 infection," Multicenter AIDS Cohort Study, *Aids*, 12:2107-2113, 1998.

Saini et al., "Molecular events regulating messenger RNA stability in eukaryotes," *Mol. Cell Biochem*, 96(1):15-23, 1990.

Saitou and Nei, *Mol. Biol. Evol.*, 4(4):406-425, 1987.

Saksena et al., "Seroepidemiologic, molecular, and phylogenetic analyses of simian T-cell leukemia viruses (STLV-1) from various naturally infected monkey species from central and western Africa," *Virology*, 198:297-310, 1994.

Sambrook et al., *Molecular Cloning—A Laboratory Manual*, Cold Spring Harbor Laboratory Press, 1989.

Samson et al., "Molecular cloning and functional expression of a new human CC-chemokine receptor gene," *Biochemistry*, 35(11):3362-3367, 1996.

Samson et al., "Resistance to HIV-1 infection in caucasian individuals bearing mutant alleles of the CCR-5 chemokine receptor gene," *Nature*, 382(6593):722-725, 1996.

Samson et al., *Genomics*, 36:522-526, 1996.

Scarlatti et al., "In vivo evolution of HIV-1 co-receptor usage and sensitivity to chemokine-mediated suppression," *Nat. Med.*, 3:1259-1265, 1997.

Schacker et al., "Biological and virologic characteristics of primary HIV infection," *Ann. Intern Med.*, 128:613-620, 1998.

Schlotterer, "Genome evolution: are microsatellites really simple sequences?," *Curr. Biol.*, 8:R132-R134, 1998.

Schmidtmayerova et al., "Chemokines and HIV replication," *Nature*, 382:767, 1996.

Schneider et al. "Arlequin: A software for population genetic data analysis. Ver 1.1.," Genetics and Biometry Lab, Dept. of Anthropology, University of Geneva, 1997.

Schwoebel et al., "Factors associated with extrapulmonary tuberculosis as an AIDS-defining disease in Europe," The Coordinators of AIDS surveillance in Austria, Belgium, France, Germany, Italy, Portugal, Switzerland, United Kingdom and the city of Amsterdam, *Tuber Lung Dis.*, 76:281-285, 1995.

Shafer and Edlin, "Tuberculosis in patients infected with human immunodeficiency virus: perspective on the past decade," *Clin. Infect. Dis.*, 22:683-704, 1996.

Shearer and Clerici, "Protective immunity against HIV infection: has nature done the experiment for us?" *Immunol. Today*, 17:21-24, 1996.

Shearer and Clerici, "Cytokine profiles in HIV type 1 disease and protection," *AIDS Res. Hum. Retroviruses*, 14(Suppl 2):S149-S152, 1998.

Shearer et al., "CCR5 HIV-1 vertical transmission,". Women and Infants Transmission Study Group. *J. Acquir. Immune Defic. Syndr. Hum. Retrovirol.*, 17:180-181, 1998.

Shirasaka et al., "In vitro study of drug-sensitivity of HIV strains isolated from patients with AIDS or ARC before and after therapy with AZT and/or 2',3'-dideoxycytidine (ddC)," *Intl. Conf. AIDS* 6:185 (abstract Th.A.263), 1990.

Simmons et al., "Potent inhibition of HIV-1 infectivity in macrophages and lymphocytes by a novel CCR5 antagonist," *Science*, 276(5310):276-279, 1997.

Skowron et al., "Alternating and intermittent regimens of Zidovudine and dideoxycytidine in patients with AIDS or AIDS-related complex," *Ann. In. Med.* 118:321-330, 1993.

Sloan et al., "Single base pair substitutions within the HLA-DRA gene promoter separate the functions of the X1 and X2 boxes," *J. Immunol,* 148(8):2591-2599, 1992.

Smale and Baltimore, *Cell,* 57:103-113, 1989.

Smith et al., "Contrasting genetic influence of CCR2 and CCR5 variants on HIV-1 infection and disease progression," Hemophilia Growth and Development Study (HGDS), Multicenter AIDS Cohort Study (MACS), Multicenter Hemophilia Cohort Study (MHCS), San Francisco City Cohort (SFCC), ALIVE Study. Science, 277(5328): 959-965, 1997.

Song et al., "Polymorphic nucleotides within the human IL-4 promoter that mediate overexpression of the gene," *J. Immunol.,* 156(2):424-429, 1996.

Sozzani et al., "Migration of dendritic cells in response to formyl peptides, C5a, and a distinct set of chemokines," *J. Immunol.,* 155(7):3292-3295, 1995.

Speck et al., "Selective employment of chemokine receptors as human immunodeficiency virus type I coreceptors determined by individual amino acids within the envelope V3 loop," *J. Virol.,* 71(9):7136-7139, 1997.

Sperling et al., "Maternal viral load, zidovudine treatment, and the risk of transmission of human immunodeficiency virus type 1 from mother to infant," Pediatric AIDS Clinical Trials Group Protocol 076 Study Group. *N. Engl. J. Med.,* 335:1621-1629, 1996.

Spijkerman et al., "Differences in progression to AIDS between injection drug users and homosexual men with documented dates of seroconversion," *Epidemiology,* 7:571-577, 1996.

Steel et al., "HLA haplotype A1 B8 DR3 as a risk factor for HIV-related disease," *Lancet,* 1:1185-1188, 1988.

Steinman, "The dendritic cell system and its role in immunogenicity," *Annu. Rev. Immunol.,* 9:271-296, 1991.

Steinman et al., "Dendritic cells: antigen presentation, accessory function and clinical relevance," *Adv. Exp. Med. Biol.,* 329:1-9, 1993.

Stephens et al., "Dating the origin of the CCR5-Delta32 AIDS-resistance allele by the coalescence of haplotypes," *Am. J. Hum. Genet.,* 62:1507-1515, 1998.

Stern et al., "Lack of awareness and treatment of hyperlipidemia in type II diabetes in a community survey," *JAMA,* 262(3):360-364, 1989.

Swofford, "PAUP: Phylogenetic analysis using parsimony, Version 3.1," Computer program distributed by the Illinois Natural History Survey, Champaign, Ill., 1993.

Takahata and Satta, *Proc. Natl. Acad. Sci. USA,* 94(9):4811-4815, 1997.

Tavares et al., "3'-Azido-3'-deoxythymidine in feline leukemia virus-infected cats: A model for therapy and prophylaxis of AIDS," *Cancer Res.* 47:3190-3194, 1987.

The Working Group on Mother-To-Child Transmission of HIV, "Rates of mother-to-child transmission of HIV-1 in Africa, America, and Europe: results from 13 perinatal studies," *J. Acquir. Immune Defic. Syndr. Hum. Retrovirol.,* 8:506-510, 1995.

Theodorou et al., "HIV-1 infection in an individual homozygous for CCR5 delta 32," Seroco Study Group, *Lancet,* 349(9060):1219-1220, 1997.

Tomlinson and Bodmer, "The HLA system and the analysis of multifactorial genetic disease," *Trends Genet.,* 11:493-498, 1995.

Tournamille et al., "Disruption of a GATA motif in the Duffy gene promoter abolishes erythroid gene expression in Duffy-negative individuals," *Nat. Genet.,* 10:224-228, 1995.

Trkola et al., "CD4-dependent, antibody-sensitive interactions between HIV-1 and its co-receptor CCR-5," *Nature,* 384(6605):184-187, 1996.

Tyagi and Kramer, "Molecular beacons: probes that fluoresce upon hybridization," *Nat. Biotechnol.,* 14:303-308, 1996.

Tyagi et al., "Multicolor molecular beacons for allele discrimination," *Nat. Biotechnol.,* 16:49-53, 1998.

Unutmaz et al., "G protein-coupled receptors in HIV and SIV entry: new perspectives on lentivirus-host interactions and on the utility of animal models," *Semin. Immunol.,* 10(3):225-236, 1998.

Van de Perre, "Mother-to-child transmission of HIV-1: the 'all mucosal' hypothesis as a predominant mechanism of transmission," *AIDS,* 13:1133-1138, 1999.

van Rij et al., "Role of CCR2 genotype in the clinical course of syncytium-inducing (SI) or non-SI human immunodeficiency virus type 1 infection and in the time to conversion to SI virus variants," *J. Infect. Dis.,* 178:1806-1811, 1998.

van Rij et al., "The role of a stromal cell-derived factor-1 chemokine gene variant in the clinical course of HIV-1 infection," *AIDS,* 12:F85-F90, 1998.

Versaw et al., "Mitogen-activated protein kinases enhance long-range activation by the beta-globin locus control region," *Proc. Natl. Acad. Sci. USA,* 95:8756-8760, 1998.

Vrang et al., "Inhibition of the reverse transcriptase from HIV by 3'-azido-3'-deoxythymidine triphosphate and its threo analogue," *Antiviral Res.* 7:139-149, 1987.

Wainberg et al., "Characterization of AZT-resistant isolates of HIV-1: Susceptibility to deoxythiacytidine and other nucleosides," *Intl. Conf. AIDS* 6:117 (abstract S.B.87), 1990.

Weatherall, "The genetics of common diseases: the implications of population variability," *Ciba Found Symp.,* 197:300-308, 1996a.

Weatherall, "Host genetics and infectious disease," *Parasitology,* 112:S23-S29, 1996b.

Weatherall et al., "The role of genomics in studying genetic susceptibility to infectious disease," *Genome Res.,* 7:967-973, 1997.

Westby et al., "The role of host immune responses in determining the outcome of HIV infection," *Immunol. Today,* 17:120-126, 1996.

White et al., "Mechanism of inhibition by Carbovir triphosphate of HIV reverse transcriptase and human DNA polymerases, compared with the action of AZT triphosphate and dideoxynucleoside triphosphates," *Intl. Conf. AIDS* 6:186 (abstract Th.A.266), 1990.

White et al., "A TIBO derivative, R82913, is a potent inhibitor of HIV-1 reverse transcriptase with heteropolymer templates," *Antiviral Res.* 16:257-266, 1991.

Winkler et al., "Genetic restriction of AIDS pathogenesis by an SDF-1 chemokine gene variant," ALIVE Study, Hemophilia Growth and Development Study (HGDS), Multicenter AIDS Cohort Study (MACS), Multicenter Hemophilia Cohort Study (MHCS), San Francisco City Cohort (SFCC). *Science,* 279:389-393, 1998.

Wong et al., "Organization and differential expression of the human monocyte chemoattractant protein 1 receptor gene. Evidence for the role of the carboxyl-terminal tail in receptor trafficking," *J. Biol. Chem.,* 272(2):1038-1045, 1997.

Wu et al., "CCR5 levels and expression pattern correlate with infectability by macrophage-tropic HIV-1, in vitro," *J. Exp. Med.,* 185(9):1681-1691, 1997.

Yang and Nielsen, *J. Mol. Evol.,* 46(4):409-418, 1998.

Yang, *Comput. Appl. Biosci.,* 13(5):555-556, 1997.

Yarchoan et al., "Administration of 3'-azido-3'-deoxythymidine, an inhibitor of HTLV-III/LAV replication, to patients with AIDS or AIDS-related complex," *Lancet* 1(8481):575-580, 1986.

Yu, Bowden, Spray, Rich and Freedman, *Hypertension* 31:906-911, 1998.

Zagury et al., "C-C chemokines, pivotal in protection against HIV type 1 infection," *Proc. Natl. Acad. Sci. USA,* 95:3857-3861, 1998.

Zhang et al., "Use of coreceptors other than CCR5 by non-syncytium-inducing adult and pediatric isolates of human immunodeficiency virus type 1 is rare in vitro," *J. Virol.,* 72:9337-9344, 1998.

Zimmerman et al., "Inherited resistance to HIV-1 conferred by an inactivating mutation in CC chemokine receptor 5: studies in populations with contrasting clinical phenotypes, defined racial background, and quantified risk," *Mol. Med.,* 3(1):23-36, 1997.

Zuker, *Science,* 244:48-52, 1989.

The invention claimed is:

1. A method of identifying a Caucasian human subject as having an increased risk of accelerated HIV-1 disease progression, comprising detecting the presence of a CCR5 haplotype pair HHE/HHE in the subject, whereby the presence of said haplotype pair HHE/HHE identifies the subject as having an increased risk of accelerated HIV-1 disease progression.

2. A method of identifying an African-American human subject as having an increased risk of accelerated HIV-1 disease progression, comprising detecting the presence of a CCR5 haplotype pair in the subject, wherein the haplotype pair is selected from the group consisting of:

a) HHC/HHF*1;
b) HHC/HHE;
c) HHC/HHC; and
d) HHC/HHD, whereby the presence of said CCR5 haplotype pair identifies the subject as having an increased risk of accelerated HIV-1 disease progression.

3. The method of claim 2, wherein the haplotype pair is HHC/HHF*1.

4. The method of claim 2, wherein the haplotype pair is HHC/HHE.

5. The method of claim 2, wherein the haplotype pair is HHC/HHC.

6. The method of claim 2, wherein the haplotype pair is HHC/HHD.

7. A method of identifying a Caucasian human subject as having an increased risk of becoming infected with an HIV-1 virus, comprising detecting the presence of a CCR5 haplotype pair HHE/HHE in the subject, whereby the presence of said CCR5 haplotype pair identifies the subject as having an increased risk of becoming infected with an HIV-1 virus.

* * * * *

UNITED STATES PATENT AND TRADEMARK OFFICE
CERTIFICATE OF CORRECTION

PATENT NO. : 7,393,634 B1
APPLICATION NO. : 10/089595
DATED : July 1, 2008
INVENTOR(S) : Ahuja et al.

It is certified that error appears in the above-identified patent and that said Letters Patent is hereby corrected as shown below:

Column 40, Line 62: Please correct "($\geqq 0.22$)"
 To read: --($\geq 0.22$)--

Column 49, Line 32: Please correct "($\geqq 20.22$)"
 To read: --($\geq 0.22$)--

Column 72, Line 9: Please correct "(AG)"
 To read: --($\Delta G$)--

Column 116, Line 48: Please correct "($\geqq 0.22$)"
 To read: --($\geq 0.22$)--

Signed and Sealed this

Sixteenth Day of September, 2008

JON W. DUDAS
*Director of the United States Patent and Trademark Office*

SEQUENCE LISTING

```
<160> NUMBER OF SEQ ID NOS: 72

<210> SEQ ID NO 1
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 1
gtgggatgag cagagaacaa aaacaaaata atccagtgag aaaagcccgt aaataaag        58

<210> SEQ ID NO 2
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 2
cagagaacaa aaacaaaata atccagtgag aaaagcccgt aaataaag                   48

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
gataattgta tgagcacttg gtg                                              23

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
ttgccttctt agagatcaca agccaaagct                                       30

<210> SEQ ID NO 5
<211> LENGTH: 49
<212> TYPE: DNA
<213> ORGANISM: Artificial Sequence
<220> FEATURE:
<223> OTHER INFORMATION: Synthetic oligonucleotide
```

<400> SEQUENCE: 5
cccacacaga tgctcaccac ccaatattat tgttctctgt aaacggaga    49

<210> SEQ ID NO 6
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 6
aacagttctt cttttaagt tgagcttaaa ataagctaga gaatagatct ctggttt    57

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
ggttaatgtg aagtccagga tcc    23

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
ggttaatgtg aagtccagga tcc    23

<210> SEQ ID NO 9
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 9
cattaagtgt attgaaggcg aaaagaatca gagaacagtt gatc    44

<210> SEQ ID NO 10
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 10
gtaaataaac cttcagacca gagatctatt ctccagctta ttttaagctc aacttttaa    59

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
gataattgta tgagcacttg gtgtttgcc    29

<210> SEQ ID NO 12

```
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 12
atcttaaaga ttatatttta agataattgt atgagcactt ggtgtttgcc agat        54

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
gttggtttaa gttggctt                                                18

<210> SEQ ID NO 14
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 14
ctccgctcta ctcgctggtg ttcatctttg gttttgtggg caacatgatg g           51

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
agttgactgg tgctttca                                                18

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
gagccaaggt cacggaagcc c                                            21

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
ggacccagga tcttagtg                                                18

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
```

```
caaaaagaag gtcttcatta cacc                                          24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
tcacaagccc acagatattt cctg                                          24

<210> SEQ ID NO 20
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 20
gatgggaaac ctgtttagct cacccgtgag c                                  31

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21
catcccacta cacagaatct gttag                                         25

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
cccgtgagcc catagttaaa actc                                          24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
tcacagggct tttcaacagt aagg                                          24

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
agatgaatgt aaatgttctt ctag                                          24

<210> SEQ ID NO 25
<211> LENGTH: 26
<212> TYPE: DNA
```

```
<213> ORGANISM: Artificial Sequence
<220> FEATURE:
<223> OTHER INFORMATION: Synthetic oligonucleotide

<400> SEQUENCE: 25 cttttaagt tgagcttaaa ataagc                                          26

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 26
cgcacctctg gtctgaaggt ttatggtgcg                                     30

<210> SEQ ID NO 27
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 27
cgcacctctg gtctgaaagt ttatttggtg cg                                  32

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
agaccagaga tctattctcc agct                                           24

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
tattgaaggc gaaaagaatc ag                                             22

<210> SEQ ID NO 30
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 30
ccggtcaact taaaagaag aactggaccg g                                    31

<210> SEQ ID NO 31
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 31
ccggtcaact taaaggaag aactggaccg g                                    31
```

<210> SEQ ID NO 32
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 32
ctccgctcta ctcgctggtg ttcatctttg gttttgtggg caacatgatg g         51

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
tcaactgacc acgaaagt                                               18

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
gagccaaggt cacggaagcc c                                           21

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 35
cctgggtcct agaatcac                                               18

<210> SEQ ID NO 36
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 36
gtgggatgag cagagaacaa aaacaaaata atccagtgag aaaagcccgt aaataaag   58

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
ctattaacat actcgtgaac cac                                         23

<210> SEQ ID NO 38
<211> LENGTH: 18
<212> TYPE: DNA
<213> ORGANISM: Artificial Sequence
<220> FEATURE:

<223> OTHER INFORMATION: Synthetic oligonucleotide

<400> SEQUENCE: 38
gttggtttaa gttggctt                                         18

<210> SEQ ID NO 39
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 39
tagaatttct aatataaaat tctattaaca tactcgtgaa ccacaaacgg tcta    54

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
caaaaagaag gtcttcatta cacc                                  24

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
agtgttcggg tgtctataaa ggac                                  24

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
tggcgacacg tagcagctta g                                     21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
ttcctggtgc cgagactagt c                                     21

<210> SEQ ID NO 44
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 44
gcggccgctt atgcacaggg tggaacaag                             29

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
tctagaccac ttgagtccgt gtca                                   24

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 46
cataaagaac ctgaacttga cc                                     22

<210> SEQ ID NO 47
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 47
tagaatttct aatataaaat tctattaaca tactcgtgaa ccacaaacgg tcta   54

<210> SEQ ID NO 48
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 48
gggaacggat gtctcagctc ttct                                   24

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 49
accaaagatg aacaccagtg agtagag                                27

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
tgtcttctca gctctgctga c                                      21

<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 51
gctccgatgt ataataattg atgt                                          24

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 52
aatacttgag attttcagat g                                             21

<210> SEQ ID NO 53
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 53
agattggact tgacacttga taatccat                                      28

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
gttttcgttt acggagtaat attg                                          24

<210> SEQ ID NO 55
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 55
gtttccgttt acagagaaca ataatattg                                     29

<210> SEQ ID NO 56
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 56
gttcatgtgt atgggagtg ggatagg                                        27

<210> SEQ ID NO 57
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 57
gcatctgtgt ggggttggg gtgggatagg                                     30

<210> SEQ ID NO 58
<211> LENGTH: 24
```

```
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (14)..(14)
<223> OTHER INFORMATION: WHEREIN R = G OR A

<400> SEQUENCE: 58
atctggagtg aagratcctg ccac                                              24

<210> SEQ ID NO 59
<211> LENGTH: 30
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (17)..(17)
<223> OTHER INFORMATION: WHEREIN Y = T OR C

<400> SEQUENCE: 59
ggaaacccat agaagayatt tggcaaacac                                        30

<210> SEQ ID NO 60
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (16)..(16)
<223> OTHER INFORMATION: WHEREIN K = G OR T

<400> SEQUENCE: 60
tttagacaac aggttktttc cgtttacaga g                                      31

<210> SEQ ID NO 61
<211> LENGTH: 31
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (16)..(16)
<223> OTHER INFORMATION: WHEREIN R = G OR A

<400> SEQUENCE: 61
gtggagaaaa agggrcaca gggttaatgt g                                       31

<210> SEQ ID NO 62
<211> LENGTH: 34
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (16)..(19)
<223> OTHER INFORMATION: WHEREIN Y = T OR C

<400> SEQUENCE: 62
agcccgtaaa taaacyttya gaccagagat ctat                                   34

<210> SEQ ID NO 63
<211> LENGTH: 31
<212> TYPE: DNA
<213> ORGANISM: Artificial Sequence
<220> FEATURE:
<223> OTHER INFORMATION: Synthetic oligonucleotide
```

```
<221> NAME/KEY: misc_feature
<222> LOCATION: (16)..(16)
<223> OTHER INFORMATION: WHEREIN R = G OR A

<400> SEQUENCE: 63
aagctcaact taaaargaag aactgttctc t                                31

<210> SEQ ID NO 64
<211> LENGTH: 925
<212> TYPE: DNA
<213> ORGANISM: Artificial Sequence
<220> FEATURE:
<223> OTHER INFORMATION: Synthetic oligonucleotide

<400> SEQUENCE: 64
ctccagatag attatatctg gagtgaagaa tcctgccacc tatgtgtctg gcatagtgtg    60
agtcctcata aatgcttact ggtttgaagg gcaacaaaat agtgaacaga gtgaaaatcc   120
ccactaagat cctgggtcca gaaaagatg ggaaacctgt ttagctcccg tgagcccata    180
gttaaaactc tttagacaac aggttgtttc cgtttacaga gaacaataat attgggtggt   240
gagcatctgt gtggggttg gggtgggata ggggatacgg ggagagtgga gaaaagggg     300 gcacagggtt aatgtgaagt ccaggatccc cctctacatt taaagttggt ttaagttggc   360
tttaattaat agcaactctt aagataatca gaattttctt aacctttag ccttactgtt    420 gaaaagccct gtgatcttgt acaaatcatt ggcttcttgg atagtaattt cttttactaa   480
aatgtgggct tttgactaga tgaatgtaaa tgttcttcta gctctgatat cctttattct   540
ttatattttc taacggattc tgtgtagagg gatgagcaga gaacaaaaac aaaataatcc   600
agtgagaaaa gcccataaat aaactttcag accagagatc tattctctag cttattttaa   660
gctcaactta aaagaagaa ctgttctctg attcttttg ccttcgatac acttaatgat     720
ttaactccac cctccttcaa agaaacagc atttcctact tttatactgt ctatatgatt    780
gacttgcaca gctcatctgg ccagaagagc tgagacatcc gttcccctac aagaaactct   840
ccccggtaag taacctctca gccgcttggc ctgttagtta gcttctgaga tgagtaaaag   900
actttacagg aaacccatag aagac                                        925

<210> SEQ ID NO 65
<211> LENGTH: 927
<212> TYPE: DNA
<213> ORGANISM: Artificial Sequence
<220> FEATURE:
<223> OTHER INFORMATION: Synthetic oligonucleotide

<400> SEQUENCE: 65
cttcagatag attatatctg gagtgaagaa tcctgccacc tatgtatctg gcatagtgtg    60
agtcctcata aatgcttact ggtttgaagg gcaacaaaat agtgaacaga gtgaaaatcc   120
ccactaagat cctgggtcca gaaaagatg ggaaacctgt ttagctcacc cgtgagccca    180
tagttaaaac tctttagaca acaggttgtt tccgtttaca gagaacaata atattgggtg   240
gtgagcatct gtgtgggggt tggggtggga taggggatac gggagagtg gagaaaaagg    300 gggcacaggg ttaatgtgaa gtccaggatc cccctctaca tttaaagttg gtttaagttg   360
gctttaatta atagcaactc ttaagataat cagaattttc ttaaccttt agccttactg    420 ttgaaaagcc ctgtgatctt gtacaaatca tttgcttctt ggatagtaat ttcttttact   480
aaaatgtggg cttttgacta gatgaatgta aatgttcttc tagctctgat atcctttatt   540
ctttatattt tctaacagat tctgtgtagt gggatgagca gagaacaaaa acaaaataat   600
```

```
ccagtgagaa aagcccgtaa ataaactttc agaccagaga tctattctct agcttatttt      660
aagctcaact taaaaagaag aactgttctc tgattctttt cgccttcaat acacttaatg      720
atttaactcc accctccttc aaaagaaaca gcatttccta cttttatact gtctatatga     780
ttgatttgca cagctcatct ggccagaaga gctgagacat ccgttcccct acaagaaact      840
ctccccggta agtaacctct cagctgcttg gcctgttagt tagcttctga gatgagtaaa      900
agactttaca ggaaacccat agaagac                                          927

<210> SEQ ID NO 66
<211> LENGTH: 927
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (374)..(374)
<223> OTHER INFORMATION: WHEREIN S = C OR G
<221> NAME/KEY: misc_feature
<222> LOCATION: (385)..(922)
<223> OTHER INFORMATION: WHEREIN R = A OR G
<221> NAME/KEY: misc_feature
<222> LOCATION: (546)..(546)
<223> OTHER INFORMATION: WHEREIN Y = C OR T

<400> SEQUENCE: 66
cttcagatag attatatctg gagtgaagaa tcctgccacc tatgtatctg gcatagtgtg      60
agtcctcata aatgcttact ggtttgaagg gcaacaaaat agtgaacaga gtgaaaatcc     120
ccactaagat cctgggtcca gaaaaagatg ggaaacctgt ttagctcacc cgtgagccca     180
tagttaaaac tctttagaca acaggttgtt tccgtttaca gagaacaata atattgggtg     240
gtgagcatct gtgtgggggt tggggtggga taggggatac ggggagagtg gagaaaaagg     300
gggcacaggg ttaatgtgaa gtccaggatc cccctctaca tttaaagttg gtttaagttg     360
gctttaatta atascaactc ttaaratat cagaattttc ttaaccttt agccttactg      420 ttgaaaagcc ctgtgatctt gtacaaatca tttgcttctt ggatagtaat ttcttttact     480
aaaatgtggg cttttgacta gatgaatgta atgttcttc tagctctgat atcctttatt      540
ctttayattt tctaacagat tctgtgtagt gggatgagca gagaacaaaa acaaaataat     600
ccagtgagaa aagcccgtaa ataaactttc agaccagaga tctattctct agcttatttt      660
aagctcaact taaaaagaag aactgttctc tgattctttt cgccttcaat acacttaatg      720
atttaactcc accctccttc aaaagaaaca gcatttccta cttttatact gtctatatga     780
ttgatttgca cagctcatct ggccagaaga gctgagacat ccgttcccct acaagaaact      840
ctccccggta agtaacctct cagctgcttg gcctgttagt tagcttctga gatgagtaaa      900
agactttaca ggaaacccat araagac                                          927

<210> SEQ ID NO 67
<211> LENGTH: 927
<212> TYPE: DNA
<213> ORGANISM: Artificial Sequence
<220> FEATURE:
<223> OTHER INFORMATION: Synthetic oligonucleotide

<400> SEQUENCE: 67
cttcagatag attatatctg gagtgaagaa tcctgccacc tatgtatctg gcatagtgtg      60
agtcctcata aatgcttact ggtttgaagg gcaacaaaat agtgaacaga gtgaaaatcc     120
ccactaagat cctgggtcca gaaaaagatg ggaaacctgt ttagctcacc cgtgagccca     180
```

```
tagttaaaac tctttagaca acaggttttt tccgtttaca gagaacaata atattgggtg    240
gtgagcatct gtgtgggggt tggggtggga taggggatac ggggagagtg gagaaaaagg    300
gggcacaggg ttaatgtgaa gtccaggatc cccctctaca tttaaagttg gtttaagttg    360
gctttaatta atagcaactc ttaagataat cagaattttc ttaaccttt agccttactg    420 ttgaaaagcc ctgtgatctt gtacaaatca tttgcttctt ggatagtaat ttcttttact    480
aaaatgtggg cttttgacta gatgaatgta aatgttcttc tagctctgat atcctttatt    540
ctttatattt tctaacagat tctgtgtagt gggatgagca gagaacaaaa acaaaataat    600
ccagtgagaa aagcccgtaa ataaactttc agaccagaga tctattctct agcttatttt    660
aagctcaact taaaagaag aactgttctc tgattctttt cgccttcaat acacttaatg    720
atttaactcc accctccttc aaaagaaaca gcatttccta cttttatact gtctatatga    780
ttgatttgca cagctcatct ggccagaaga gctgagacat ccgttcccct acaagaaact    840
ctccccggta agtaacctct cagctgcttg gcctgttagt tagcttctga gatgagtaaa    900
agactttaca ggaaacccat agaagac                                        927

<210> SEQ ID NO 68
<211> LENGTH: 927
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (239)..(756)
<223> OTHER INFORMATION: WHEREIN Y = C OR T

<400> SEQUENCE: 68
cttcagatag attatatctg gagtgaagaa tcctgccacc tatgtatctg gcatagtgtg     60
agtcctcata aatgcttact ggtttgaagg gcaacaaaat agtgaacaga gtgaaaatcc    120
ccactaagat cctgggtcca gaaaaagatg ggaaacctgt ttagctcacc cgtgagccca    180
tagttaaaac tctttagaca acaggttttt tccgtttaca gagaacaata atattgggyg    240
gtgagcatct gtgtgggggt tggggtggga taggggatac ggggagagtg gagaaaaagg    300
gggcacaggg ttaatgtgaa gtccaggatc cccctctaca tttaaagttg gtttaagttg    360
gctttaatta atagcaactc ttaagataat cagaattttc ttaaccttt agccttactg    420 ttgaaaagcc ctgtgatctt gtacaaatca tttgcttctt ggatagtaat ttcttttact    480
aaaatgtggg cttttgacta gatgaatgta aatgttcttc tagctctgat atcctttatt    540
ctttatattt tctaacagat tctgtgtagt gggatgagca gagaacaaaa acaaaataat    600
ccagtgagaa aagcccgtaa ataaactttc agaccagaga tctattctct agcttatttt    660
aagctcaact taaaggaag aactgttctc tgattctttt cgccttcaat acacttaatg    720
atttaactcc accctccttc aaaagaaaca gcattyccta cttttatact gtctatatga    780
ttgatttgca cagctcatct ggccagaaga gctgagacat ccgttcccct acaagaaact    840
ctccccggta agtaacctct cagctgcttg gcctgttagt tagcttctga gatgagtaaa    900
agactttaca ggaaacccat agaagac                                        927

<210> SEQ ID NO 69
<211> LENGTH: 927
<212> TYPE: DNA
<213> ORGANISM: Artificial Sequence
<220> FEATURE:
<223> OTHER INFORMATION: Synthetic oligonucleotide
```

<221> NAME/KEY: misc_feature
<222> LOCATION: (45)..(524)
<223> OTHER INFORMATION: WHEREIN Y = C OR T

<400> SEQUENCE: 69

```
cttcagatag attatatctg gagtgaagaa tcctgccacc tatgyatctg gcatagtgtg      60
agtcctcata aatgcttact ggtttgaagg gcaacaaaat agtgaacaga gtgaaaatcc     120
ccactaagat cctgggtcca gaaaaagatg ggaaacctgt ttagctcacc cgtgagccca     180
tagttaaaac tctttagaca acaggttttt tccgtttaca gagaacaata atattgggtg     240
gtgagcatct gtgtggggt tggggtggga taggggatac gggagagtg gagaaaaagg      300
gggcacaggg ttaatgtgaa gtccaggatc ccctctaca tttaaagttg gtttaagttg     360
gctttaatta atagcaactc ytaagataat cagaattttc ttaacctttt agccttactg     420
ttgaaaagcc ctgtgatctt gtacaaatca tttgcttctt ggatagtaat ttcttttact     480
aaaatgtggg cttttgacta gatgaatgta atgttcttc tagytctgat atcctttat      540
ctttatattt tctaacagat tctgtgtagt gggatgagca gagaacaaaa acaaaataat     600
ccagtgagaa aagcccgtaa ataaactttt agaccagaga tctattctct agcttatttt     660
aagctcaact taaaaagaag aactgttctc tgattctttt cgccttcaat acacttaatg     720
atttaactcc accctccttc aaagaaaca gcatttccta cttttatact gtctatatga     780
ttgatttgca cagctcatct ggccagaaga gctgagacat ccgttcccct acaagaaact     840
ctccccggta agtaacctct cagctgcttg gcctgttagt tagcttctga gatgagtaaa     900
agactttaca ggaaacccat agaagac                                         927
```

<210> SEQ ID NO 70
<211> LENGTH: 927
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (177)..(494)
<223> OTHER INFORMATION: WHEREIN Y = C OR T

<400> SEQUENCE: 70

```
cttcagatag attatatctg gagtgaagaa tcctgccacc tatgtatctg gcatagtgtg      60
agtcctcata aatgcttact ggtttgaagg gcaacaaaat agtgaacaga gtgaaaatcc     120
ccactaagat cctgggtcca gaaaaagatg ggaaacctgt ttagctcacc cgtgagycca     180
tagttaaaac tctttagaca acaggttgtt tccgtttaca gagaacaata atattgggtg     240
gtgagcatct gtgtggggt tggggtggga taggggatac gggagagtg gagaaaaagg      300
ggacacaggg ttaatgtgaa gtccaggatc ccctctaca tttaaagttg gtttaagttg     360
gctttaatta atagcaactc ttaagataat cagaattttc ttaaccttty agccttactg     420
ttgaaaagcc ctgygatctt gtacaaatca tttgcttctt ggatagtaat ttcttttact     480
aaaatgtggg cttytgacta gatgaatgta atgttcttc tagctctgat atcctttat      540
ctttatattt tctaacagat tctgtgtagt gggatgagca gagaacaaaa acaaaataat     600
ccagtgagaa aagcccgtaa ataaaccttc agaccagaga tctattctct agcttatttt     660
aagctcaact taaaaagaag aactgttctc tgattctttt cgccttcaat acacttaatg     720
atttaactcc accctccttc aaagaaaca gcatttccta cttttatact gtctatatga     780
ttgatttgca cagctcatct ggccagaaga gctgagacat ccgttcccct acaagaaact     840
```

| | | |
|---|---|---|
| ctccccggta agtaacctct cagctgcttg gcctgttagt tagcttctga gatgagtaaa | 900 | |
| agactttaca ggaaacccat agaagac | 927 | |

<210> SEQ ID NO 71
<211> LENGTH: 927
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (94)..(895)
<223> OTHER INFORMATION: WHEREIN R = A OR G
<221> NAME/KEY: misc_feature
<222> LOCATION: (209)..(880)
<223> OTHER INFORMATION: WHEREIN Y = C OR T

<400> SEQUENCE: 71

| | |
|---|---|
| cttcagatag attatatctg gagtgaagaa tcctgccacc tatgtatctg gcatagtgtg | 60 |
| agtcctcata aatgcttact ggtttgaagg gcarcaaaat agtgaacaga gtgaaaatcc | 120 |
| ccactaagat cctgggtcca gaaaaagatg ggaaacctgt ttagctcacc cgtgagccca | 180 |
| tagttaaaac tctttagacr acaggttgyt tccgtttaca gagaacaata atattgggtg | 240 |
| gtgagcatct gtgtgggggt tggggtggga taggggatac ggggagagtg grgaaaaagg | 300 |
| ggacacaggg ttaatgtgaa gtccaggatc cccctctaca tttaaagttg gtttaagttg | 360 |
| rctttaatta atagcaactc ttaagataat cagaattttc ttaacctttt agccttactg | 420 |
| ttgaaaagcc ctgtgatctt gtacaaatca tttgcttctt ggatagtaat ttcttttact | 480 |
| aaaatgtggg cttttgacta gatgaatgta aatgttcttc tagctctgat atcctttatt | 540 |
| ctttatattt tctaacagat tctgtgtagt gggatgagca gagaacaaaa acaaaataat | 600 |
| ccagtgagaa aagcccgtaa ataaaccttc agaccagaga tctattctct agcttatttt | 660 |
| aagctcaact taaaagaag aactgytctc tgattctttt cgccttcaat acacttaatg | 720 |
| atttaactcc accctccttc aaaagaaaca gcatttccta cttttatact gyctatatga | 780 |
| ttgatttgca cagctcatct ggccagaaga gctgagacat ccgttcccct acaagaaact | 840 |
| ctccccggta agtaacctct cagctgcttg gcctgttagy tagcttctgr gatgrgtaaa | 900 |
| agactttaca ggaaacccat agaagat | 927 |

<210> SEQ ID NO 72
<211> LENGTH: 927
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: (718)..(925)
<223> OTHER INFORMATION: WHEREIN R = A OR G

<400> SEQUENCE: 72

| | |
|---|---|
| cttcagatag attatatctg gagtgaagga tcctgccacc tatgtatctg gcatagtgtg | 60 |
| agtcctcata aatgcttact ggtttgaagg gcaacaaaat agtgaacaga gtgaaaatcc | 120 |
| ccactaagat cctgggtcca gaaaaagatg ggaaacctgt ttagctcacc cgtgagccca | 180 |
| tagttaaaac tctttagaca acaggttgtt tccgtttaca gagaacaata atattgggtg | 240 |
| gtgagcatct gtgtgggggt tggggtggga taggggatac ggggagagtg gagaaaaagg | 300 |
| ggacacaggg ttaatgtgaa gtccaggatc cccctctaca tttaaagttg gtttaagttg | 360 |
| gctttaatta atagcaactc ttaagataat cagaattttc ttaacctttt agccttactg | 420 |

```
-continued ttgaaaagcc ctgtgatctt gtacaaatca tttgcttctt ggatagtaat ttcttttact      480
aaaatgtggg cttttgacta gatgaatgta aatgttcttc tagctctgat atcctttatt      540
ctttatattt tctaacagat tctgtgtagt gggatgagca gagaacaaaa acaaaataat      600
ccagtgagaa aagcccgtaa ataaaccttc agaccagaga tctattctct agcttatttt      660
aagctcaact taaaagaag aactgttctc tgattctttt cgccttcaat acacttartg       720
atttaactcc accctccttc aaaagaaaca gcatttccta cttttatact gtctatatga      780
ttgatttgca cagctcatct ggccagaaga gctgagacat ccgttcccct acaagaaact      840
ctccccggta agtaacctct cagctgcttg gcctgttagt tagcttctga ratgagtaaa      900
agactttaca ggaaacccat agaarac                                          927
```